(12) United States Patent
He et al.

(10) Patent No.: US 11,458,122 B2
(45) Date of Patent: Oct. 4, 2022

(54) METHODS FOR TREATING DISEASES AND NERVE INJURIES

(71) Applicant: CHILDREN'S HOSPITAL MEDICAL CENTER, Cincinnati, OH (US)

(72) Inventors: Xuelian He, Cambridge, MA (US); Qing Lu, Cincinnati, OH (US); Liguo Zhang, Cincinnati, OH (US)

(73) Assignee: CHILDREN'S HOSPITAL MEDICAL CENTER, Cincinnati, OH (US)

( * ) Notice: Subject to any disclaimer, the term of this patent is extended or adjusted under 35 U.S.C. 154(b) by 82 days.

(21) Appl. No.: 16/637,295

(22) PCT Filed: Aug. 8, 2018

(86) PCT No.: PCT/US2018/045727
§ 371 (c)(1),
(2) Date: Feb. 7, 2020

(87) PCT Pub. No.: WO2019/032652
PCT Pub. Date: Feb. 14, 2019

(65) Prior Publication Data
US 2020/0230106 A1 Jul. 23, 2020

Related U.S. Application Data

(60) Provisional application No. 62/543,044, filed on Aug. 9, 2017.

(51) Int. Cl.
| | |
|---|---|
| *A61K 31/415* | (2006.01) |
| *A61P 25/28* | (2006.01) |
| *A61K 9/00* | (2006.01) |
| *A61K 31/167* | (2006.01) |
| *A61K 31/4353* | (2006.01) |
| *A61K 45/06* | (2006.01) |

(52) U.S. Cl.
CPC .......... *A61K 31/415* (2013.01); *A61K 9/0019* (2013.01); *A61K 9/0053* (2013.01); *A61K 31/167* (2013.01); *A61K 31/4353* (2013.01); *A61K 45/06* (2013.01); *A61P 25/28* (2018.01)

(58) Field of Classification Search
CPC .................................................... A61K 31/415
See application file for complete search history.

(56) References Cited

U.S. PATENT DOCUMENTS

| | | | | |
|---|---|---|---|---|
| 2004/0077591 | A1* | 4/2004 | Dangond | A61K 31/19 514/54 |
| 2007/0078083 | A1* | 4/2007 | Barlow | A61P 27/02 514/8.3 |
| 2007/0219244 | A1* | 9/2007 | Jenssen | C07C 231/02 514/313 |
| 2012/0276073 | A1 | 11/2012 | Schachner et al. | |
| 2013/0210899 | A1 | 8/2013 | Wood | |
| 2013/0317003 | A1* | 11/2013 | Jacques | A61P 25/28 514/210.21 |
| 2014/0080802 | A1 | 3/2014 | Holson et al. | |
| 2016/0097036 | A1 | 4/2016 | Chaurasia et al. | |

OTHER PUBLICATIONS

Li et al. J. Pharmacol Exp Ther., 2010, 334(1): 106-15 (abstract).*
Soragni et al. CAS: 163: 438461, 2014.*
Yoshizumi et al. CAS: 160: 451487, 2013.*
Li et al. (2010) "An Apolipoprotein E-Mimetic Stimulates Axonal Regeneration and Remyelination after Peripheral Nerve Injury" The Journal of Pharmacology and Experimental Therapeutics, vol. 334, No. 1, pp. 106-115.
International Search Report from PCT/US2018/045727, dated Oct. 19, 2018, 3 pages.
Written Opinion from PCT/US2018/045727, dated Oct. 19, 2018, 5 pages.
Arthur-Farraj et al. (2012) "c-Jun reprograms Schwann cells of injured nerves to generate a repair cell essential for regeneration" Neuron, vol. 75, pp. 633-647.
Bei et al. (2016) "Restoration of Visual Function by Enhancing Conduction" Regenerated Axons Cell, vol. 164, pp. 219-232.
Benraiss et al. (2016) "Human glia can both induce and rescue aspects of disease phenotype in Huntington disease" Nature Communications, vol. 7, Article 11758 (13 pages).
Bittner et al., (2014) "Myelin oligodendrocyte glycoprotein (MOG35-55) induced experimental autoimmune encephalomyelitis (EAE) in C57BL/6 mice" J Vis Exp., vol. 86, Article 51275 (5 pages).
Brugger et al. (2015) "HDAC1/2-Dependent P0 Expression Maintains Paranodal and Nodal Integrity Independently of Myelin Stability through Interactions with Neurofascins" PLoS Biol, vol. 13, vol. 9, Article el002258 (32 pages).
Brugger et al. (2017) "Delaying histone deacetylase response to injury accelerates conversion into repair Schwann cells and nerve regeneration" Nat Commun, vol. 8, Article 14272 (16 pages).
Cattin et al. (2015) "Macrophage-Induced Blood Vessels Guide Schwann Cell-Mediated Regeneration of Peripheral Nerves" Cell, vol. 162, pp. 1127-1139.
Chen et al. (2007) "Peripheral regeneration" Annu Rev Neurosci, vol. 30, pp. 209-233.

(Continued)

*Primary Examiner* — Rei Tsang Shiao
(74) *Attorney, Agent, or Firm* — ALGM LLP; Harry J. Guttman

(57) ABSTRACT

Some embodiments of the invention include methods for treating an animal for disease or nerve damage, comprising administration of a composition comprising a myelination enhancing inhibitor to the animal. Other embodiments of the invention include methods for treating an animal for disease or nerve damage, comprising administration of a composition comprising an HDAC3 inhibitor to the animal. Still other embodiments of the invention include methods for treating an animal for MS or nerve damage, comprising administration of a composition comprising an HDAC3 inhibitor to the animal. Additional embodiments of the invention are also discussed herein.

27 Claims, 69 Drawing Sheets

(56) References Cited

OTHER PUBLICATIONS

Chen et al. (2011) "HDAC-mediated deacetylation of NF-kappaB is critical for Schwann cell myelination" Nat Neurosci, vol. 14, pp. 437-441.
Cho et al. (2013) "Injury-induced HDAC5 nuclear export is essential for axon regeneration" Cell, vol. 155, pp. 894-908.
Choudhary et al. (2009) "Lysine acetylation targets protein complexes and co-regulates major cellular functions" Science, vol. 325, pp. 834-840.
Cotter et al. (2010) "Dlg1-PTEN interaction regulates myelin thickness to prevent damaging peripheral nerve overmyelination" Science, vol. 328, pp. 1415-1418.
Creyghton et al., (2010) "Histone H3K27ac separates active from poised enhancers and predicts developmental state" Proc Natl Acad Sci U S A, vol. 107, pp. 21931-21936.
De Souza et al. (2015) "HDAC Inhibitors as Novel Anti-Cancer Therapeutics" Recent Pat Anticancer Drug Discov, vol. 10, pp. 145-162.
Deng et al. (2017) "A reciprocal regulatory loop between TAZ/YAP and G-protein Galphas regulates Schwann cell proliferation and myelination" Nat Commun, vol. 8, Article 15161 (15 pages).
Deumens et al. (2010) "Repairing injured peripheral nerves: Bridging the gap" Prog Neurobial, vol. 92, pp. 245-276.
Doerflinger et al. (2003) "Inducible site-specific recombination in myelinating cells" Genesis, vol. 35, pp. 63-72.
Emery et al. (2015) "Transcriptional and Epigenetic Regulation of Oligodendrocyte Development and Myelination in the Central Nervous System" Cold Spring Harb Perspect Biol, vol. 7, Article a020461 (21 pages).
Erjala et al. (2006) "Signaling via ErbB2 and ErbB3 associates with resistance and epidermal growth factor receptor (EGFR) amplification with sensitivity to EGFR inhibitor gefitinib in head and neck squamous cell carcinoma cells" Clin Cancer Res, vol. 12, pp. 4103-4111.
Feltri et al. (2005) "Laminins and their receptors in Schwann cells and hereditary neuropathies" J Peripher Nerv Syst, vol. 10, pp. 128-143.
Feltri et al. (2015) "How Schwann Cells Sort Axons: New Concepts" Neuroscientist, vol. 22, No. 3, pp. 252-265.
Fernando et al. (2016) "Optimal myelin elongation relies on YAP activation by axonal growth and inhibition by Crb3/Hippo pathway" Nat Commun, vol. 7, Article 12186 (14 pages).
Finzsch et al. (2010) "Sox10 is required for Schwann cell identity and progression beyond the immature Schwann cell stage" J Cell Biol, vol. 189, pp. 701-712.
Fledrich et al. (2014) "Soluble neuregulin-1 modulates disease pathogenesis in rodent models of Charcot-Marie-Tooth disease IA" Nat Med, vol. 20, pp. 1055-1061.
Greer et al. (2015) "Histone Deacetylases Positively Regulate Transcription through the Elongation Machinery" Cell Rep, vol. 13, pp. 1444-1455.
Grove et al. (2017) "YAP/TAZ initiate and maintain Schwann cell myelination" Elife, vol. 6, Article e20982 (27 pages).
Gutmann et al. (2015) "Update on Charcot-Marie-Tooth disease" Curr Opin Neural, vol. 28, pp. 462-467.
Quintes et al. (2016) "Zeb2 is essential for Schwann cell differentiation, myelination and nerve repair" Nat Neurosci, vol. 19, pp. 1050-1059.
Rai et al. (2008) "HDAC inhibitors correct frataxin deficiency in a Friedreich ataxia mouse model" PLoS One, vol. 3, No. 4, Article e1958 (8 pages).
Sadoul et al. (2008) "Regulation of protein turnover by acetyltransferases and deacetylases" Biochimie, vol. 90, pp. 306-312.
Salzer (2015) "Schwann cell myelination" Cold Spring Harb Perspect Biol, vol. 7, Article a020529 (26 pages).
Scherer et al. (2008) "Molecular mechanisms of inherited demyelinating neuropathies" Glia, vol. 56, pp. 1578-1589.
Schroder (1972) "Altered ratio between axon diameter and myelin sheath thickness in regenerated nerve fibers" Brain Res, vol. 45, pp. 49-65.
Sheean et al. (2014) "Activation of MAPK overrides the termination of myelin growth and replaces Nrg1/ErbB3 signals during Schwann cell development and myelination" Genes Dev, vol. 28, pp. 290-303.
Sherman et al. (2005) "Mechanisms of axon ensheathment and myelin growth" Nat Rev Neurosci, vol. 6, pp. 683-690.
Stolt et al. (2016) "Schwann cells and their transcriptional network: Evolution of key regulators of peripheral myelination" Brain Res, vol. 1641, Part A, pp. 101-110.
Suter et al. (2003) "Disease mechanisms in inherited neuropathies" Nat Rev Neurosci, vol. 4, pp. 714-726.
Suzuki (2013) "Peripheral neuropathy in the elderly" Handb Clin Neurol, vol. 115, pp. 803-813.
Svaren et al. (2008) "The molecular machinery of myelin gene transcription in Schwann cells" Glia, vol. 56, pp. 1541-1551.
Svennigsen et al. (2013) "Repair of the Peripheral Nerve-Remyelination that Works" Brain Sci, vol. 3, pp. 1182-1197.
Taveggia et al. (2005) "Neuregulin-1 type III determines the ensheathment fate of axons" Neuron, vol. 47, pp. 681-694.
Topilko et al. (1994) "Krox-20 controls myelination in the peripheral nervous system" Nature, vol. 371, pp. 796-799.
Trivedi et al. (2018) "Design, synthesis and biological screening of 2-aminobenzamides as selective HDAC3 inhibitors with promising anticancer effects" European Journal of Pharmaceutical Sciences, vol. 124, pp. 165-181.
Wang et al. (2009) "Genome-wide mapping of HATs and HDACs reveals distinct functions in active and inactive genes" Cell, vol. 138, pp. 1019-1031.
Watkins et al. (2008) "Distinct stages of myelination regulated by gamma-secretase and astrocytes in a rapidly myelinating CNS coculture system" Neuron, vol. 60, pp. 555-569.
Weider et al. (2012) "Chromatin-remodeling factor brg1 is required for schwann cell differentiation and myelination" Dev Cell, vol. 23, pp. 193-201.
Woodhoo et al. (2009) "Notch controls embryonic Schwann cell differentiation, postnatal myelination and adult plasticity" Nat Neurosci, vol. 12, pp. 839-847.
Wu et al. (2016) "Zeb2 recruits HDAC-NuRD to inhibit Notch and controls Schwann cell differentiation and remyelination" Nat Neurosci, vol. 19, pp. 1060-1072.
Xia et al. (2017) "Proteomic Analysis of HDAC3 Selective Inhibitor in the Regulation of Inflammatory Response of Primary Microglia" Neural Plasticity, vol. 2017, Article 6237351 (13 pages).
Yagi et al. (2007) "Transcription factor TEAD4 specifies the trophectoderm lineage at the beginning of mammalian development" Development, vol. 134, pp. 3827-3836.
Yao et al. (2011) "Beyond histone and deacetylase: an overview of cytoplasmic histone deacetylases and their nonhistone substrates" J Biomed Biotechnol, vol. 2011, Article 146493 (15 pages).
Zhang et al. (2016) "Hdac3 Interaction with p300 Histone Acetyltransferase Regulates the Oligodendrocyte and Astrocyte Lineage Fate Switch" Dev Cell, vol. 36, pp. 316-330.
Zhou et al. (2016) "Promoting peripheral myelin repair" Exp Neurol, vol. 283, pp. 573-580.
Haberland et al. (2009) "The many roles of histone deacetylases in development and physiology: implications for disease and therapy" Nat Rev Genet, vol. 10, pp. 32-42.
He et al. (2010) "Yy1 as a molecular link between neuregulin and transcriptional modulation of peripheral myelination" Nat Neurosci, vol. 13, pp. 1472-1480.
He et al. (2016) "Intrinsic Control of Axon Regeneration" Neuron, vol. 90, pp. 437-451.
He et al. (2018) "A Histone Deacetylase 3-Dependent Pathway Delimits Peripheral Myelin Growth and Functional Regeneration" Nature Medicine, vol. 24, No. 3, pp. 338-351.
Huang et al. (2015) "Expression pattern of neuregulin-1 type III during the development of the peripheral nervous system" Neural Regen Res, vol. 10, pp. 65-70.
Hung et al. (2012) "The nucleosome remodeling and deacetylase chromatin remodeling (NuRD) complex is required for peripheral nerve myelination" J Neurosci, vol. 32, pp. 1517-1527.

(56) References Cited

OTHER PUBLICATIONS

Jacob et al. (2011) "HDAC1 and HDAC2 control the transcriptional program of myelination and the survival of Schwann cells" Nat Neurosci, vol. 14, pp. 429-436.
Jaegle et al. (2003) "The POU proteins Brn-2 and Oct-6 share important functions in Schwann cell development" Genes Dev, vol. 17, pp. 1380-1391.
Jessen et al. (2015) "Schwann Cells: Development and Role in Nerve Repair" Cold Spring Harb Perspect Biol, vol. 7, Article a020487 (15 pages).
Jia et al. (2016) "The Effects of Pharmacological Inhibition of Histone Deacetylase 3 (HDAC3) in Huntington's Disease Mice" PLoS One, vol. 11, Article e0152498 (14 pages).
Jiang et al. (2014) "HDAC3 controls gap2/mitosis progression in adult neural stem/progenitor cells by regulating CDK1 levels" Proc Natl Acad Sci U S A, vol. 111, pp. 13541-13546.
Kang et al. (2013) "Motor axon regeneration and muscle reinnervation in young adult and aged animals" J Neurosci, vol. 33, pp. 19480-19491.
Koontz et al. (2013) "The Hippo effector Yorkie controls normal tissue growth by antagonizing scalloped-mediated default repression" Dev Cell, vol. 25, pp. 388-401.
Langfelder et al. (2008) "WGCNA: an R package for weighted correlation network analysis" BMC Bioinformatics, vol. 9, Article 559 (13 pages).
Lappe-Siefke et al. (2003) "Disruption of Cnp1 uncouples oligodendroglial functions in axonal support and myelination" Nat Genet, vol. 33, pp. 366-374.
Li et al. (2016) "HDACs and HDAC Inhibitors in Cancer Development and Therapy" Cold Spring Harb Perspect Med, vol. 6, Article 026831 (34 pages).
Limpert et al. (2013) "NF-kappaB forms a complex with the chromatin remodeler BRG1 to regulate Schwann cell differentiation" J Neurosci, vol. 33, pp. 2388-2397.
Lundborg (2000) "25-year perspective of peripheral nerve surgery: evolving neuroscientific concepts and clinical significance" J Hand Surg Am, vol. 25A, pp. 391-414.
Lutz et al. (2014) "Contrasting the glial response to axon injury in the central and peripheral nervous systems" Dev Cell, vol. 28, pp. 7-17.
Ma et al. (2015) "Regulation of Peripheral Nerve Myelin Maintenance by Gene Repression through Polycomb Repressive Complex 2" J Neurosci, vol. 35, pp. 8640-8652.
Ma et al. (2016) "Epigenomic reprogramming in peripheral nerve injury" Neural Regen Res, vol. 11, pp. 1930-1931.
Malvaez et al. (2013) "HDAC3-selective inhibitor enhances extinction of cocaine-seeking behavior in a persistent manner," PNAS, vol. 110, pp. 2647-2652.
Michailov et al. (2004) "Axonal neuregulin-1 regulates myelin sheath thickness" Science, vol. 304, pp. 700-703.
Monk et al. (2009) "A G protein-coupled receptor is essential for Schwann cells to initiate myelination" Science, vol. 325, pp. 1402-1405.
Monk et al. (2015) "New insights on schwann cell development" Glia, vol. 63, No. 8, pp. 1376-1393.
Montgomery et al. (2008) "Maintenance of cardiac energy metabolism by histone deacetylase 3 in mice" J Clin Invest, vol. 118, pp. 3588-3597.
Mottamal et al. (2015) "Histone deacetylase inhibitors in clinical studies as templates for new anticancer agents" Molecules, vol. 20, pp. 3898-3941.
Nave et al. (2007) "Mechanisms of disease: inherited demyelinating neuropathies—from basic to clinical research" Nat Clin Pract Neurol, vol. 3, pp. 453-464.
Nave et al. (2014) "Myelination of the nervous system: mechanisms and functions" Annu Rev Cell Dev Biol, vol. 30, pp. 503-533.
Nodari et al. (2008) "Alpha6beta4 integrin and dystroglycan cooperate to stabilize the myelin sheath" J Neurosci, vol. 28, pp. 6714-6719.
Norrmen et al. (2013) "Akt/mTOR signalling in myelination" Biochem Soc Trans, vol. 41, pp. 944-950.
Noseda et al. (2013) "DDIT4/REDD1/RTP801 is a novel negative regulator of Schwann cell myelination" J Neurosci, vol. 33, pp. 15295-15305.
Okumura et al. (2006) "PCAF modulates PTEN activity" J Biol Chem, vol. 281, pp. 26562-26568.
Painter et al. (2014) "Diminished Schwann cell repair responses underlie age-associated impaired axonal regeneration" Neuron, vol. 83, pp. 331-343.
Parikshak et al. (2015) "Systems biology and gene networks in neurodevelopmental and neurodegenerative disorders" Nat Rev Genet, vol. 16, pp. 441-458.
Parrinello et al. (2010) "EphB signaling directs peripheral nerve regeneration through Sox2-dependent Schwann cell sorting" Cell, vol. 143, pp. 145-155.
Pereira et al. (2012) "Molecular mechanisms regulating myelination in the peripheral nervous system" Trends Neurosci, vol. 35, pp. 123-134.
Poitelon et al. (2016) "YAP and TAZ control peripheral myelination and the expression of laminin receptors in Schwann cells" Nat Neurosci, vol. 19, pp. 879-887.
Schmitt et al. (2014) "Histone deacetylase 3 (HDAC3) plays an important role in retinal ganglion cell death after acute optic nerve injury" Molecular Neurodegeneration, vol. 9, Article 39 (15 pages).
Soragni et al. (2014) "Epigenetic Therapy for Friedreich Ataxia" Ann Neurol., vol. 76, No. 4, pp. 489-508.
Sredni et al. (2013) "Histone deacetylases expression in atypical teratoid rhabdoid tumors" Childs Nerv Syst, vol. 29, pp. 5-9.
Yoshizumi et al. (2013) "Valproate prevents dysregulation of spinal glutamate and reduces the development of hypersensitivity in rats after peripheral nerve injury" J Pain., vol. 14, Article 11 (16 pages).
Zhang et al. (2011) "Role of HDAC3 on p53 Expression and Apoptosis in T Cells of Patients with Multiple Sclerosis" PLoS ONE, vol. 6, No. 2, Article e16795 (11 pages).

* cited by examiner

D

E

R

S

F

G

V

W

Z

AA

AB

AC

AD

AE

AF

AG

AH

D

E

F

O

P18

P

P105

U

V

AB

AC

AD

AE

AF

AG

C

D

E

F

G

H

I

J

K

T

U

V

W

X

Y

C

D

O

P

Q

R

S

T

METHODS FOR TREATING DISEASES AND NERVE INJURIES

CROSS-REFERENCE TO RELATED APPLICATIONS

This application is a National Stage Entry of International Application No. PCT/US2018/045727 filed Aug. 8, 2018, entitled "METHODS FOR TREATING DISEASES AND NERVE INJURY" which is herein incorporated by reference in its entirety, and which claims the benefit of U.S. Provisional Application No. 62/543,044, filed Aug. 9, 2017 entitled "Histone Deacetylase 3-Dependent Pathway Delimits Peripheral Myelin Growth and Functional Regeneration" which is herein incorporated by reference in its entirety.

BACKGROUND

Diseases (e.g., related to nerve function) and nerve injury are not uncommon in the US and worldwide. However, effective treatments for diseases or nerve injury remain a challenge. For example, current treatments for nerve injuries (e.g., spinal or PNS injury), such as by transection or crushing, are limited or ineffective. There is a need to develop effective treatments for nerve injuries. In another example, there is no effective therapy to halt or slow the progression of multiple sclerosis (MS). MS is a prevalent demyelinating disease in the central nervous system (CNS) of both children and adults. There is a need for novel therapeutic modalities that can treat MS. And, more generally, there is a need to treat diseases (e.g., related to nerve function) and nerve injury.

Some embodiments of the invention include methods for treating an animal for disease or nerve damage, comprising administration of a composition comprising a myelination enhancing inhibitor to the animal. Other embodiments of the invention include methods for treating an animal for disease or nerve damage, comprising administration of a composition comprising an HDAC3 inhibitor to the animal. Still other embodiments of the invention include methods for treating an animal for MS or nerve damage, comprising administration of a composition comprising an HDAC3 inhibitor to the animal. Additional embodiments of the invention are also discussed herein.

SUMMARY

Some embodiments of the invention include methods for treating an animal for disease or nerve injury, comprising administration of a composition comprising a myelination enhancing inhibitor to the animal. In other embodiments, the myelination enhancing inhibitor is an HDAC3 (histone deacetylase 3) inhibitor, an HDAC (histone deacetylase) inhibitor, a demethylase inhibitor, or a methyltransferase inhibitor. In still other embodiments, the myelination enhancing inhibitor is an HDAC3 inhibitor. In some embodiments, the myelination enhancing inhibitor is CUDC-907, Quisinostat, RG2833, CUDC-101, Resminostat, 4SC-202, Mocetinostat, Entinostat, Citarinostat, Abexinostat, Pracinostat, apicidin, PDA106, RGFP966, CAY10398, chidamide, LAQ824, SAHA, GSK-J4, JIB-04, UNC0631, or UNC0646. In yet other embodiments, the myelination enhancing inhibitor is apicidin, PDA106, RGFP966, CAY10398, chidamide, LAQ824, SAHA, GSK-J4, JIB-04, UNC0631, or UNC0646. In some embodiments, the myelination enhancing inhibitor is CUDC-907, Quisinostat, RG2833, CUDC-101, Resminostat, 4SC-202, Mocetinostat, Entinostat, Citarinostat, Abexinostat, Pracinostat, apicidin, PDA106, or RGFP966. In yet other embodiments, the myelination enhancing inhibitor is PDA106 or RGFP966. In some embodiments, the method comprises more than one administration of the composition comprising the myelination enhancing inhibitor to the animal. In other embodiments, the amount of the myelination enhancing inhibitor is from about 0.0001% (by weight total composition) to about 99%. In still other embodiments, the composition further comprises a formulary ingredient. In yet other embodiments, the composition is a pharmaceutical composition. In some embodiments, the administration comprises parenteral administration, mucosal administration, intravenous administration, depot injection, subcutaneous administration, topical administration, intradermal administration, oral administration, sublingual administration, intranasal administration, or intramuscular administration. In other embodiments, the administration comprises a depot injection or an oral administration. In some embodiments, if there is more than one administration at least one composition used for at least one administration is different from the composition of at least one other administration. In other embodiments, the myelination enhancing inhibitor of the composition is administered to the animal in an amount of from about 0.005 mg/kg animal body weight to about 100 mg/kg animal body weight. In still other embodiments, the animal is a human, a rodent, or a primate. In yet other embodiments, the animal is in need of treatment of disease or nerve injury.

In some embodiments, the method is for treating myelopathy, spinal cord injury, myelitis, vascular myelopathy, cervical spondylotic myelopathy, spondylosis, spinal stenosis, demyelinating disease, any disease of the nervous system where the myelin sheath of a neuron is damaged, CNS demyelinating disease, PNS demyelinating disease, genetic demyelinating disease, infectious demyelinating disease, autoimmune demyelinating disease, demyelinating myelinoclastic disease, demyelinating leukodystrophic disease, Devic's disease, CNS neuropathies, diseases resulting in vitamin B12 deficiency, central pontine myelinolysis, myelopathies, tabes *dorsalis*, leukoencephalopathies, progressive multifocal leukoencephalopathy, leukodystrophies, optic neuritis, transverse myelitis, neuromyelitis optica, Guillain-Barré syndrome, chronic inflammatory demyelinating polyneuropathy, anti-MAG peripheral neuropathy, Charcot-Marie-Tooth disease, Hereditary neuropathy with liability to pressure palsy, copper deficiency associated conditions, peripheral neuropathy, myelopathy, optic neuropathy, progressive inflammatory neuropathy, multiple sclerosis (MS), MS-type clinically isolated syndrome, relapsing-remitting MS, primary progressive MS, secondary progressive MS, traumatic brain injury, acquired brain injury, hypoxic ischemic brain injury, strokes, periventricular leukomalacia (PVL), white-matter brain injury, CNS nerve injury, PNS nerve injury, crush nerve injury, or transection nerve injury. In still other embodiments, the method is for treating MS, MS-type clinically isolated syndrome, relapsing-remitting MS, primary progressive MS, or secondary progressive MS. In yet other embodiments, the method is for treating inflammation, remyelination, or both in MS, MS-type clinically isolated syndrome, relapsing-remitting MS, primary progressive MS, or secondary progressive MS. In some embodiments, the method is for treating inflammation and remyelination in MS, MS-type clinically isolated syndrome, relapsing-remitting MS, primary progressive MS, or secondary progressive MS. In other embodiments, the method is for treating CNS demyelinating disease, PNS demyelinating disease, MS, traumatic brain injury, acquired brain injury, hypoxic ischemic brain injury, strokes, periventricular leukomalacia (PVL), white-matter brain injury, CNS nerve injury, PNS nerve injury, crush nerve injury, or transection nerve injury. In yet other embodiments, the method is for treating CNS demyelinating disease, PNS demyelinating disease, MS, CNS nerve injury, PNS nerve injury, crush nerve injury, or transection nerve injury. In still other embodiments, the method is for treating CNS nerve injury, PNS nerve injury, crush nerve injury, or transection nerve injury. In yet other embodiments, the method is for treating crush nerve injury or transection nerve injury. In some embodiments, the method further comprises one or more other treatments.

Some embodiments of the invention include methods for treating an animal for MS or nerve injury, comprising administration of a composition comprising an HDAC3 inhibitor to the animal.

Other embodiments of the invention include methods for treating an animal for MS or nerve injury, comprising administration of a composition comprising PDA106 or RGFP966 to the animal.

Other embodiments of the invention are also discussed herein.

BRIEF DESCRIPTION OF THE DRAWINGS

The following drawings form part of the present specification and are included to further demonstrate certain aspects of the present invention. The invention may be better understood by reference to one or more of these drawings in combination with the description of specific embodiments presented herein.

μm. (O) Effects of pharmacological inhibition of HDAC3 on myelination at different stages: Quantification of hypermyelinated axons in sciatic nerves from Veh- and PDA106-treated mice at P24. (Data are presented as mean±s.e.m.; n=3 animals/group; two-tailed unpaired Student's t-test; P=0.0061, t=5.228, d.f.=4). (P) Effects of pharmacological inhibition of HDAC3 on myelination at different stages: Upper: Schematic diagram showing drug treatment scheme. Mice were treated with Veh or PDA106 from P14 to P21. Sciatic nerves were harvested at P24. Bottom: Representative toluidine blue-stained images of cross sections of sciatic nerves from Veh- and PDA106-treated mice. Arrow indicates hypermyelinated axons. n=3 animals/group, with 5 images for each mouse. Scale bars: 20 μm. (Q) Effects of pharmacological inhibition of HDAC3 on myelination at different stages: Quantification of hypermyelinated axons in sciatic nerves from Veh- and PDA106-treated mice at P24. (Data are presented as mean±s.e.m.; n=3 animals/group; two-tailed unpaired Student's t-test; P=0.0073, t=5.027, d.f.=4). (R) Effects of pharmacological inhibition of HDAC3 on myelination at different stages: Representative images of longitudinal cryosections of sciatic nerves from Veh- and P7 or P14 started PDA106-treated mice Immunostaining was performed at P24 with EGR2 (red) and DAPI (blue). n=3 animals/group, with 5 images for each mouse. Scale bar: 20 μm. (S) Effects of pharmacological inhibition of HDAC3 on myelination at different stages: Quantifications at P24 of EGR2$^+$ cells in sciatic nerves from Veh- and P7 or P14 started PDA106-treated mice. (Data are presented as mean±s.e.m.; n=3 animals/group; one-way ANOVA with Tukey's multiple comparisons test; $F_{(2, 6)}=0.697$, $P_{Veh\ versus\ P7\ treated}=0.5197$, $P_{Veh\ versus\ P14\ treated}=0.9323$, $P_{P7\ treated\ versus\ P14\ treated}=0.7196$). n.s., not significant, *P<0.05, P<0.01, *P<0.001.

Figure 2:
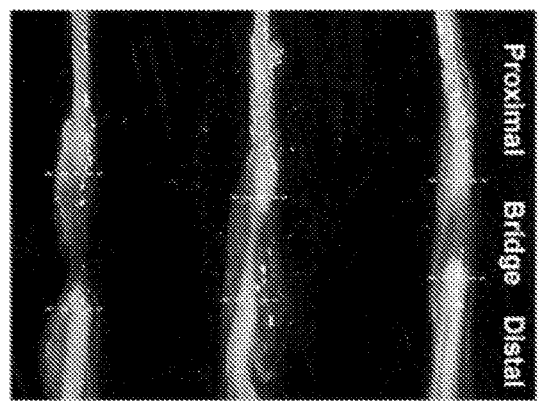
Figure 2:
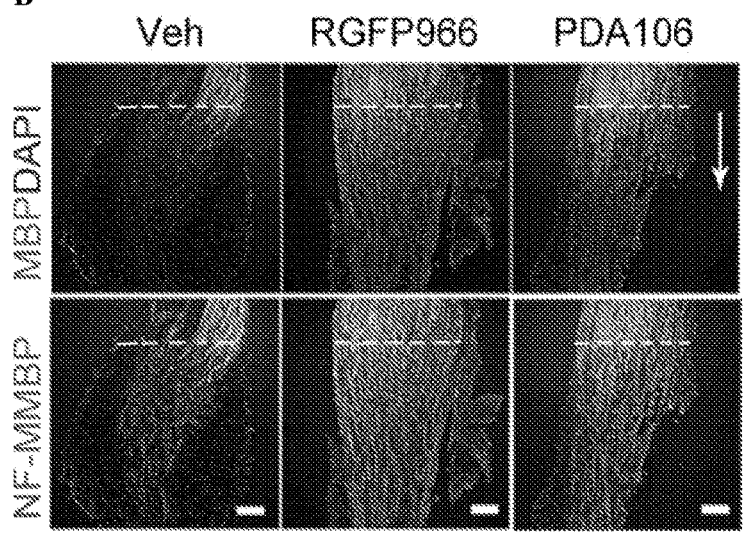
Figure 2:
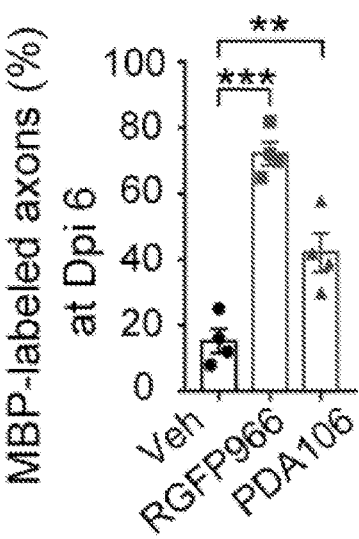
Figure 2:
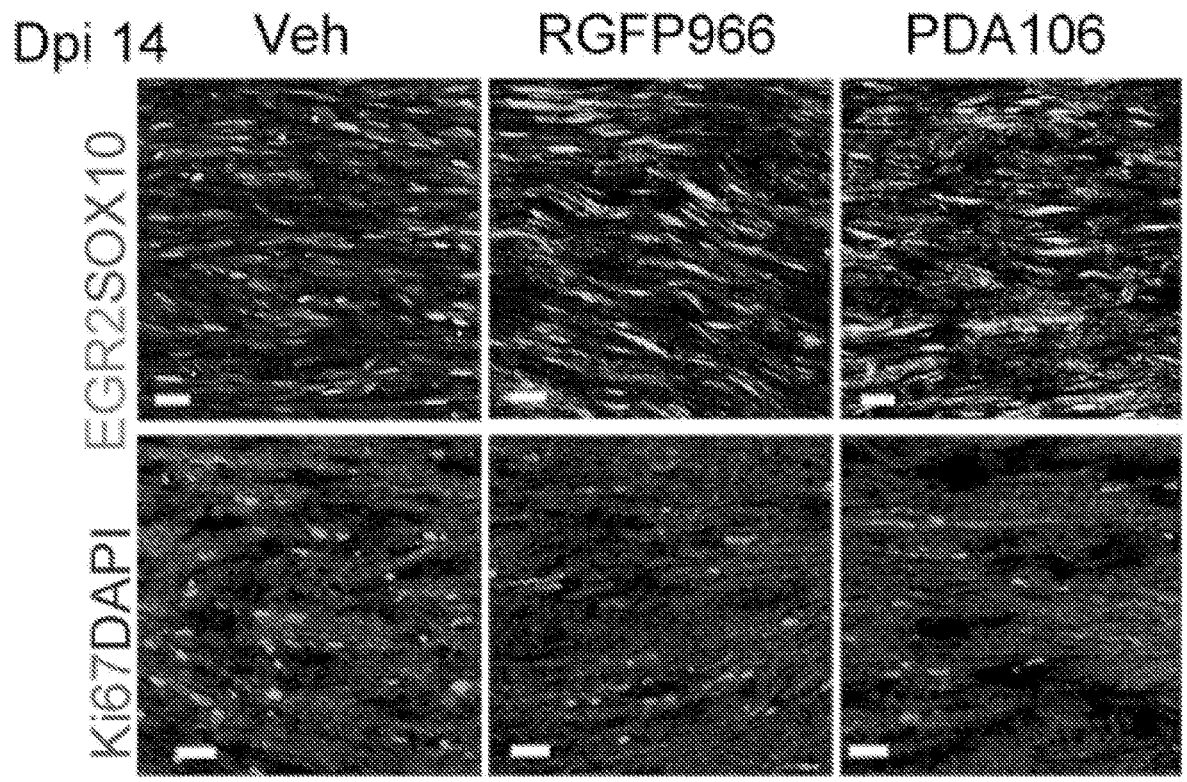
Figure 2:
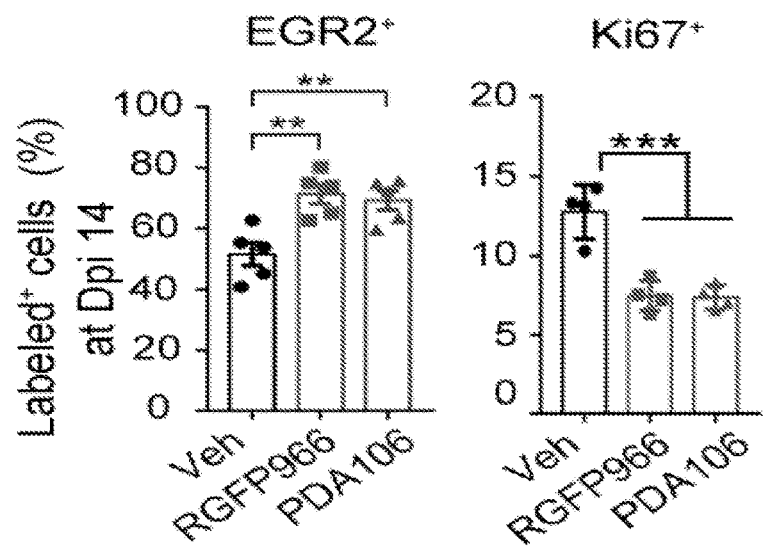
Figure 2:
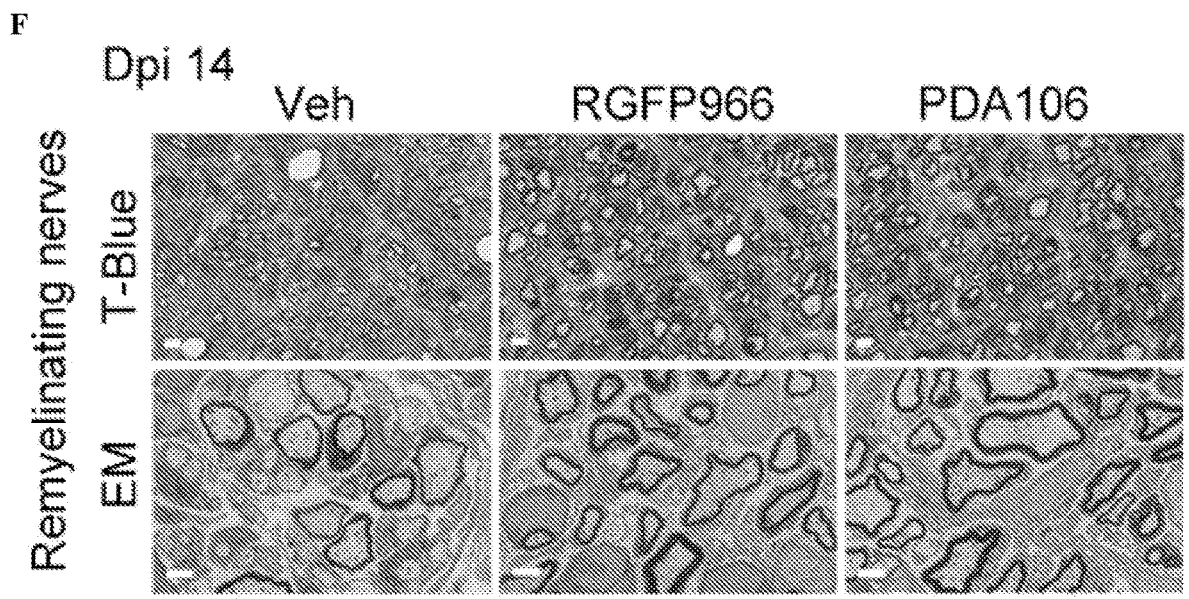
Figure 2:
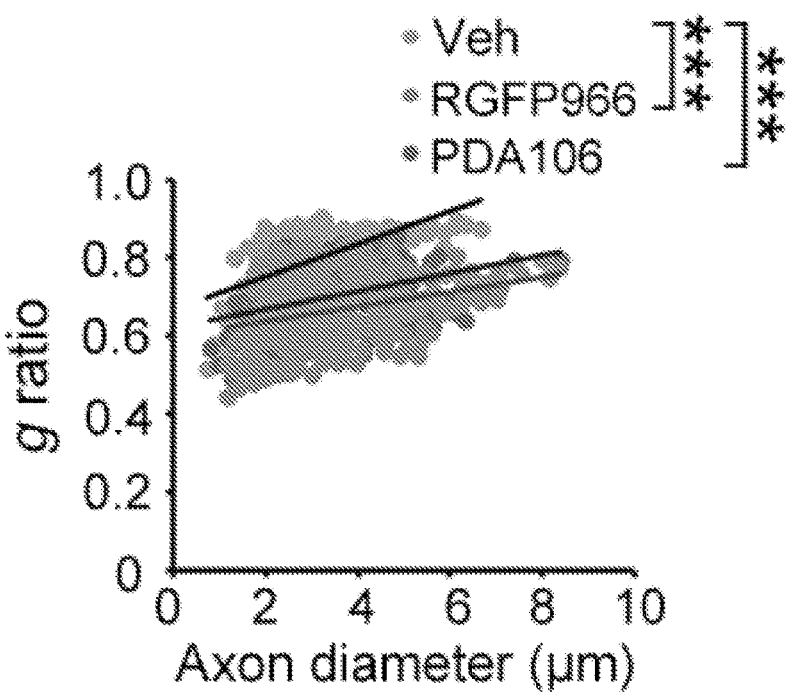
Figure 2:
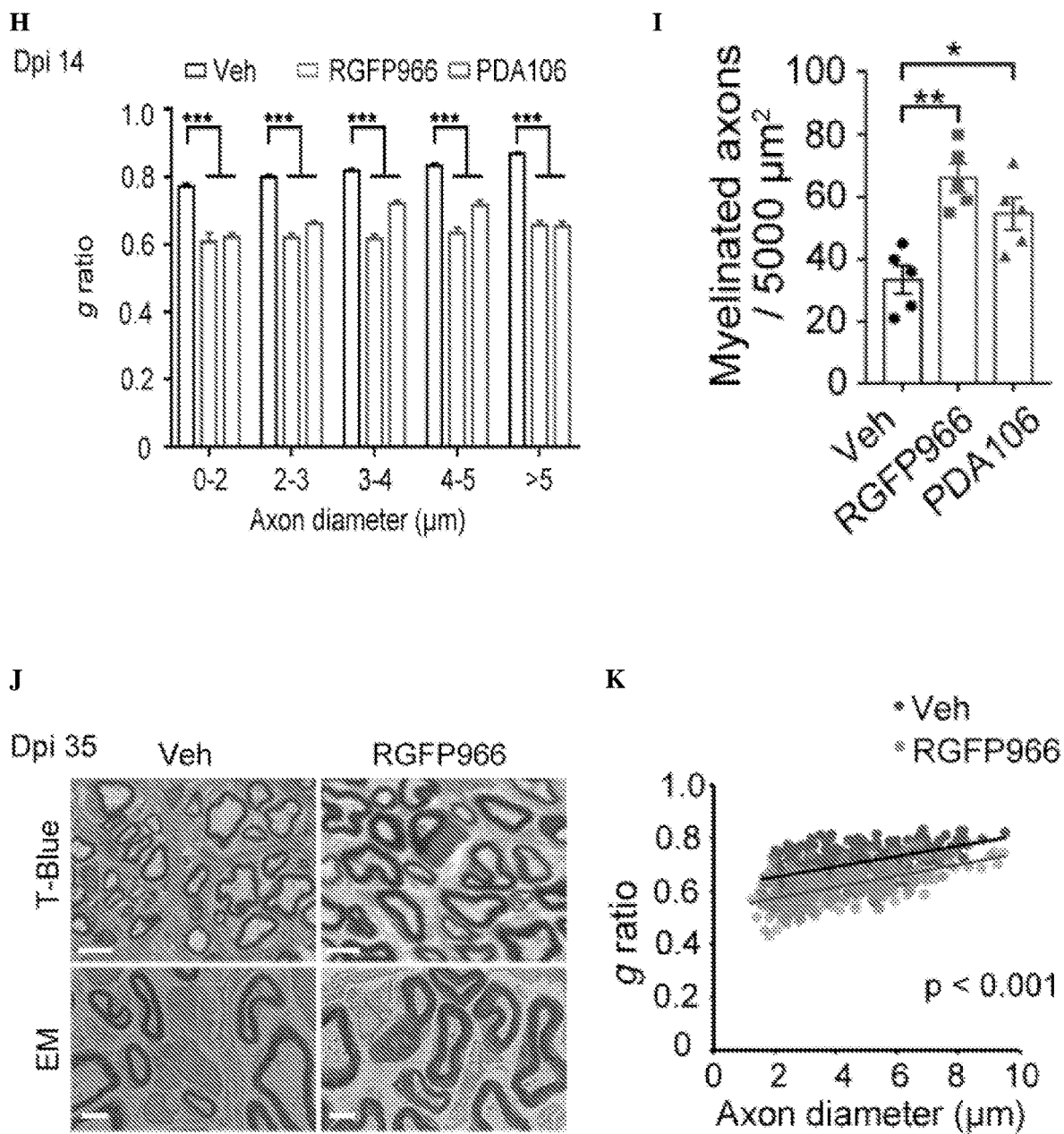
Figure 2:
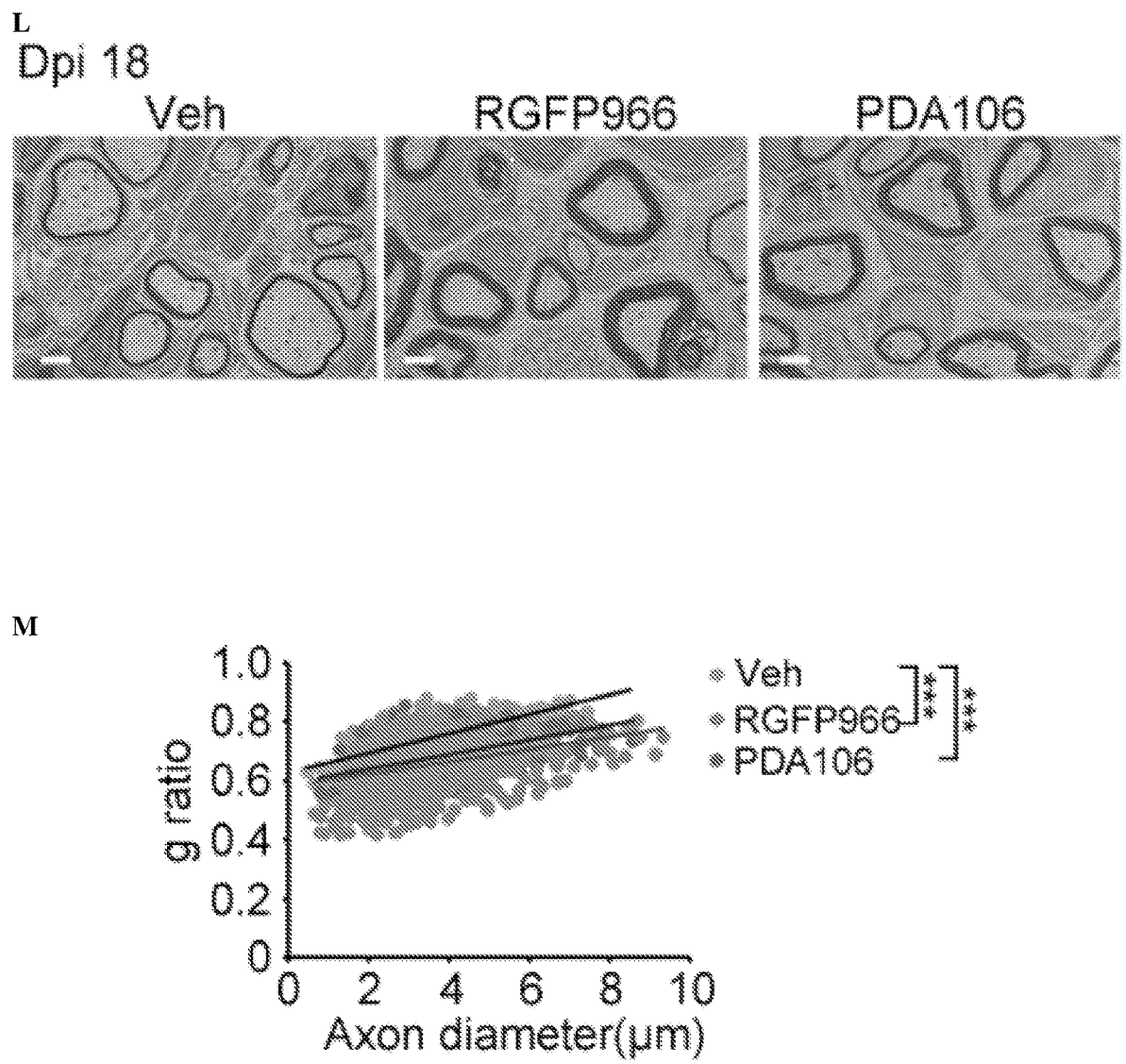
Figure 2:
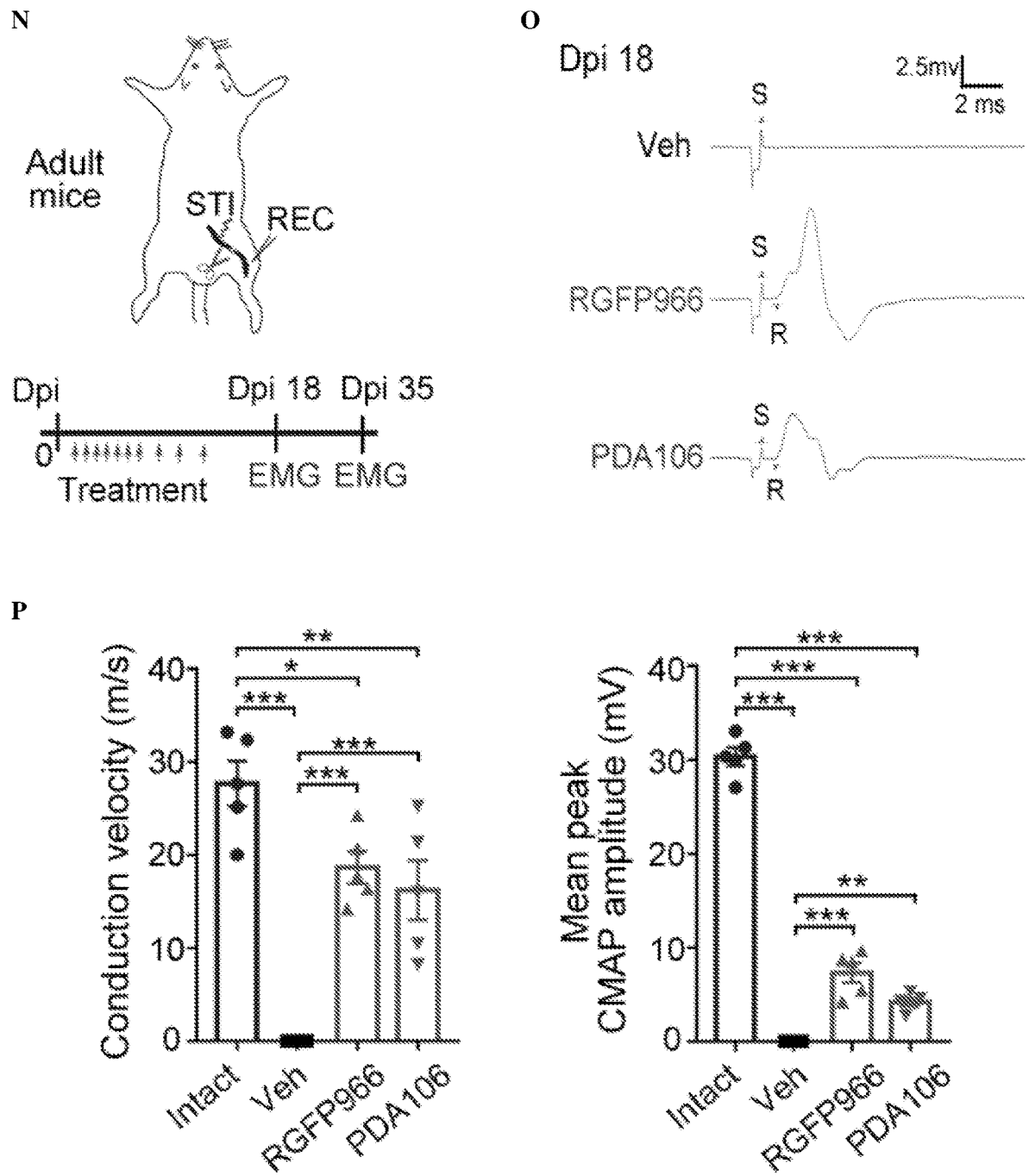
Figure 2:
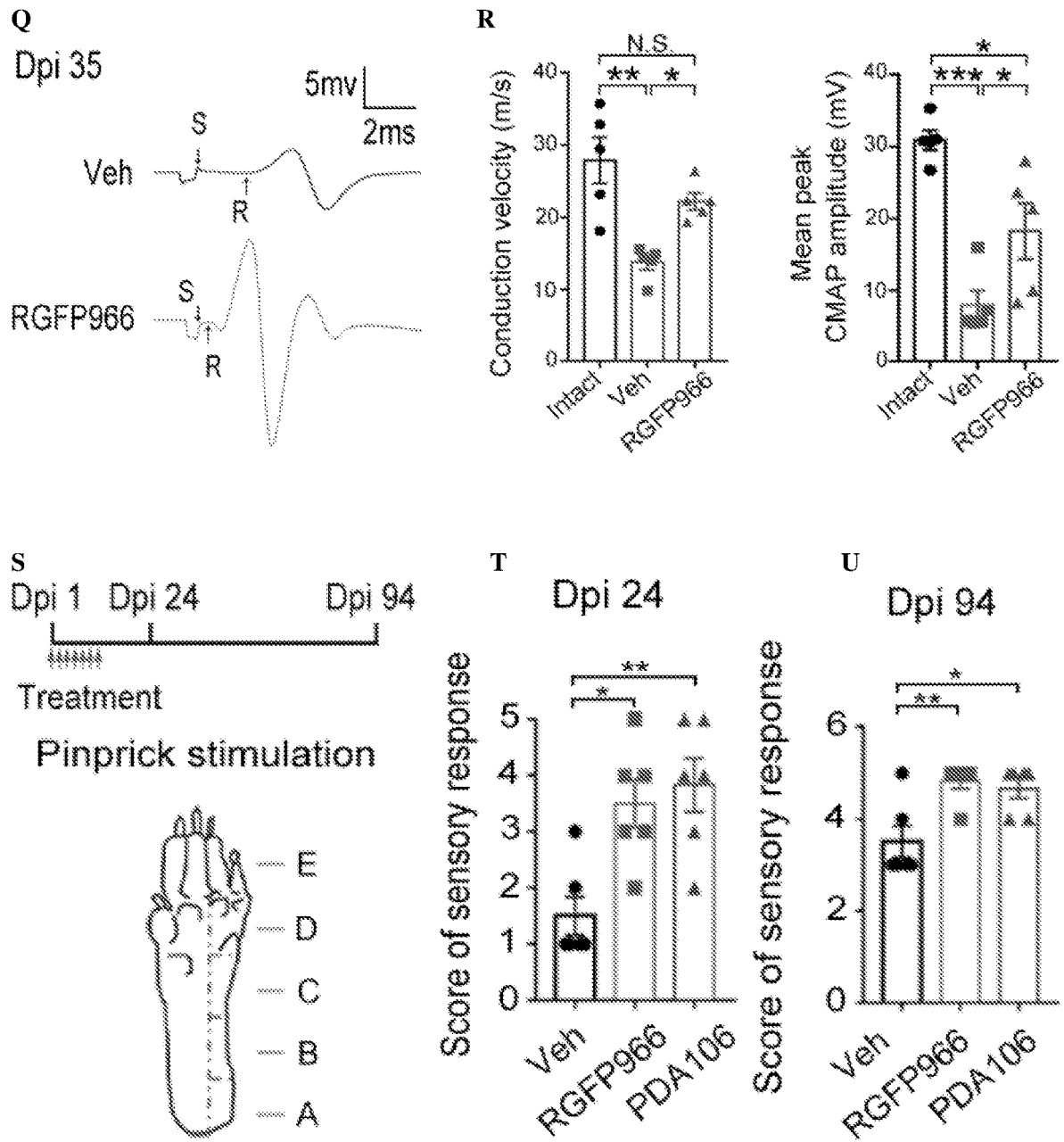
Figure 2:
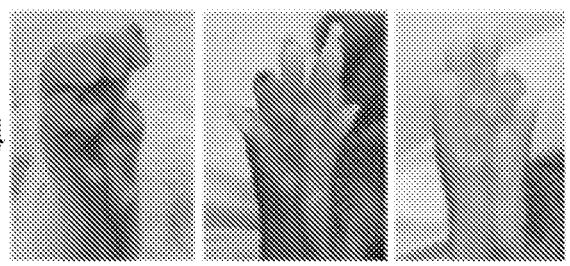
Figure 2:
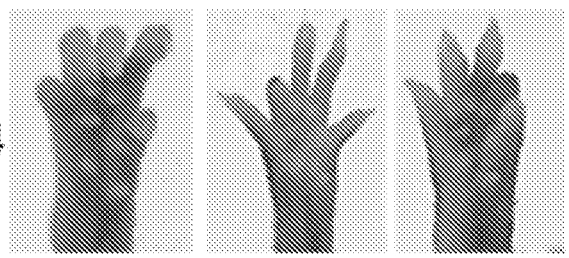
Figure 2:
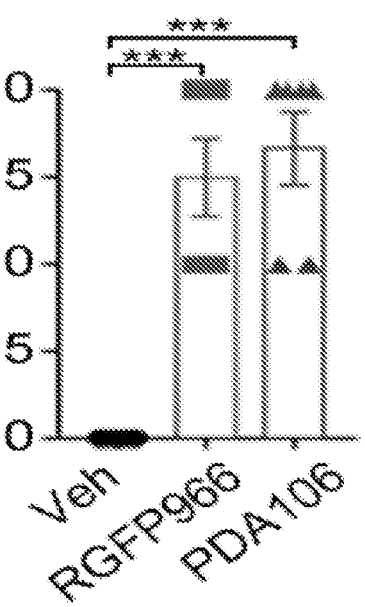
Figure 2:
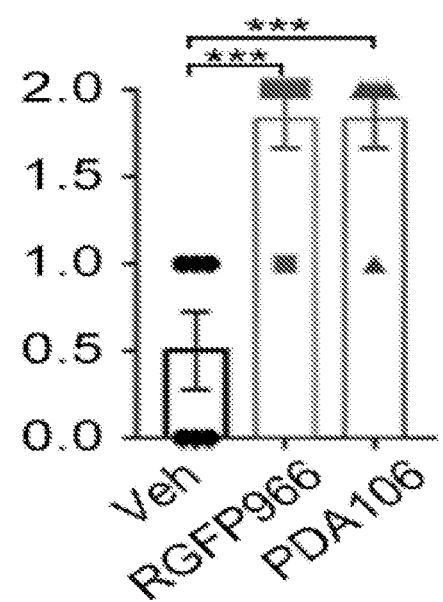
Figure 2:
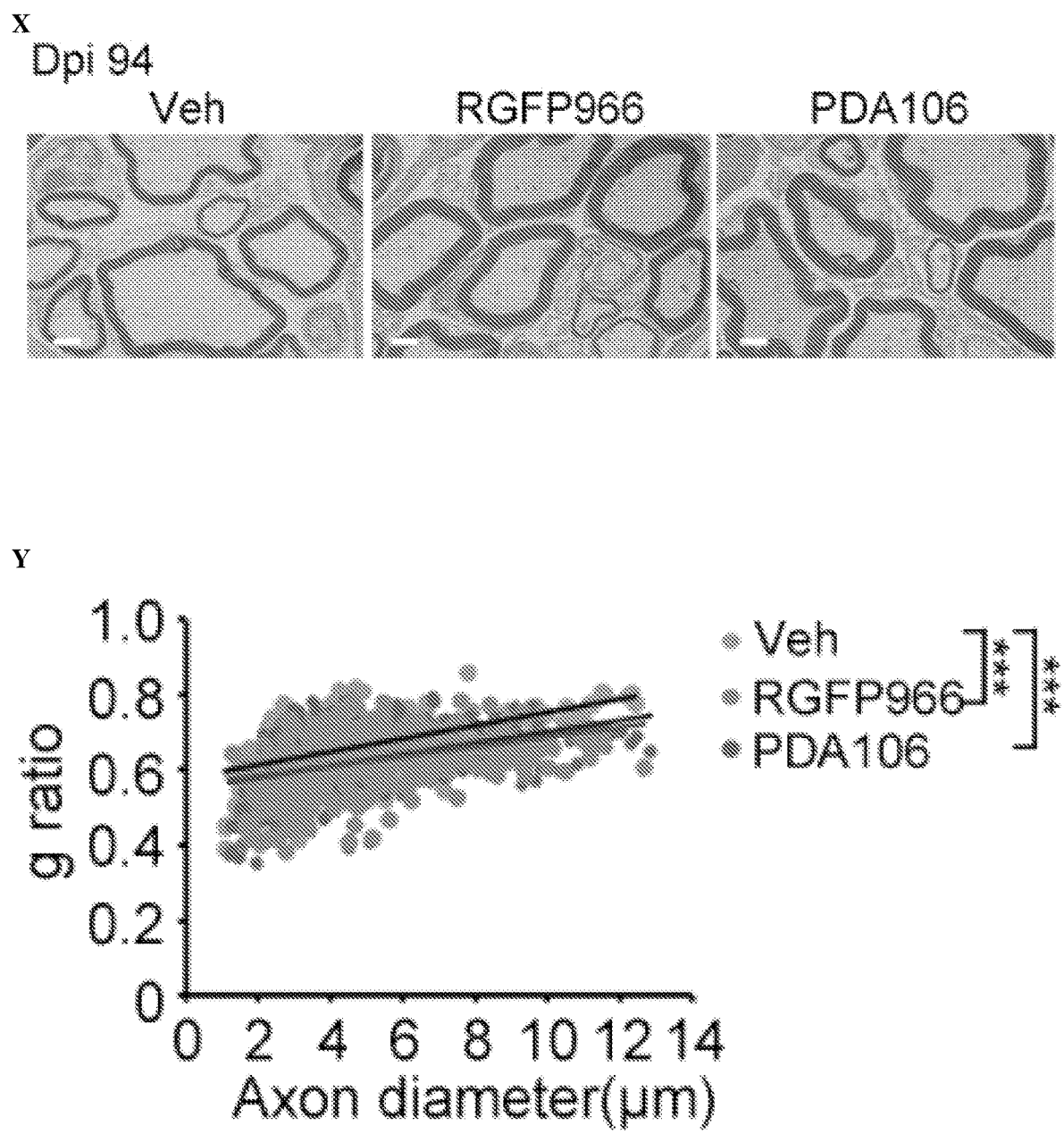
Figure 2:
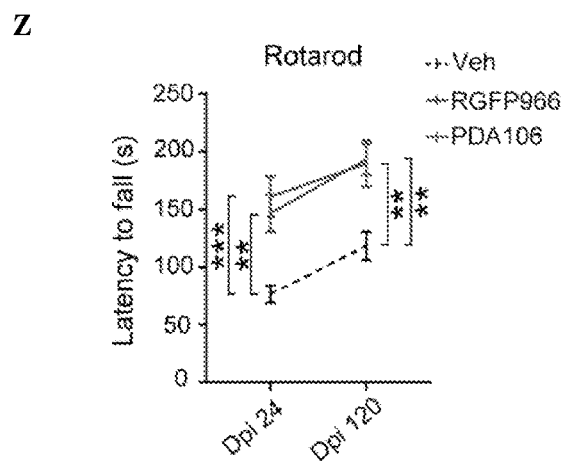
Figure 2:
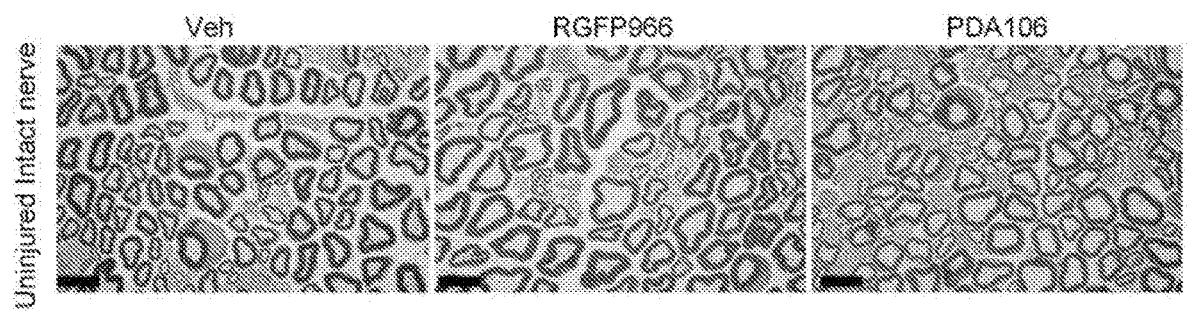
Figure 2:
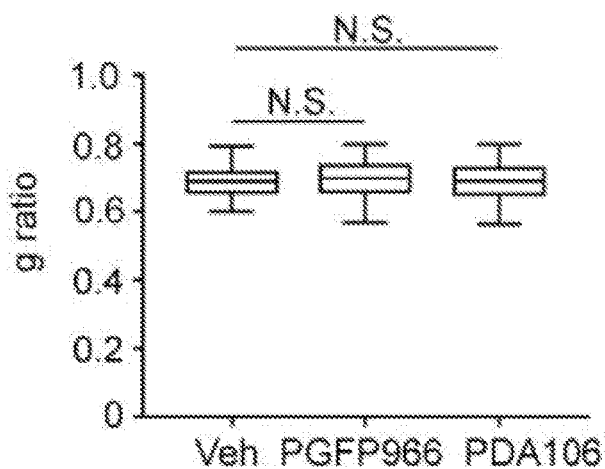
Figure 2:
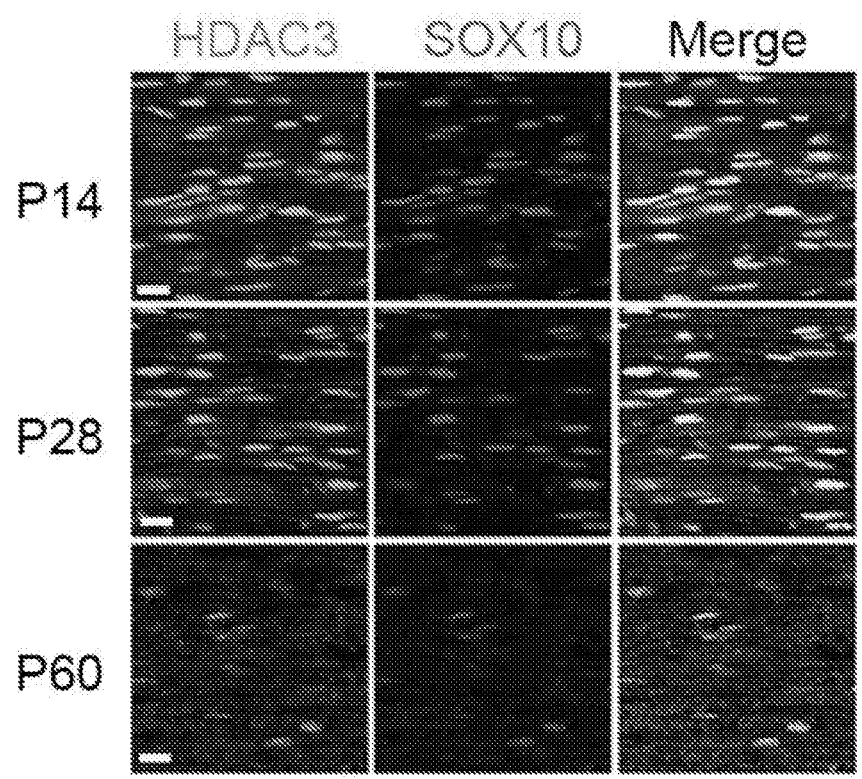
Figure 2:
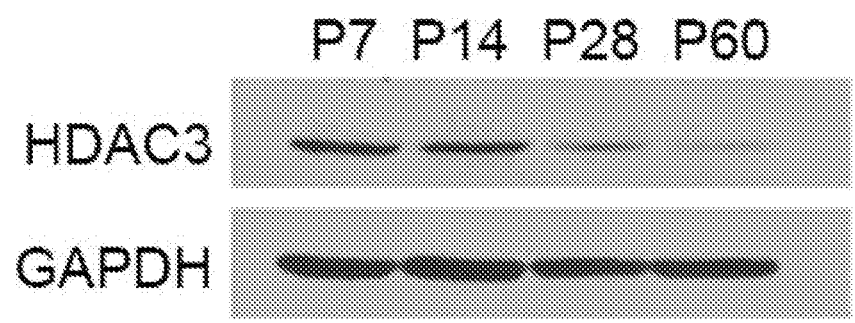
Figure 2:
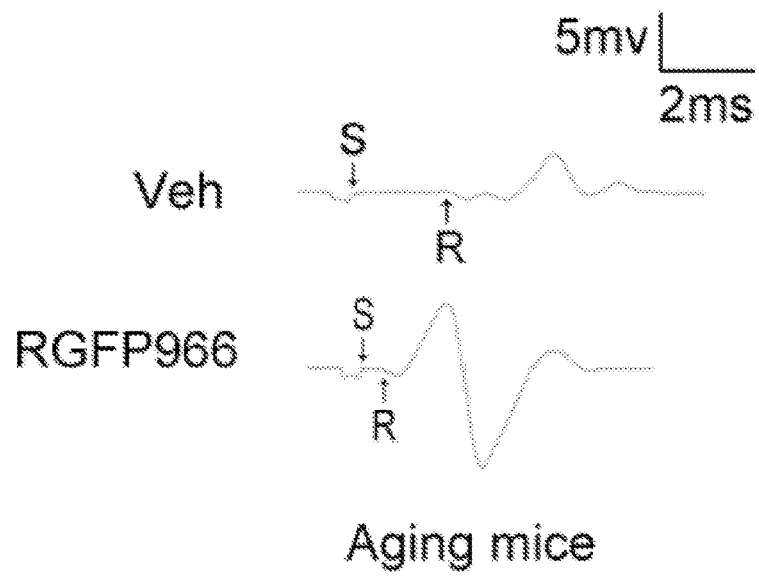
Figure 2:
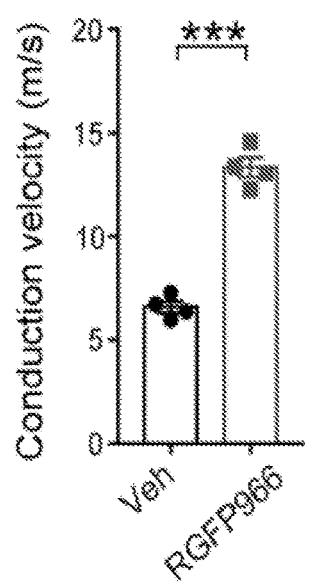
Figure 2:
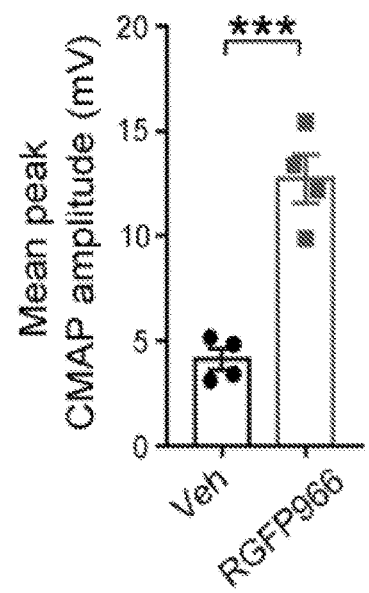
Figure 2:
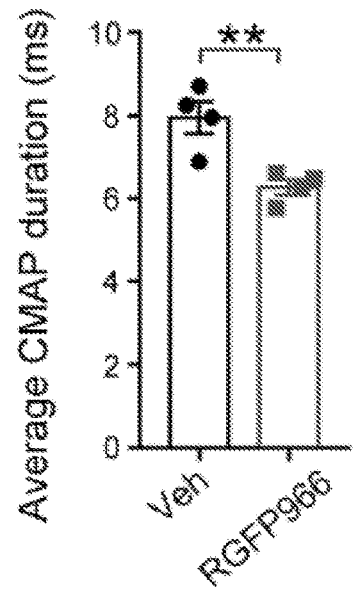

FIG. 2: HDAC3 inhibitor treatment enhances SCs remyelination and functional recovery after sciatic nerve transection. (A) Representative bright field images of injured sciatic nerves at Dpi 6. Mice (~8 week-old) were treated i.p. with Veh, RGFP966, or PDA106 beginning the day after sciatic nerve transection. Bridge tissues were indicated between two dashed lines. n=4 animals/group. (B) Representative images of longitudinal sections of tissue bridges (regions under the dashes lines) from injured sciatic nerves after indicated treatment at Dpi 7 immunostained for neurofilament M (NF), MBP, and counterstained with DAPI. Arrow indicates proximal to distal direction. n=4 animals/group. Scale bar, 50 μm. (C) Percentage of MBP-colocalized NF$^+$ axons within the tissue bridge after treatment indicated. (Data are presented as mean±s.e.m.; n=4 animals/group; one-way ANOVA with Tukey's multiple comparisons test; $F_{(2, 9)}=40.64$, $P_{Veh\ versus\ RGFP966}<0.0001$, $P_{Veh\ versus\ PDA106}=0.0053$). (D) Representative images of longitudinal cryosections of injured sciatic nerves at 14 Dpi immunostained with EGR2 (green) and SOX10 (red) (upper), or Ki67 (green) and DAPI (blue) (bottom). n=5 or 4 animals/group, with 5 images for each mouse. Scale bar, 20 μm. (E) Percentage of EGR2$^+$ cells (left) or Ki67$^+$ (right) in injured sciatic nerves of Veh- and HDAC3 inhibitor-treated mice at Dpi 14. (Data are presented as mean±s.e.m.; n=5 or 4 animals/group; one-way ANOVA with Tukey's multiple comparisons test; EGR2, $F_{(2, 12)}=9.912$, $P_{Veh\ versus\ RGFP966}=0.0042$, $P_{Veh\ versus\ PDA106}=0.0091$; Ki67, $F_{(2, 9)}=25.95$, $P_{Veh\ versus\ RGFP966}=0.0004$, $P_{Veh\ versus\ PDA106}=0.0004$). (F) Representative toluidine blue-stained images (upper) and electron micrographs (bottom) of cross sections of regenerating tissue bridge in sciatic nerves from vehicle and compound-treated mice at Dpi 14. n=5 animals/group, with 10 images for each mouse. Scale bars: 5 μm in upper and 2 μm in bottom. (G) Quantification of g ratios of axons of regenerated sciatic nerves from Veh-, RGFP966-, and PDA106-treated mice at Dpi 14. (Data are presented as mean±s.e.m.; n=308 axons from 3 control mice, 300 axons from 3 RGFP966 treated mice and 322 axons from 3 PDA106 treated mice; one-way ANOVA with Tukey's multiple comparisons test; $F_{(2, 927)}=294.3$, $P_{Veh\ versus\ RGFP966}<0.0001$, $P_{Veh\ versus\ PDA106}<0.0001$). (H) Effects of pharmacological inhibition of HDAC3 on remyelination: Quantification of g ratios of groups of axons with the indicated diameters at Dpi 14. (Data are presented as mean±s.e.m.; n=3 animals/group; one-way ANOVA with Tukey's multiple comparisons test; 0-2 μm, $F_{(2, 114)}=59.91$, $P_{Veh\ versus\ RGFP966}<0.0001$, $P_{Veh\ versus\ PDA106}<0.0001$; 2-3 μm, $F_{(2, 337)}=137.8$, $P_{Veh\ versus\ RGFP966}<0.0001$, $P_{Veh\ versus\ PDA106}<0.0001$; 3-4 μm, $F_{(2, 227)}=89.09$, $P_{Veh\ versus\ RGFP966}<0.0001$, $P_{Veh\ versus\ PDA106}<0.0001$; 4-5 μm, $F_{(2, 122)}=31.72$, $P_{Veh\ versus\ RGFP966}<0.0001$, $P_{Veh\ versus\ PDA106}<0.0001$; >5 μm, $F_{(2, 82)}=47.03$, $P_{Veh\ versus\ RGFP966}<0.0001$, $P_{Veh\ versus\ PDA106}<0.0001$). (I) Quantification of myelinated axons of injured sciatic nerves from Veh-, RGFP966-, and PDA106-treated mice at Dpi 14. (Data are presented as mean±s.e.m.; n=5 animals/group; one-way ANOVA with Tukey's multiple comparisons test; $F_{(2, 12)}=12.05$, $P_{Veh\ versus\ RGFP966}=0.0011$, $P_{Veh\ versus\ PDA106}=0.022$). (J) Representative toluidine blue-stained images (upper) and electron micrographs (bottom) of regenerated sciatic nerve cross sections from Veh- and RGFP966-treated mice at Dpi 35. n=5 animals/group, with 10 images for each mouse. Scale bars: 5 μm in upper and 2 μm in bottom. (K) Quantification of g ratios of the axons of regenerated sciatic nerves from Veh- and RGFP966-treated mice at Dpi 35. (Data are presented as mean±s.e.m.; n=303 axons from 3 mice for each group; two-tailed unpaired Student's t-test; P<0.0001, t=15.29, d.f.=604). (L) Effects of pharmacological inhibition of HDAC3 on remyelination: Representative electron micrographs of regenerated sciatic nerve cross sections from Veh- and HDAC3 inhibitors-treated mice at Dpi 18. n=3 animals/group, with 5 images for each mouse. Scale bars: 2 μm. (M) Effects of pharmacological inhibition of HDAC3 on remyelination: Quantification of g ratios of the axons of regenerated sciatic nerves from Veh- and HDAC3 inhibitors-treated mice at Dpi 18. (Data are presented as mean±s.e.m.; n=408 axons from 3 control mice, 574 axons from 3 RGFP966 treated mice and 546 axons from 3 PDA106 treated mice; one-way ANOVA with Tukey's multiple comparisons test; $F_{(2, 1525)}=153$, $P_{Veh\ versus\ RGFP966}<0.0001$, $P_{Veh\ versus\ PDA106}<0.0001$). (N) Schematic diagram depicting sciatic nerve transection and electrophysiological analysis. Mice were treated daily for the first week and then every two days until Dpi 14. Electrophysiological analyses were performed at Dpi 18 and Dpi 35. (0) Representative recordings of CMAPs of regenerated sciatic nerves at Dpi 18 from Veh-, RGFP966-, and PDA106-treated mice (S, stimulus; R, initiation of CMAP response). n=5 animals/group. (P) Quantification of the conduction velocity and mean peak of CMAP amplitude of intact or injured sciatic nerves from Veh- and RGFP966-treated mice. (Data are presented as mean±s.e.m.; n=5 animals/group; one-way ANOVA with Tukey's multiple comparisons test; conduction velocity, $F_{(3, 16)}=27.75$, $P_{Intact\ versus\ Veh}<0.0001$, $P_{Intact\ versus\ RGFP966}=0.046$, $P_{Intact\ versus\ PDA106}=0.0096$, $P_{Veh\ versus\ RGFP966}<0.0001$, $P_{Veh\ versus\ PDA106}=0.0004$; mean peak of CMAP amplitude, $F_{(3, 16)}=335.2$, $P_{Intact\ versus\ Veh}<0.0001$, $P_{Intact\ versus\ RGFP966}<0.0001$, $P_{Intact\ versus\ PDA106}<0.0001$, $P_{Veh\ versus\ RGFP966}<0.0001$, $P_{Veh\ versus\ PDA106}=0.0055$). (Q) HDAC3 inhibitor treatment enhances functional recovery after sciatic nerve transection: Representative recordings of CMAPs of regenerated sciatic nerves at Dpi 35 from Veh- and RGFP966-treated mice (S, stimulus; R, initiation of CMAP response). n=5 animals/group. (R) HDAC3 inhibitor treatment enhances functional recovery after sciatic nerve transection: Quantification of the conduction velocity and mean peak of CMAP amplitude of injured sciatic nerves from Veh- and RGFP966-treated mice. (Data are presented as mean±s.e.m.; n.s., not significant; n=5 animals/group; one-way ANOVA with Tukey's multiple comparisons test; conduction velocity, $F_{(2,\ 12)}=11.88$, $P_{Intact\ versus\ Veh}=0.0011$, $P_{Intact\ versus\ RGFP966}=0.1697$, $P_{Veh\ versus\ RGFP966}=0.0331$; mean peak of CMAP amplitude, $F_{(2,\ 12)}=18.77$, $P_{Intact\ versus\ Veh}=0.0001$, $P_{Intact\ versus\ RGFP966}=0.0142$, $P_{Veh\ versus\ RGFP966}=0.0439$). (S) Treatment scheme for HDAC3 inhibitors for ten days (upper) and pinprick stimulation to the plantar surface of the paw (lower panel). (T,U) Quantification of pinprick stimulation assays for sensory recovery in vehicle and HDAC3 inhibitor-treated mice at Dpi 24 (T) and 94 (U). (Data are presented as mean±s.e.m.; n=6 animals/group; one-way ANOVA with Tukey's multiple comparisons test; Dpi 24, $F_{(2,\ 15)}=9.053$, $P_{Veh\ versus\ RGFP966}=0.011$, $P_{Veh\ versus\ PDA106}=0.0036$; Dpi 94, $F_{(2,\ 15)}=8.382$, $P_{Veh\ versus\ RGFP966}=0.0051$, $P_{Veh\ versus\ PDA106}=0.013$). (V) Photographs of paws of uninjured mice, and the mice at Dpi 24 and 94 with nerve transection treated with vehicle and HDAC3 inhibitors for 10 days. (W) Quantification of toe spreading reflex in vehicle and HDAC3 inhibitor-treated mice at Dpi 24 and 94. (Data are presented as mean±s.e.m.; n=6 animals/group; one-way ANOVA with Tukey's multiple comparisons test; Dpi 24, $F_{(2,\ 15)}=26.76$, $P_{Veh\ versus\ RGFP966}<0.0001$, $P_{Veh\ versus\ PDA106}<0.0001$; Dpi 94, $F_{(2,\ 15)}=16.84$, $P_{Veh\ versus\ RGFP966}=0.0004$, $P_{Veh\ versus\ PDA106}=0.0004$). (X) Effects of inhibition of HDAC3 on remyelination: Representative electron micrographs of regenerated sciatic nerve cross sections from Veh- and HDAC3 inhibitors-treated mice at Dpi 94. n=3 animals/group, with 5 images for each mouse. Scale bars: 2 μm. (Y) Effects of inhibition of HDAC3 on remyelination: Quantification of g ratios of the axons of regenerated sciatic nerves from Veh- and HDAC3 inhibitors-treated mice at Dpi 94. (Data are presented as mean±s.e.m.; n=407 axons from 3 control mice, 364 axons from 3 RGFP966 treated mice and 436 axons from 3 PDA106 treated mice; one-way ANOVA with Tukey's multiple comparisons test; $F_{(2,\ 1201)}=26.69$, $P_{Veh\ versus\ RGFP966}<0.0001$, $P_{Veh\ versus\ PDA106}<0.0001$). (Z) Latency (s) to fall off the accelerating rotarod of vehicle and HDAC3 inhibitor-treated mice at Dpi 24 and 120. (Data are presented as mean±s.e.m.; n=8 animals/group; one-way ANOVA with Tukey's multiple comparisons test; Dpi 24, $F_{(2,\ 21)}=10.04$, $P_{Veh\ versus\ RGFP966}=0.0008$, $P_{Veh\ versus\ PDA106}=0.0043$; Dpi 120, $F_{(2,\ 21)}=7.392$, $P_{Veh\ versus\ RGFP966}=0.0073$, $P_{Veh\ versus\ PDA106}=0.0051$). (AA) Treatment with HDAC3 inhibitors does not affect myelin thickness of the intact sciatic nerves in adult mice: Representative electron micrographs of intact sciatic nerves from Veh-, RGFP966-, and PDA106-treated adult mice at Dpi 35. n=3 animals/group, with 5 images for each mouse. Scale bars: 2 μm. (AB) Treatment with HDAC3 inhibitors does not affect myelin thickness of the intact sciatic nerves in adult mice: Box plots of g ratios of the intact sciatic nerves from Veh-, RGFP966-, and PDA106-treated mice at Dpi 35. (Data are presented as mean±s.e.m.; n=203 axons from 3 control mice, 202 axons from 3 RGFP966 treated mice and 200 axons from 3 PDA106 treated mice; Whiskers show the minimum and maximum, boxes extend from the first to the third quartiles with cross lines at the medians; one-way ANOVA with Tukey's multiple comparisons test, $F_{(2,\ 602)}=2.48$, $P_{Veh\ versus\ RGFP966}=0.0679$, $P_{Veh\ versus\ PDA106}=0.5701$). (AC) HDAC3 expression in sciatic nerves at postnatal and adult stages: Immunofluorescence labeling for HDAC3 (green) and SOX10 (red) in sciatic nerves at indicated stages. n=5 animals/group, with 5 images for each mouse. Scale bars: 20 μm. (AD) HDAC3 expression in sciatic nerves at postnatal and adult stages: Western blots for HDAC3 expression in sciatic nerves at indicated stages. n=3 independent experiments. GAPDH was detected as a loading control. (AE) HDAC3 inhibitor treatment enhances functional recovery after sciatic nerve transection in aging mice: Wildtype aging mice at 10-12 months of age were treated daily for the first week and then every two days until Dpi 14 beginning the day after sciatic nerve transection. Representative recordings of CMAPs of regenerated sciatic nerves at Dpi 35 from Veh- and RGFP966-treated mice (S, stimulus; R, initiation of CMAP response). n=4 animals/group. (AF-AH) HDAC3 inhibitor treatment enhances functional recovery after sciatic nerve transection in aging mice: quantification of the conduction velocity (AF), mean peak of CMAP amplitude (AG), and average CMAP duration (AH) of injured sciatic nerves from Veh- and RGFP966-treated mice. (Data are presented as mean±s.e.m.; n=4 animals/group; two-tailed unpaired Student's t-test; AF, P<0.0001, t=12.11, d.f.=6; AG, P=0.0005, t=6.764, d.f.=6; AH, P=0.0077, t=3.933, d.f.=6). n.s., not significant, *P<0.05, P<0.01, *P<0.001.

Figure 3:
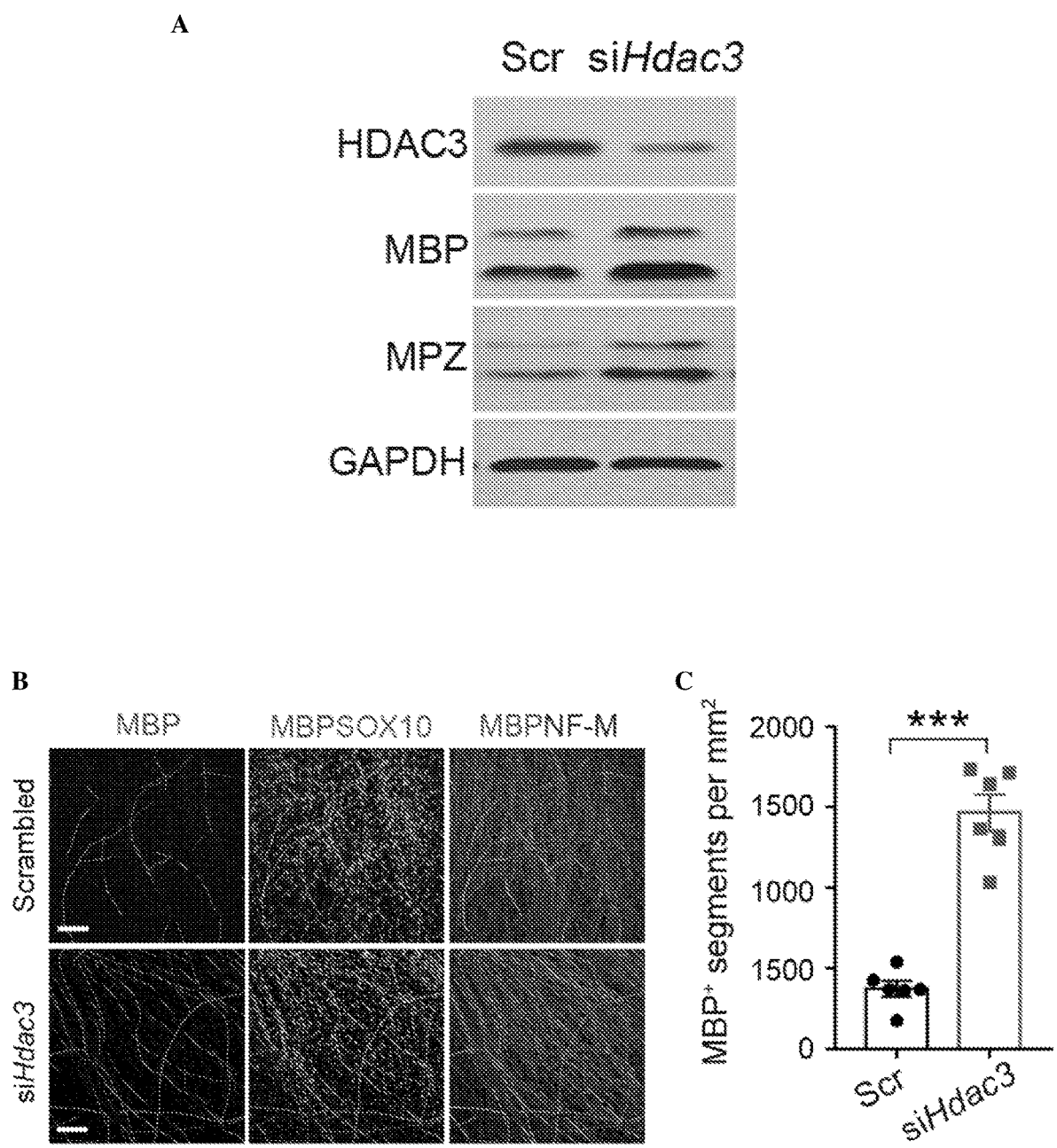
Figure 3:
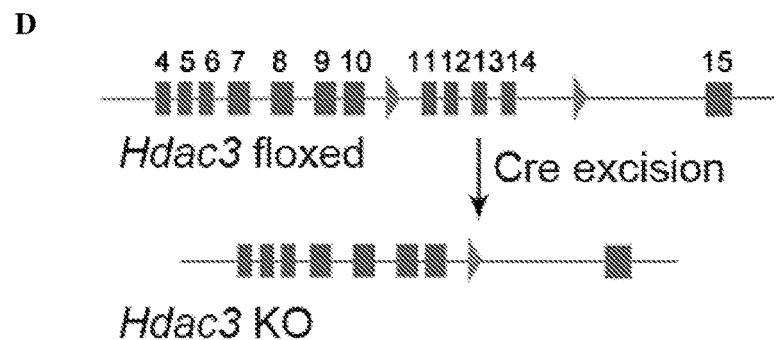
Figure 3:
Figure 3:
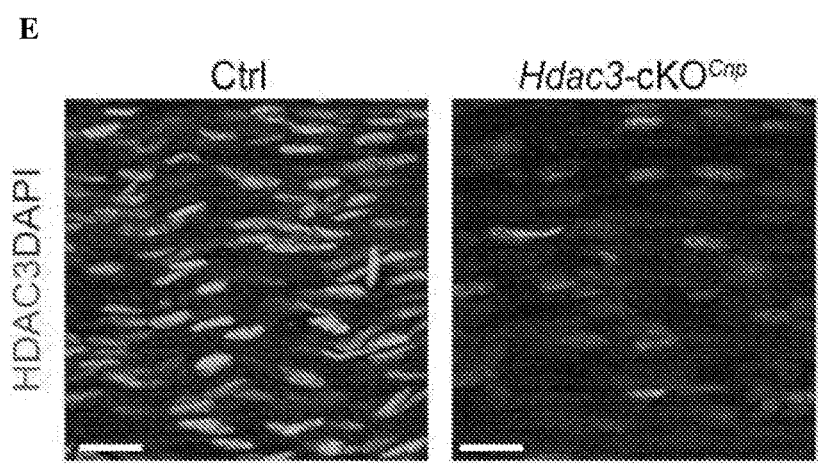
Figure 3:
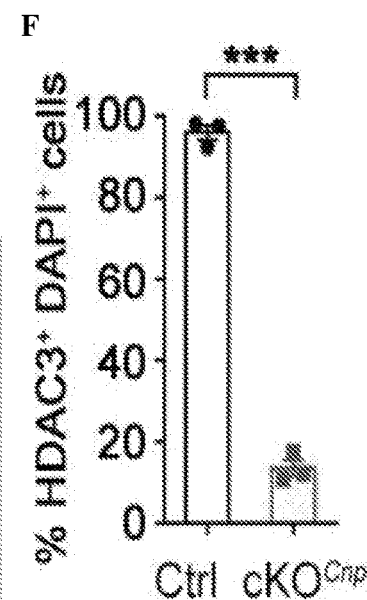
Figure 3:
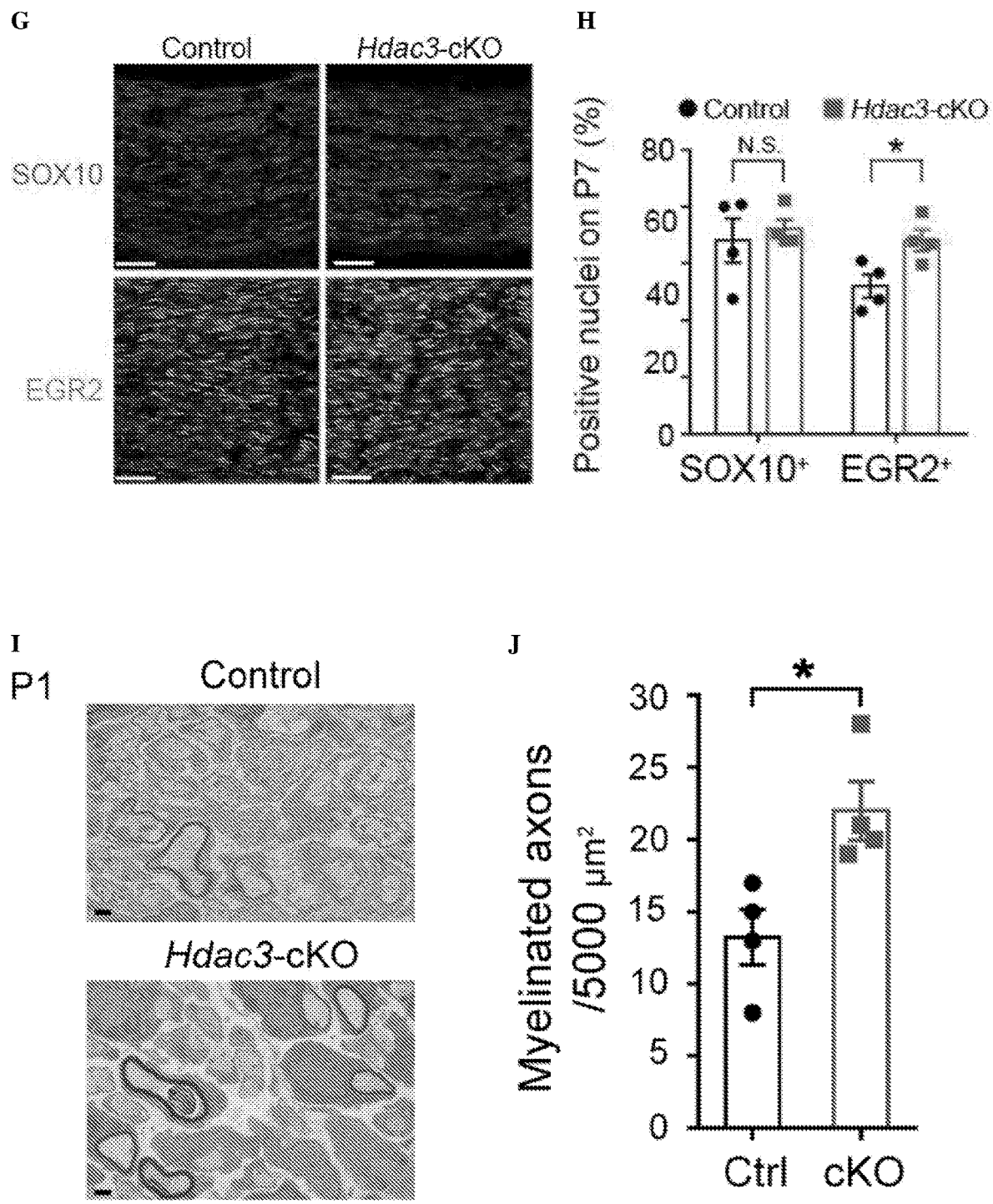
Figure 3:
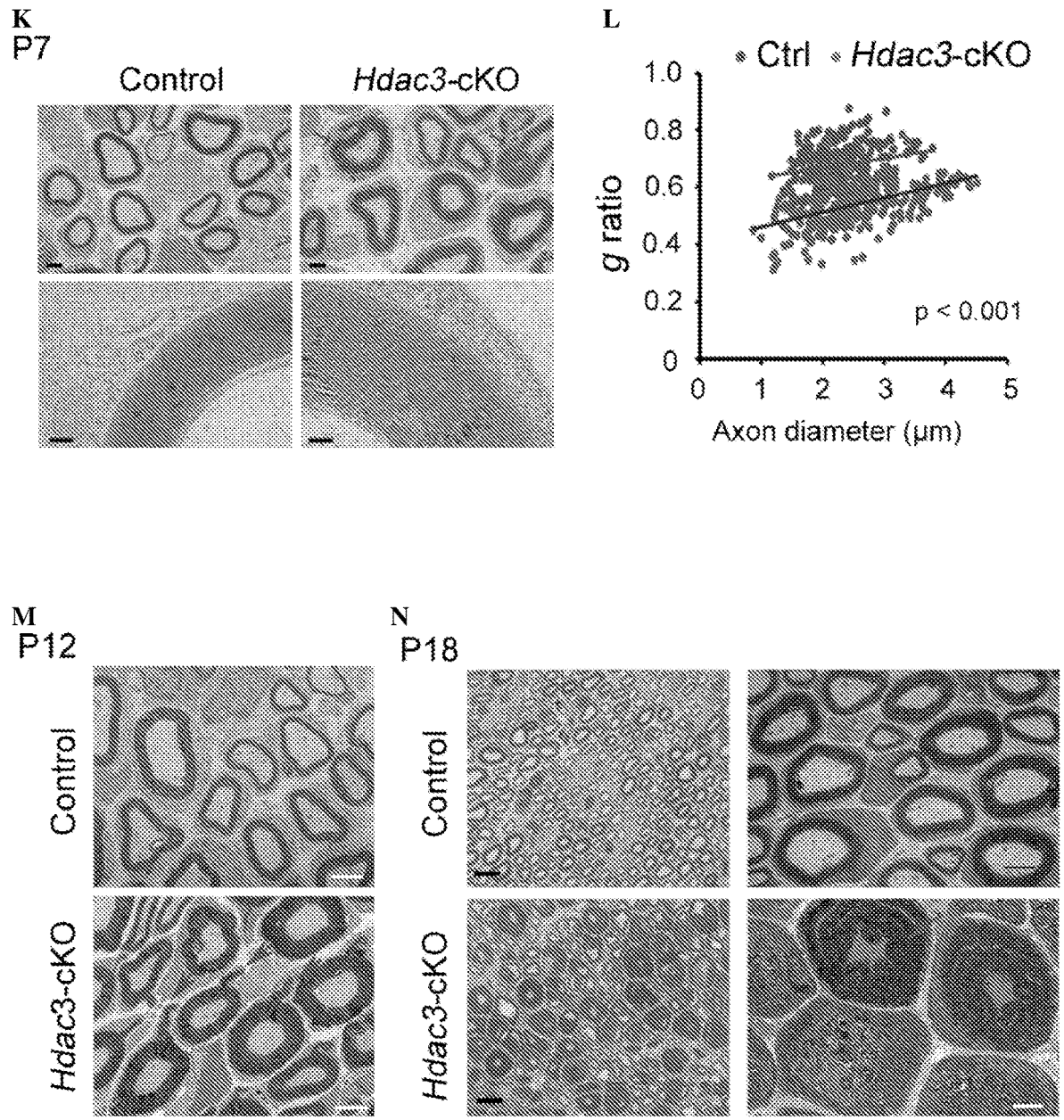
Figure 3:
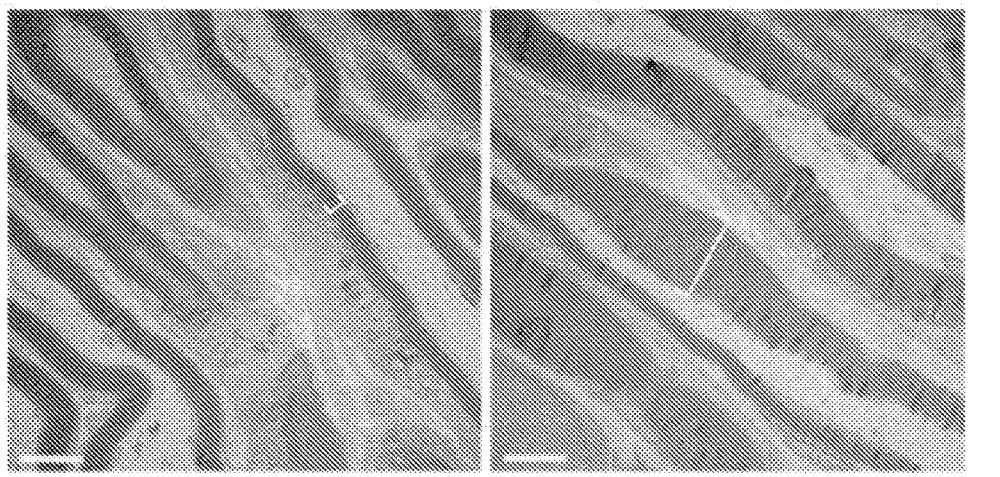
Figure 3:
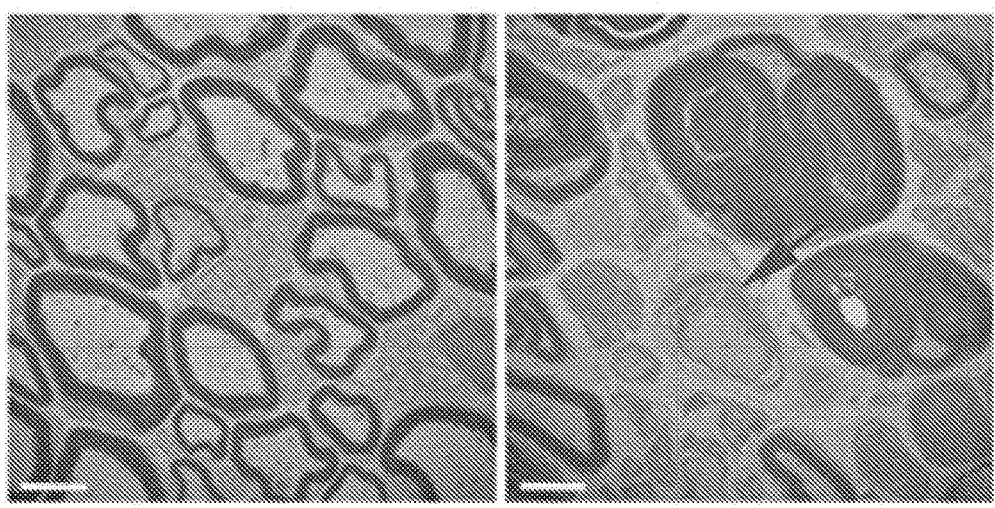
Figure 3:
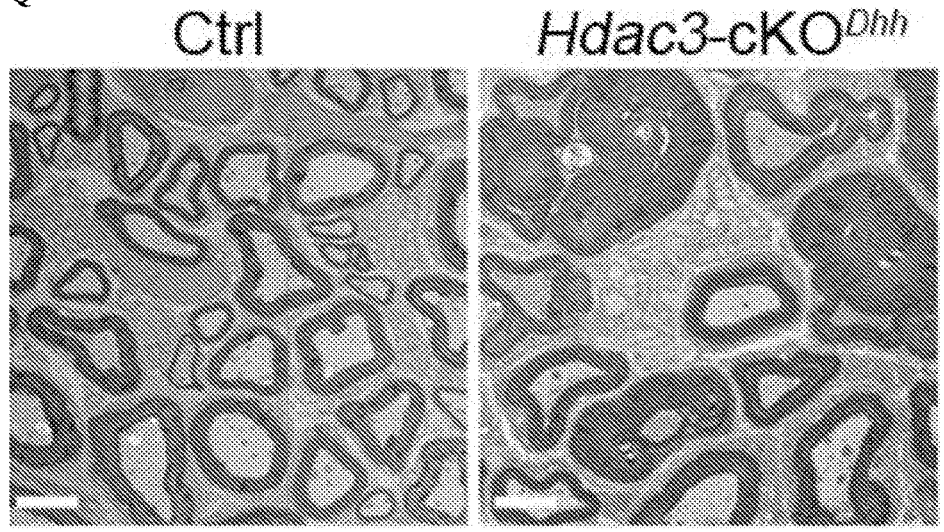
Figure 3:
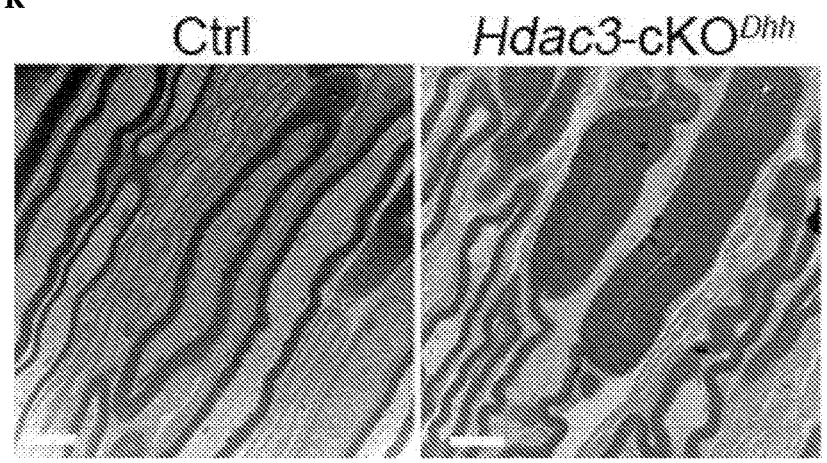
Figure 3:
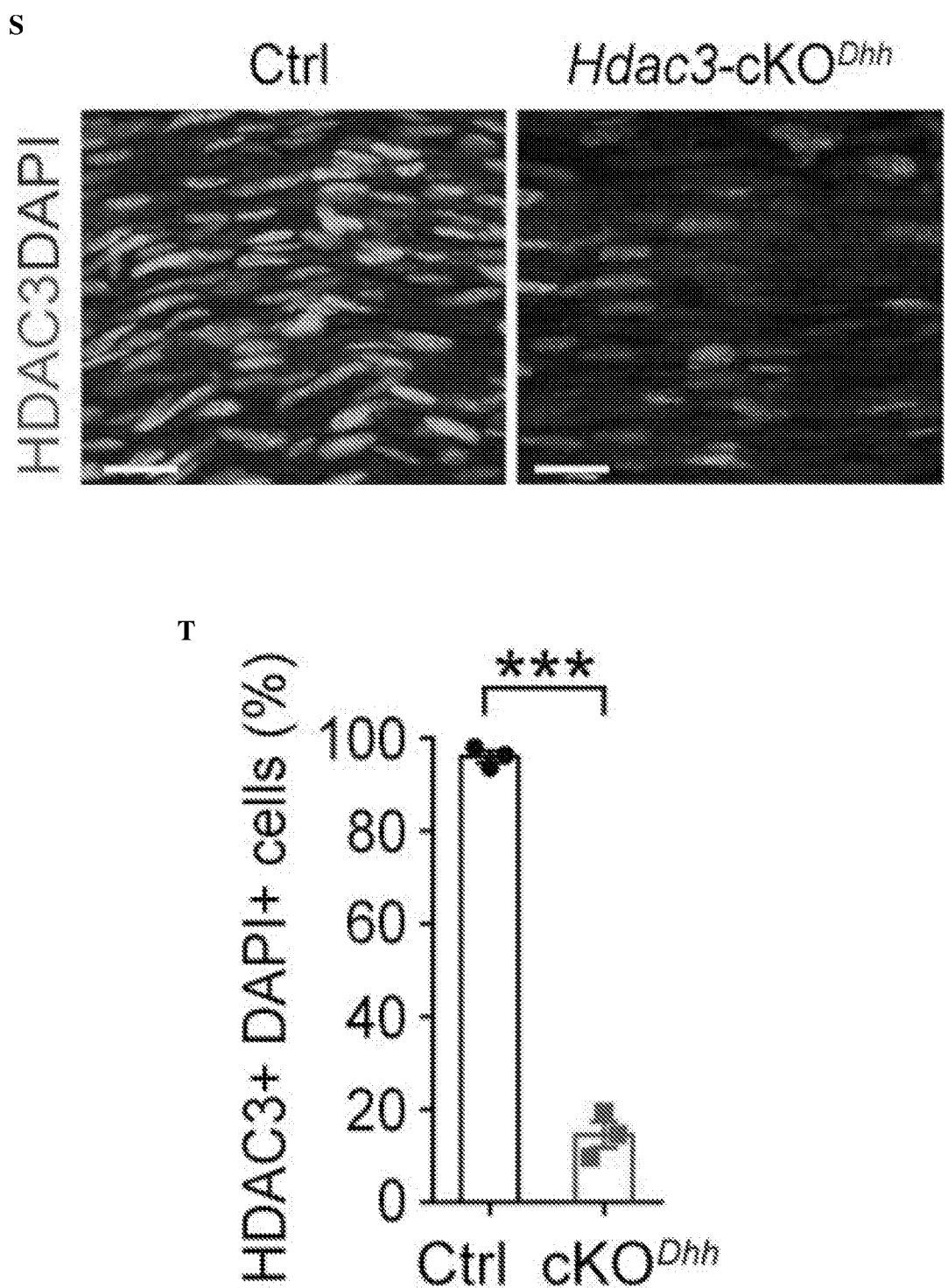
Figure 3:
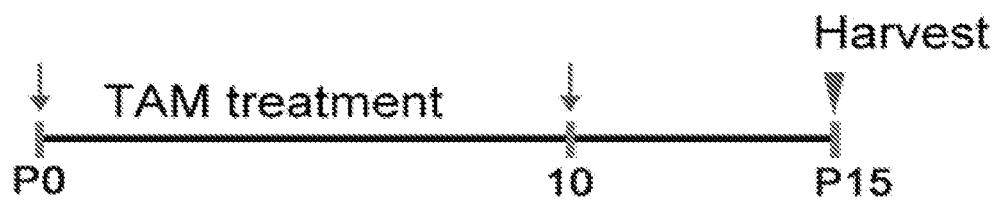
Figure 3:
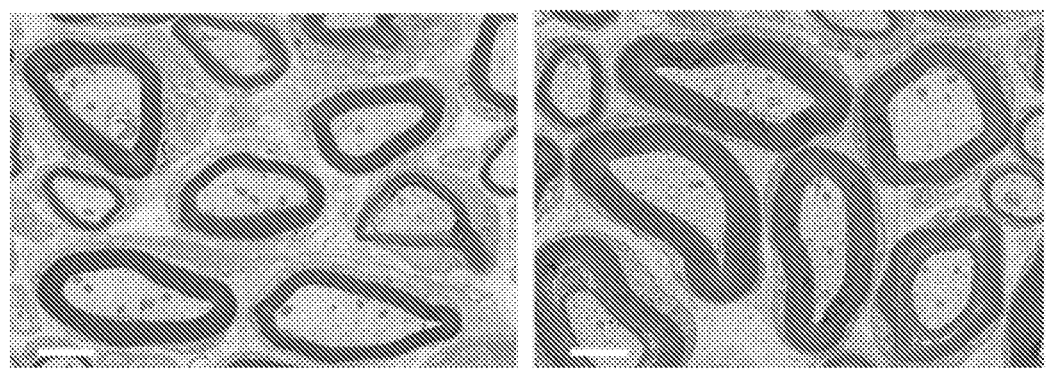
Figure 3:
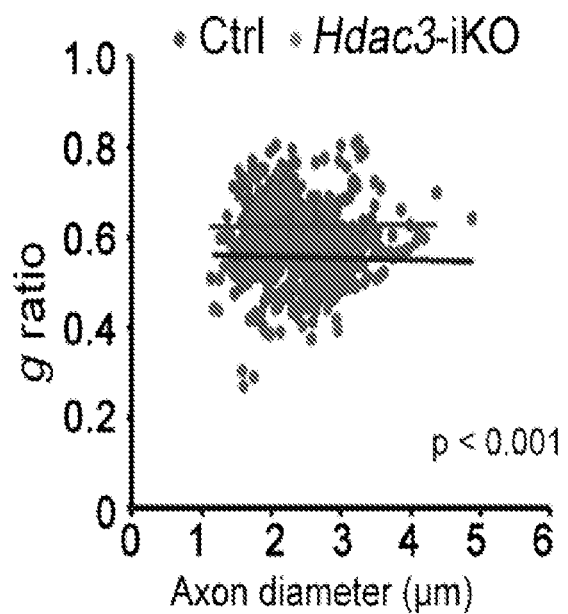
Figure 3:
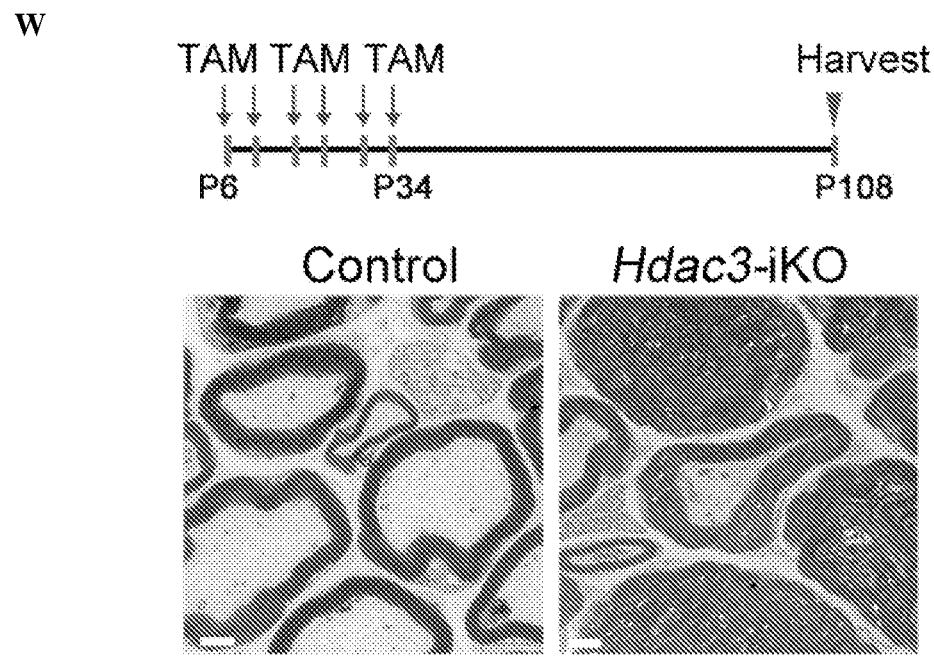
Figure 3:
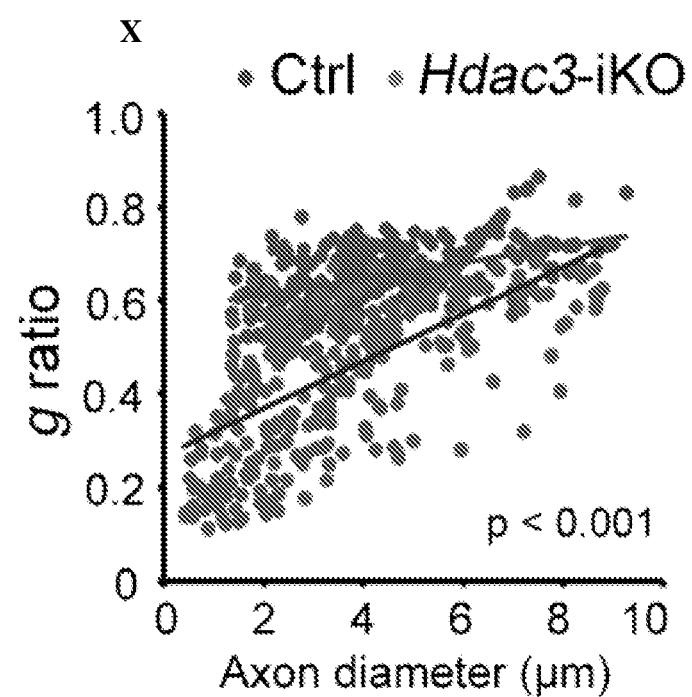
Figure 3:
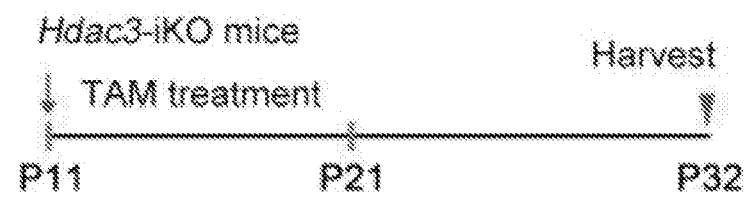
Figure 3:
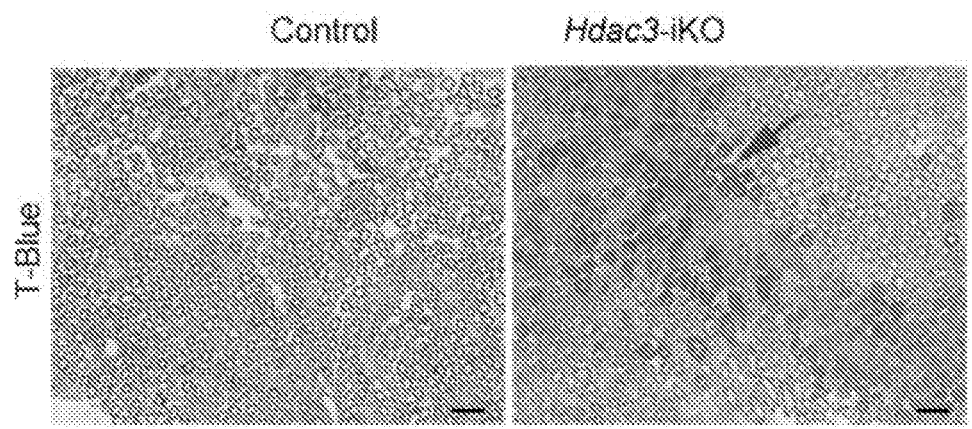
Figure 3:
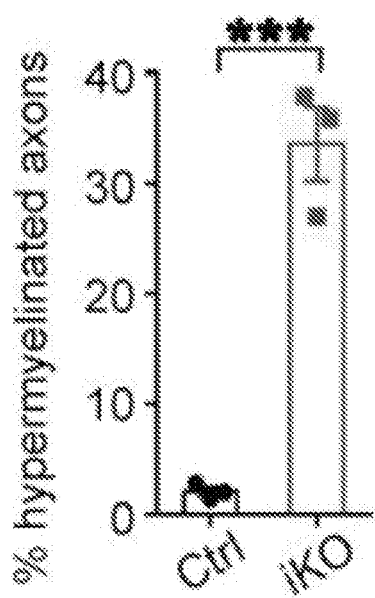
Figure 3:
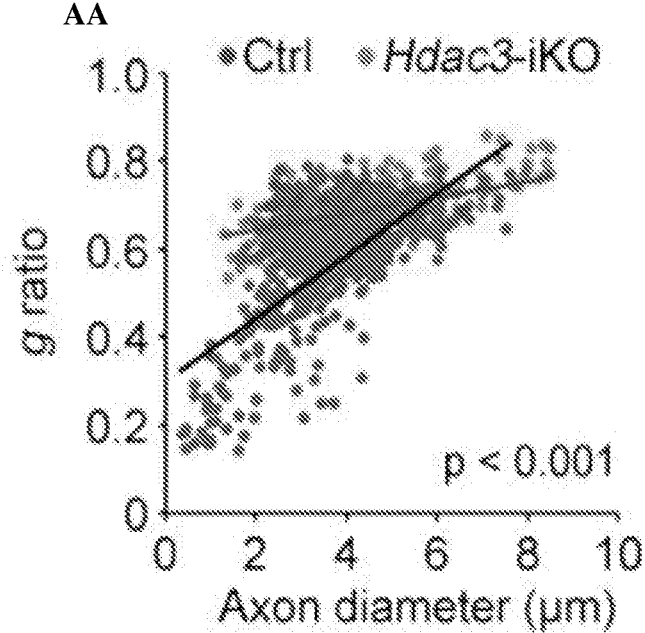
Figure 3:
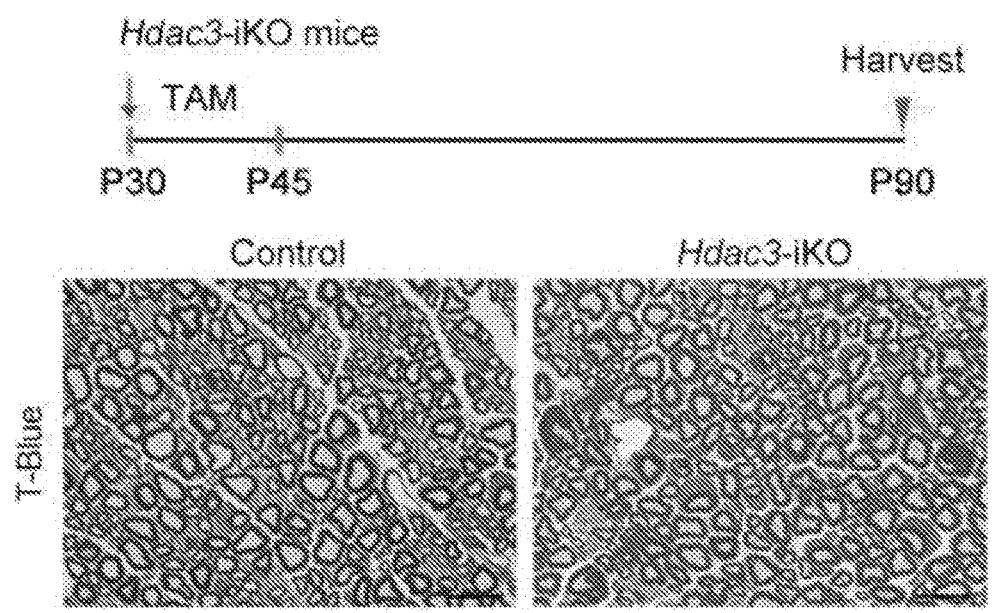
Figure 3:
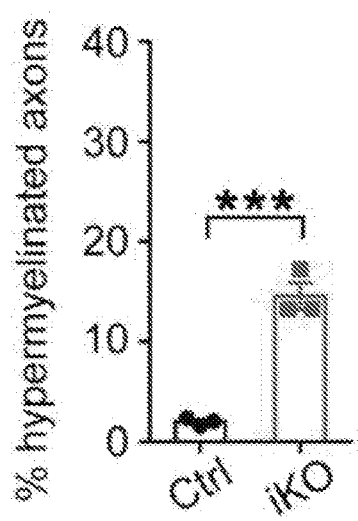
Figure 3:
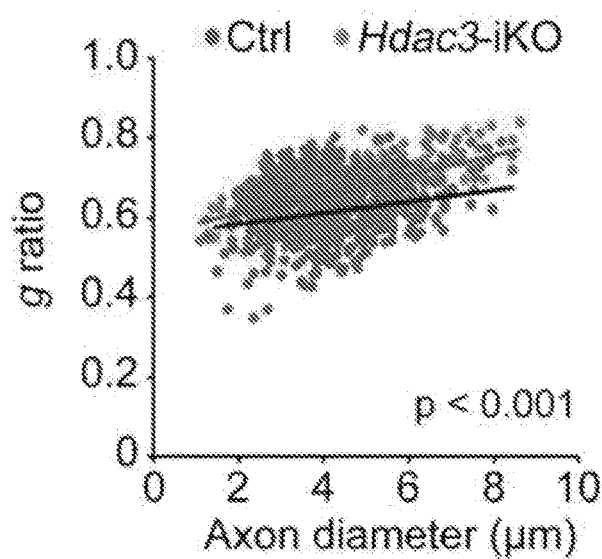
Figure 3:
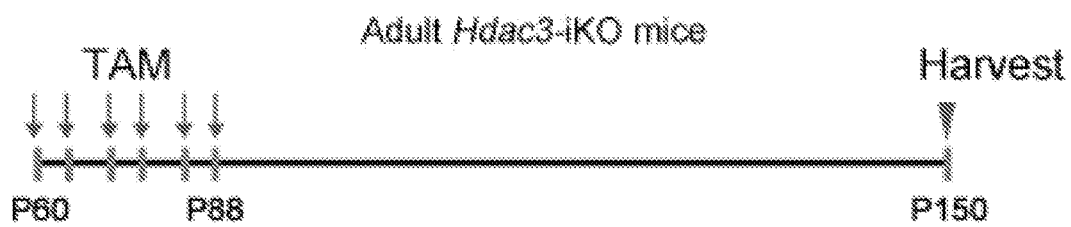
Figure 3:
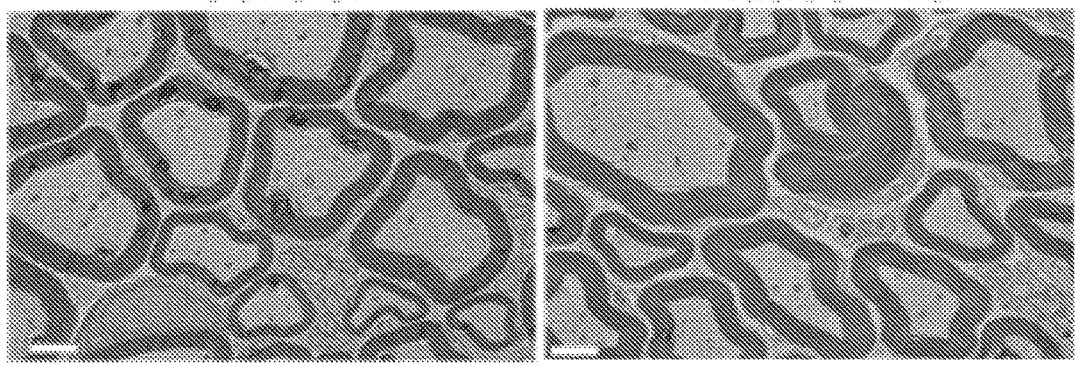
Figure 3:
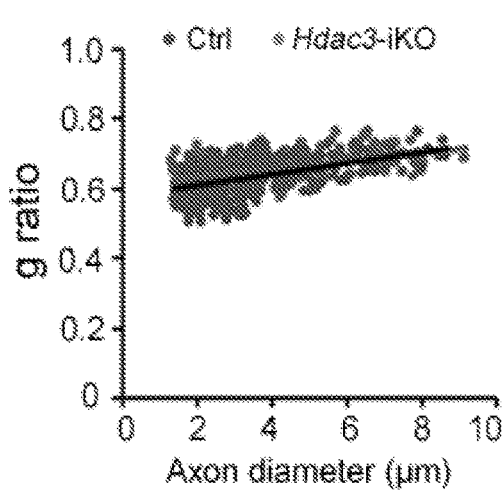
Figure 3:
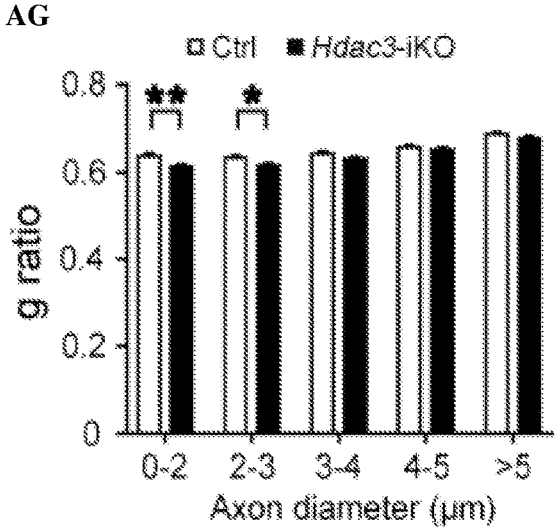

FIG. 3: Hdac3 ablation can lead to hypermyelination during peripheral nerve development. (A) Western blots of HDAC3, MPZ, and MBP in co-cultures of DRGs and SCs treated with siHdac3 or control siRNA. n=2 independent experiments. GAPDH was detected as a loading control. (B) Rat SCs treated with siHdac3 or control siRNA were seeded onto rat DRGs. After 10 days, co-cultures were immunostained for MBP, SOX10, and neurofilament-M (NF-M). n=6 independent experiments, with 10 images for each experiment. Scale bars: 100 μm. (C) Quantitation of MBP+ segment numbers in myelinating co-cultures of DRGs and SCs treated with siHdac3 or scrambled control siRNA (Scr). (Data are presented as mean±s.e.m.; n=6 independent experiments; two-tailed unpaired Student's t-test; P<0.0001, t=8.79, d.f.=10). (D) Upper: A schematic diagram shows Cre-mediated excision of floxed Hdac3 exons 11-14. Bottom: Western blots of sciatic nerves showing a marked decreased HDAC3 in Hdac3-cKO mice compared to controls at P21. n=3 independent experiments. GAPDH was detected as a loading control. (E) Recombination efficiency in the sciatic nerves of Hdac3-cKO mice driven by Cnp-Cre: Representative images of longitudinal cryosections of sciatic nerves from control and Hdac3-cKO mice at P8 immunostained for HDAC3 (green) and SOX10 (red). n=3 animals/group, with 5 images for each mouse. Scale bar, 20 μm. (F) Recombination efficiency in the sciatic nerves of Hdac3-cKO mice driven by Cnp-Cre: Percentage of HDAC3+ cells among DAPI nuclei in control and Hdac3-cKO sciatic nerves at P8. (Data are presented as mean±s.e.m.; n=3 animals/group; two-tailed unpaired Student's t-test; P<0.0001, t=30.28, d.f.=4). (G) Increase of EGR2+ differentiated SCs in HDAC3-deficient sciatic nerves: Immunofluorescence labeling for SOX10 (red) and EGR2 (green) in control and Hdac3-iKO sciatic nerves at P7. n=4 animals/group, with 5 images for each mouse. Scale bars: 50 (H) Increase of EGR2+ differentiated SCs in HDAC3-deficient sciatic nerves: Percentage of SOX10$^+$ and EGR2$^+$ SCs among DAPI nuclei in control and Hdac3-iKO sciatic nerves at P7. (Data are presented as mean±s.e.m.; n=4 animals/group; two-tailed unpaired Student's t-test; SOX10, P=0.6492, t=0.4786, d.f.=6; EGR2, P=0.0276, t=2.894, d.f.=6). (I) Electron microscopy analysis of cross sections of control and Hdac3-cKO sciatic nerves at P1. n=4 animals/group, with 10 images for each mouse. Scale bars: 1 µm. (J) Quantification of myelinated axons per 5000 µm$^2$ of P1 sciatic nerves from control and Hdac3-cKO mice. (Data are presented as mean±s.e.m.; n=4 animals/group; two-tailed unpaired Student's t-test; P=0.0207, t=3.114, d.f.=6). (K) Upper: Electron microscopy analysis of cross sections of control and Hdac3-cKO sciatic nerves at P7. Arrows indicate regions of thick myelin sheaths in Hdac3-cKO mice. Scale bars: 2 µm. Bottom: High magnification images of myelin wrapped around axons of similar diameter. Note that the ultrastructure and periodicity of myelin wraps are similar in the control and mutant mice. n=3 animals/group, with 10 images for each mouse. Scale bars: 0.2 µm. (L) Quantification of g ratios of axons at P7 from control and Hdac3-cKO mice. (Data are presented as mean±s.e.m.; n=250 axons from 3 control mice and 252 axons from 3 cKO mice; two-tailed unpaired Student's t-test; P<0.0001, t=19.91, d.f.=500). (M) Representative electron micrographs of cross sections of sciatic nerves of control and Hdac3-cKO mice at P12. n=4 animals/group, with 10 images for each mouse. Arrows indicate myelin out-foldings. Scale bars: 2 µm. (N) Representative light microscopic images and electron micrographs of sciatic nerve cross sections from control and Hdac3-cKO mice at P18. Arrow indicates excessive myelin. n=4 animals/group, with 10 images for each mouse. Scale bars: 10 µm (left) and 4 µm (right). (O) Hdac3-deficient mice can develop hypermyelination at P18 and progressive demyelination at adult stage in peripheral nerves. Representative electron micrographs of longitudinal sections of sciatic nerves from control and Hdac3-cKO mice at P18. The brackets indicate the thickness of myelin sheath. n=4 animals/group, with 5 images for each mouse. Scale bars: 2 µm. (P) Hdac3-deficient mice can develop hypermyelination at P18 and progressive demyelination at adult stage in peripheral nerves. Representative electron micrographs of cross sections of sciatic nerves of control and Hdac3-cKO mice at P105. Arrow indicates a demyelinated axon. n=4 animals/group, with 5 images for each mouse. Scale bars: 2 µm. (Q, R) Mice with Hdac3 ablation in Dhh-Cre-expressing SCs can exhibit hypermyelination. Electron micrographs of (Q) cross sections and (R) longitudinal sections of sciatic nerves from control (Hdac3$^{fl/fl}$) and Hdac3-cKO (Hdac3$^{fl/fl}$; Dhh-Cre$^{+/-}$) mice at P28. Colored regions mark axons. n=3 animals/group, with 5 images for each mouse. Scale bars: 2 µm. (S) Mice with Hdac3 ablation in Dhh-Cre-expressing SCs can exhibit hypermyelination. Representative images of longitudinal cryosections of sciatic nerves from control and Hdac3cKO mice at P8 immunostained for HDAC3 (green) and SOX10 (red). n=3 animals/group, with 5 images for each mouse. Scale bar, 20 µm. (T) Mice with Hdac3 ablation in Dhh-Cre-expressing SCs can exhibit hypermyelination. Percentage of HDAC3$^+$ cells among DAPI nuclei in control and Hdac3-cKO sciatic nerves at P8. (Data are presented as mean±s.e.m.; n=3 animals/group; two-tailed unpaired Student's t-test; P<0.0001, t=26.71, d.f.=4). (U) Upper: A diagram of tamoxifen administration scheme. Tamoxifen was injected i.p. into lactating dams once per day till P10. Sciatic nerves were harvested at P15. Bottom: Representative electron micrographs of cross sections of sciatic nerves from control heterozygotes and Hdac3-iKO mice. n=4 animals/group with 10 images for each mouse. Scale bars: 2 µm. (V) Quantification of g ratios of axons at P15 from control and Hdac3-iKO mice. (Data are presented as mean±s.e.m.; n=303 axons from 3 control mice and 305 axons from 3 iKO mice; two-tailed unpaired Student's t-test; P<0.0001, t=11.09, d.f.=606). (W) Upper: Schematic diagram showing tamoxifen treatment scheme. Mice were treated with tamoxifen from P6 to P10, from P18 to P22, and from P30 to 34. Sciatic nerves were harvested at P108. Bottom: Representative electron micrographs of cross sections of sciatic nerves from control and Hdac3-iKO mice. n=4 animals/group with 10 images for each mouse. Scale bars: 2 µm. (X) Quantification of g ratios of axons at P108 from control and Hdac3-iKO mice. (Data are presented as mean±s.e.m.; n=302 axons from 3 control mice and 304 axons from 3 iKO mice; two-tailed unpaired Student's t-test; P<0.0001, t=21.79, d.f.=604). (Y) Inducible deletion of Hdac3 at different stages can lead to hypermyelination. Upper: Schematic diagram showing tamoxifen treatment scheme. Mice were treated with tamoxifen from P11 to P21 and sciatic nerves were harvested at P32. Bottom: Representative toluidine blue-stained images of semi-thin cross-sections of sciatic nerves from control and Hdac3-iKO mice. n=3 animals/group, with 5 images for each mouse. Scale bars: 20 µm. (Z) Inducible deletion of Hdac3 at different stages can lead to hypermyelination. Quantification of hypermyelinated axons at P32 from control and Hdac3-iKO mice. (Data are presented as mean±s.e.m.; n=3 animals/group; two-tailed unpaired Student's t-test; P=0.0007, t=9.342, d.f.=4). (AA) Inducible deletion of Hdac3 at different stages can lead to hypermyelination. Quantification of g ratios of axons at P32 from control and Hdac3iKO mice. (Data are presented as mean±s.e.m.; n=415 axons from 3 control mice and 392 axons from 3 iKO mice; two-tailed unpaired Student's t-test; P<0.0001, t=18.95, d.f.=805). (AB) Inducible deletion of Hdac3 at different stages can lead to hypermyelination. Upper: Schematic diagram showing tamoxifen treatment scheme. Mice were treated with tamoxifen from P30 to P45 and sciatic nerves were harvested at P90. Bottom: Representative toluidine blue-stained images of semi-thin cross-sections of sciatic nerves from control and Hdac3-iKO mice. n=3 animals/group, with 5 images for each mouse. Scale bars: 20 µm. (AC) Inducible deletion of Hdac3 at different stages can lead to hypermyelination. Quantification of hypermyelinated axons at P90 from control and Hdac3-iKO mice. (Data are presented as mean±s.e.m.; n=3 animals/group; two-tailed unpaired Student's t-test; P=0.0007, t=9.373, d.f.=4). (AD) Inducible deletion of Hdac3 at different stages can lead to hypermyelination. Quantification of g ratios of axons at P90 from control and Hdac3-iKO mice. (Data are presented as mean±s.e.m.; n=426 axons from 3 control mice and 351 axons from 3 iKO mice two-tailed unpaired Student's t-test; P<0.0001, t=8.498, d.f.=775). (AE) Effect of Hdac3 ablation in adult mice on peripheral myelination. Upper: A diagram of tamoxifen administration scheme. Adult control and Hdac3-iKO mice were treated with tamoxifen from P60 to P64, from P72 to P76, and from P84 to 88. Sciatic nerves were harvested at P150. Bottom: Representative electron micrographs of cross sections of sciatic nerves from control and Hdac3-iKO mice at P150. n=3 animals/group, with 5 images for each mouse. Scale bars: 2 µm. (AF) Effect of Hdac3 ablation in adult mice on peripheral myelination. Dot plot of g ratios of axons at P150 from control and Hdac3-iKO mice (n=3 animals/group). (AG) Effect of Hdac3 ablation in adult mice on peripheral myelination. Quantification of g ratios of groups of axons with the indicated diameters at P150. (Data are presented as mean±s.e.m.; n=3 animals/ group; two-tailed unpaired Student's ttest; 0-2 μm, P=0.0041, t=2.934, d.f.=112; 2-3 μm, P=0.0148, t=2.461, d.f.=182). n.s., not significant, *P<0.05, P<0.01, *P<0.001.

Figure 4:
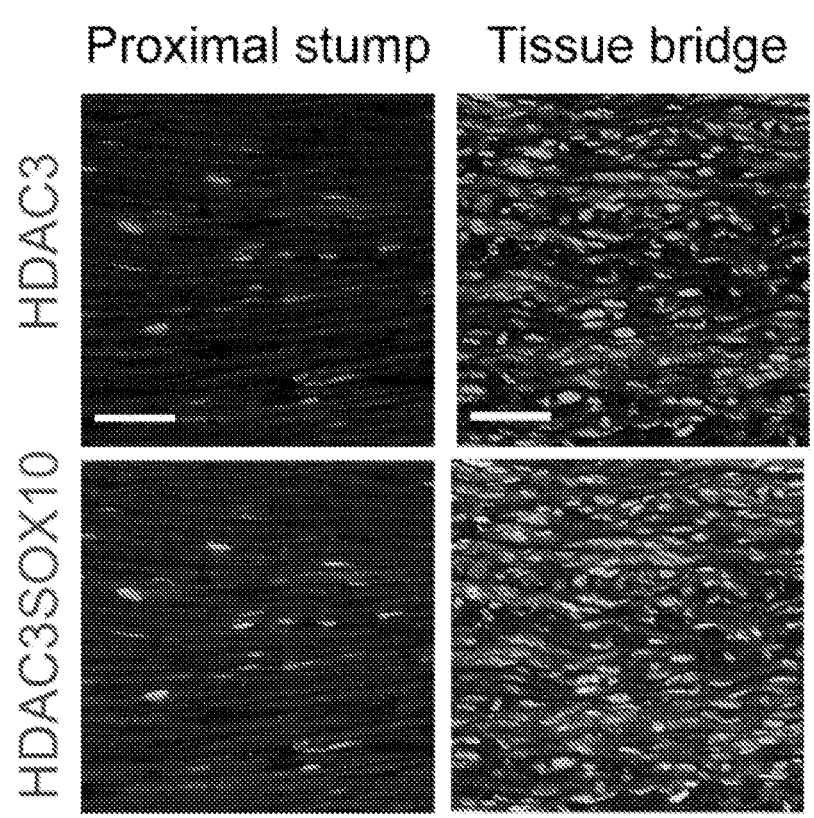
Figure 4:
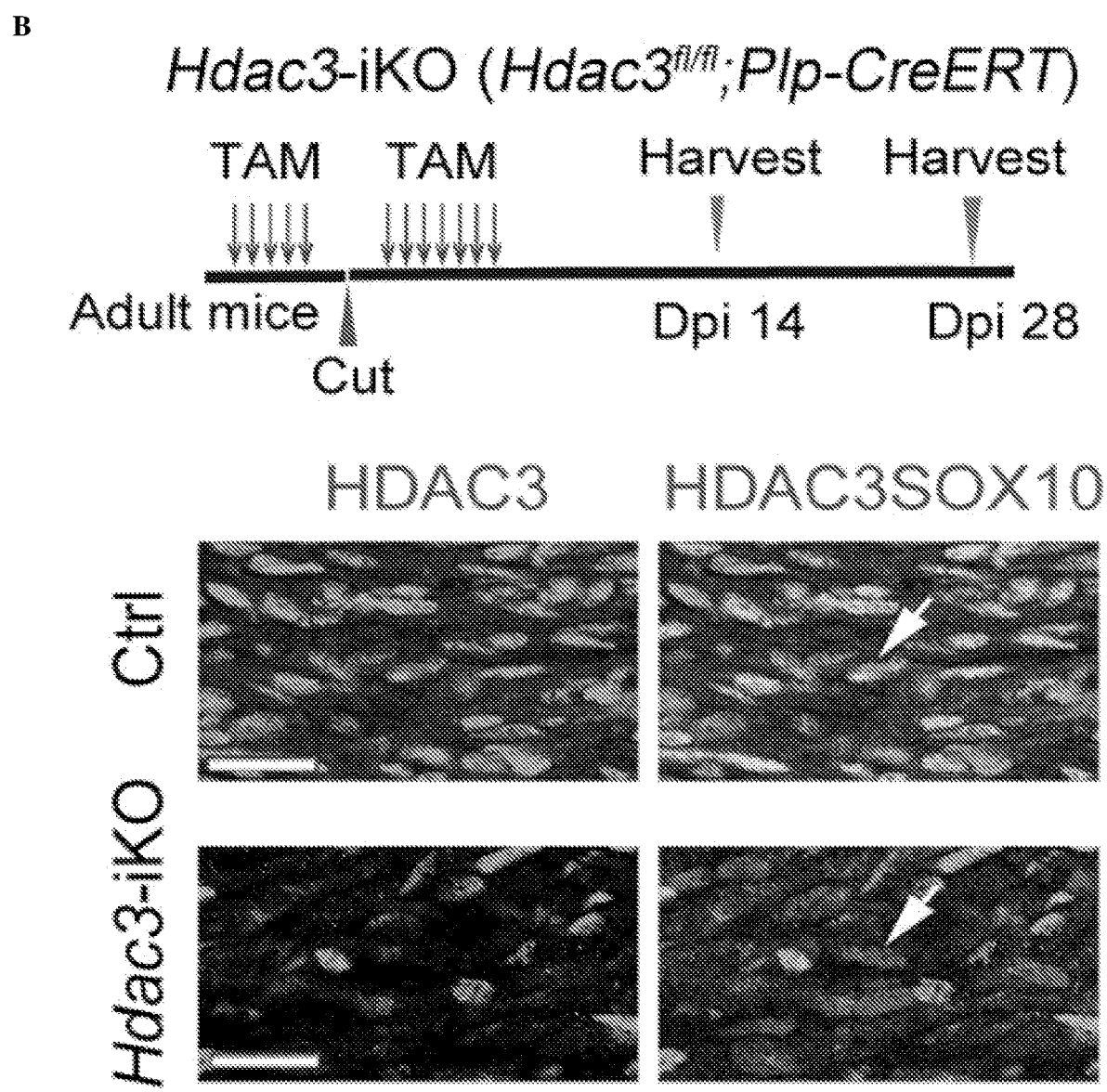
Figure 4:
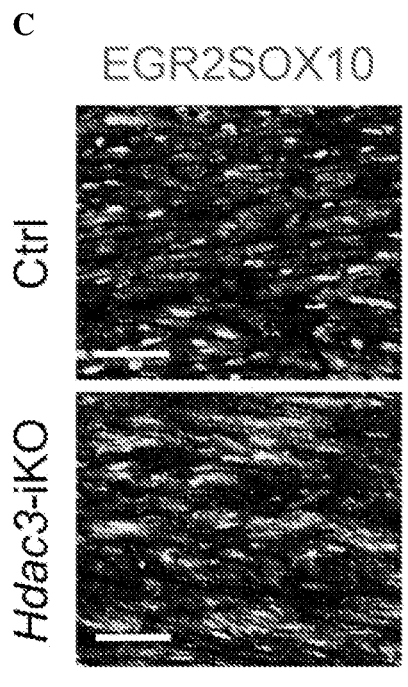
Figure 4:
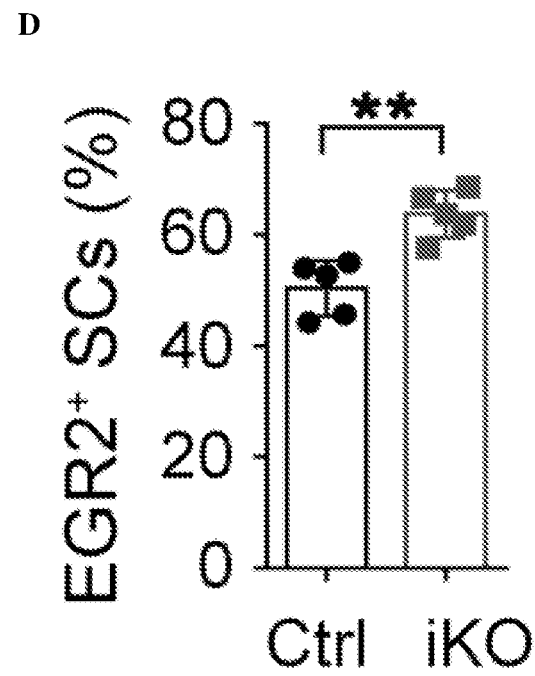
Figure 4:
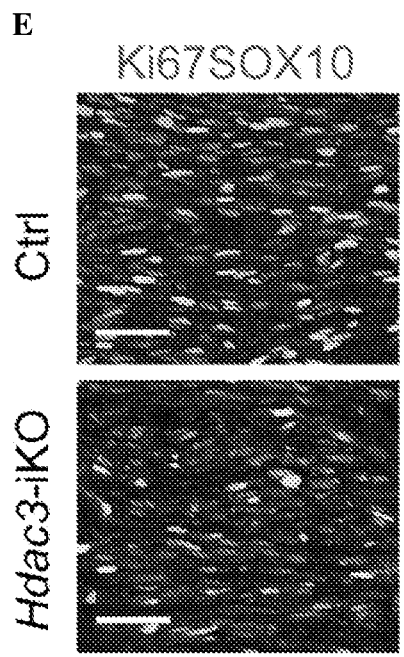
Figure 4:
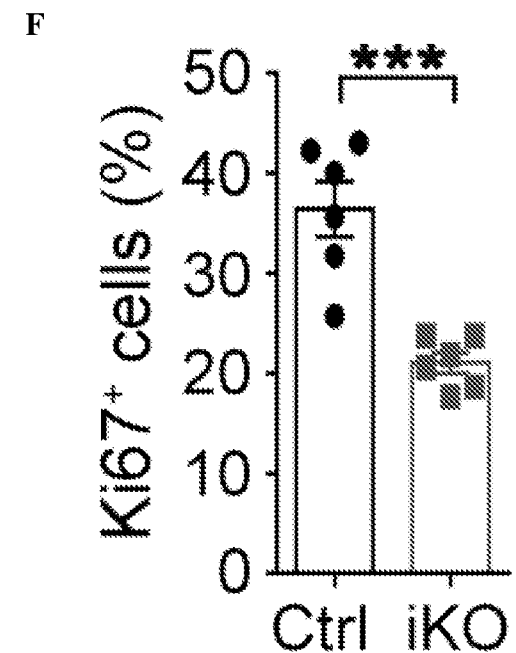
Figure 4:
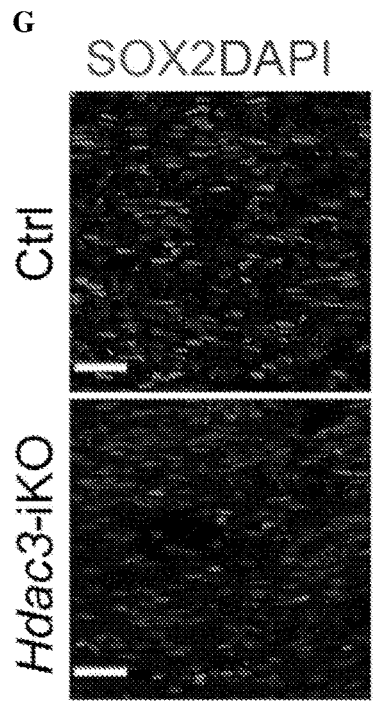
Figure 4:
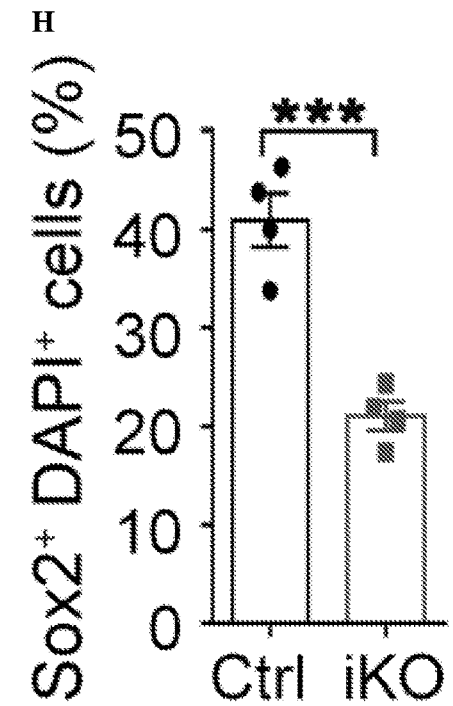
Figure 4:
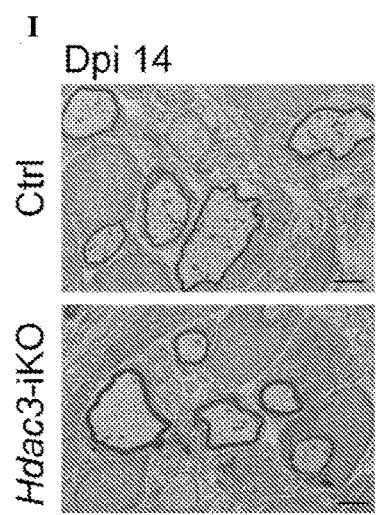
Figure 4:
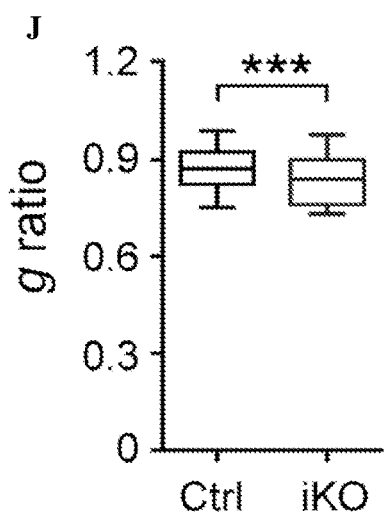
Figure 4:
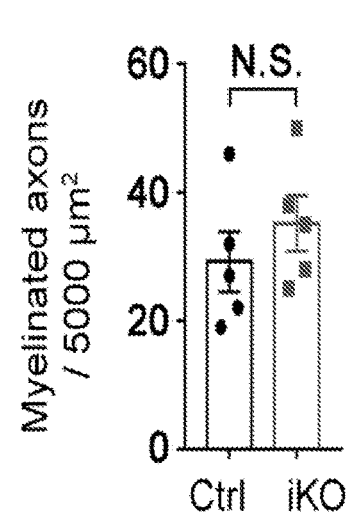
Figure 4:
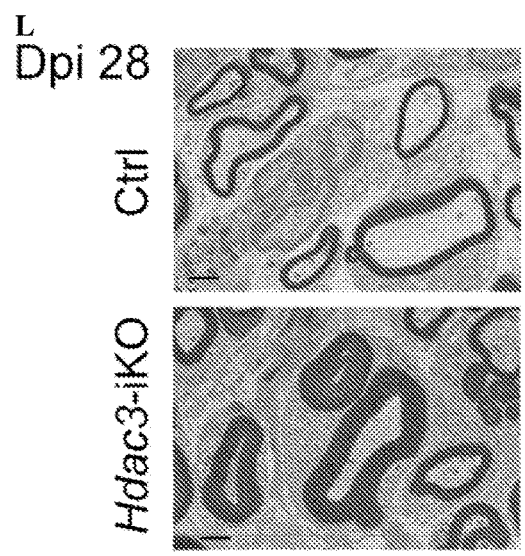
Figure 4:
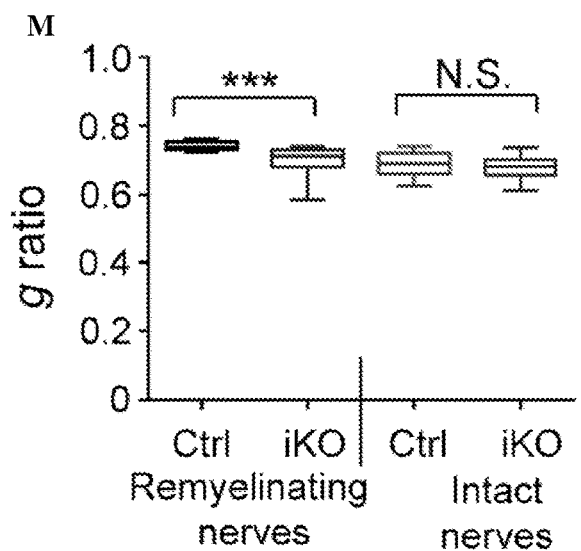
Figure 4:
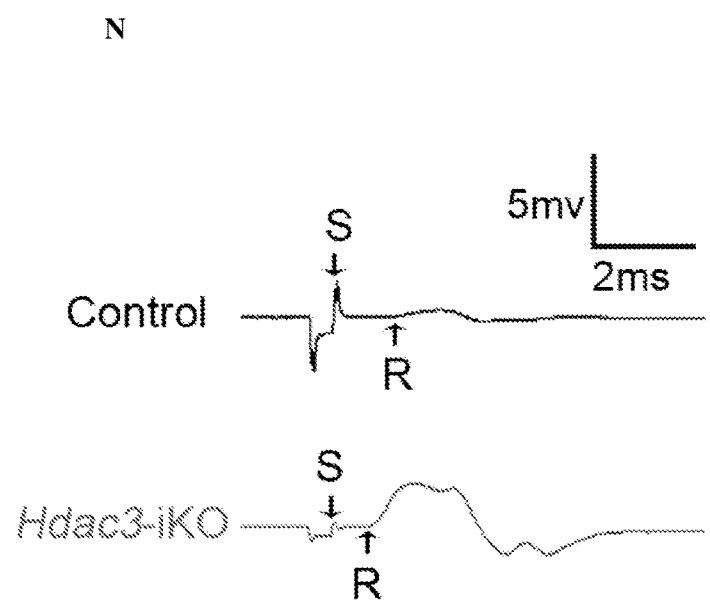
Figure 4:
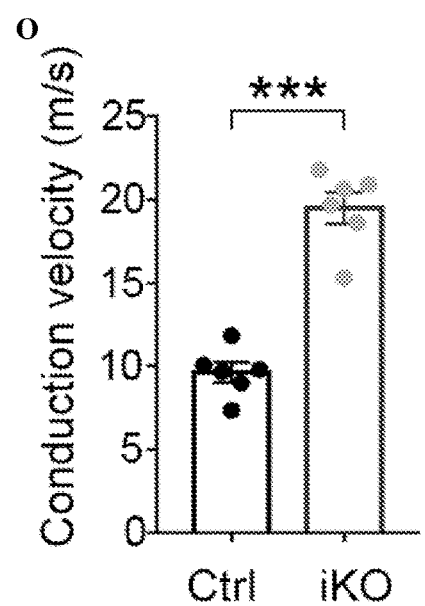
Figure 4:
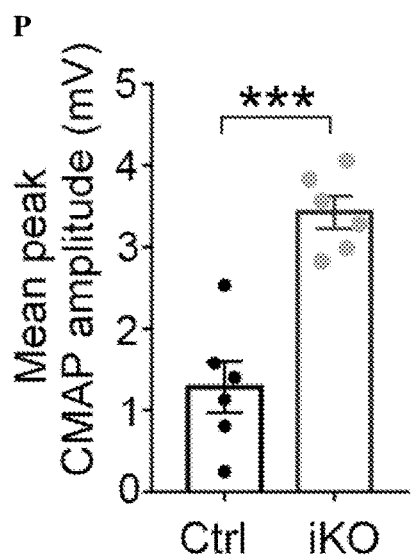
Figure 4:
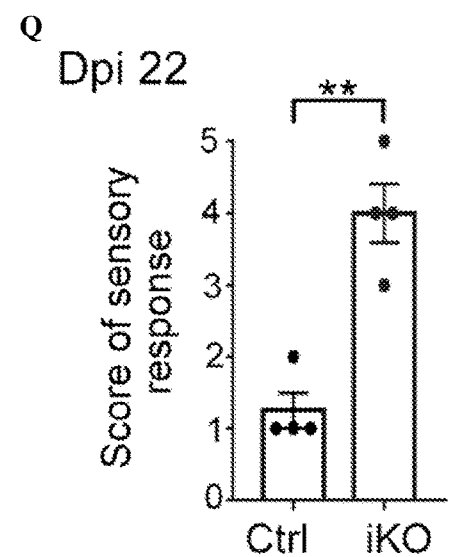
Figure 4:
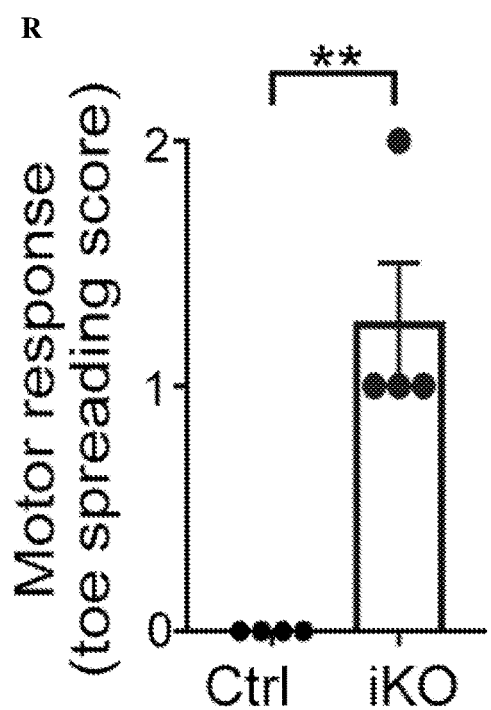
Figure 4:
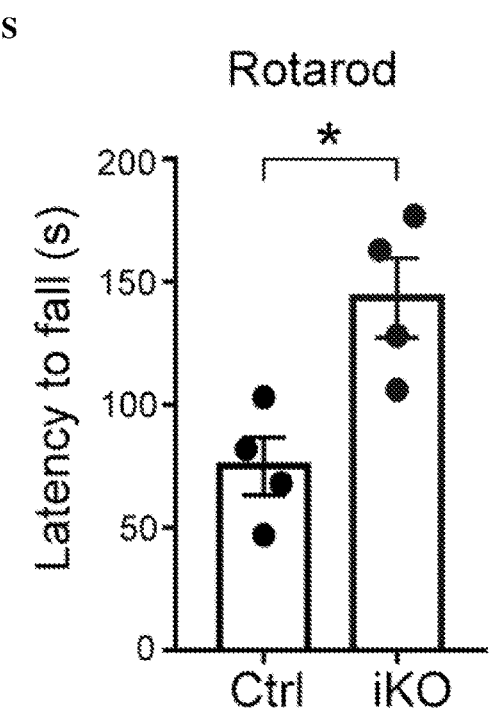

FIG. 4: Ablation of Hdac3 promotes remyelination after nerve injury. (A) Immunofluorescence labeling for HDAC3 (green) and SOX10 (red) in sciatic nerves from wild-type animals on day 14 post injury shows re-expression of HDAC3 in SCs in the lesion area following nerve cut. SCs in the intact proximal stump nerves show minimal HDAC3 immunoreactivity. n=5 animals/group, with 5 images for each mouse. Scale bars: 50 (B) Upper: Diagram showing the nerve transection scheme in control (Hdac3$^{fl/+}$; Plp1-Cre-ERT) and Hdac3-iKO (Hdac3$^{fl/fl}$; Plp1-CreERT) mice. Tamoxifen was injected i.p. into 8 week-old mice for 5 days followed by a 7-day rest prior to nerve cut injury; mice were then treated with tamoxifen for 7 days after injury. Bottom: Immunofluorescence labeling for SOX10 (red) and HDAC3 (green) in control and Hdac3-iKO sciatic nerves in the regenerating site at 14 Dpi. n=5 animals/group, with 5 images for each mouse. Arrows indicate the absence of HDAC3 in SOX10$^+$ SCs. Scale bars: 20 μm. (C) Immunofluorescence labeling for EGR2 (green) and SOX10 (red) in control and Hdac3-iKO sciatic nerves in the regenerating region at Dpi 14. n=5 animals/group, with 5 images for each mouse. Scale bars: 50 (D) Quantification of EGR2$^+$ SCs in the regenerating area in control and Hdac3-iKO sciatic nerves at Dpi 14. (Data are presented as mean±s.e.m.; n=5 animals/group; two-tailed unpaired Student's t-test; P<0.0019, t=4.554, d.f.=8). (E) Immunofluorescence labeling for Ki67 (green) and SOX10 (red) in control and Hdac3-iKO sciatic nerves in the regenerating region at Dpi 14. n=6 animals/group, with 5 images for each mouse. Scale bars: 50 (F) Quantification of Ki67$^+$ SCs in the regenerating area in control and Hdac3-iKO sciatic nerves at Dpi 14. (Data are presented as mean±s.e.m.; n=6 animals/group; two-tailed unpaired Student's t-test; P<0.0004, t=5.222, d.f.=10). (G,H) Immunolabeling for SOX2 (red) and counterstaining with DAPI in control and Hdac3-iKO sciatic nerves in the regenerating region at Dpi 14 (G). Scale bars: 50 μm. Panel H shows quantification of the percentage of SOX2$^+$ cells in (G). (Data are presented as mean±s.e.m.; n=4 animals/group, with 5 images for each mouse; two-tailed unpaired Student's t-test; P<0.0007, t=6.43, d.f.=6). (I) Electron micrographs of transverse sections of control and Hdac3-iKO at Dpi 14. n=5 animals/group, with 5 images for each mouse. Scale bars: 2 μm. (J) Box plots of g ratios of sciatic nerves from control and Hdac3-iKO mice 14 Dpi at remyelinated regions. (Data are presented as mean±s.e.m.; n=102 remyelinated axons from 3 control mice and 104 remyelinated axons from 3 iKO mice; Whiskers show the minimum and maximum, boxes extend from the first to the third quartiles with cross lines at the medians; two-tailed unpaired Student's t-test; P=0.0002, t=3.8, d.f.=204). (K) Quantification of the number of myelinated axons per μm$^2$ at remyelinated regions from control and Hdac3-iKO mice at Dpi 14. (Data are presented as mean±s.e.m. n=5 animals/ group; two-tailed unpaired Student's t-test; P<0.3799, t=0.9294, d.f.=8). (L) Electron micrographs of transverse sections of control and Hdac3-iKO at Dpi 28. n=5 animals/group, with 5 images for each mouse. Scale bars: 2 μm. (M) Box plots of g ratios of remyelinating sciatic nerves from control and Hdac3-icKO mice at 28 Dpi. (Data are presented as mean±s.e.m.; n=150 remyelinated axons from 3 mice for each group; group; Whiskers show the minimum and maximum, boxes extend from the first to the third quartiles with cross lines at the medians; one-way ANOVA with Tukey's multiple comparisons test; $F_{(3, 596)}$=108.1, Remyelinating nerves, $P_{Ctrl\ versus\ iKO}$<0.0001; Intact nerves, $P_{Ctrl\ versus\ iKO}$=0.0675). (N) Representative recordings of CMAPs of regenerated sciatic nerves at Dpi 20 from control and Hdac3-iKO mice (S, stimulus; R, initiation of CMAP response). n=6 animals/group. (O,P) Quantification of the conduction velocity (O) and mean peak of CMAP amplitude (P) of injured sciatic nerves from control and Hdac3-icKO mice. (Data are presented as mean±s.e.m.; n=6 animals/ group; two-tailed unpaired Student's t-test; 0, P<0.0001, t=8.856, d.f.=10; P, P=0.0002, t=5.754, d.f.=10). (Q,R) Quantification of pinprick stimulation assays (Q) for sensory functions and toe spreading reflex (R) for motor functions in control and Hdac3-iKO mice at Dpi 22. (Data are presented as mean±s.e.m.; n=4 animals/group; two-tailed unpaired Student's t-test; q, P=0.0012, t=5.745, d.f.=6; r, P=0.0025, t=5, d.f.=6). (S) Latency (seconds) to fall off the accelerating rotarod of control and Hdac3-iKO mice at Dpi 22. (Data are presented as mean±s.e.m.; n=4 animals/group; two-tailed unpaired Student's t-test; P=0.016, t=3.42, d.f.=6). n.s., not significant, *P<0.05, P<0.01, *P<0.001.

Figure 5:
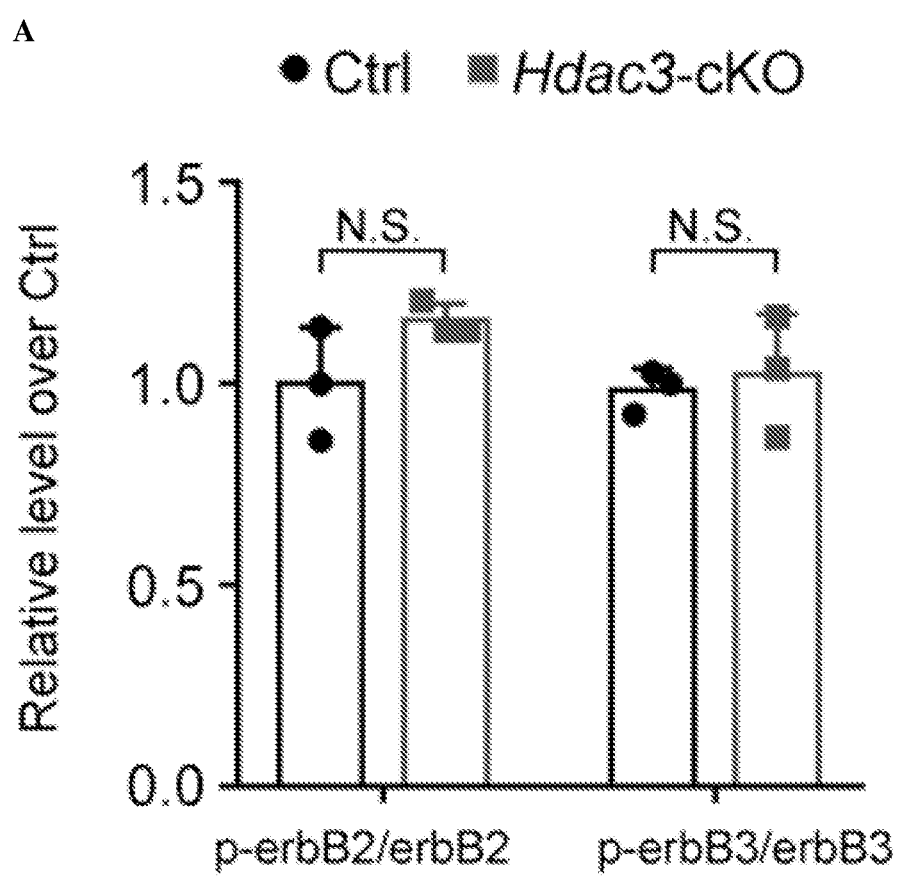
Figure 5:
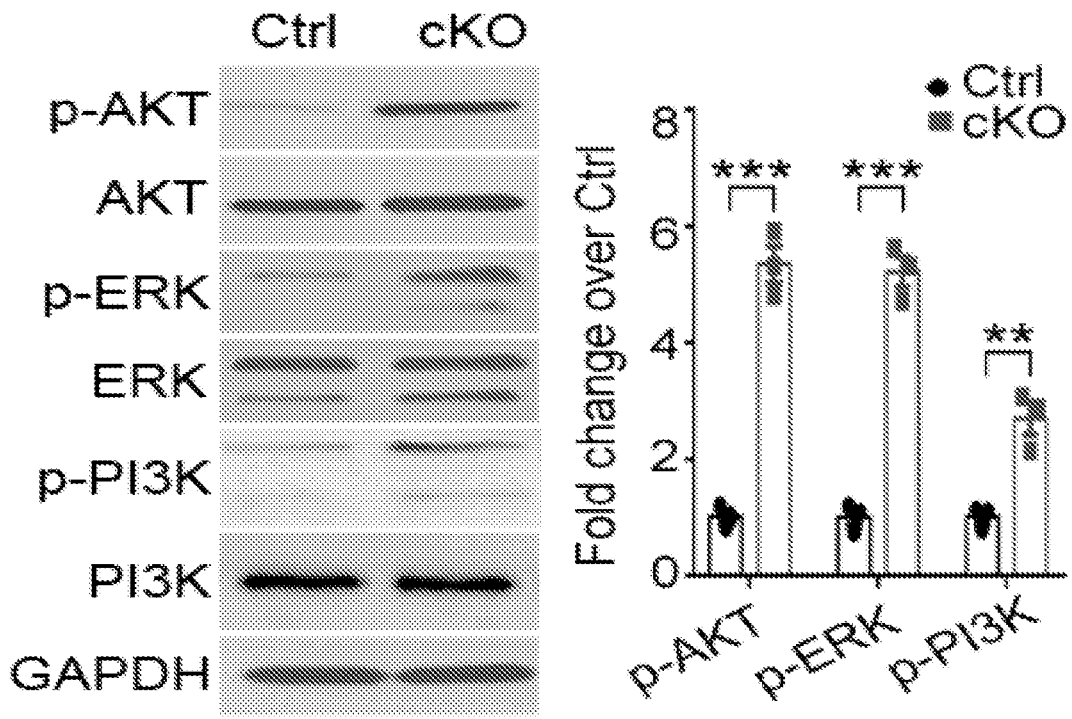
Figure 5:
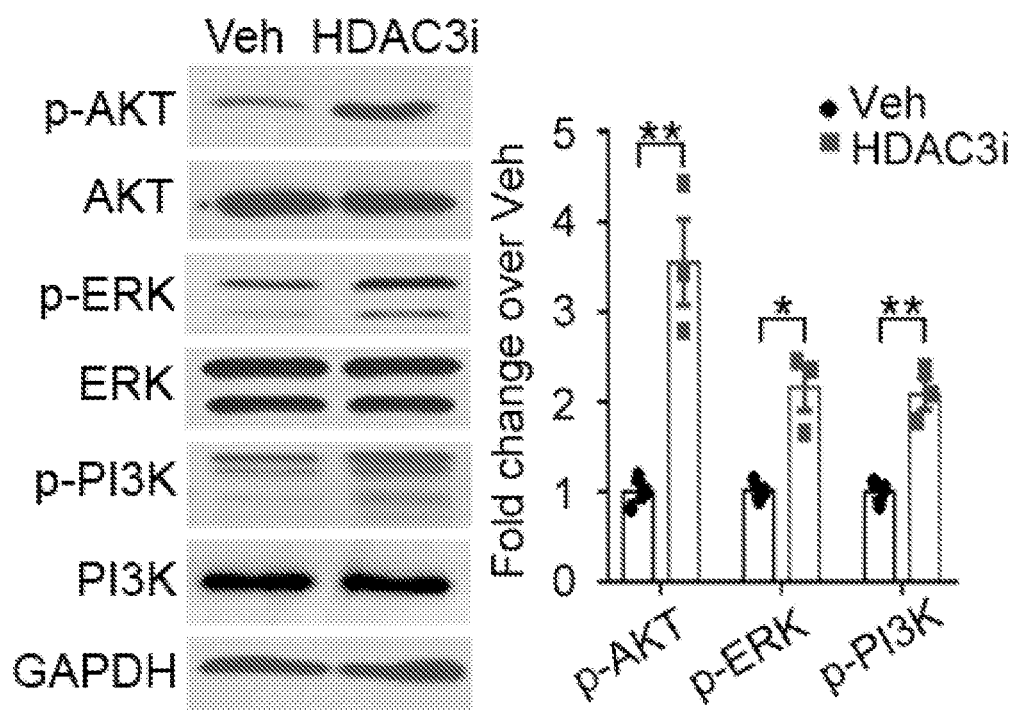
Figure 5:
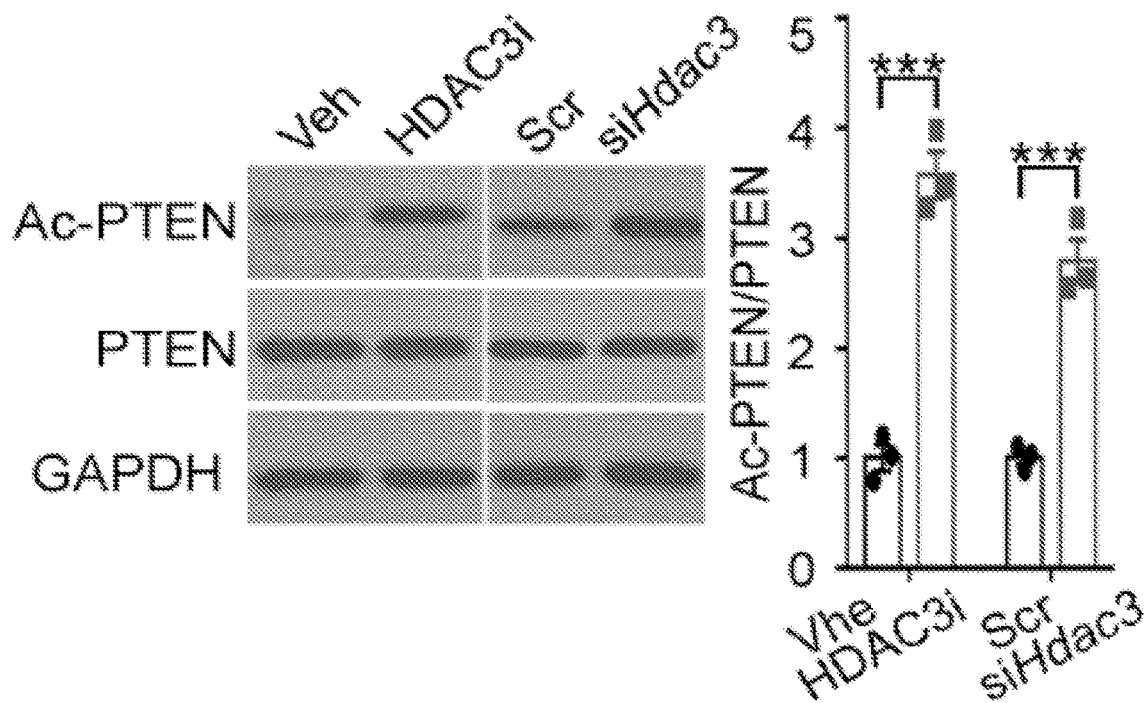
Figure 5:
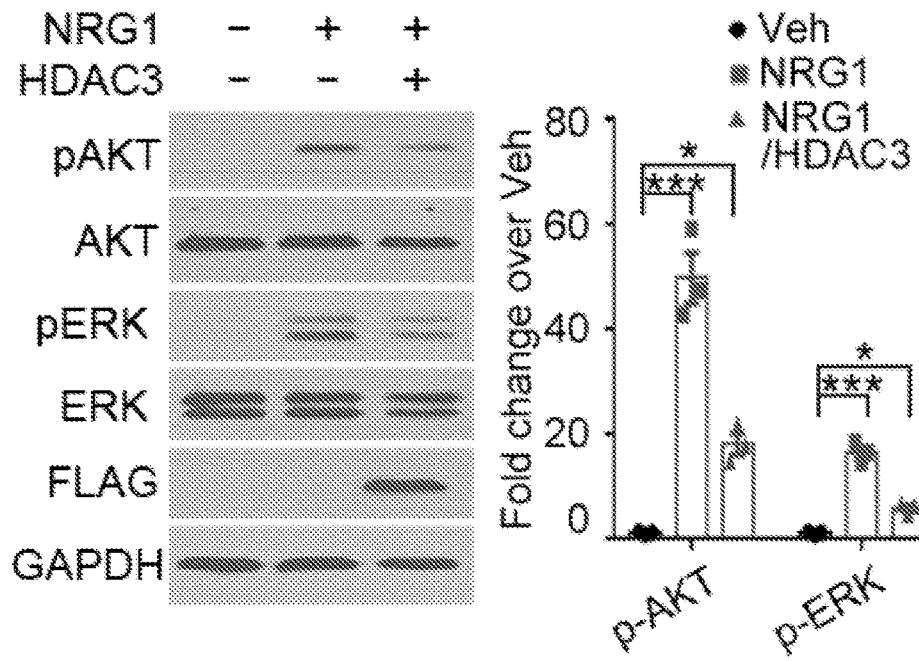
Figure 5:
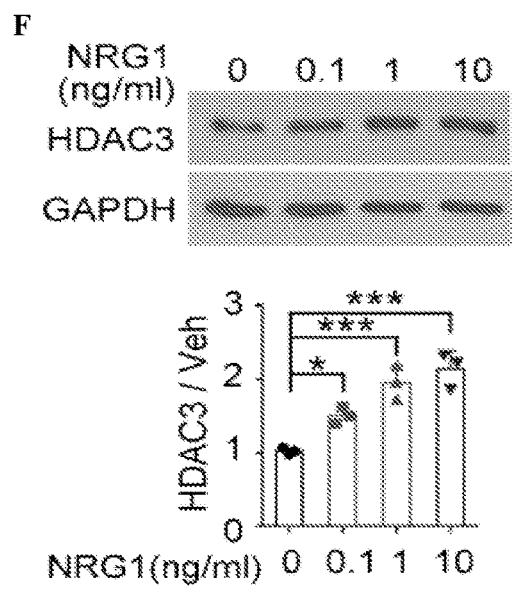
Figure 5:
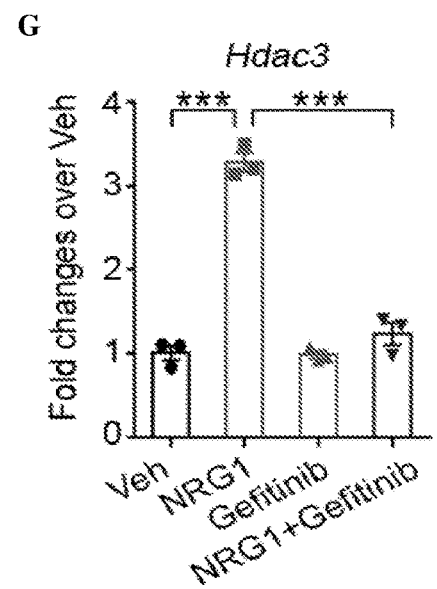
Figure 5:
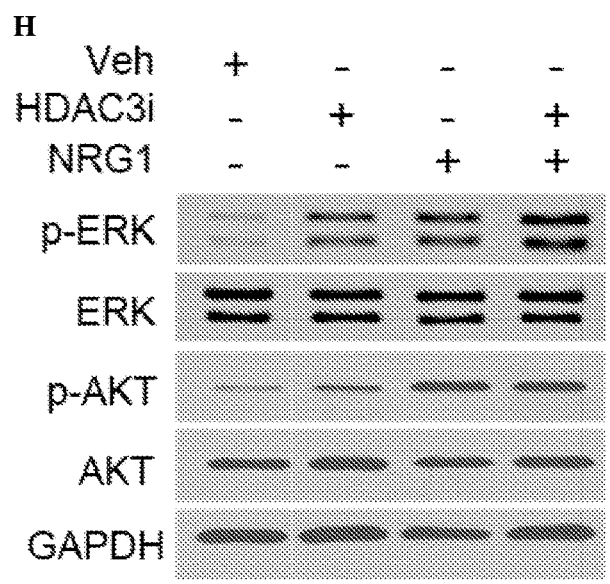
Figure 5:
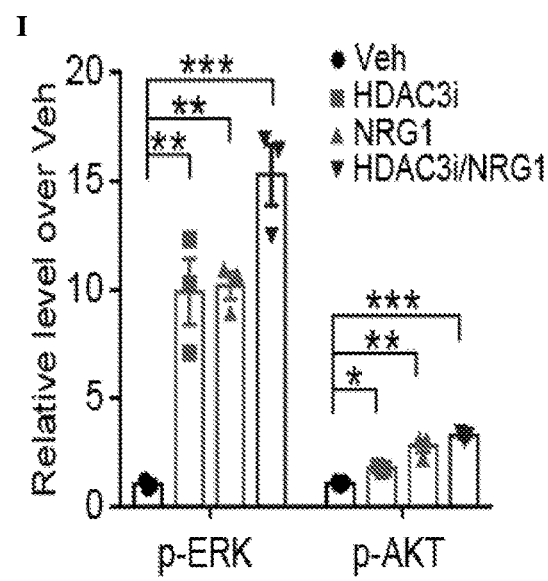
Figure 5:
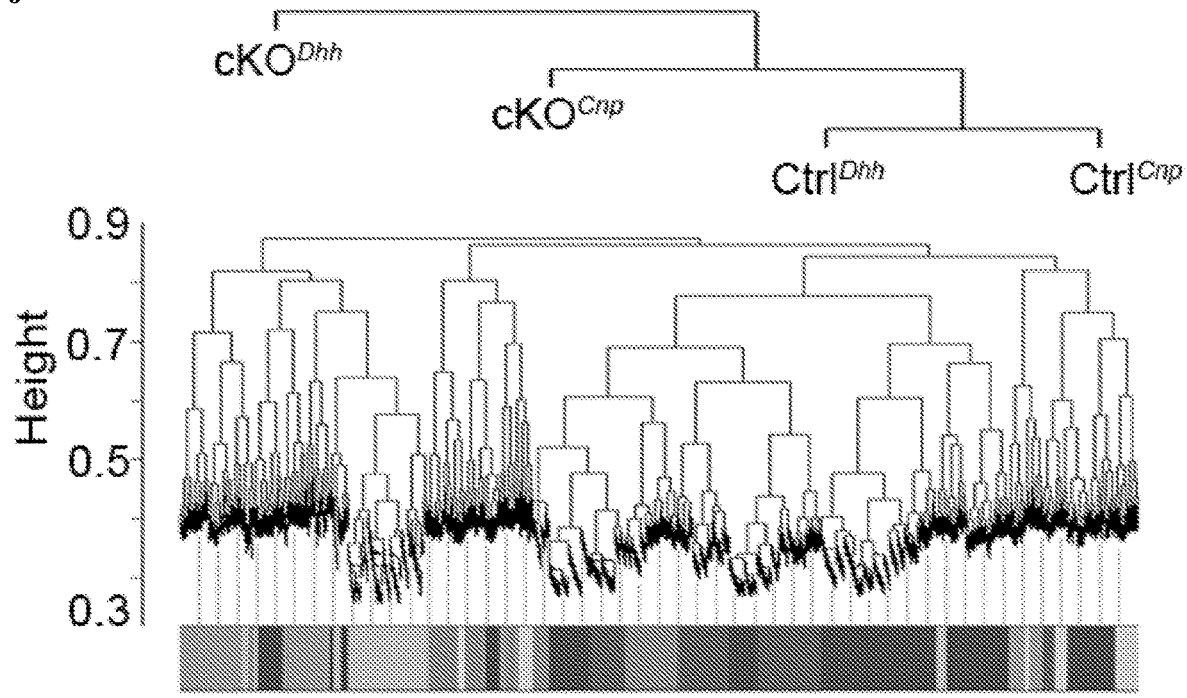
Figure 5:
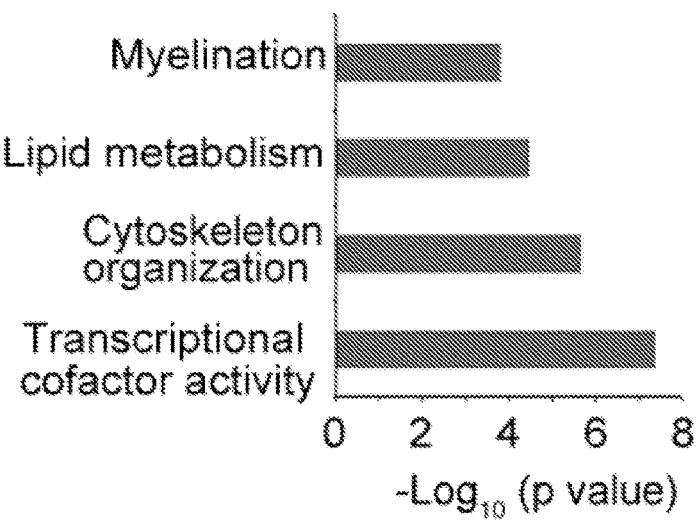
Figure 5:
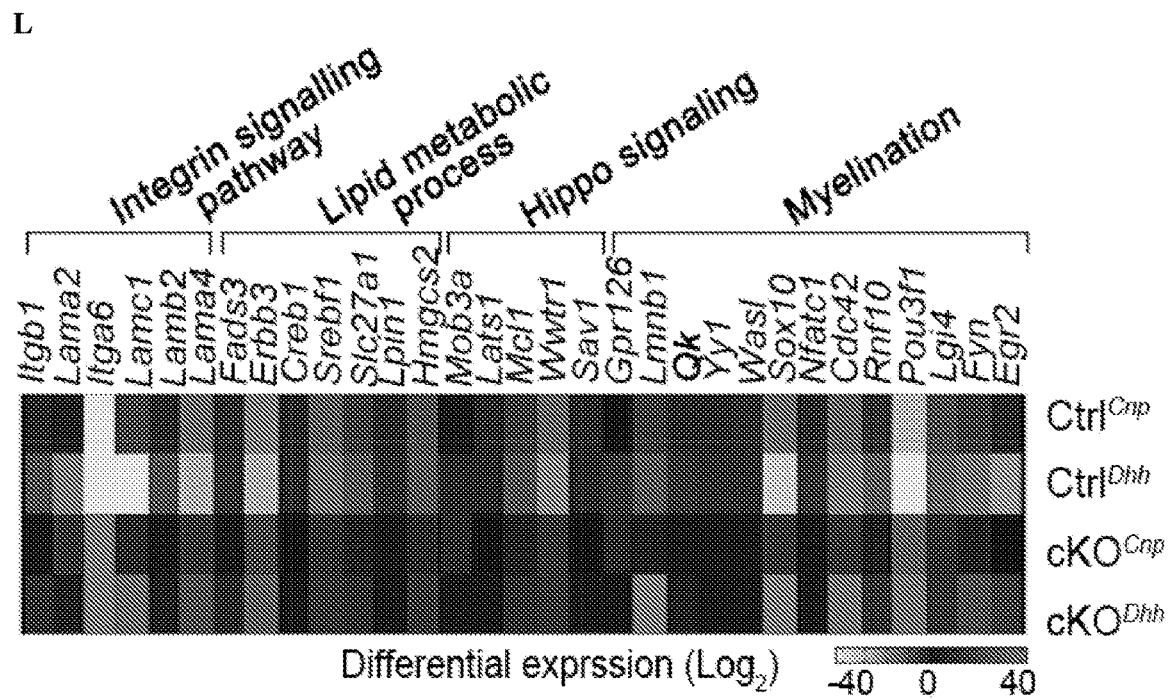
Figure 5:
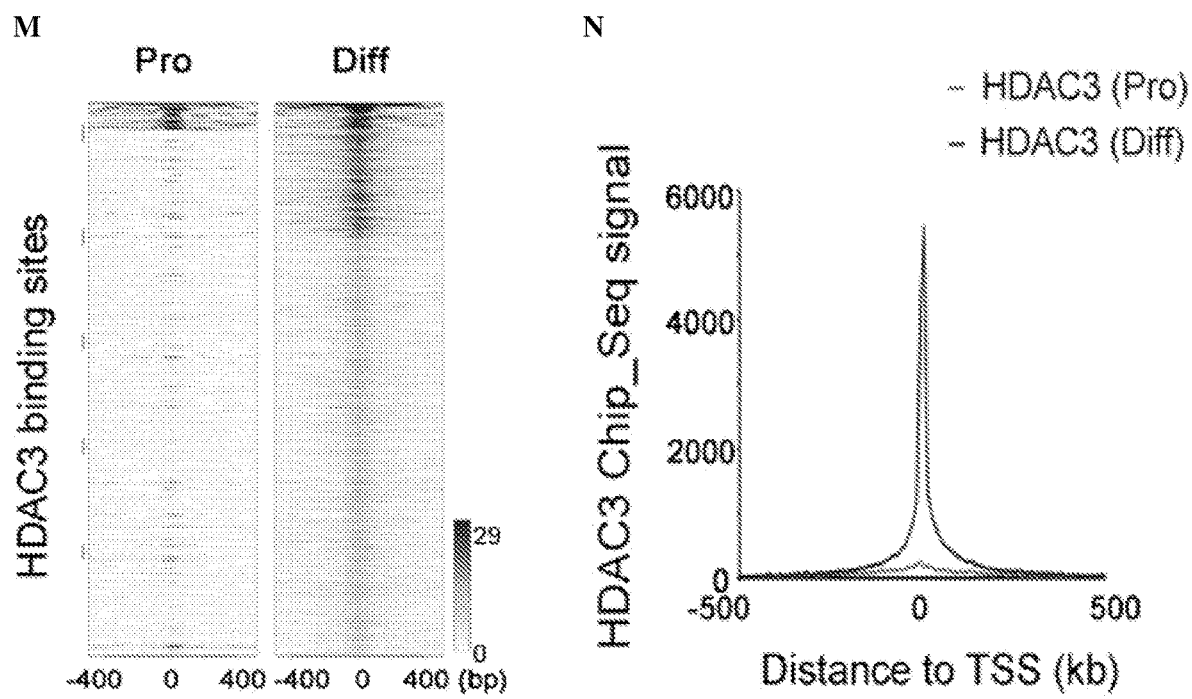
Figure 5:
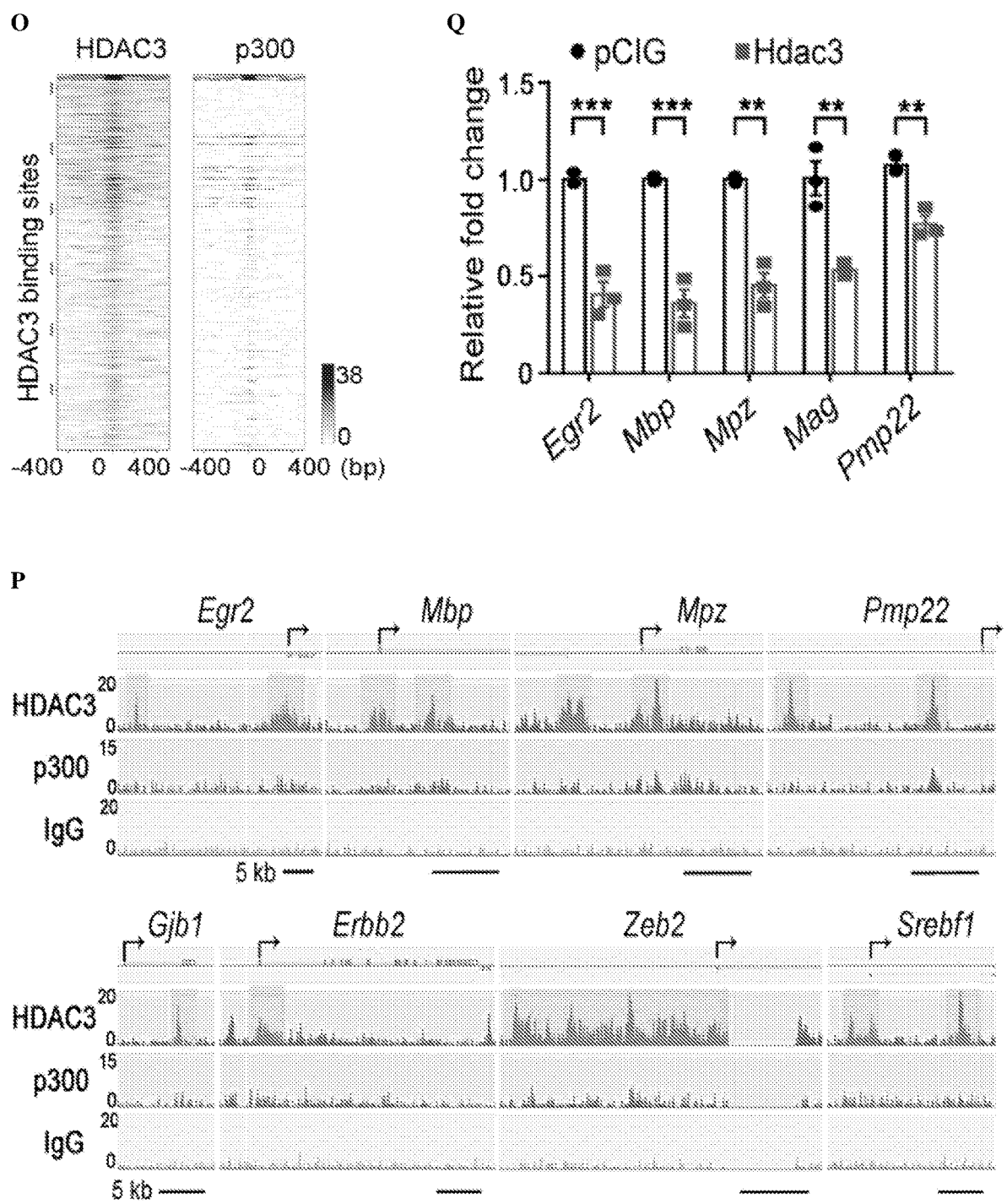
Figure 5:
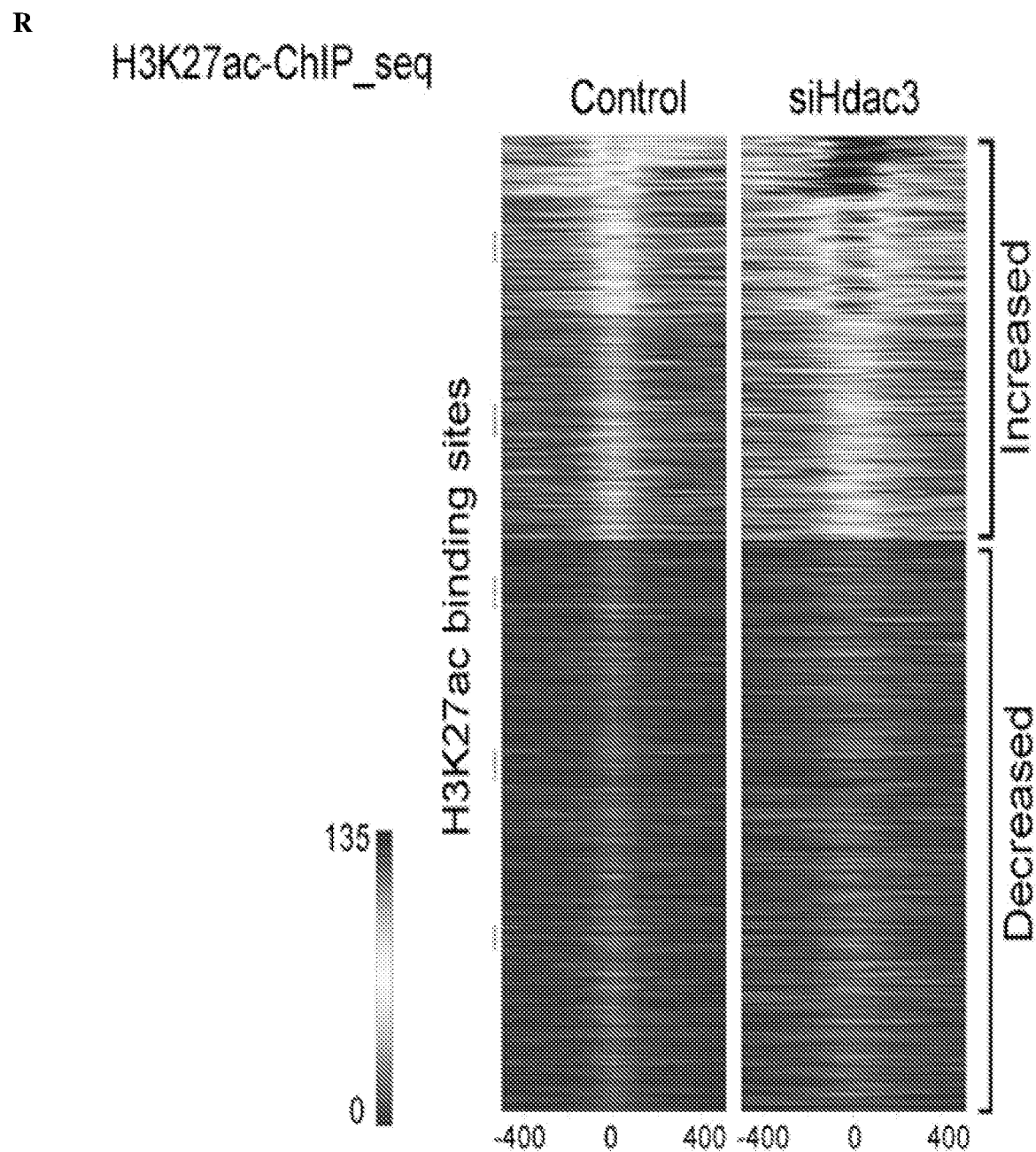
Figure 5:
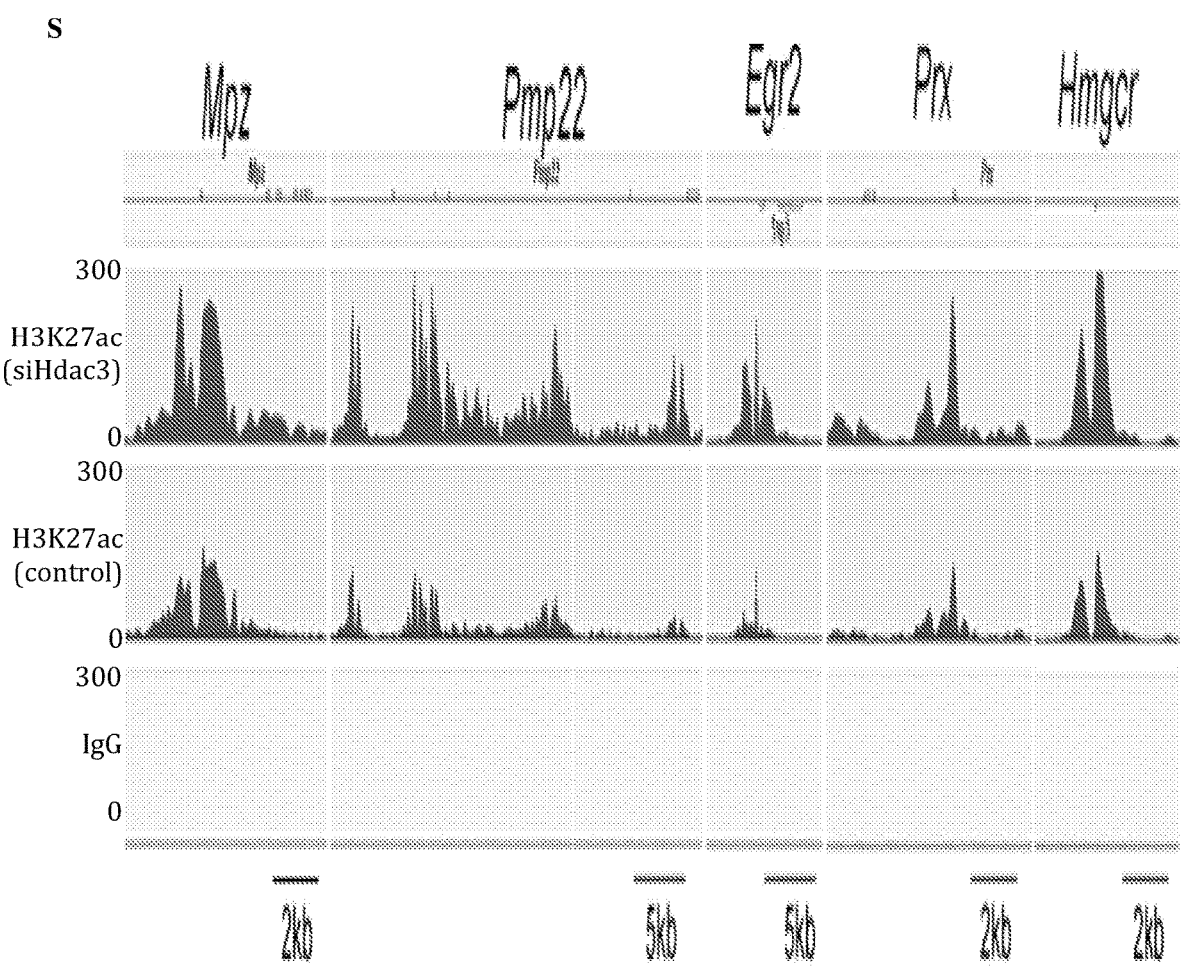
Figure 5:
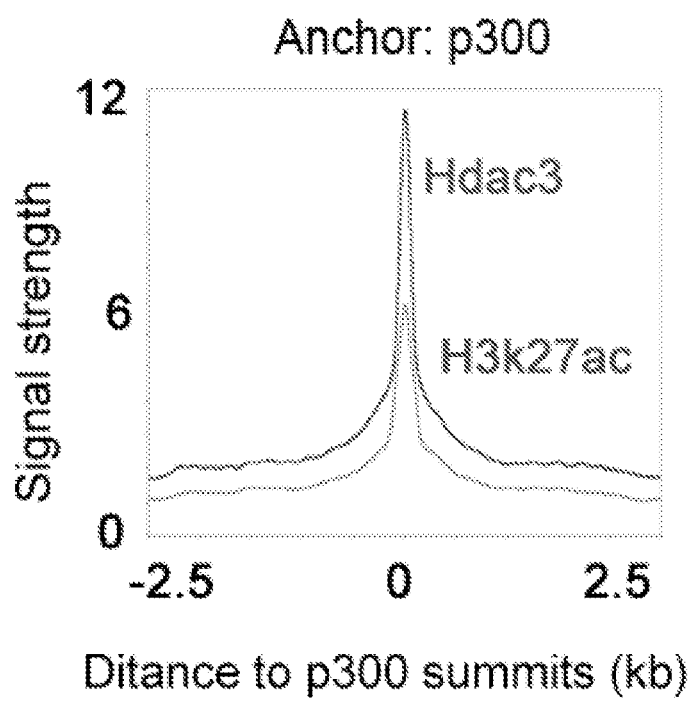
Figure 5:
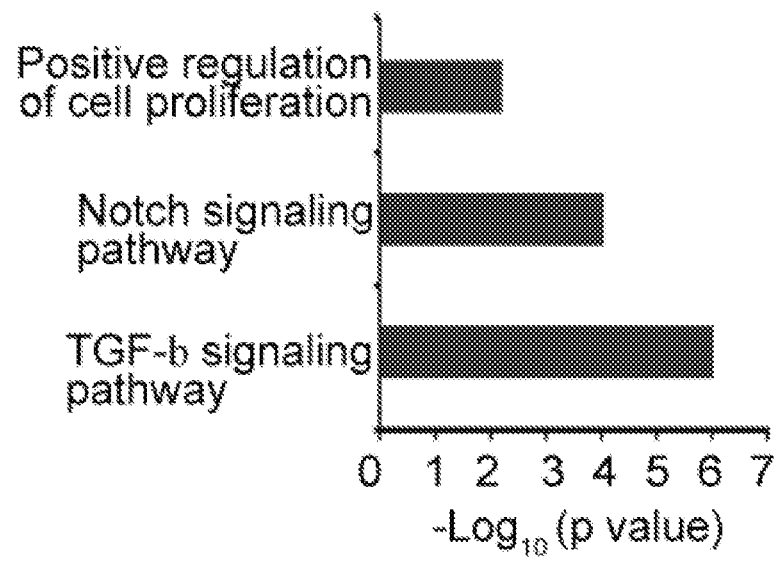
Figure 5:
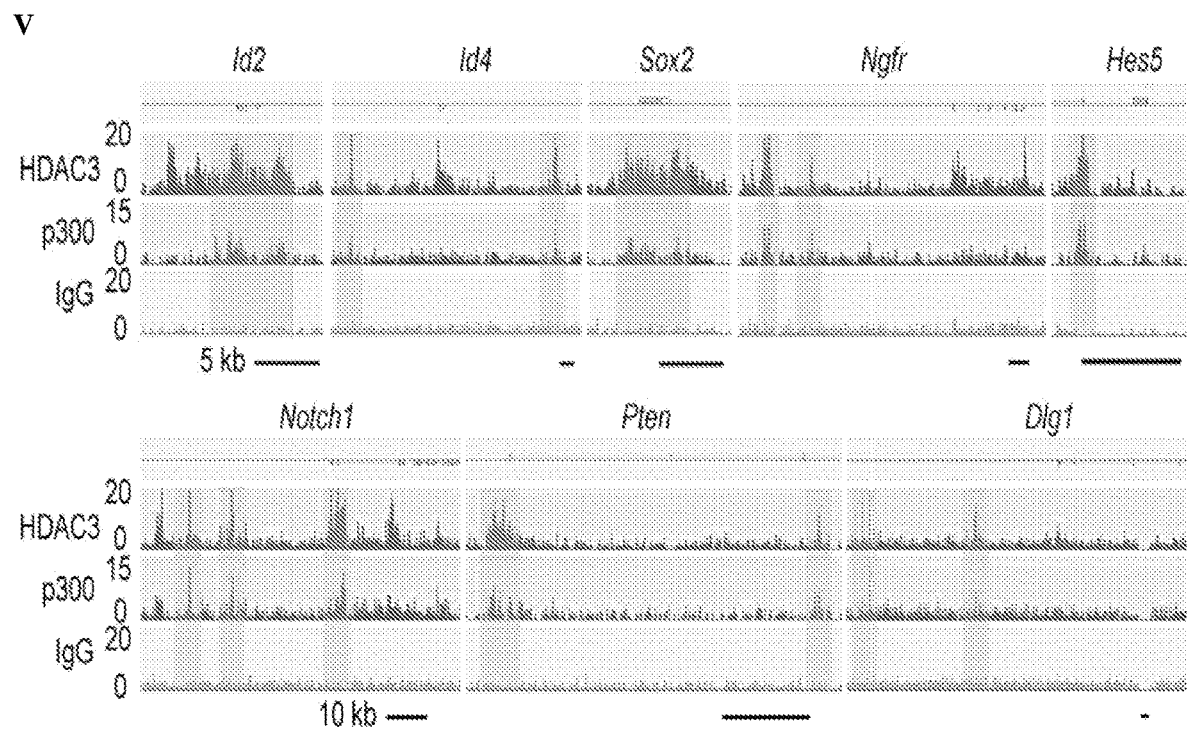
Figure 5:
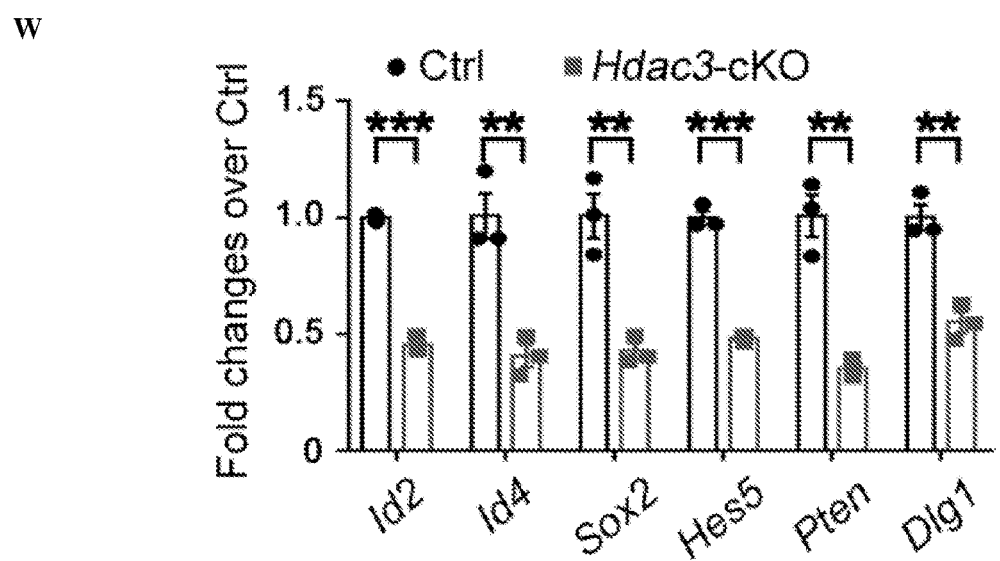
Figure 5:
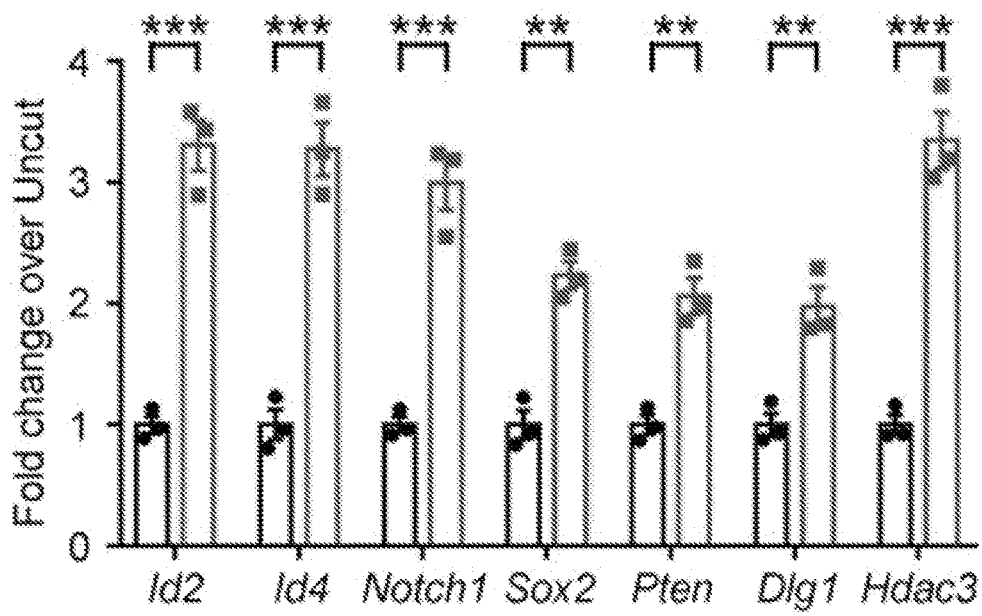
Figure 5:
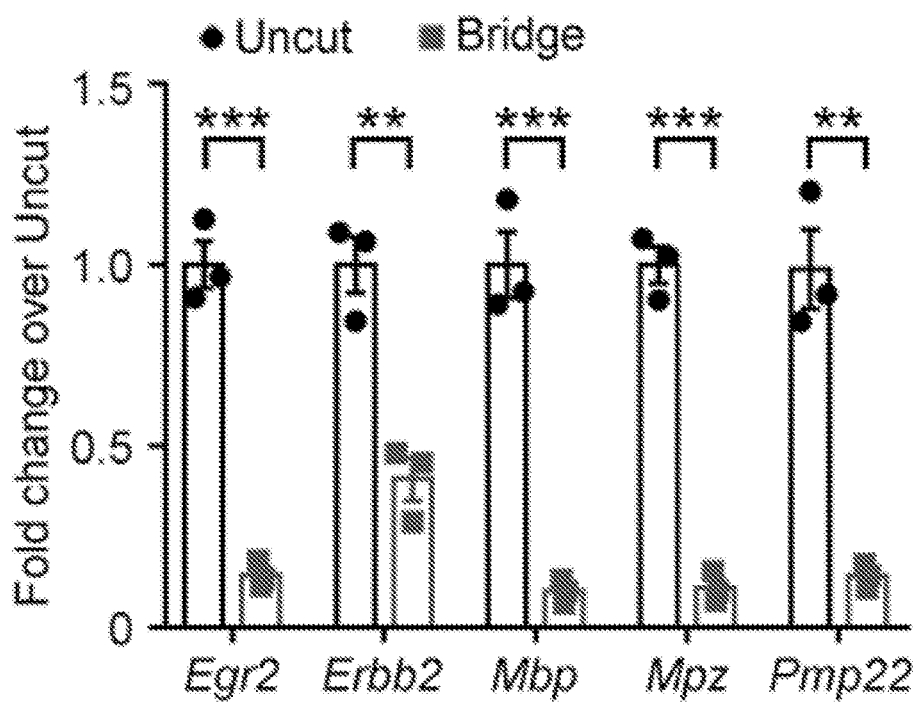

FIG. 5: Activation of PI3K/AKT pathway promotes myelination in Hdac3-mutant sciatic nerves. (A) NRG1 receptor erbB2/3 activity is comparable between control and Hdac3-cKO sciatic nerves. Quantification of the ratio between p-erbB2/3 and erbB2/3 analyzed by western blot analysis of control and Hdac3-cKO sciatic nerves at P13 (Data are presented as mean±s.e.m.; n=3 animals/group; two-tailed unpaired Student's t-test). (B,C) Representative western blots (left) and quantifications (right) of p-AKT, p-ERK, p-PI3K in sciatic nerves of control and Hdac3-cKO mice at P13 (B) and rat SC cultures treated with PDA106 (C). The band densities of phospho-forms were normalized with total AKT, ERK, PI3K, respectively. GAPDH: loading control. (Data are presented as mean±s.e.m.; n=3 independent western blot experiments; two-tailed unpaired Student's t-test; a, P-AKT, P=0.0002, t=12.91, d.f.=4; P-ERK, P=0.0001, t=14.17, d.f.=4; P-PI3K, P=0.005, t=5.583, d.f.=4; b, P-AKT, P=0.006, t=5.222, d.f.=4; P-ERK, P=0.0118, t=4.392, d.f.=4; P-PI3K, P=0.005, t=5.708, d.f.=4). (D) Representative western blots (left) and quantifications (right) of Ac-PTEN and PTEN in SC cultures treated with PDA106 or transfected with siHdac3. GAPDH: loading control. (Data are presented as mean±s.e.m.; n=3 independent western blot experiments; two-tailed unpaired Student's t-test; $P_{HDAC3i\ versus\ Veh}$=0.0004, $t_{HDAC3i\ versus\ Veh}$=10.63, d.f.=4; $P_{siHDAC3\ versus\ Scr}$=0.00097, $t_{siHDAC3\ versus\ Scr}$=8.673, d.f.=4). (E) Representative western blots (left) and quantifications (right) of p-AKT, AKT, p-ERK and ERK in rat SC cultures treated with NRG1 with or without Hdac3 overexpression. p-AKT and p-ERK were normalized to AKT and ERK, respectively. (Data are presented as mean±s.e.m.; n=3 independent western blot experiments; one-way ANOVA with Tukey's multiple comparisons test; P-AKT, $F_{(2, 6)}$=66.62, $P_{Veh\ versus\ NRG1}$<0.0001, $P_{Veh\ versus\ NRG1+HDAC3}$=0.017; P-ERK, ANOVA $F_{(2, 6)}$=109.2, $P_{Veh\ versus\ NRG1}$<0.0001, $P_{Veh\ versus\ NRG1+HDAC3}$=0.0106). (F) Representative western blot (upper panel) of HDAC3 in SC cultures treated with indicated concentrations of NRG1 for 1 hr. GAPDH as a loading control. Lower panel shows relative expression over mock treatment. (Data are presented as mean±s.e.m. n=3 independent western blot experiments; one-way ANOVA with Tukey's multiple comparisons test; $F_{(3, 8)}$=23.72; $P_{0\ versus\ 0.1}$=0.0415, $P_{0\ versus\ 1}$=0.0009, $P_{0\ versus\ 10}$=0.0003). (G) q-PCR showing expression of Hdac3 in primary SCs treated with vehicle, NRG1, gefitinib or combined NRG1 and gefitinib. (Data are presented as mean±s.e.m.; n=3 independent experiments; one-way ANOVA with Tukey's multiple comparisons test; $F_{(3, 8)}$=125.8; $P_{NRG1\ versus\ Veh}$<0.0001, $P_{NRG1\ versus\ Gefitinib}$<0.0001, $P_{NRG1\ versus\ NRG1+Gefitinib}$<0.0001). (H,I) Rat SCs treated with vehicle, PDA106, NRG1 or combined PDA106 and NRG1 were subjected to western blot analysis (H). GAPDH as a loading control. Panel I shows relative expression level over Veh treatment. p-AKT and p-ERK were normalized to AKT and ERK, respectively. (Data are presented as mean±s.e.m.; n=3 independent western blot experiments; one-way ANOVA with Tukey's multiple comparisons test; P-ERK, $F_{(3, 8)}$=29.83; $P_{Veh\ versus\ HDAC3i}$=0.0018, $P_{Veh\ versus\ NRG1}$=0.0015, $P_{Veh\ versus\ HDAC3i+NRG1}$<0.0001; P-AKT, $F_{(3, 8)}$=41.62; $P_{Veh\ versus\ HDAC3i}$=0.0494, $P_{Veh\ versus\ NRG1}$=0.0002, $P_{Veh\ versus\ HDAC3i+NRG1}$<0.0001). (J) Gene dendrogram based on RNA-seq datasets of Hdac3-cKO$^{Cnp}$ and Hdac3-cKO$^{Dhh}$ and corresponding control (Hdac3$^{fl/fl}$) sciatic nerves at P6. Bottom: co-expression modules were color-coded among Hdac3-mutant sciatic nerves and corresponding controls. (K) Gene ontology showing that the genes associated with myelination, lipid metabolism, cytoskeleton organization, and transcription cofactor activity were upregulated in Hdac3-cKO as compared to control sciatic nerves at P6. (L) Heatmap showing representative upregulated genes in each category of interest from RNA-seq analysis of Ctrl$^{Cnp}$, Ctrl$^{Dhh}$, cKO$^{Cnp}$, and cKO$^{Dhh}$ sciatic nerves at P6. Each RNA sample was pooled from 6 animals per genotype and sequenced once. (M) HDAC3 directly targets and represses expression of myelin-associated genes. Heatmaps of HDAC3-binding signals obtained by ChIP-seq in SCs under proliferation (Pro) and differentiation (Diff) conditions. Each line on y axis represents a genomic region ±0.4 kb flanking HDAC3 summits (N) HDAC3 can directly target and repress expression of myelin-associated genes. The distribution pattern of HDAC3-binding signals in SCs under proliferation (Pro) and differentiation (Diff) conditions mapped to the transcription start site (TSS) of their closest Ensembl annotated genes. (O) Heatmaps of HDAC3 and p300 ChIP-seq signals in rat SCs grown under differentiation conditions. Each line on y axis represents a genomic region ±0.4 kb flanking HDAC3 summits (P) HDAC3 can directly target and repress expression of myelin-associated genes. Representative ChIP-seq signals of myelin-associated genes (upper panel) and pro-myelinating transcriptional regulators (lower panel) that are targeted by HDAC3 but not p300. n=2 independent experiments with similar results. (Q) HDAC3 can directly target and repress expression of myelin-associated genes. q-PCR showing expression of myelination-related genes in SCs that express control GFP-expressing pCIG and Hdac3-expressing vectors. (Data are presented as mean±s.e.m.; n=3 independent experiments; two-tailed unpaired Student's t-test; Egr2, P=0.00097, t=8.679, d.f.=4; Mbp, P=0.0009, t=8.93, d.f.=4; Mpz, P=0.0011, t=8.329, d.f.=4; Mag, P=0.0062, t=5.268, d.f.=4; Pmp22, P=0.004, t=5.925, d.f.=4). (R) Knockdown of HDAC3 can elevate H3K27ac signals in the regulatory elements of myelination-associated genes in SCs. Heatmaps of H3K27ac signals obtained by ChIP-seq in mock control or siHdac3 transfected SCs. Each line on y axis represents a genomic region ±400 bp flanking H3K27ac summits in control SCs. (S) Knockdown of HDAC3 can elevate H3K27ac signals in the regulatory elements of myelination-associated genes in SCs. Genome browser view of the distribution of H3K27ac signals on the myelination-associated Mpz, Pmp22, Egr2, Prx and Hmgcr gene loci. Note that an increase in H3K27ac signals in the enhancer/promoter elements in SCs transfected with Hdac3 siRNA. The ChIP-seq experiments were performed once using a pool of control or siHdac3 transfected SCs (10 petri dishes per group). (T) ChIP-seq enrichment analysis of the binding profiles of HDAC3 and H3K27ac around p300 peak summits in rat SCs under differentiation conditions. (U) Gene ontology reveals that the downregulated genes targeted by both HDAC3 and p300 (HDAC3 peaks within 5 kb of TSS) were enriched in regulation of cell proliferation, Notch and TGF-β signaling pathway components. (V) ChIP signals over representative gene loci of negative regulators of myelination that are targeted by both HDAC3 and p300. n=2 independent experiments. (W) q-PCR showing reduced expression of myelination-inhibitory genes in the sciatic nerves of control and Hdac3-cKO mice at P7. (Data are presented as mean±s.e.m.; n=3 independent experiments; two-tailed unpaired Student's t-test; Id2, P<0.0001, t=23.59, d.f.=4; Id4, P=0.0051, t=5.558, d.f.=4; Sox2, P=0.0044, t=5.791, d.f.=4; Hes5, P<0.0001, t=16.51, d.f.=4; Pten, P=0.0022, t=7.007, d.f.=4; Dlg1, P=0.0029, t=6.485, d.f.=4). (X,Y) Expression of myelination-related genes in the regenerating sites in sciatic nerves. q-PCR analysis of expression of myelination-inhibitory genes (X) and myelination-associated genes (Y) in the regenerating sites of sciatic nerves at Dpi 14. (Data are presented as mean±s.e.m.; n=3 independent experiments (uncut nerves and bridge tissues from 3 animals/experiment); two-tailed unpaired Student's t-test; X, Id2, P=0.0005, t=10.44, d.f.=4; Id4, P=0.0008, t=9.051, d.f.=4; Notch1, P=0.00098, t=8.656, d.f.=4; Sox2, P=0.0017, t=7.528, d.f.=4; Pten, P=0.0032, t=6.309, d.f.=4; Dlg1, P=0.0066, t=5.185, d.f.=4; Hdac3, P=0.0008, t=9.522, d.f.=4; Y, Egr2, P=0.0002, t=15.28, d.f.=4; Erbb2, P=0.0038, t=6.045, d.f.=4; Mbp, P=0.0006, t=9.641, d.f.=4; Mpz, P<0.0001, t=15.95, d.f.=4; Pmp22, P=0.0016, t=7.607, d.f.=4). n.s., not significant, *P<0.05, P<0.01, *P<0.001.

Figure 6:
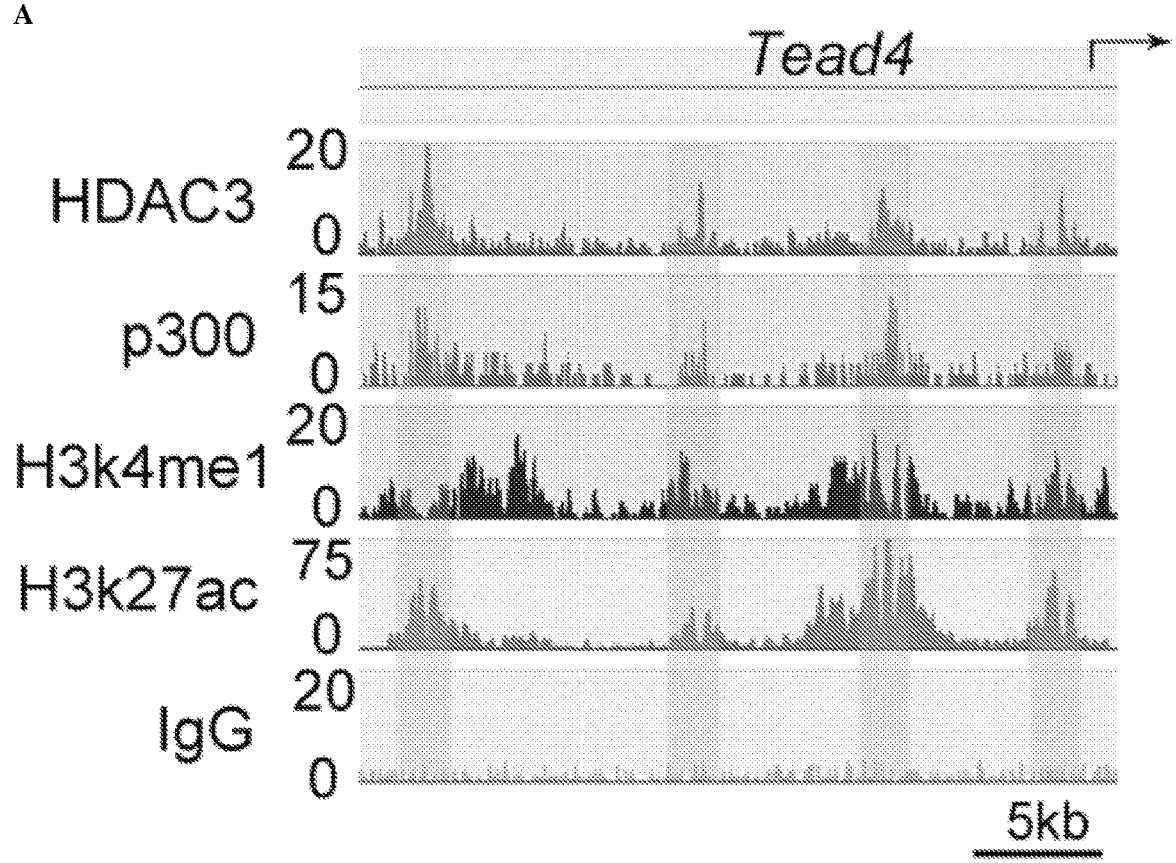
Figure 6:
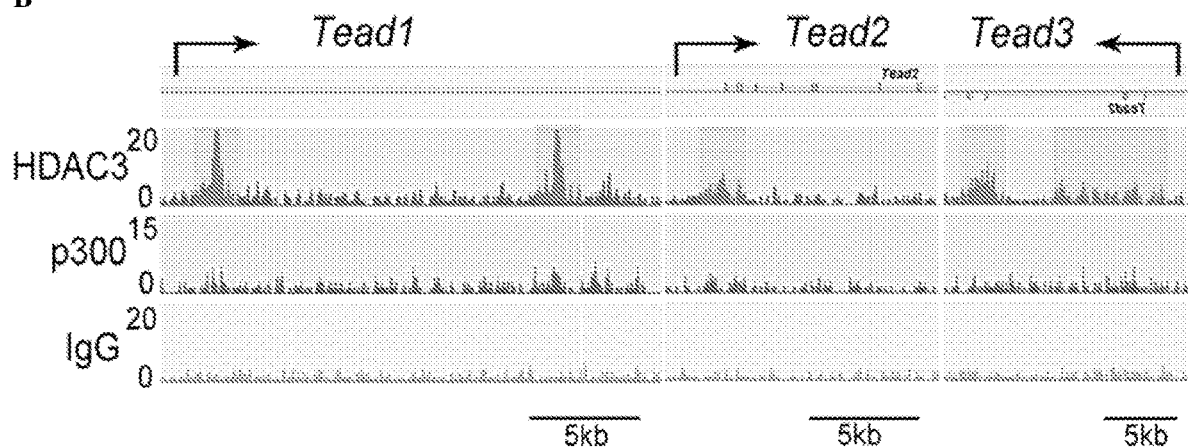
Figure 6:
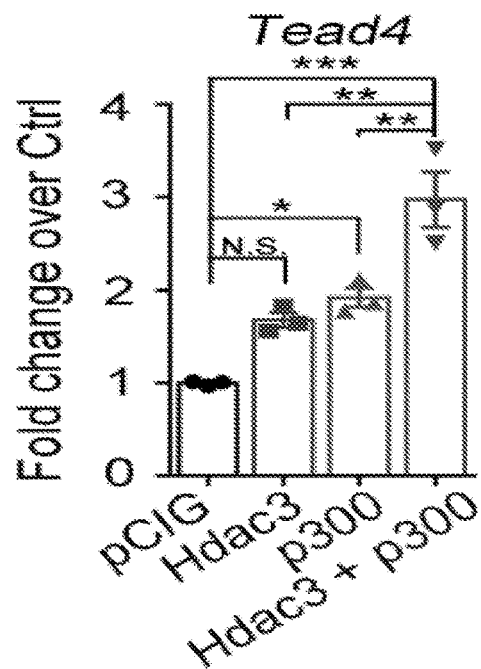
Figure 6:
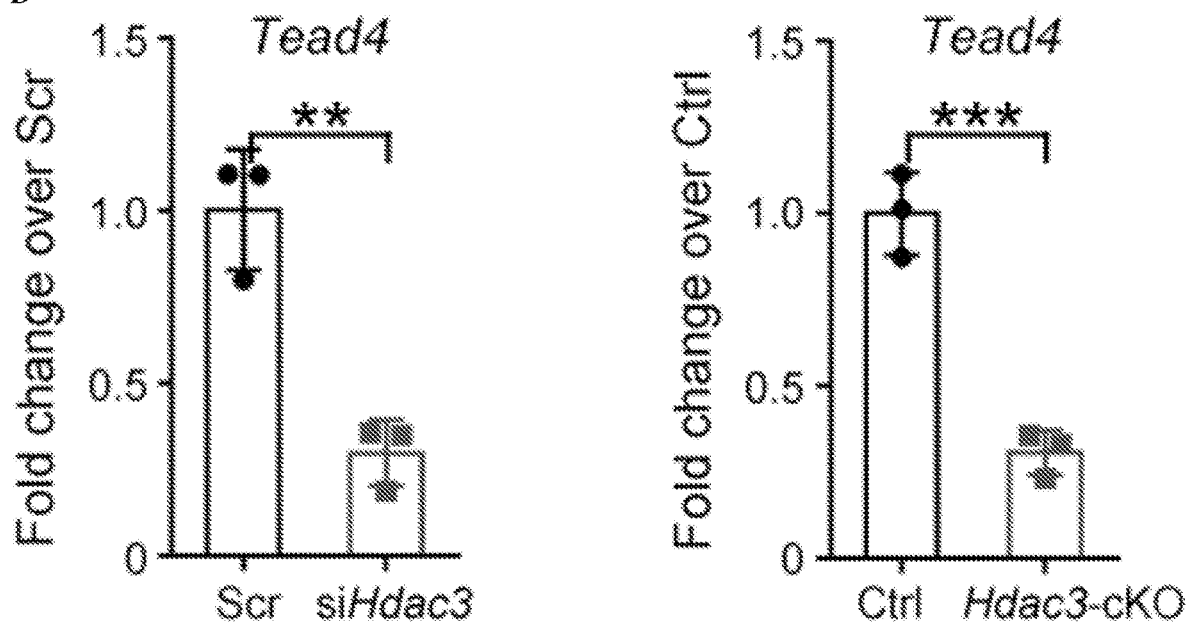
Figure 6:
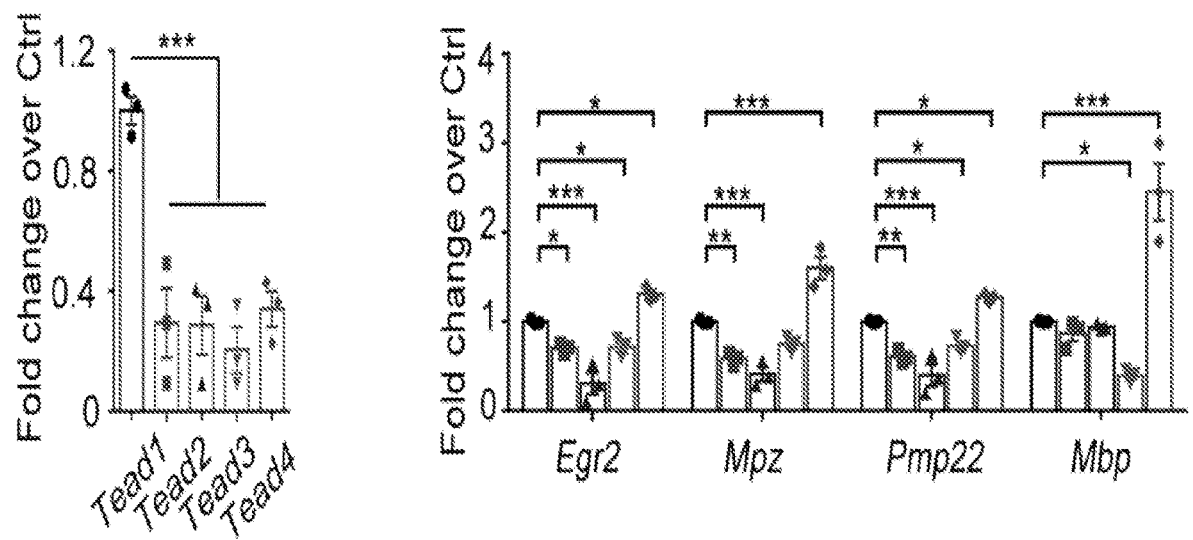
Figure 6:
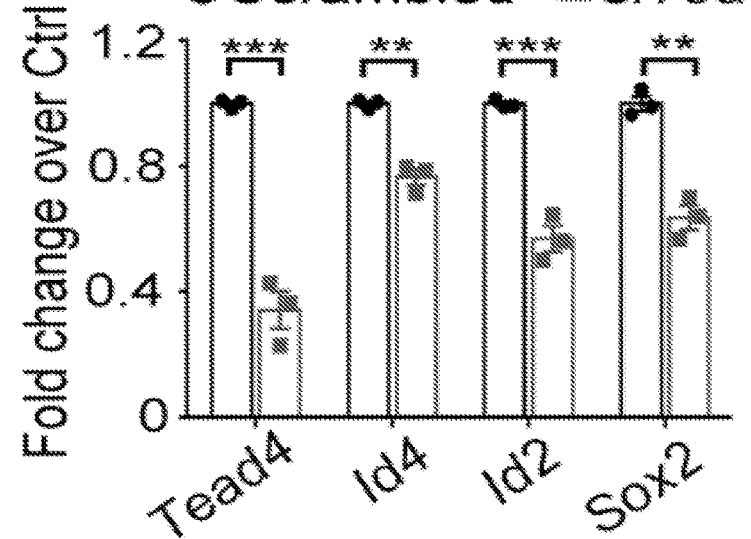
Figure 6:
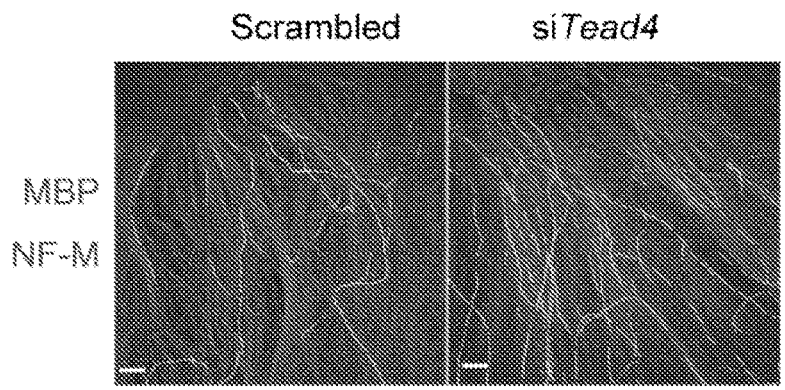
Figure 6:
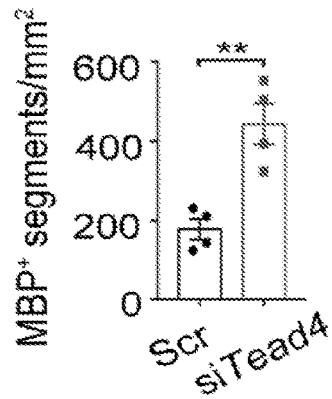
Figure 6:
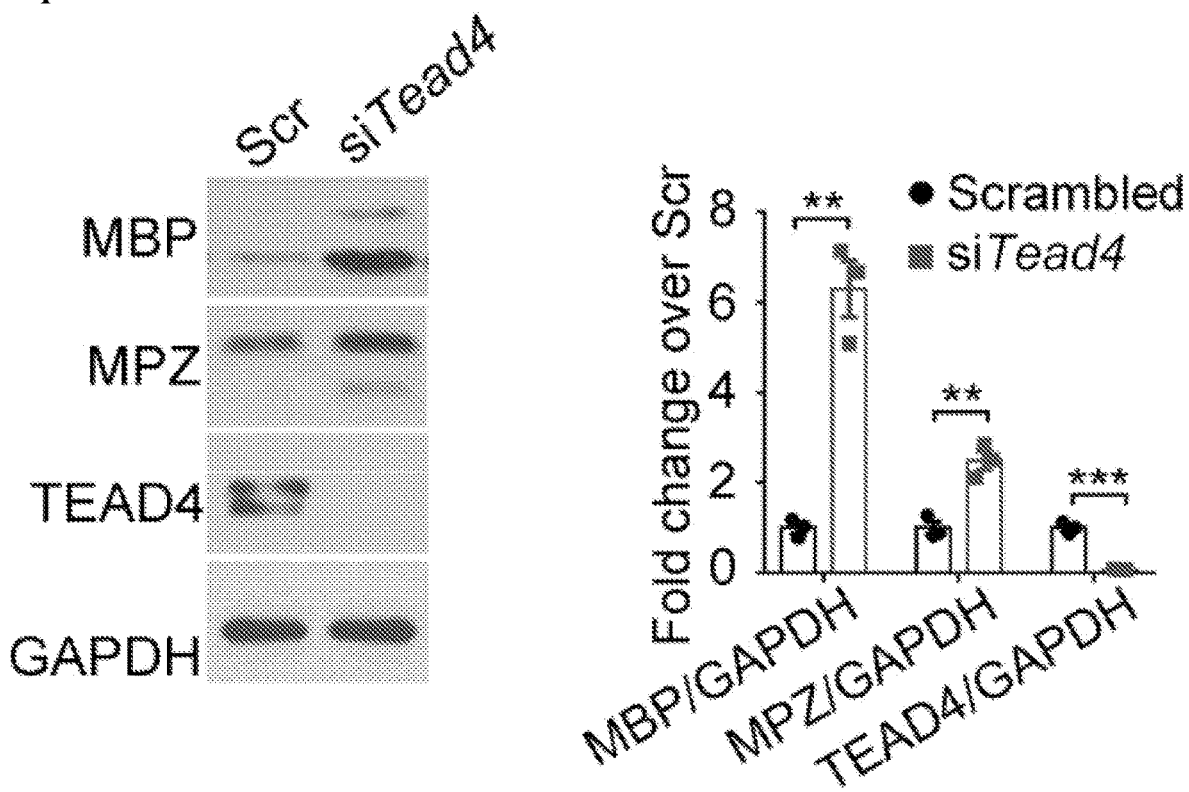
Figure 6:
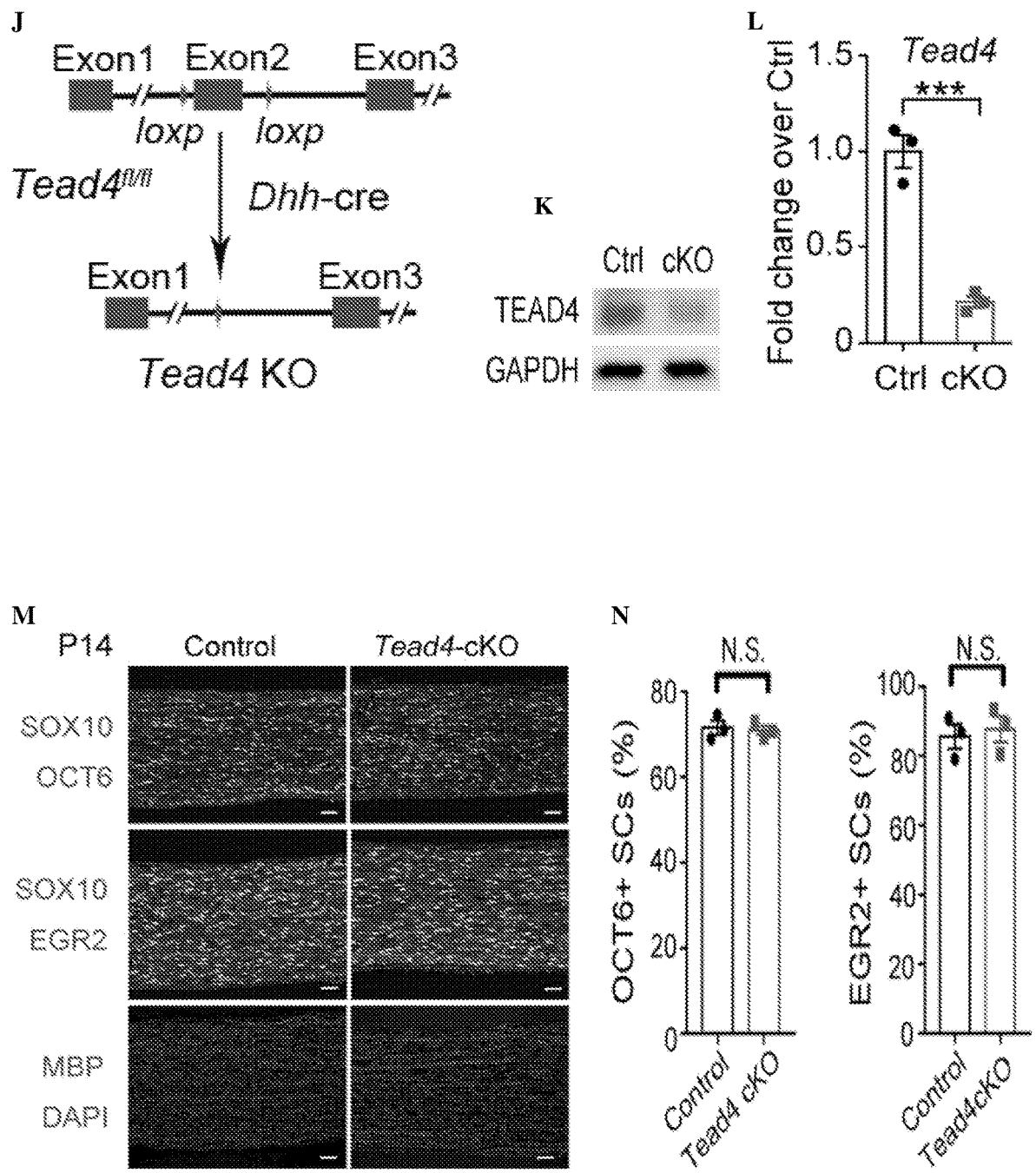
Figure 6:
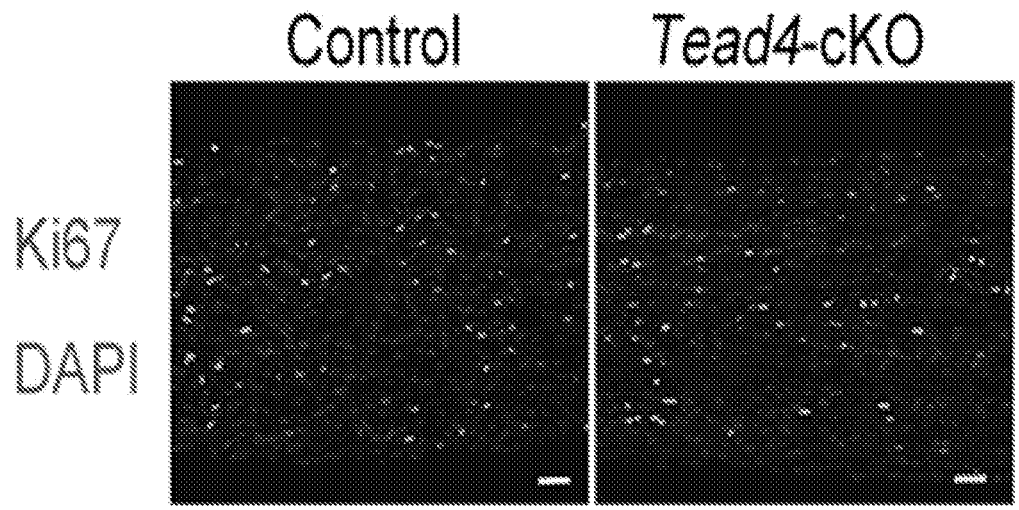
Figure 6:
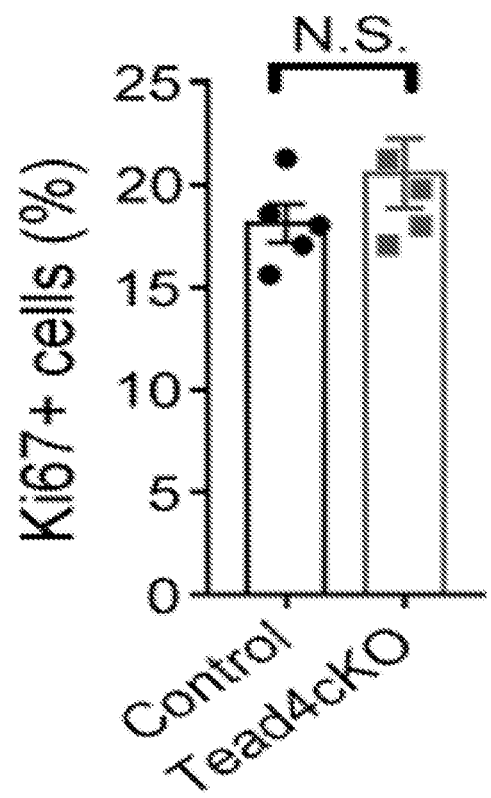
Figure 6:
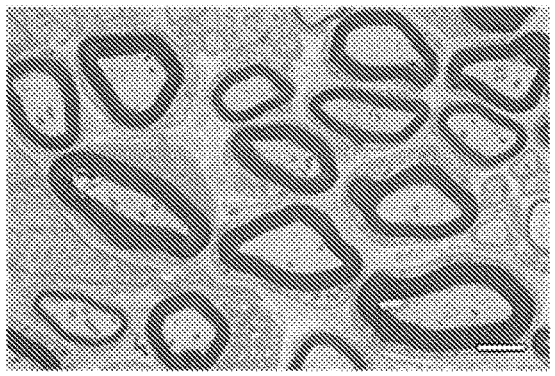
Figure 6:
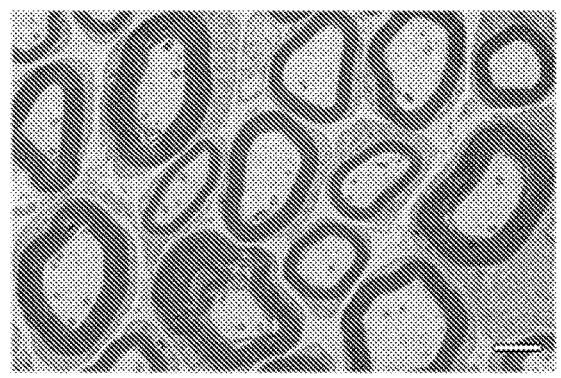
Figure 6:
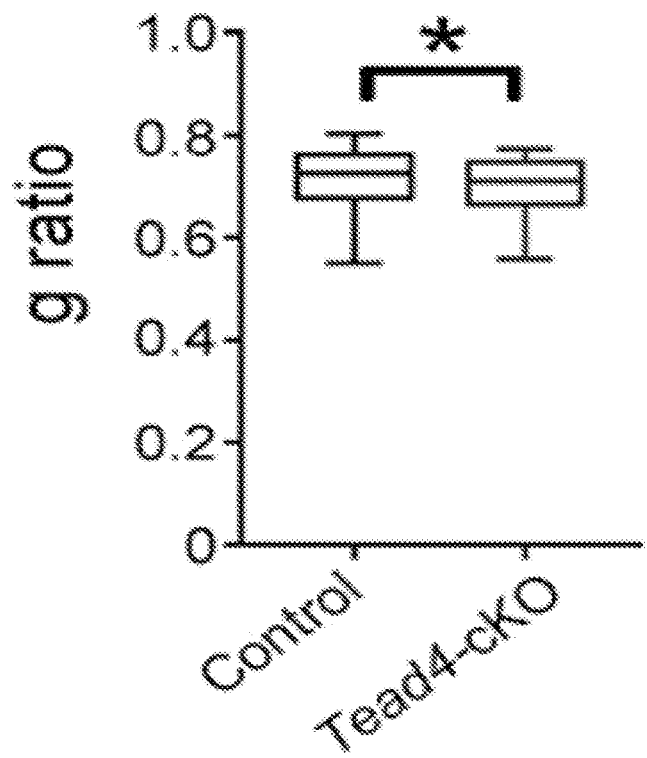
Figure 6:
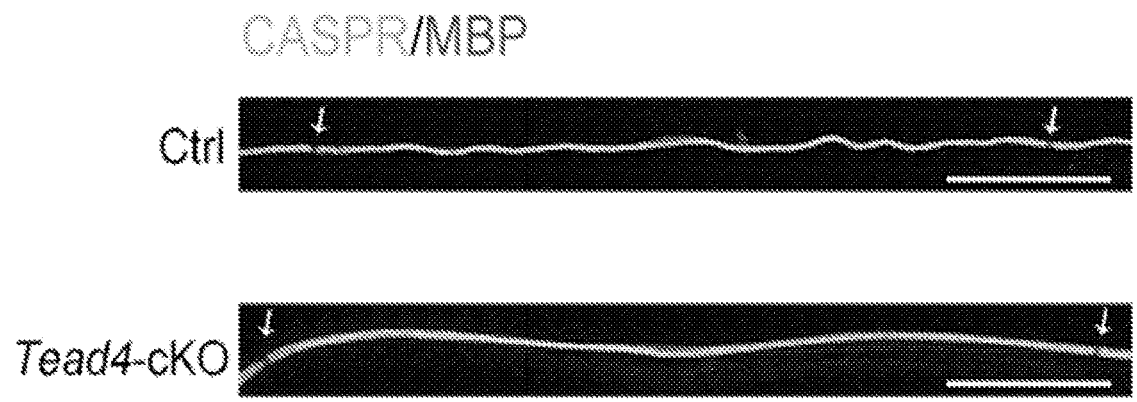
Figure 6:
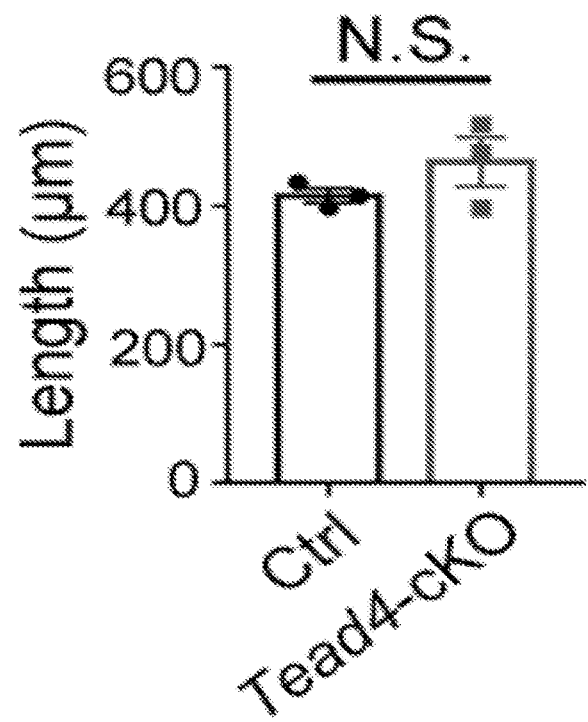
Figure 6:
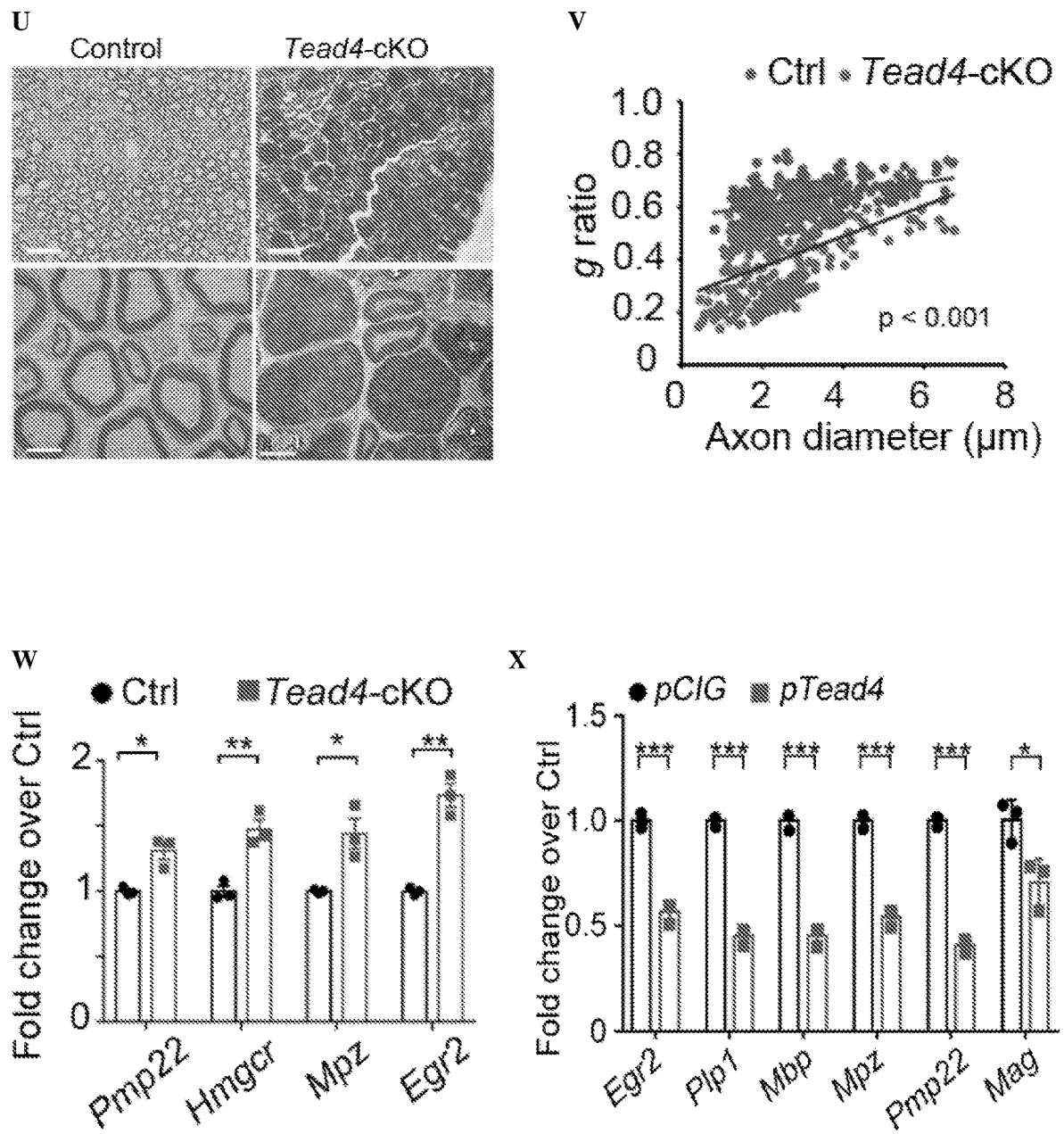
Figure 6:
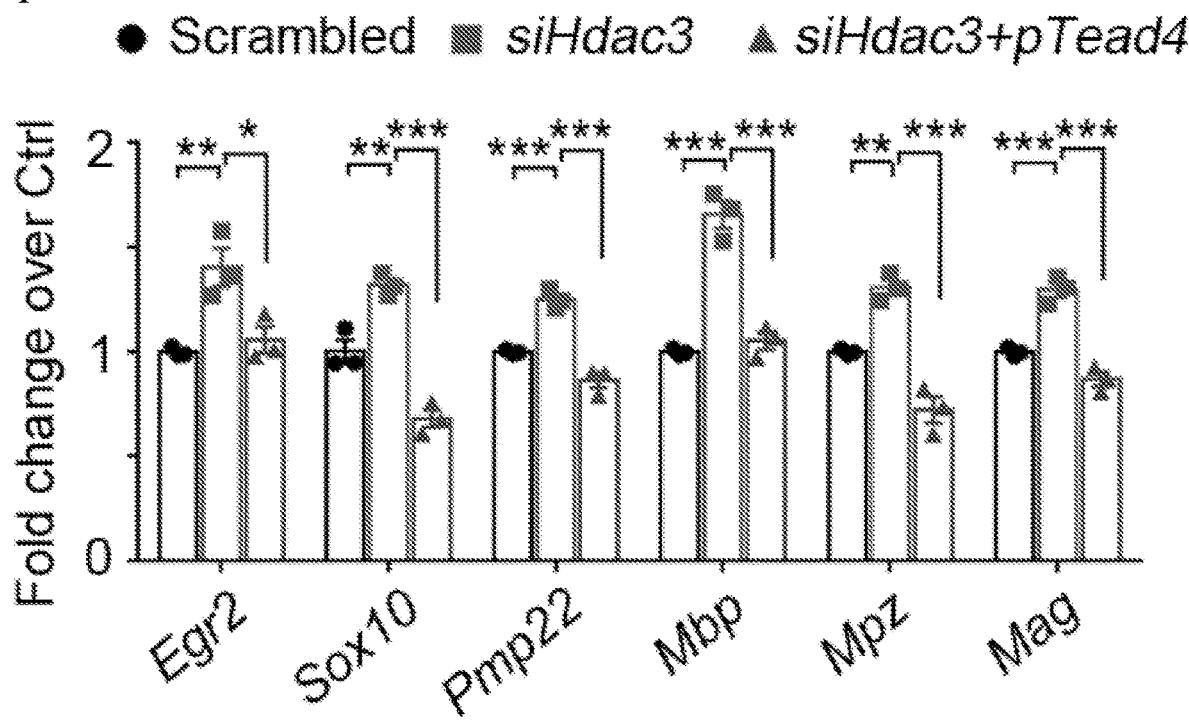
Figure 6:
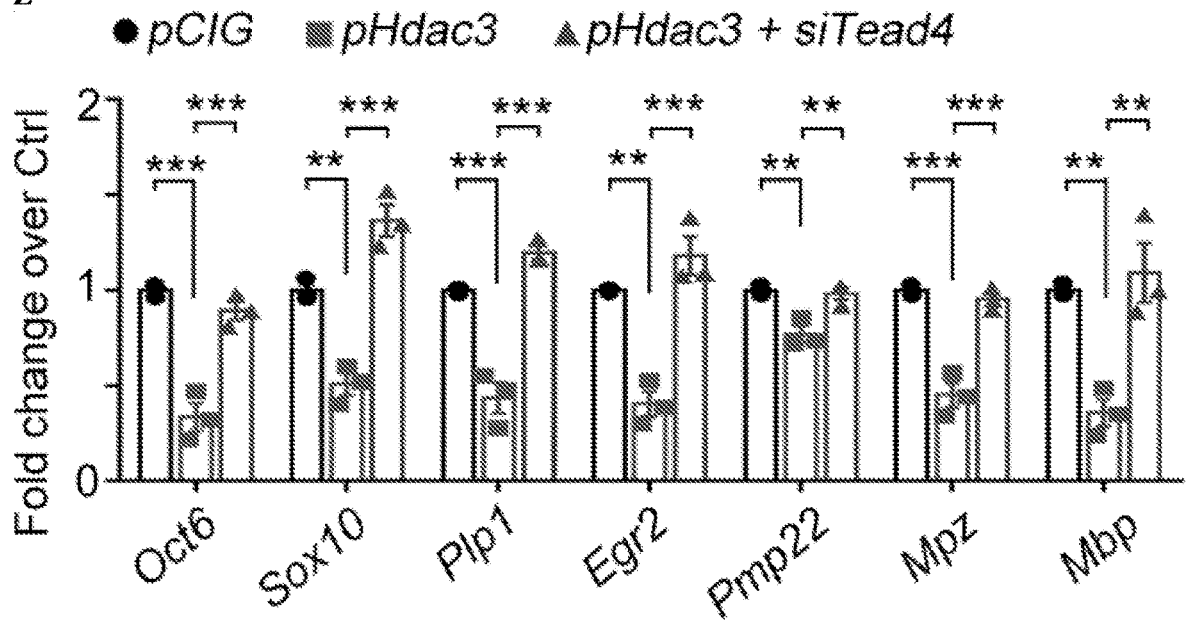

FIG. 6: HDAC3 can inhibit myelinogenesis by activating an inhibitory factor TEAD4. (A) Genome browser view of the distribution of HDAC3, p300, H3K4me1, and H3K27ac marks on the Tead4 locus. n=2 independent experiments for ChIP-seq of HDAC3, p300 and IgG. n=1 for histone markers. (B) HDAC3 and p300 genomic occupancy on the gene loci of TEAD family members. Genome browser view of the distribution of HDAC3 and p300 signals on the Tead1, Tead2, and Tead3 loci. Note that HDAC3 binding was mainly detected in these gene loci. n=2 independent experiments with similar results. (C) qRT-PCR analysis of Tead4 expression in SCs transfected with control vector or vectors for expression of Hdac3 or both Hdac3 and p300. (Data are presented as mean±s.e.m.; n=3 independent experiments; one-way ANOVA with Tukey's multiple comparisons test; $F_{(3, 8)}$=25.48; $P_{pCIG\ versus\ Hdac3}$=0.0705, $P_{pCIG\ versus\ p300}$=0.0164, $P_{pCIG\ versus\ Hdac3+p300}$=0.0001, $P_{Hdac3\ versus\ Hdac3+p300}$=0.0022, $P_{p300\ versus\ Hdac3+p300}$=0.0077). (D) HDAC3 and p300 genomic occupancy on the gene loci of TEAD family members. qRT-PCR analyses of Tead4 expression in siHdac3-treated SCs (left) or sciatic nerves of Hdac3-cKO mice (right). (Data are presented as mean±s.e.m.; n=3 independent experiments; two-tailed unpaired Student's t-test; left, P=0.0037, t=6.083, d.f.=4; right, P=0.001, t=8.707, d.f.=4). (E) Left: qRT-PCR validation of inhibition of Tead1-4 expression with indicated siRNAs. Right: qRT-PCR analyses of Egr2, Mpz, Pmp22, and Mbp in SCs treated with indicated siRNAs. (Data are presented as mean±s.e.m.; n=3 independent experiments; one-way ANOVA with Tukey's multiple comparisons test; Left, $F_{(4, 10)}=15.72$, $P_{Scr\ versus\ Tead1}=0.0009$, $P_{Scr\ versus\ Tead2}=0.0009$, $P_{Scr\ versus\ Tead3}=0.0004$, $P_{Scr\ versus\ Tead4}=0.001$; Right, Egr2, $F_{(4, 10)}=31.07$, $P_{Scr\ versus\ Tead1}=0.0333$, $P_{Scr\ versus\ Tead2}=0.0001$, $P_{Scr\ versus\ Tead3}=0.0398$, $P_{Scr\ versus\ Tead4}=0.0281$; Mpz, $F_{(4, 10)}=40.63$, $P_{Scr\ versus\ Tead1}=0.0076$, $P_{Scr\ versus\ Tead2}=0.0007$, $P_{Scr\ versus\ Tead4}=0.0006$; Pmp22, $F_{(4, 10)}=28.81$, $P_{Scr\ versus\ Tead1}=0.0048$, $P_{Scr\ versus\ Tead2}=0.0002$, $P_{Scr\ versus\ Tead3}=0.041$, $P_{Scr\ versus\ Tead4}=0.0399$; Mbp, $F_{(4, 10)}=27.26$, $P_{Scr\ versus\ Tead3}=0.0499$, $P_{Scr\ versus\ Tead4}=0.0002$). (F) qRT-PCR analyses of Id4, Id2, and Sox2 in siTead4-treated SCs. (Data are presented as mean±s.e.m.; n=3 independent experiments; two-tailed unpaired Student's t-test; Tead4, P=0.0004, t=11.12, d.f.=4; Id4, P=0.0011, t=8.44, d.f.=4; Id2, P=0.0005, t=10.09, d.f.=4; Sox2, P=0.0013, t=8.069, d.f.=4). (G) Rat SCs transfected with siTead4 or a control siRNA were seeded onto rat DRGs. After 10 days, co-cultures were stained for MBP and NF-M. n=3 independent experiments, with 10 images for each experiment. Scale bars: 100 µm. (H) Quantitation of MBP segments formed in myelinating co-cultures of DRGs and SCs transfected with siTead4 or control siRNA. (Data are presented as mean±s.e.m.; n=4 independent experiments; two-tailed unpaired Student's t-test; P=0.0037, t=4.591, d.f.=6). (I) Western blot (left) of TEAD4, MPZ, and MBP in myelinating co-cultures of DRGs and SCs transfected with siTead4 or control siRNA. GAPDH served as a loading control. Right, relative siTead4-induced expression of the indicated protein over the expression induced by the scrambled control. The corresponding band densities were normalized to GAPDH. (Data are presented as mean±s.e.m. n=three independent western blot experiments; two-tailed unpaired Student's t-test; MBP, P=0.0011, t=8.412, d.f.=4; MPZ, P=0.0042, t=5.885, d.f.=4; TEAD4, P=0.0002, t=13.2, d.f.=4). (J) A schematic diagram showing excision of the floxed exon 2 of the Tead4 allele upon recombination mediated by SC-expressing Dhh-Cre. (K) Western blot of sciatic nerves showing a marked decreased TEAD4 in Tead4-cKO mice compared to controls at P120. GAPDH as a loading control. n=3 independent western blot experiments. (L) qRT-PCR analysis of Tead4 expression in sciatic nerves of control or Tead4-cKO mice. (Data are presented as mean±s.e.m.; n=3 independent experiments; two-tailed unpaired Student's t-test; P=0.0009, t=8.774, d.f.=4). (M) Myelination in Tead4-cKO mice at early postnatal stages. Longitudinal sections of sciatic nerves from Tead4-cKO and control mice at P14 were immunostained with SOX10, OCT6, EGR2, and MBP. n=3 animals/group, with 5 images for each mouse. Scale bars: 50 µm. (N) Myelination in Tead4-cKO mice at early postnatal stages. Quantification of OCT6+ and EGR2+ SCs among SOX10+ SCs in P14 control and Tead4-cKO sciatic nerves. (Data are presented as mean±s.e.m.; n=3 animals/group; two-tailed unpaired Student's t-test; OCT6, P=0.7902, t=0.2844, d.f.=4; EGR2, P=0.7019, t=0.4113, d.f.=4). (O) Myelination in Tead4-cKO mice at early postnatal stages. Immunofluorescence labeling for Ki67 (green) in P14 sciatic nerves from control and Tead4-cKO nerves. DAPI (blue) was used to stain nuclei. n=3 animals/group, with 5 images for each mouse. Scale bars: (P) Myelination in Tead4-cKO mice at early postnatal stages. Quantification of Ki67+ SCs in P14 control and Tead4-cKO sciatic nerves. (Data are presented as mean±s.e.m.; n=3 animals/group; two-tailed unpaired Student's t-test; P=0.2425, t=1.262, d.f.=8). (Q) Myelination in Tead4-cKO mice at early postnatal stages. Electron microscopy analysis of cross sections of control and Tead4-cKO sciatic nerves at P14. n=3 animals/group, with 5 images for each mouse. Scale bars: 2 µm. (R) Myelination in Tead4-cKO mice at early postnatal stages. Quantification of g ratios at P14 from control and Tead4-cKO sciatic nerves. (Data are presented as mean±s.e.m.; n=161 axons from 3 control mice and 133 axons from 3 cKO (S) mice; Whiskers show the minimum and maximum, boxes extend from the first to the third quartiles with cross lines at the medians; two-tailed unpaired Student's t-test; P=0.0103, t=2.581, d.f.=292). (S) Ablation of Tead4 appears to exert no significant effect on myelin elongation. Representative images of teased fibers of sciatic nerves from control and Tead4-cKO mice at P14 immunostained for MBP (red), CASPR (green) to visualize nodes of Ranvier by staining paranodes), and DAPI (blue). Arrows indicate the location of the nodes. n=3 animals/group, with 5 images for each mouse. Scale bar, 100 µm. (T) Ablation of Tead4 appears to exert no significant effect on myelin elongation. Quantification of internode lengths of teased fibers from sciatic nerves of Ctrl or Tead4-cKO mice. (Data are presented as mean±s.e.m.; n=3 animals/group; twotailed unpaired Student's t-test; P=0.2576, t=1.319, d.f.=4). (U) Cross sections from control and Tead4-cKO sciatic nerves at P120 imaged with light microscopy after toluidine blue staining (upper) and with electron microscopy (bottom). n=3 animals/group, with 5 images for each mouse. Scale bars: 10 µm in upper and 4 µm in lower panel. (V) Quantification of g ratios from control and Tead4-cKO mice at P120. (Data are presented as mean±s.e.m.; n=303 axons from 3 mice for each group; two-tailed unpaired Student's t-test; P<0.0001, t=25.51, d.f.=604). (W) qRT-PCR analysis of Pmp22, Hmgcr, Mpz, and Egr2 expression in Tead4-cKO sciatic nerves at P120. (Data are presented as mean±s.e.m.; n=3 animals/group; two-tailed unpaired Student's t-test; Pmp22, P=0.0106, t=4.532, d.f.=4; Hmgcr, P=0.0049, t=5.619, d.f.=4; Mpz, P=0.0191, t=3.798, d.f.=4; Egr2, P=0.0014, t=7.916, d.f.=4). (X) qRT-PCR analysis of Egr2, Plp1, Mbp, Mpz, Pmp22 and Mag expression in SCs overexpress Tead4. (Data are presented as mean±s.e.m.; n=3 independent experiments; two-tailed unpaired Student's t-test; Egr2, P=0.0003, t=12, d.f.=4; Plp1, P<0.0001, t=19.58, d.f.=4; Mbp, P<0.0001, t=15.65, d.f.=4; Mpz, P=0.0001, t=14.88, d.f.=4; Pmp22, P<0.0001, t=24.77, d.f.=4; Mag, P=0.0264, t=3.435, d.f.=4). (Y) qRT-PCR analysis of expression of myelination-associated genes in SCs treated with siHdac3 and transfected with control or Tead4 expression vectors. (Data are presented as mean±s.e.m.; n=3 independent experiments; one-way ANOVA with Tukey's multiple comparisons test; Egr2, $F_{(2, 6)}=11.52$, $P_{Scr\ versus\ siHdac3}=0.0079$, $P_{siHdac3\ versus\ siHdac3+pTead4}=0.0159$; Sox10, $F_{(2, 6)}=52.54$, $P_{Scr\ versus\ siHdac3}=0.004$, $P_{siHdac3\ versus\ siHdac3+pTead4}=0.0001$; Pmp22, $F_{(2, 6)}=57.59$, $P_{Scr\ versus\ siHdac3}=0.0009$, $P_{siHdac3\ versus\ siHdac3+pTead4}=0.0001$; Mbp, $F_{(2, 6)}=63.97$, $P_{Scr\ versus\ siHdac3}=0.0001$, $P_{siHdac3\ versus\ siHdac3+pTead4}=0.0002$; Mpz, $F_{(2, 6)}=47.15$, $P_{Scr\ versus\ siHdac3}=0.004$, $P_{siHdac3\ versus\ siHdac3+pTead4}=0.0001$; Mag, $F_{(2, 6)}=56.23$, $P_{Scr\ versus\ siHdac3}=0.0007$, $P_{siHdac3\ versus\ siHdac3+pTead4}=0.0001$). (Z) qRT-PCR analysis of expression of myelination-associated genes in SCs that overexpress HDAC3 treated with either control siRNA or siTead4. (Data are presented as mean±s.e.m.; n=3 independent experiments; one-way ANOVA with Tukey's multiple comparisons test; Oct6, $F_{(2, 6)}=46.18$, $P_{Scr\ versus\ pHdac3}=0.0002$, $P_{pHdac3\ versus\ pHdac3+siTead4}=0.0005$; Sox10, $F_{(2, 6)}=48.37$, $P_{Scr}$ versus $pHdac3$=0.0025, $P_{pHdac3}$ versus $pHdac3+siTead4$=0.0001; Plp1, $F_{(2, 6)}$=58.43, $P_{Scr}$ versus $pHdac3$=0.0005, $P_{pHdac3}$ versus $pHdac3+siTead4$=0.0001; Egr2, $F_{(2, 6)}$=34.41, $P_{Scr}$ versus $pHdac3$=0.0016, $P_{pHdac3}$ versus $pHdac3+siTead4$=0.0004; Pmp22, $F_{(2, 6)}$=15.21, $P_{Scr}$ versus $pHdac3$=0.0046, $P_{pHdac3}$ versus $pHdac3+siTead4$=0.0067; Mpz, $F_{(2, 6)}$=50.16, $P_{Scr}$ versus $pHdac3$=0.0002, $P_{pHdac3}$ versus $pHdac3+siTead4$=0.0003; Mbp, $F_{(2, 6)}$=16.23, $P_{Scr}$ versus $pHdac3$=0.0068, $P_{pHdac3}$ versus $pHdac3+siTead4$=0.0035). n.s., not significant, *P<0.05, P<0.01, *P<0.001.

Figure 7:
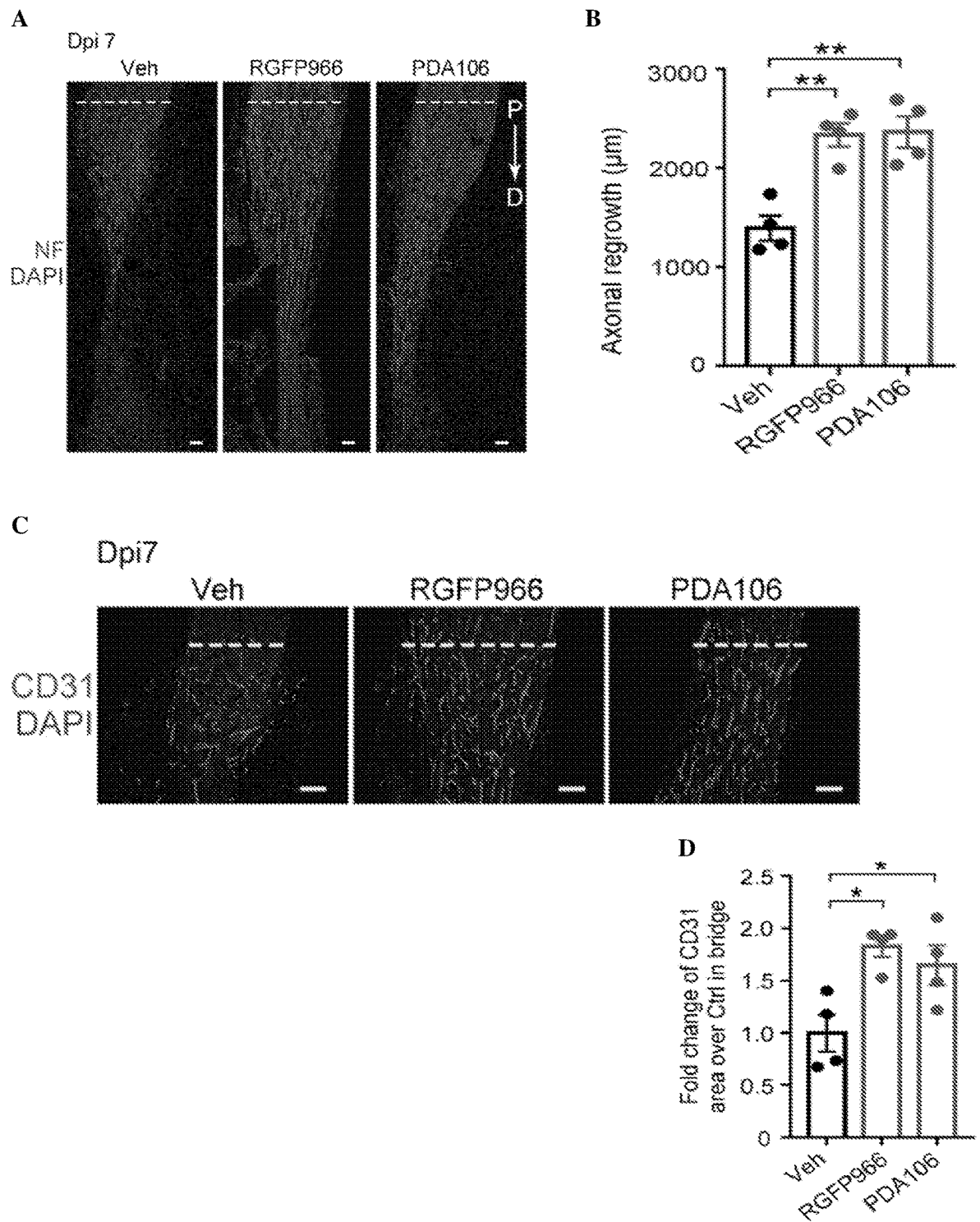
Figure 7:
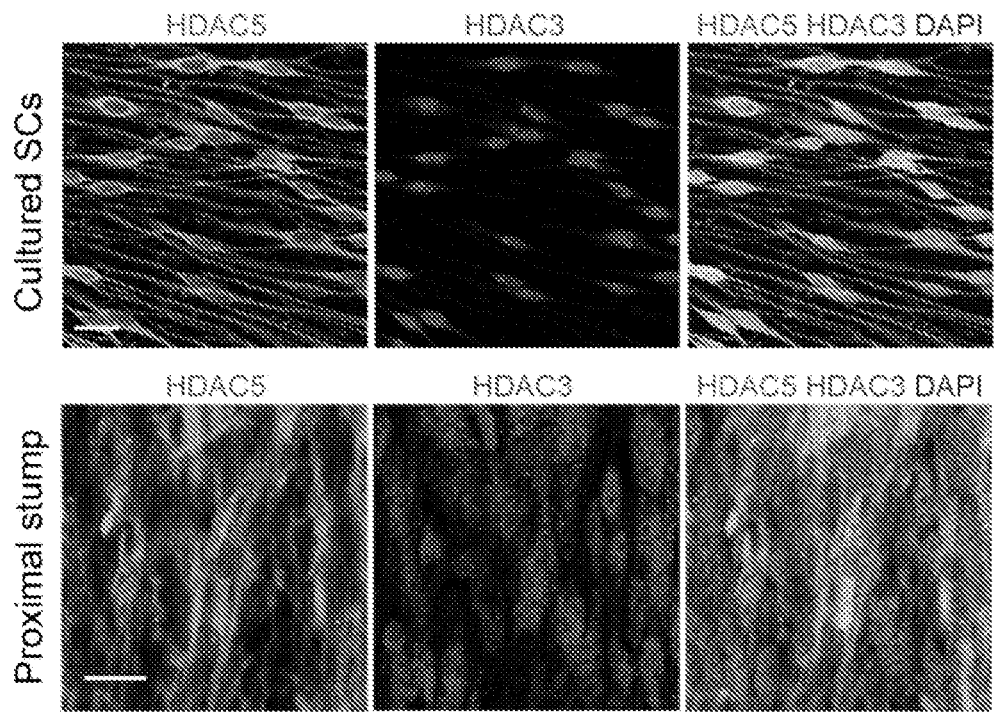
Figure 7:
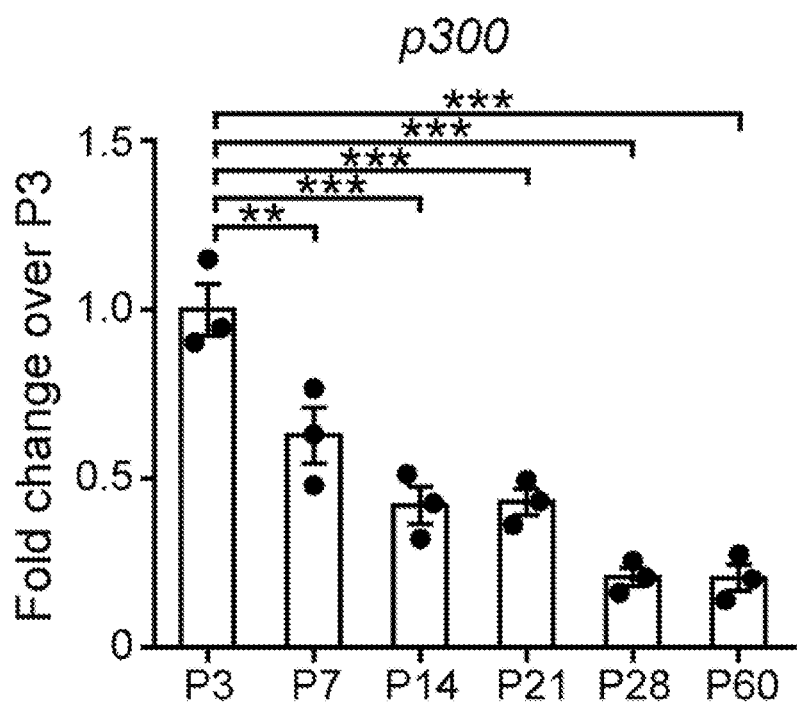
Figure 7:
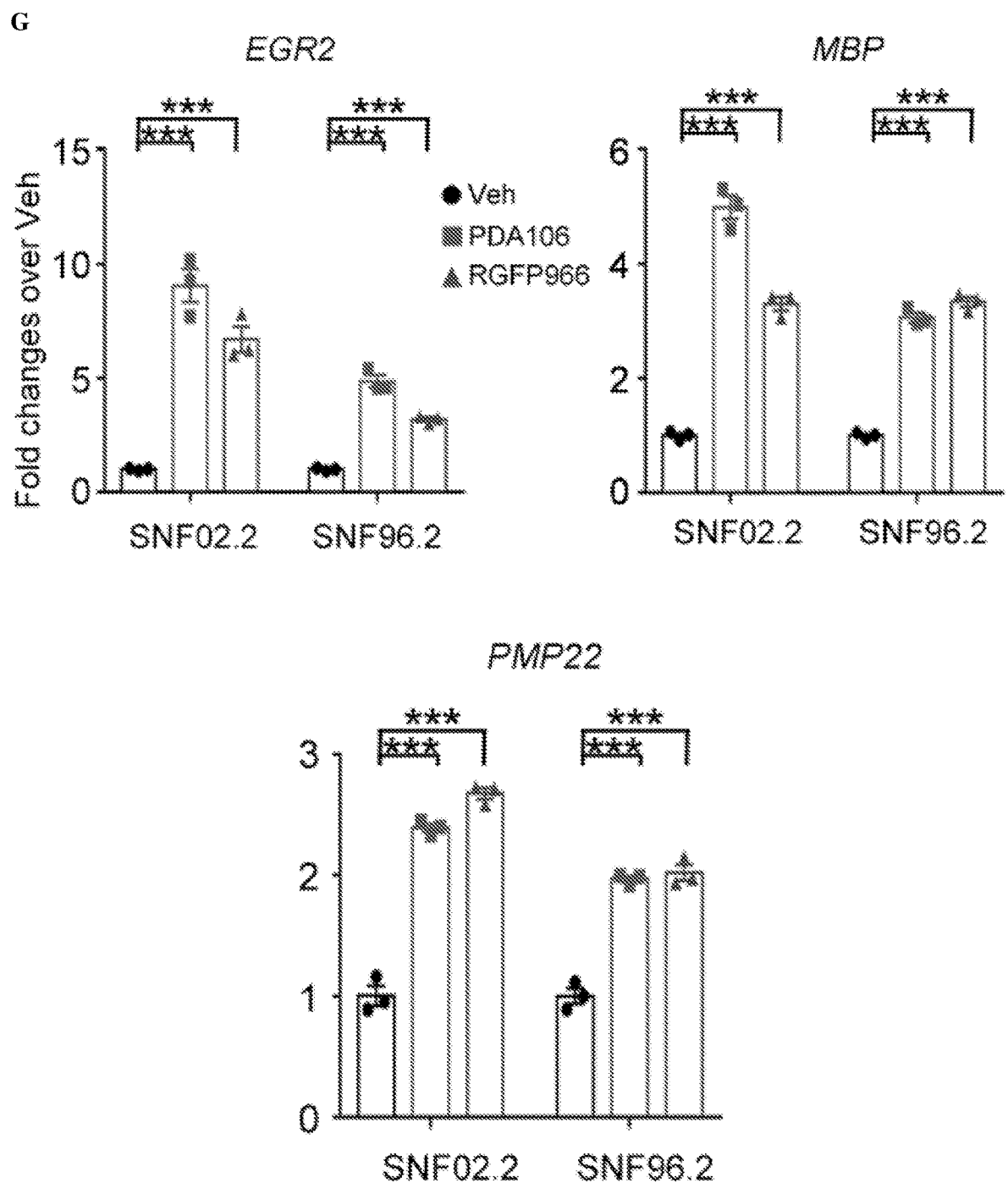

FIG. 7: (A) Effects of HDAC3 inhibition on axon regrowth and blood vessel formation. Representative images of longitudinal cryosections of tissue bridges (regions under the dashes lines) from injured sciatic nerves after indicated treatment at Dpi 7 immunostained for neurofilament M (NF; red) and counterstained with DAPI (blue). P: proximal; D: distal. n=4 animals/group. Scale bars, 100 µm. (B) Effects of HDAC3 inhibition on axon regrowth and blood vessel formation. Quantification of regenerating axons at different distances caudal to the lesion sites. (Data are presented as mean±s.e.m.; n=4 animals/group; One-way ANOVA with Tukey's multiple comparisons test; $F_{(2, 9)}$=16.22, $P_{Veh\ versus\ RGFP966}$=0.0023, $P_{Veh\ versus\ PDA106}$=0.0019). (C) Effects of HDAC3 inhibition on axon regrowth and blood vessel formation. Representative images of longitudinal cryosections of tissue bridges (regions under the dashes lines) from injured sciatic nerves after indicated treatment at Dpi 7 immunostained for CD31 (red) and counterstained with DAPI (blue). n=3 animals/group. Scale bar, 100 µm. (D) Effects of HDAC3 inhibition on axon regrowth and blood vessel formation. Quantification of CD31$^+$ area within the bridge. (Data are presented as mean±s.e.m.; n=4 animals/group; One way ANOVA with Tukey's multiple comparisons test; $F_{(2, 9)}$=6.579, $P_{Veh\ versus\ RGFP966}$=0.0171, $P_{Veh\ versus\ PDA106}$=0.0452). *P<0.05; **P<0.01. (E) Expression of HDAC5 and HDAC3 in SC and injured sciatic nerves. Representative images of cultured rat SCs (upper) and tissue bridges in injured sciatic nerves at Dpi 6 (low) was immunostained with HDAC5 (green), HDAC3 (red) and DAPI (blue). Results are representative of 5 independent experiments, with 5 images for each experiment. Scale bar: 20 µm. (F) p300 expression pattern during peripheral nerve development. qPCR quantification of p300 expression in murine sciatic nerve at different stages. (Data are presented as mean±s.e.m.; n=3 animals/group; One way ANOVA with Tukey's multiple comparisons test; $F_{(5, 12)}$=27.65, $P_{P3\ versus\ P7}$=0.0058, $P_{P3\ versus\ P14}$=0.0001, $P_{P3\ versus\ P21}$=0.0001, $P_{P3\ versus\ P28}$<0.0001, $P_{P3\ versus\ P60}$<0.0001). (G) Upregulation of myelin gene expression in human SC lines treated with HDAC3 inhibitors. Transcript levels of the myelination-associated genes EGR2, MBP and PMP22, assayed by qRT-PCR, in human neurofibroma-derived Schwann cell lines SNF02.2 and SNF96.2 treated with the HDAC3 inhibitors PDA106 and RGFP966, were normalized to those in Vehicle treated cells. (Data are presented as mean±s.e.m.; n=3 independent experiments; one-way ANOVA with Tukey's multiple comparisons test; EGR2, SNF02.2, $F_{(2, 6)}$=61.27, $P_{Veh\ versus\ PDA106}$<0.0001, $P_{Veh\ versus\ RGFP966}$=0.0007; SNF96.2, $F_{(2, 6)}$=138.7, $P_{Veh\ versus\ PDA106}$<0.0001, $P_{Veh\ versus\ RGFP966}$=0.0002; MBP, SNF02.2, $F_{(2, 6)}$=212.4, $P_{Veh\ versus\ PDA106}$<0.0001, $P_{Veh\ versus\ RGFP966}$<0.0001; SNF96.2, $F_{(2, 6)}$=318.1, $P_{Veh\ versus\ PDA106}$<0.0001, $P_{Veh\ versus\ RGFP966}$<0.0001; PMP22, SNF02.2, $F_{(2, 6)}$=242, $P_{Veh\ versus\ PDA106}$<0.0001, $P_{Veh\ versus\ RGFP966}$<0.0001; SNF96.2, $F_{(2, 6)}$=108.9, $P_{Veh\ versus\ PDA106}$<0.0001, $P_{Veh\ versus\ RGFP966}$<0.0001). n.s., not significant, *P<0.05, P<0.01, *P<0.001.

Figure 8:
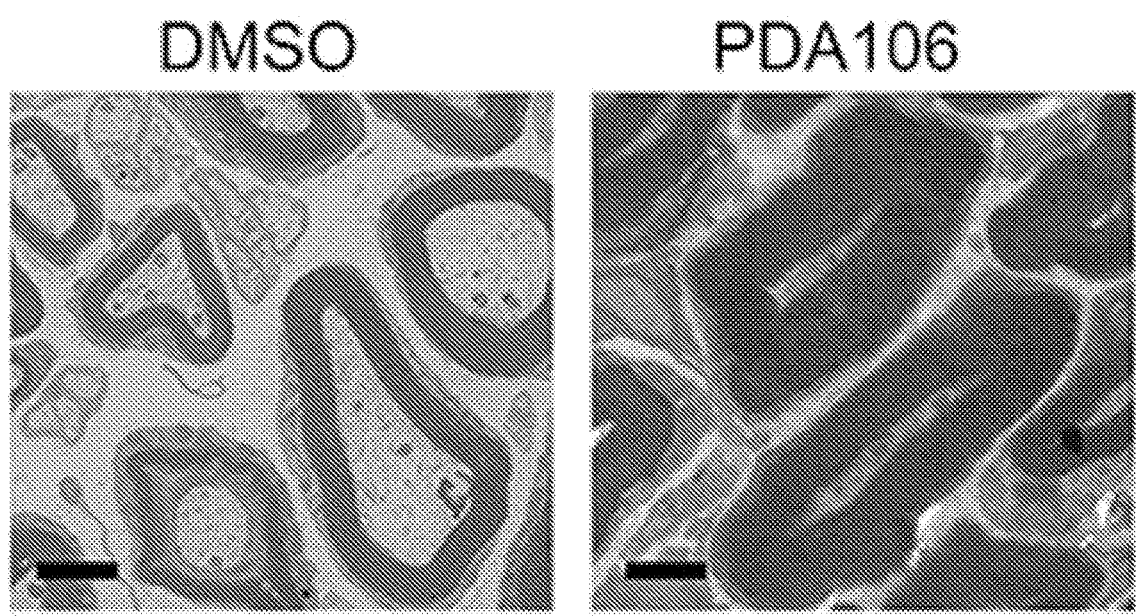
Figure 8:
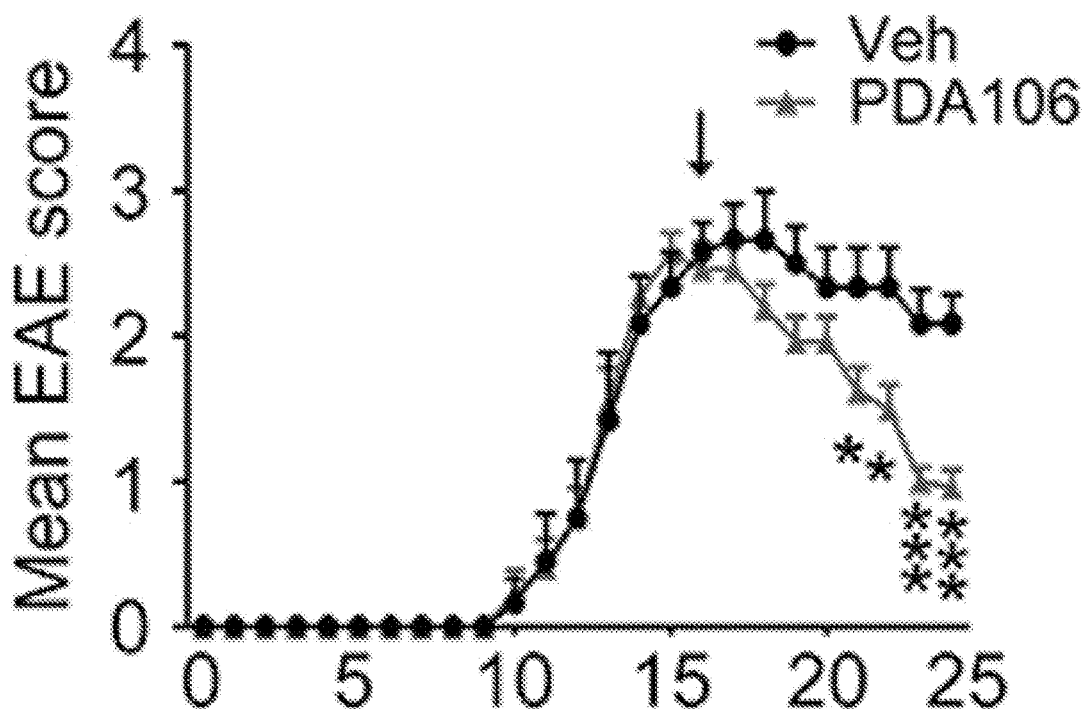
Figure 8:
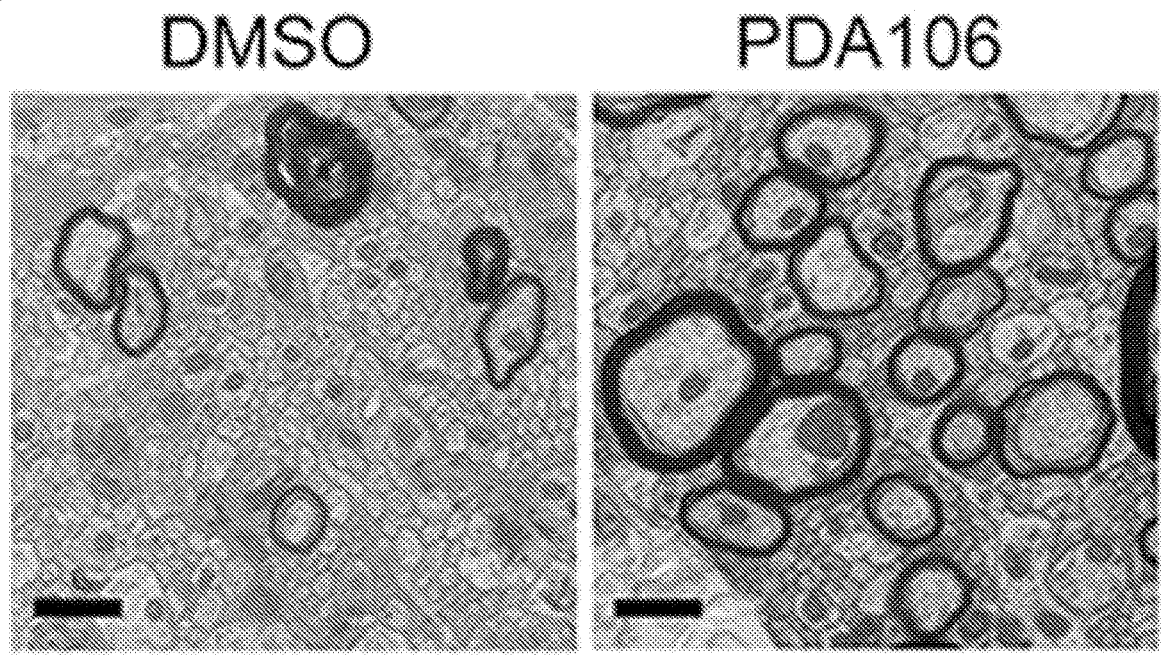

FIG. 8: HDAC3 inhibitor treatment can promote myelination and reduces clinical score. (A) HDAC3 inhibitor treatment can promote myelination in Schwann cells in sciatic nerves. Representative electron micrographs of sciatic nerve cross-sections at P15 from mice treated with vehicle or an HDAC3 inhibitor PDA106 from P3-P8. (B) Clinical score in chronic progressive demyelinating EAE mice treated with DMSO or PDA106 daily for 10 days beginning at the peak of disease at post-immunization day (PID) 15 (black arrow). (C) EM images of the lesion areas at PID 25 in ventral spinal cords of mice treated with DMSO or PDA106. *p<0.05, ***p<0.001, two-tailed unpaired Student's t-test.

Figure 9:
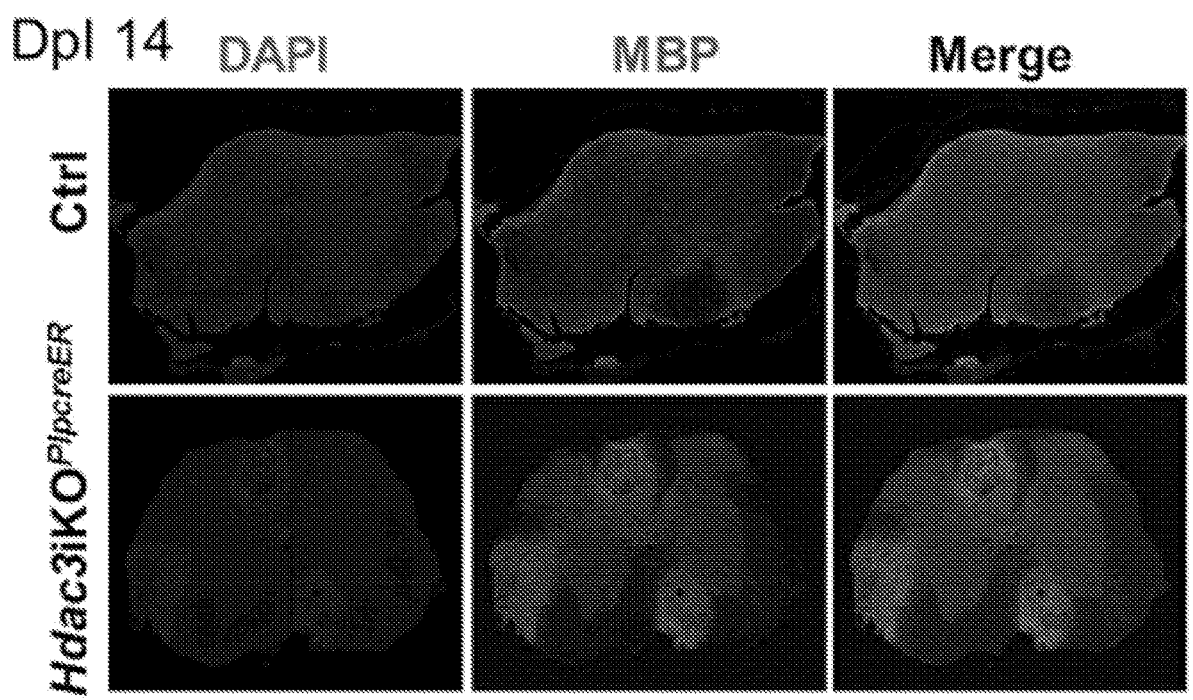

FIG. 9: HDAC3iKO can promote remyelination in LPC-induced demyelination lesions Immunostaining of MBP in LPC-induced lesion regions at days post LPC lesions (Dp1) 14 in spinal cord of Ctrl and HDAC3iKO$^{PlpcreET}$ mice.

Figure 10:
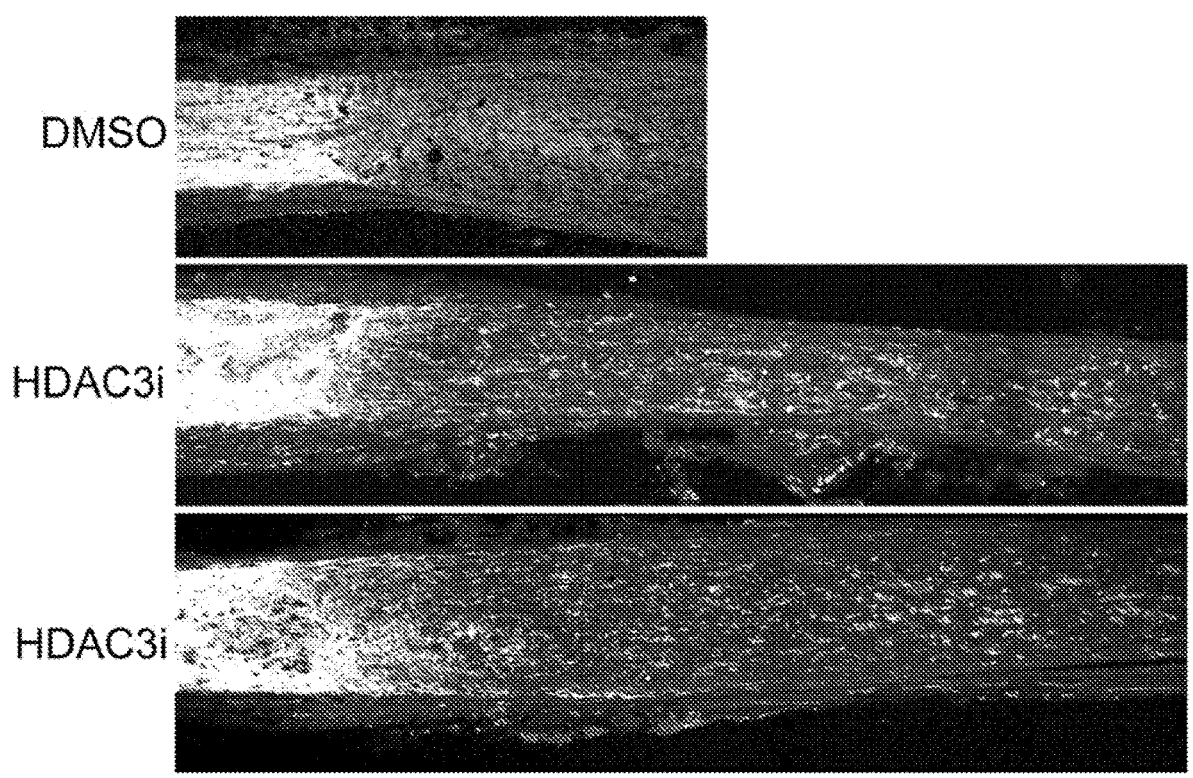

FIG. 10: Inhibition of HDAC3 can promote axon regeneration in the central nervous system.

Figure 11:
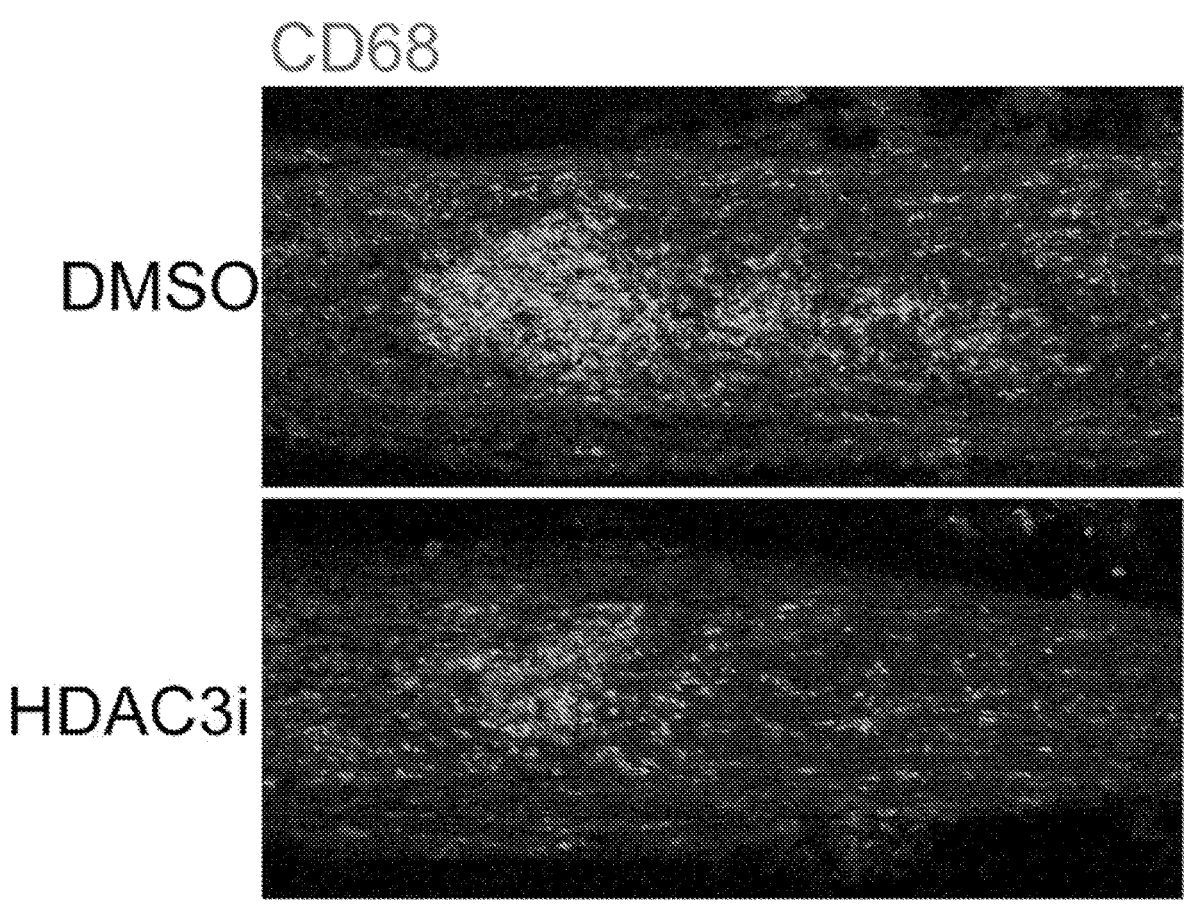

FIG. 11: Inhibition of HDAC3 can decrease inflammation after nerve injury.

DETAILED DESCRIPTION

While embodiments encompassing the general inventive concepts may take diverse forms, various embodiments will be described herein, with the understanding that the present disclosure is to be considered merely exemplary, and the general inventive concepts are not intended to be limited to the disclosed embodiments.

Some embodiments of the invention include methods for treating an animal for disease or nerve damage, comprising administration of a composition comprising a myelination enhancing inhibitor to the animal. Other embodiments of the invention include methods for treating an animal for disease or nerve damage, comprising administration of a composition comprising an HDAC3 inhibitor to the animal. Still other embodiments of the invention include methods for treating an animal for MS or nerve damage, comprising administration of a composition comprising an HDAC3 inhibitor to the animal. Additional embodiments of the invention are also discussed herein.

A "myelination enhancing inhibitor" is defined herein as an inhibitor of an enzyme or process, such that the inhibition will lead to an increase in myelination (e.g., increasing myelination on the axon sheath). In some embodiments, the myelination enhancing inhibitor can lead to axon re-growth. Examples of myelination enhancing inhibitors include but are not limited to HDAC3 (histone deacetylase 3) inhibitors (e.g., apicidin, PDA106, RGFP966, CUDC-907 (CAS Number 1339928-25-4; N-hydroxy-2-(((2-(6-methoxypyridin-3-yl)-4-morpholinothieno[3,2-d]pyrimidin-6-yl)methyl) (methyl)amino)pyrimidine-5-carboxamide), Quisinostat (JNJ-26481585; CAS Number 875320-31-3; N-Hydroxy-2-[4-({[(1-methyl-1H-indol-3-yl)methyl]amino}methyl)-1-piperidinyl]-5-pyrimidinecarboxamide), RG2833 (RGFP109; CAS Number 1215493-56-3; N-[6-[(2-aminophenyl)amino]-6-oxohexyl]-4-methyl-benzamide), CUDC-101 (CAS Number 1012054-59-9; 7-[[4-(3-Ethynylphenylamino)-7-methoxyquinazolin-6-yl]oxy]-N-hydroxyheptanamide), Resminostat (CAS Number 864814-88-0; 4SC-201; RAS2410; (2E)-3-[1-({4-[(Dimethylamino)methyl]phenyl}sulfonyl)-1H-pyrrol-3-yl]-N-hydroxyacrylamide), 4SC-202 (CAS Number 910462-43-0; (E)-N-(2-aminophenyl)-3-[1-[4-(1-methylpyrazol-4-yl)phenyl]sulfonylpyrrol-3-yl]prop-2-enamide), Mocetinostat (MGCD0103; MG0103; CAS Number 726169-73-9; N-(2-Aminophenyl)-4-[[(4-pyridin-3-ylpyrimidin-2-yl)amino]methyl] benzamide), Entinostat (MS-275; CAS Number 209783-80-2; 3-pyridinylmethyl [[4-[[(2-aminophenyl)amino]carbonyl] phenyl]methyl]carbamate), Citarinostat (ACY-241; HDAC-IN-2; CAS Number 1316215-12-9; 2-((2-chlorophenyl) (phenyl)amino)-N-(7-(hydroxyamino)-7-oxoheptyl) pyrimidine-5-carboxamide), Abexinostat (PCI-24781; CRA-024781; CAS Number 783355-60-2; 3-[(Dimethylamino)methyl]-N-{2-[4-(hydroxycarbamoyl)phenoxy]ethyl}-1-benzofuran-2-carboxamide), Pracinostat (SB939; CAS Number 929016-96-6; (E)-3-(2-Butyl-1-(2-(diethylamino)ethyl)-1H-benzo[d]imidazol-5-yl)-N-hydroxyacrylamide)), HDAC (histone deacetylase) inhibitors (e.g., CAY10398, chidamide, LAQ824, and SAHA), demethylase inhibitors (e.g., GSK-J4 and JIB-04), and methyltransferase inhibitors (e.g., UNC0631 and UNC0646). Table A shows inhibitor type and identifying information for several compounds. In some embodiments, myelination enhancing inhibitors can inhibit (e.g., fully inhibit or partially inhibit) one or more of HDAC3, HDAC, demethylase, and methyltransferase by, for example, reducing the activity or expression of an enzyme (e.g., HDAC3, HDAC, demethylase, or methyltransferase). In other embodiments, myelination enhancing inhibitors (e.g., HDAC3 inhibitors) can be antagonists (e.g., antagonists of one or more of HDAC3, HDAC, demethylase, and methyltransferase), partial antagonists (e.g., partial antagonists of one or more of HDAC3, HDAC, demethylase, and methyltransferase), inverse agonists (e.g., inverse antagonists of one or more of HDAC3, HDAC, demethylase, and methyltransferase), partial inverse agonists (e.g., partial inverse antagonists of one or more of HDAC3, HDAC, demethylase, and methyltransferase), or combinations thereof. In certain embodiments, inhibition (e.g., by a myelination enhancing inhibitor, an HDAC3 inhibitor, or another inhibitor) can occur using any suitable mechanism, such as but not limited to blockading an enzyme (e.g., partially or fully blocking other molecules from accessing one or more receptor sites), an antagonist mechanism, a partial antagonist mechanism, an inverse agonist mechanism, a partial inverse agonist mechanism, or a combination thereof. In some embodiments, the myelination enhancing inhibitor can be in the form of a salt, an ester, or a solvate. In other embodiments, the myelination enhancing inhibitor (e.g., HDAC3 inhibitor) can be in various forms, such as uncharged molecules, components of molecular complexes, or non-irritating pharmacologically acceptable salts, including but not limited to hydrochloride, hydrobromide, sulphate, phosphate, nitrate, borate, acetate, maleate, tartrate, and salicylate. In some instances, for acidic compounds, salts can include metals, amines, or organic cations (e.g. quaternary ammonium). Esters can include any suitable esters such as but not limited to when an —OH group is replaced by an —O-alkyl group, where alkyl can be but is not limited to methyl, ethyl, propyl, or butyl. Solvates can include any suitable solvent (e.g., water, alcohols, ethanol) complexed (e.g., reversibly associated) with the molecule (e.g., myelination enhancing inhibitor).

TABLE A

| Compound name | Inhibitor types (exemplary) | CAS number/other identifying information |
|---|---|---|
| Apicidin | HDAC3 inhibitor | OSI 2040; CAS Number 183506-66-3; Cyclo[(2S)-2-amino-8-oxodecanoyl-1-methoxy-L-tryptophyl-L-isoleucyl-(2R)-2-piperidinexcarbonyl] |
| CAY10398 | HDAC inhibitor; HDAC1 inhibitor | MD 85; PX 089274; CAS Number 193551-00-7; 4-(dimethylamino)-N-[6-(hydroxyamino)-6-oxohexyl]-benzamide |
| Chidamide | HDAC inhibitor; benzamide HDAC inhibitor | HBI-8000; Epidaza; CAS Number 743420-02-2; N-(2-amino-5-fluorophenyl)-4-[[[1-oxo-3-(3-pyridinyl)-2-propen-1-yl]amino]methyl]-benzamide |
| GSK-J4 | Demethylase inhibitor; a histone demethylase KDM6B/JMJD3 inhibitor; Histone lysine demethylase (KDM) inhibitor | CAS Number 1373423-53-0; Ethyl 3-((6-(4,5-dihydro-1H-benzo[d]azepin-3(2H)-yl)-2-(pyridin-2-yl)pyrimidin-4-yl)amino)propanoate |
| JIB-04 | Demethylase inhibitor; pan-selective inhibitor of histone demethylase; inhibitor of Jumonji family of histone demethylases | CAS Number 199596-05-9; (E)-N-(5-Chloro-pyridin-2-yl)-N'-(phenyl-pyridin-2-yl-methylene)-hydrazine |
| LAQ824 | HDAC inhibitor | Dacinostat; NVP-LAQ824; CAS Number 404951-53-7; (2E)-N-hydroxy-3-[4-[[(2-hydroxyethyl)[2-(1H-indol-3-yl)ethyl]amino]methyl]phenyl]-2-propenamide |
| PDA106 | HDAC3 inhibitor | Pimelic diphenylamide 106; RGFA 8; TC-H 106; CAS Number 937039-45-7; N1-(2-Aminophenyl)-N7-(4-methylphenyl)-heptanediamide |
| RGFP966 | HDAC3 selective inhibitor | CAS Number 1396841-57-8; (2E)-N-(2-Amino-4-fluorophenyl)-3-[(2E)-1-(3-phenyl-2-propen-1-yl)-1H-pyrazol-4-yl]-2-propenamide |
| SAHA | HDAC inhibitor; inhibitor of class I, II, and IV HDAC | Suberoylanilide hydroxamic acid; Vorinostat; CAS Number 149647-78-9; N-hydroxy-N'-phenyl-octanediamide |
| UNC0631 | Methyltransferase inhibitor; G9a/GLP-mediated dimethylation of histone 3 | CAS Number 1320288-19-4; N-[1-(cyclohexylmethyl)-4-piperidinyl]-2-[hexahydro-4-(1-methylethyl)-1H-1,4-diazepin-1-yl]-6-methoxy-7-[3-(1-piperidinyl)propoxy] 4-quinazolinamine |
| UNC0646 | Methyltransferase inhibitor; selective inhibitor of the methyltransferase G9a | CAS Number 1320288-17-2; N-(1-Cyclohexyl-4-piperidinyl)-2-[hexahydro-4-(1-methylethyl)-1H-1,4-diazepin-1-yl]-6-methoxy-7[3-(1-piperidinyl)propoxy]-4-quinazolinamine |

Treatments of Disease

Some embodiments of the invention include treatment of disease, nerve injury, or both in an animal comprising administering a myelination enhancing inhibitor resulting in inhibiting HDAC3, inhibiting HDAC, inhibiting demethylase, or inhibiting methyltransferase. Inhibiting HDAC3 can occur by any suitable method including but not limited to administering an HDAC3 inhibitor (e.g., small molecule or antibody). Inhibiting HDAC can occur by any suitable method including but not limited to administering an HDAC inhibitor (e.g., small molecule or antibody). Inhibiting demethylase can occur by any suitable method including but not limited to administering a demethylase inhibitor (e.g., small molecule or antibody). Inhibiting methyltransferase can occur by any suitable method including but not limited to administering a methyltransferase inhibitor (e.g., small molecule or antibody).

Some embodiments of the invention include treatment of disease, treatment of nerve injury (e.g., to the central nervous system (CNS) or the peripheral nervous system (PNS)), or both in an animal comprising administering a myelination enhancing inhibitor (e.g., HDAC3 inhibitor, PDA106, or RGFP966). Administration to the animal can be accomplished by any number of suitable administration routes or formulations. Animals include but are not limited to mammals, primates, monkeys (e.g., macaque, rhesus macaque, or pig tail macaque), humans, canine, feline, bovine, porcine, avian (e.g., chicken), mice, rabbits, and rats. As used herein, the term "subject" refers to both human and animal subjects.

In some embodiments the age of the animal can be young or old. In other embodiments, the age of the animal (e.g., human) can be about 0.1, about 0.5, about 1, about 2, about 3, about 4, about 5, about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, or about 150 years old. In certain embodiments, the animal can be no more than about 2 years old, no more than about 5 years old, no more than about 10 years old, no more than about 20 years old, at least about 40 years old, at least about 50 years old, at least about 65 years old, at least about 80 years old, or at least about 100 years old.

In some embodiments, the amount of a myelination enhancing inhibitor (e.g., HDAC3 inhibitor, PDA106, or RGFP966) administered to an animal (e.g., via a composition or a pharmaceutical composition) can be, but is not limited to about 0.005 mg/kg, about 0.01 mg/kg, about 0.05 mg/kg, about 0.1 mg/kg, about 0.5 mg/kg, about 0.6 mg/kg, about 0.7 mg/kg, about 0.8 mg/kg, about 0.9 mg/kg, about 1.0 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 2.0 mg/kg, about 2.1 mg/kg, about 2.2 mg/kg, about 2.3 mg/kg, about 2.4 mg/kg, about 2.5 mg/kg, about 2.6 mg/kg, about 2.7 mg/kg, about 2.8 mg/kg, about 2.9 mg/kg, about 3.0 mg/kg, about 3.1 mg/kg, about 3.2 mg/kg, about 3.3 mg/kg, about 3.4 mg/kg, about 3.5 mg/kg, about 3.6 mg/kg, about 3.7 mg/kg, about 3.8 mg/kg, about 3.9 mg/kg, about 4.0 mg/kg, about 4.1 mg/kg, about 4.2 mg/kg, about 4.3 mg/kg, about 4.4 mg/kg, about 4.5 mg/kg, about 5.0 mg/kg, about 5.5 mg/kg, about 6.0 mg/kg, about 6.5 mg/kg, about 7.0 mg/kg, about 7.5 mg/kg, about 10 mg/kg, about 20 mg/kg, about 30 mg/kg, about 40 mg/kg, about 50 mg/kg, about 80 mg/kg, about 100 mg/kg, about 150 mg/kg, about 200 mg/kg, about 250 mg/kg, no more than about 20.0 mg/kg, no more than about 10.0 mg/kg, no more than about 5.0 mg/kg, no more than about 4.5 mg/kg, no more than about 4.4 mg/kg, no more than about 4.3 mg/kg, no more than about 4.2 mg/kg, no more than about 4.1 mg/kg, no more than about 4.0 mg/kg, no more than about 3.9 mg/kg, no more than about 3.8 mg/kg, no more than about 3.7 mg/kg, no more than about 3.6 mg/kg, no more than about 3.5 mg/kg, no more than about 3.4 mg/kg, no more than about 3.3 mg/kg, no more than about 3.2 mg/kg, no more than about 3.1 mg/kg, no more than about 3.0 mg/kg, no more than about 2.9 mg/kg, no more than about 2.8 mg/kg, no more than about 2.7 mg/kg, no more than about 2.6 mg/kg, no more than about 2.5 mg/kg, no more than about 2.4 mg/kg, no more than about 2.3 mg/kg, no more than about 2.2 mg/kg, no more than about 2.1 mg/kg, no more than about 2.0 mg/kg, no more than about 1.9 mg/kg, no more than about 1.8 mg/kg, no more than about 1.7 mg/kg, no more than about 1.6 mg/kg, no more than about 1.5 mg/kg, no more than about 1.4 mg/kg, no more than about 1.3 mg/kg, no more than about 1.2 mg/kg, no more than about 1.1 mg/kg, no more than about 1.0 mg/kg, no more than about 0.9 mg/kg, no more than about 0.8 mg/kg, no more than about 0.7 mg/kg, no more than about 0.6 mg/kg, or no more than about 0.5 mg/kg animal body weight. The animal (e.g., human) body weight can be about 2 kg, about 5 kg, about 10 kg, about 15 kg, about 20 kg, about 25 kg, about 30 kg, about 35 kg, about 40 kg, about 45 kg, about 50 kg, about 55 kg, about 60 kg, about 65 kg, about 70 kg, about 75 kg, about 80 kg, about 85 kg, about 90 kg, about 95 kg, about 100 kg, about 150 kg, about 200 kg, from about 2 kg to about 200 kg, from about 10 kg to about 100 kg, from about 10 kg to about 85 kg, from about 45 kg to about 100 kg, or from about 45 kg to about 85 kg. These amounts (e.g., dosages) can be used as an effective amount or a therapeutically effective amount.

Nerve injury (e.g., from disease, crushing injury, or transection injury) to the CNS or nerve injury to the PNS (e.g., from disease, crushing injury, or transection injury) that can be treated in an animal (e.g., mammals, porcine, canine, avian (e.g., chicken), bovine, feline, primates, rodents, monkeys, rabbits, mice, rats, and humans) using a myelination enhancing inhibitor (e.g., HDAC3 inhibitor, PDA106, or RGFP966) include, but are not limited to repairing nerve damage (e.g., in the CNS or PNS), improving nerve function (e.g., in the CNS or PNS), improving action potential (e.g., in the CNS or PNS), re-connecting axons (e.g., in the CNS or PNS), repairing axons (e.g., in the CNS or PNS), promoting myelination (e.g., in the CNS or PNS), increasing the extent of myelination (e.g., in the CNS or PNS), increasing the extent of myelination on the myelin sheath (e.g., in the CNS or PNS), reducing inflammation (e.g., in the CNS or PNS), reducing inflammation near (e.g., no more than about 1 mm, no more than about 3 mm, no more than about 5 mm, or no more than about 10 mm) or at an axon (e.g., in the CNS or PNS), traumatic brain injury, acquired brain injury (e.g., hypoxic ischemic brain injury), strokes, or periventricular leukomalacia (PVL; e.g., white-matter brain injury).

Diseases that can be treated in an animal (e.g., mammals, porcine, canine, avian (e.g., chicken), bovine, feline, primates, rodents, monkeys, rabbits, mice, rats, and humans) using a myelination enhancing inhibitor (e.g., HDAC3 inhibitor, PDA106, or RGFP966) include, but are not limited to myelopathy (e.g., spinal cord injury, myelitis, vascular myelopathy, cervical spondylotic myelopathy, spondylosis, spinal stenosis), demyelinating disease (e.g., any disease of the nervous system where the myelin sheath of a neuron is damaged), CNS demyelinating disease, PNS demyelinating disease, genetic demyelinating disease, infectious demyelinating disease, autoimmune demyelinating disease, demyelinating myelinoclastic disease, demyelinating leukodystrophic disease, Devic's disease, CNS neuropathies (e.g., diseases resulting in vitamin B12 deficiency), central pontine myelinolysis, myelopathies (e.g., tabes *dorsalis*), leukoencephalopathies (e.g., progressive multifocal leukoencephalopathy), leukodystrophies, optic neuritis, transverse myelitis, neuromyelitis optica, Guillain-Barré syndrome, chronic inflammatory demyelinating polyneuropathy, anti-MAG peripheral neuropathy, Charcot-Marie-Tooth disease, Hereditary neuropathy with liability to pressure palsy, copper deficiency associated conditions (e.g., peripheral neuropathy, myelopathy, and optic neuropathy), progressive inflammatory neuropathy, multiple sclerosis (MS) (e.g., treating inflammation, remyelination, or both), MS-type clinically isolated syndrome (e.g., treating inflammation, remyelination, or both), relapsing-remitting MS (e.g., treating inflammation, remyelination, or both), primary progressive MS (e.g., treating inflammation, remyelination, or both), secondary progressive MS (e.g., treating inflammation, remyelination, or both), traumatic brain injury, acquired brain injury (e.g., hypoxic ischemic brain injury), strokes, or periventricular leukomalacia (PVL; e.g., white-matter brain injury).

The route of administration for treatment can be of any suitable route. Administration routes can be, but are not limited to the oral route, the parenteral route, the cutaneous route, the nasal route, the rectal route, the vaginal route, and the ocular route. In other embodiments, the administration route can be parenteral administration, a mucosal administration, intravenous administration, depot injection, subcutaneous administration, topical administration, intradermal administration, oral administration, sublingual administration, intranasal administration, or intramuscular administration. The choice of administration route can depend on the compound identity (e.g., the physical and chemical properties of the compound) as well as the age and weight of the animal, the particular disease or injury (e.g., in the CNS or PNS; transection vs. crushing injury), and the severity of the disease or injury (e.g., stage or severity of disease or injury). Of course, combinations of administration routes can be administered, as desired.

Some embodiments of the invention include a method for providing a subject with a composition comprising a myelination enhancing inhibitor (e.g., HDAC3 inhibitor, PDA106, or RGFP966) (e.g., a pharmaceutical composition) which comprises one or more administrations of one or more such compositions; the compositions may be the same or different if there is more than one administration.

Animals that can be treated include but are not limited to mammals, rodents, primates, monkeys (e.g., macaque, rhesus macaque, pig tail macaque), humans, canine, feline, porcine, avian (e.g., chicken), bovine, mice, rabbits, and rats. As used herein, the term "subject" refers to both human and animal subjects. In some instances, the animal is in need of the treatment (e.g., by showing signs of disease or nerve injury).

In some embodiments, diseases or nerve injuries that can be treated in an animal (e.g., mammals, porcine, canine, avian (e.g., chicken), bovine, feline, primates, rodents, monkeys, rabbits, mice, rats, and humans) using a myelination enhancing inhibitor (e.g., HDAC3 inhibitor, PDA106, or RGFP966) (e.g., by a composition comprising a myelination enhancing inhibitor) include, but are not limited to the nerve injuries described herein and the diseases described herein.

As used herein, the term "treating" (and its variations, such as "treatment") is to be considered in its broadest context. In particular, the term "treating" does not necessarily imply that an animal is treated until total recovery. Accordingly, "treating" includes amelioration of the symptoms, relief from the symptoms or effects associated with a condition, decrease in severity of a condition, or preventing, preventively ameliorating symptoms, or otherwise reducing the risk of developing a particular condition. As used herein, reference to "treating" an animal includes but is not limited to prophylactic treatment and therapeutic treatment. Any of the compositions (e.g., pharmaceutical compositions) described herein can be used to treat an animal.

As related to treating disease or nerve injury (e.g., CNS demyelinating disease, PNS demyelinating disease, MS, CNS nerve injury, PNS nerve injury, crush nerve injury, or transection nerve injury), treating can include but is not limited to prophylactic treatment and therapeutic treatment. As such, treatment can include, but is not limited to: preventing disease or nerve injury (e.g., CNS demyelinating disease, PNS demyelinating disease, MS, CNS nerve injury, PNS nerve injury, crush nerve injury, or transection nerve injury); reducing the risk of disease or nerve injury (e.g., CNS demyelinating disease, PNS demyelinating disease, MS, CNS nerve injury, PNS nerve injury, crush nerve injury, or transection nerve injury); ameliorating or relieving symptoms of disease or nerve injury (e.g., CNS demyelinating disease, PNS demyelinating disease, MS, CNS nerve injury, PNS nerve injury, crush nerve injury, or transection nerve injury); eliciting a bodily response against disease or nerve injury (e.g., CNS demyelinating disease, PNS demyelinating disease, MS, CNS nerve injury, PNS nerve injury, crush nerve injury, or transection nerve injury); inhibiting the development or progression of disease or nerve injury (e.g., CNS demyelinating disease, PNS demyelinating disease, MS, CNS nerve injury, PNS nerve injury, crush nerve injury, or transection nerve injury); inhibiting or preventing the onset of symptoms associated with disease or nerve injury (e.g., CNS demyelinating disease, PNS demyelinating disease, MS, CNS nerve injury, PNS nerve injury, crush nerve injury, or transection nerve injury); reducing the severity of disease or nerve injury (e.g., CNS demyelinating disease, PNS demyelinating disease, MS, CNS nerve injury, PNS nerve injury, crush nerve injury, or transection nerve injury); causing a regression of disease or nerve injury (e.g., CNS demyelinating disease, PNS demyelinating disease, MS, CNS nerve injury, PNS nerve injury, crush nerve injury, or transection nerve injury) or one or more of the symptoms associated with disease or nerve injury (e.g., CNS demyelinating disease, PNS demyelinating disease, MS, CNS nerve injury, PNS nerve injury, crush nerve injury, or transection nerve injury); causing remission of disease or nerve injury (e.g., CNS demyelinating disease, PNS demyelinating disease, MS, CNS nerve injury, PNS nerve injury, crush nerve injury, or transection nerve injury); or preventing relapse of disease or nerve injury (e.g., CNS demyelinating disease, PNS demyelinating disease, MS, CNS nerve injury, PNS nerve injury, crush nerve injury, or transection nerve injury). In some embodiments, treating does not include prophylactic treatment of one or both of disease or nerve injury (e.g., CNS demyelinating disease, PNS demyelinating disease, MS, CNS nerve injury, PNS nerve injury, crush nerve injury, or transection nerve injury).

Treatment of an animal (e.g., human) can occur using any suitable administration method (such as those disclosed herein) and using any suitable amount of a myelination enhancing inhibitor (e.g., HDAC3 inhibitor, PDA106, or RGFP966). In some embodiments, methods of treatment comprise treating an animal for disease or nerve injury (e.g., CNS demyelinating disease, PNS demyelinating disease, MS, CNS nerve injury, PNS nerve injury, crush nerve injury, or transection nerve injury). Some embodiments of the invention include a method for treating a subject (e.g., an animal such as a human or primate) with a composition comprising a myelination enhancing inhibitor (e.g., HDAC3 inhibitor, PDA106, or RGFP966) (e.g., a pharmaceutical composition) which comprises one or more administrations of one or more such compositions; the compositions may be the same or different if there is more than one administration.

In some embodiments, the method of treatment includes administering an effective amount of a composition comprising a myelination enhancing inhibitor (e.g., HDAC3 inhibitor, PDA106, or RGFP966). As used herein, the term "effective amount" refers to a dosage or a series of dosages sufficient to affect treatment (e.g., to treat disease or nerve injury, e.g., CNS demyelinating disease, PNS demyelinating disease, MS, CNS nerve injury, PNS nerve injury, crush nerve injury, or transection nerve injury) in an animal and include dosages disclosed herein (e.g., those disclosed above). In some embodiments, an effective amount can encompass a therapeutically effective amount, as disclosed herein. In certain embodiments, an effective amount can vary depending on the subject and the particular treatment being affected. The exact amount that is required can, for example, vary from subject to subject, depending on the age and general condition of the subject, the particular adjuvant being used (if applicable), administration protocol, and the like. As such, the effective amount can, for example, vary based on the particular circumstances, and an appropriate effective amount can be determined in a particular case. An effective amount can, for example, include any dosage or composition amount disclosed herein. In some embodiments, an effective amount of a myelination enhancing inhibitor (e.g., HDAC3 inhibitor, PDA106, or RGFP966) (which can be administered to an animal such as mammals, primates, monkeys or humans) can be an amount of about 0.005 to about 50 mg/kg body weight, about 0.005 to about 80 mg/kg body weight, about 0.005 to about 100 mg/kg body weight, about 0.01 to about 15 mg/kg body weight, about 0.1 to about 10 mg/kg body weight, about 0.5 to about 7 mg/kg body weight, about 0.005 mg/kg, about 0.01 mg/kg, about 0.05 mg/kg, about 0.1 mg/kg, about 0.5 mg/kg, about 1.0 mg/kg, about 1.5 mg/kg, about 2.0 mg/kg, about 2.5 mg/kg, about 3.0 mg/kg, about 3.5 mg/kg, about 4.0 mg/kg, about 4.5 mg/kg, about 5.0 mg/kg, about 5.5 mg/kg, about 6 mg/kg, about 6.5 mg/kg, about 7.0 mg/kg, about 7.5 mg/kg, about 8.0 mg/kg, about 10 mg/kg, about 12 mg/kg, about 15 mg/kg, about 20 mg/kg, about 30 mg/kg, about 40 mg/kg, about 50 mg/kg, about 80 mg/kg, about 100 mg/kg, or about 150 mg/kg. In regard to some embodiments, the dosage can be about 0.1 mg/kg human body weight, about 0.5 mg/kg human body weight, about 1.0 mg/kg human body weight, about 1.5 mg/kg human body weight, about 2.0 mg/kg human body weight, about 2.5 mg/kg human body weight, about 3.0 mg/kg human body weight, about 3.5 mg/kg human body weight, about 4.0 mg/kg human body weight, about 4.5 mg/kg human body weight, about 5.0 mg/kg human body weight, about 10 mg/kg human body weight, about 50 mg/kg human body weight, about 80 mg/kg human body weight, about 100 mg/kg human body weight, or about 200 mg/kg human body weight. In some instances, an effective amount of a myelination enhancing inhibitor (e.g., HDAC3 inhibitor, PDA106, or RGFP966) (which can be administered to an animal such as mammals, rodents, mice, rabbits, feline, porcine, or canine) can be an amount of about 0.005 to about 50 mg/kg body weight, about 0.005 to about 100 mg/kg body weight, about 0.005 to about 200 mg/kg body weight, about 0.01 to about 15 mg/kg body weight, about 0.1 to about 10 mg/kg body weight, about 0.5 to about 7 mg/kg body weight, about 0.005 mg/kg, about 0.01 mg/kg, about 0.05 mg/kg, about 0.1 mg/kg, about 0.5 mg/kg, about 1.0 mg/kg, about 1.5 mg/kg, about 2.0 mg/kg, about 2.5 mg/kg, about 3.0 mg/kg, about 3.5 mg/kg, about 4.0 mg/kg, about 4.5 mg/kg, about 5.0 mg/kg, about 5.5 mg/kg, about 6 mg/kg, about 6.5 mg/kg, about 7.0 mg/kg, about 7.5 mg/kg, about 8.0 mg/kg, about 10 mg/kg, about 20 mg/kg, about 30 mg/kg, about 40 mg/kg, about 50 mg/kg, about 80 mg/kg, about 100 mg/kg, about 150 mg/kg, about 200 mg/kg, or about 250 mg/kg. The amount of a myelination enhancing inhibitor (e.g., HDAC3 inhibitor, PDA106, or RGFP966) can be any amount disclosed herein (e.g., an amount disclosed in the previous sentences). In some embodiments, an effective amount of a myelination enhancing inhibitor (e.g., HDAC3 inhibitor, PDA106, or RGFP966) (which can be administered to an animal such as mammals, primates, monkeys or humans) can be an amount of about 1 to about 1000 mg/kg body weight, about 5 to about 500 mg/kg body weight, about 10 to about 200 mg/kg body weight, about 25 to about 100 mg/kg body weight, about 0.1 mg/kg, about 0.5 mg/kg, about 1.0 mg/kg, about 1.5 mg/kg, about 2.0 mg/kg, about 2.5 mg/kg, about 3.0 mg/kg, about 3.5 mg/kg, about 4.0 mg/kg, about 4.5 mg/kg, about 5.0 mg/kg, about 5.5 mg/kg, about 6 mg/kg, about 6.5 mg/kg, about 7.0 mg/kg, about 7.5 mg/kg, about 8.0 mg/kg, about 10 mg/kg, about 25 mg/kg, about 50 mg/kg, about 100 mg/kg, about 150 mg/kg, about 200 mg/kg, about 300 mg/kg, about 400 mg/kg, about 500 mg/kg, about 600 mg/kg, about 700 mg/kg, about 800 mg/kg, about 900 mg/kg, or about 1000 mg/kg. In regard to some conditions, the dosage can be about 0.1 mg/kg human body weight, about 0.5 mg/kg human body weight, about 1.0 mg/kg human body weight, about 1.5 mg/kg human body weight, about 2.0 mg/kg human body weight, about 2.5 mg/kg human body weight, about 3.0 mg/kg human body weight, about 3.5 mg/kg human body weight, about 4.0 mg/kg human body weight, about 4.5 mg/kg human body weight, about 5.0 mg/kg human body weight, about 10 mg/kg human body weight, about 20 mg/kg human body weight, about 80 mg/kg human body weight, or about 100 mg/kg human body weight. In some instances, an effective amount of a myelination enhancing inhibitor (e.g., HDAC3 inhibitor, PDA106, or RGFP966) (which can be administered to an animal such as mammals, rodents, mice, rabbits, feline, porcine, or canine) can be an amount of about 1 to about 1000 mg/kg body weight, about 5 to about 500 mg/kg body weight, about 10 to about 200 mg/kg body weight, about 25 to about 100 mg/kg body weight, about 0.1 mg/kg, about 0.5 mg/kg, about 1.0 mg/kg, about 1.5 mg/kg, about 2.0 mg/kg, about 2.5 mg/kg, about 3.0 mg/kg, about 3.5 mg/kg, about 4.0 mg/kg, about 4.5 mg/kg, about 5.0 mg/kg, about 5.5 mg/kg, about 6 mg/kg, about 6.5 mg/kg, about 7.0 mg/kg, about 7.5 mg/kg, about 8.0 mg/kg, about 10 mg/kg, about 25 mg/kg, about 50 mg/kg, about 80 mg/kg, about 100 mg/kg, about 150 mg/kg, about 200 mg/kg, about 300 mg/kg, about 400 mg/kg, about 500 mg/kg, about 600 mg/kg, about 700 mg/kg, about 800 mg/kg, about 900 mg/kg, or about 1000 mg/kg.

"Therapeutically effective amount" means an amount effective to achieve a desired and/or beneficial effect (e.g., enhancing myelination). A therapeutically effective amount can be administered in one or more administrations. For some purposes of this invention, a therapeutically effective amount is an amount appropriate to treat an indication (e.g., to treat disease, such as MS, or nerve damage). By treating an indication is meant achieving any desirable effect, such as one or more of palliate, ameliorate, stabilize, reverse, slow, or delay disease (e.g., MS) progression, increase the quality of life, or to prolong life. Such achievement can be measured by any suitable method, such as but not limited to measurement of the extent of myelination (e.g., g ratio), extent of motor function (e.g., toe spreading, latency to fall), action potential, nerve function, nerve conduction velocity, nerve CMAP amplitude, nerve CMAP duration, number of myelinated axons per area, extent of axonal regrowth, clinical EAE score, an MS progression test (e.g., using one or more of Expanded Disability Status Scale, Functional System Score, or Multiple Sclerosis Functional Composite), or any suitable method to assess the progression of the disease, (e.g., MS) or nerve damage (e.g., CNS nerve damage or PNS nerve damage).

In some embodiments, other treatments are optionally included, and can be used with the inventive treatments described herein (e.g., administering a myelination enhancing inhibitor (e.g., HDAC3 inhibitor, PDA106, or RGFP966)). Other treatments can comprise any known treatment (e.g., MS treatment) that is suitable to treat the disease or nerve injury. Some treatments can include related surgeries.

In some embodiments, additional optional treatments (e.g., as an "other treatment") can also include one or more of surgical intervention, hormone therapies, immunotherapy, adjuvant systematic therapies, and MS therapies.

Compositions Used for Treating

In certain embodiments, the myelination enhancing inhibitor (e.g., HDAC3 inhibitor, PDA106, or RGFP966) can be part of a composition and can be in an amount (by weight of the total composition) of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, or no more than about 99.99%, from about 0.0001% to about 99%, from about 0.0001% to about 50%, from about 0.01% to about 95%, from about 1% to about 95%, from about 10% to about 90%, or from about 25% to about 75%.

In some embodiments, the myelination enhancing inhibitor (e.g., HDAC3 inhibitor, PDA106, or RGFP966) can be purified or isolated in an amount (by weight of the total composition) of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, no more than about 99.99%, from about 0.0001% to about 99%, from about 0.0001% to about 50%, from about 0.01% to about 95%, from about 1% to about 95%, from about 10% to about 90%, or from about 25% to about 75%.

Some embodiments of the present invention include compositions comprising the myelination enhancing inhibitor (e.g., HDAC3 inhibitor, PDA106, or RGFP966). In certain embodiments, the composition is a pharmaceutical composition, such as compositions that are suitable for administration to animals (e.g., mammals, primates, monkeys, humans, canine, feline, porcine, mice, rabbits, or rats). In some instances, the pharmaceutical composition is non-toxic, does not cause side effects, or both. In some embodiments, there may be inherent side effects (e.g., it may harm the patient or may be toxic or harmful to some degree in some patients).

"Therapeutically effective amount" means an amount effective to achieve a desired and/or beneficial effect. An effective amount can be administered in one or more administrations. For some purposes of this invention, a therapeutically effective amount is an amount appropriate to treat an indication (e.g., to treat disease, such as MS, or nerve damage). By treating an indication is meant achieving any desirable effect, such as one or more of palliate, ameliorate, stabilize, reverse, slow, or delay disease (e.g., MS) progression, increase the quality of life, or to prolong life. Such achievement can be measured by any suitable method, such as but not limited to measurement of the extent of myelination (e.g., g ratio), extent of motor function (e.g., toe spreading, latency to fall), action potential, nerve function, nerve conduction velocity, nerve CMAP amplitude, nerve CMAP duration, number of myelinated axons per area, extent of axonal regrowth, clinical EAE score, an MS progression test (e.g., using one or more of Expanded Disability Status Scale, Functional System Score, or Multiple Sclerosis Functional Composite), or any suitable method to assess the progression of the disease, (e.g., MS) or nerve damage (e.g., CNS nerve damage or PNS nerve damage).

In some embodiments, the myelination enhancing inhibitor (e.g., HDAC3 inhibitor, PDA106, or RGFP966) can be part of a pharmaceutical composition and can be in an amount of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, no more than about 99.99%, from about 0.001% to about 99%, from about 0.001% to about 50%, from about 0.1% to about 99%, from about 1% to about 95%, from about 10% to about 90%, or from about 25% to about 75%. In some embodiments, the pharmaceutical composition can be presented in a dosage form which is suitable for the topical, subcutaneous, intrathecal, intraperitoneal, oral, parenteral, rectal, cutaneous, nasal, vaginal, or ocular administration route. In other embodiments, the pharmaceutical composition can be presented in a dosage form which is suitable for parenteral administration, a mucosal administration, intravenous administration, depot injection (e.g., solid or oil based), subcutaneous administration, topical administration, intradermal administration, oral administration, sublingual administration, intranasal administration, or intramuscular administration. The pharmaceutical composition can be in the form of, for example, tablets, capsules, pills, powders granulates, suspensions, emulsions, solutions, gels (including hydrogels), pastes, ointments, creams, plasters, drenches, delivery devices, suppositories, enemas, injectables, implants, sprays, aerosols or other suitable forms.

In some embodiments, the pharmaceutical composition can include one or more formulary ingredients. A "formulary ingredient" can be any suitable ingredient (e.g., suitable for the drug(s), for the dosage of the drug(s), for the timing of release of the drugs(s), for the disease, for the disease state, or for the delivery route) including, but not limited to, water (e.g., boiled water, distilled water, filtered water, pyrogen-free water, or water with chloroform), sugar (e.g., sucrose, glucose, mannitol, sorbitol, xylitol, or syrups made therefrom), ethanol, glycerol, glycols (e.g., propylene glycol), acetone, ethers, DMSO, surfactants (e.g., anionic surfactants, cationic surfactants, zwitterionic surfactants, or nonionic surfactants (e.g., polysorbates)), oils (e.g., animal oils, plant oils (e.g., coconut oil or *arachis* oil), or mineral oils), oil derivatives (e.g., ethyl oleate, glyceryl monostearate, or hydrogenated glycerides), excipients, preservatives (e.g., cysteine, methionine, antioxidants (e.g., vitamins (e.g., A, E, or C), selenium, retinyl palmitate, sodium citrate, citric acid, chloroform, or parabens, (e.g., methyl paraben or propyl paraben)), or combinations thereof. For example, parenteral administration, a mucosal administration, intravenous administration, depot injection (e.g., solid or oil based), subcutaneous administration, topical administration, intradermal administration, oral administration, sublingual administration, intranasal administration, or intramuscular administration, could include one or more formulary ingredients.

In certain embodiments, pharmaceutical compositions can be formulated to release the myelination enhancing inhibitor (e.g., HDAC3 inhibitor, PDA106, or RGFP966) substantially immediately upon the administration or any substantially predetermined time or time after administration. Such formulations can include, for example, controlled release formulations such as various controlled release compositions and coatings. For example, a parenteral administration, a mucosal administration, intravenous administration, depot injection (e.g., solid or oil based), subcutaneous administration, topical administration, intradermal administration, oral administration, sublingual administration, intranasal administration, or intramuscular administration, could be used for a controlled release (e.g., of myelination enhancing inhibitor, HDAC3 inhibitor, PDA106, or RGFP966), and in some instances, could be administered once per hour (or once per day, several times per day, more than once per day, once per week, several times per week, once per three months, once per six months, or once per year).

Other formulations (e.g., formulations of a pharmaceutical composition) can, in certain embodiments, include those incorporating the drug (or control release formulation) into food, food stuffs, feed, or drink. For example, the myelination enhancing inhibitor (e.g., HDAC3 inhibitor, PDA106, or RGFP966) could be administered orally once per day, twice per day, three times per day, more than once per day, once per two days, or once per week.

Some embodiments of the invention can include methods of treating an organism for disease or nerve injury (e.g., CNS demyelinating disease, PNS demyelinating disease, MS, CNS nerve injury, PNS nerve injury, crush nerve injury, or transection nerve injury). In certain embodiments, treating comprises administering the myelination enhancing inhibitor (e.g., HDAC3 inhibitor, PDA106, or RGFP966). In other embodiments, treating comprises administering the myelination enhancing inhibitor (e.g., HDAC3 inhibitor, PDA106, or RGFP966) to an animal that is effective to treat disease or nerve injury (e.g., CNS demyelinating disease, PNS demyelinating disease, MS, CNS nerve injury, PNS nerve injury, crush nerve injury, or transection nerve injury). In some embodiments, a composition or pharmaceutical composition comprises the myelination enhancing inhibitor (e.g., HDAC3 inhibitor, PDA106, or RGFP966) which can be administered to an animal (e.g., mammals, primates, monkeys, or humans) in an amount of about 0.005 to about 100 mg/kg body weight, about 0.005 to about 50 mg/kg body weight, about 0.01 to about 15 mg/kg body weight, about 0.1 to about 10 mg/kg body weight, about 0.5 to about 7 mg/kg body weight, about 0.005 mg/kg, about 0.01 mg/kg, about 0.05 mg/kg, about 0.1 mg/kg, about 0.5 mg/kg, about 1.0 mg/kg, about 1.5 mg/kg, about 2.0 mg/kg, about 2.5 mg/kg, about 3.0 mg/kg, about 3.5 mg/kg, about 4.0 mg/kg, about 4.5 mg/kg, about 5 mg/kg, about 5.5 mg/kg, about 6 mg/kg, about 6.5 mg/kg, about 7 mg/kg, about 7.5 mg/kg, about 8 mg/kg, about 10 mg/kg, about 12 mg/kg, or about 15 mg/kg. In regard to some conditions, the dosage can be about 0.5 mg/kg human body weight, about 1.0 mg/kg human body weight, about 1.5 mg/kg human body weight, about 2.0 mg/kg human body weight, about 2.5 mg/kg human body weight, about 3.0 mg/kg human body weight, about 3.5 mg/kg human body weight, about 4.0 mg/kg human body weight, about 4.5 mg/kg human body weight, about 5.0 mg/kg human body weight, about 6.5 mg/kg human body weight, about 10 mg/kg human body weight, about 50 mg/kg human body weight, about 80 mg/kg human body weight, or about 100 mg/kg human body weight. In some instances, some animals (e.g., mammals, mice, rabbits, feline, porcine, or canine) can be administered a dosage of about 0.005 to about 200 mg/kg body weight, about 0.005 to about 50 mg/kg body weight, about 0.01 to about 15 mg/kg body weight, about 0.1 to about 10 mg/kg body weight, about 0.5 to about 7 mg/kg body weight, about 0.005 mg/kg, about 0.01 mg/kg, about 0.05 mg/kg, about 0.1 mg/kg, about 1.0 mg/kg, about 1.5 mg/kg, about 2.0 mg/kg, about 2.5 mg/kg, about 3.0 mg/kg, about 3.5 mg/kg, about 4.0 mg/kg, about 4.5 mg/kg, about 5.0 mg/kg, about 10 mg/kg, about 20 mg/kg, about 30 mg/kg, about 40 mg/kg, about 50 mg/kg, about 80 mg/kg, about 100 mg/kg, about 150 mg/kg, about 200 mg/kg, or about 250 mg/kg. Of course, those skilled in the art will appreciate that it is possible to employ many concentrations in the methods of the present invention, and using, in part, the guidance provided herein, will be able to adjust and test any number of concentrations in order to find one that achieves the desired result in a given circumstance. In other embodiments, the myelination enhancing inhibitor (e.g., HDAC3 inhibitor, PDA106, or RGFP966) can be administered in combination with one or more other therapeutic agents to treat a given disease or nerve injury (e.g., CNS demyelinating disease, PNS demyelinating disease, MS, CNS nerve injury, PNS nerve injury, crush nerve injury, or transection nerve injury).

In some embodiments, the compositions can include a unit dose of one or more the myelination enhancing inhibitor (e.g., HDAC3 inhibitor, PDA106, or RGFP966) in combination with a pharmaceutically acceptable carrier and, in addition, can include other medicinal agents, pharmaceutical agents, carriers, adjuvants, diluents, and excipients. In certain embodiments, the carrier, vehicle or excipient can facilitate administration, delivery and/or improve preservation of the composition. In other embodiments, the one or more carriers, include but are not limited to, saline solutions such as normal saline, Ringer's solution, PBS (phosphate-buffered saline), and generally mixtures of various salts including potassium and phosphate salts with or without sugar additives such as glucose. Carriers can include aqueous and non-aqueous sterile injection solutions that can contain antioxidants, buffers, bacteriostats, bactericidal antibiotics, and solutes that render the formulation isotonic with the bodily fluids of the intended recipient; and aqueous and non-aqueous sterile suspensions, which can include suspending agents and thickening agents. In other embodiments, the one or more excipients can include, but are not limited to water, saline, dextrose, glycerol, ethanol, or the like, and combinations thereof. Nontoxic auxiliary substances, such as wetting agents, buffers, or emulsifiers may also be added to the composition. Oral formulations can include such normally employed excipients as, for example, pharmaceutical grades of mannitol, lactose, starch, magnesium stearate, sodium saccharine, cellulose, and magnesium carbonate.

The presently-disclosed subject matter is further illustrated by the following specific but non-limiting examples. The following examples may include compilations of data that are representative of data gathered at various times during the course of development and experimentation related to the present invention.

EXAMPLES

Example Set A

Materials and Methods

Additional methods and materials, and related discussion, can be found at HE et al., "A Histone Deacetylase 3-Dependent Pathway Delimits Peripheral Myelin Growth and Functional Regeneration" Nature Medicine (2018) Vol. 24, No. 3, pp. 338-351 (doi:10.1038/nm.4483) and related supplementary materials ("He at el. 2018"), which is herein incorporated by reference in its entirety.

Animals

Mice homozygous for floxed alleles of Hdac3 (Hdac3$^{fl/fl}$) (Montgomery R L, et al. Maintenance of cardiac energy metabolism by histone deacetylase 3 in mice. J Clin Invest. 2008; 118:3588-3597) and Tead4 (Tead4$^{fl/fl}$) (Yagi R, et al. Transcription factor TEAD4 specifies the trophectoderm lineage at the beginning of mammalian development. Development. 2007; 134:3827-3836) were crossed with mice carrying Dhh-Cre (Jaegle M, et al. The POU proteins Brn-2 and Oct-6 share important functions in Schwann cell development. Genes Dev. 2003; 17:1380-1391) or Cnp-Cre (Lappe-Siefke C, et al. Disruption of Cnp1 uncouples oligodendroglial functions in axonal support and myelination. Nat Genet. 2003; 33:366-374) to generate Hdac3 and Tead4 mutant mice, respectively. Inducible knockout mice were generated by crossing Hdac3$^{fl/fl}$ mice with the inducible Cre recombinase Cre-ERT under the control of the Plp promoter (Pip-CreERT) (Doerflinger N H, Macklin W B, Popko B. Inducible site-specific recombination in myelinating cells. Genesis. 2003; 35:63-72) followed by tamoxifen injection. Animals of either sex were used in the study and litter-mates were used as controls unless otherwise indicated. The mouse strains used in this study were generated and maintained on a mixed C57Bl/6; 129Sv background and housed in a vivarium with a 12-hour light/dark cycle. All studies applied with all relevant animal use guidelines and ethical regulations. All animal use and study protocols were approved by the Institutional Animal Care and Use Committee at the Cincinnati Children's Hospital Medical Center, USA.

Primary Rat SC Culture

Rat SCs from sciatic nerves of newborn rats (1-2 days old) were isolated as described previously (Wu L M, et al. Zeb2 recruits HDAC-NuRD to inhibit Notch and controls Schwann cell differentiation and remyelination. Nat Neurosci. 2016; 19:1060-1072, which is herein incorporated by reference in its entirety). SCs were grown in DMEM/10% FBS (Life Technologies), supplemented with 10 ng/ml neuregulin 1 (NRG1 type III; 396-HB-050; R&D Systems), and 5 µM forskolin (Sigma, F6886), plus L-glutamine and penicillin/streptomycin, hereafter denoted as SC proliferation medium. Cells between passages 2 and 5 were used in all experiments. >95% SC purity was achieved, assessed by positive SOX10 and S100β immunoreactivity. To initiate differentiation, SCs were cultured in differentiation medium containing DMEM/0.5% FBS and 1 mM dibutyl cyclic AMP (Sigma, D0627) with L-glutamine and penicillin/streptomycin, for the length of time indicated in the text, depending on the assays used. Human neurofibroma-derived Schwann cell lines SNF02.2 (ATCC CRL-2885) and SNF96.2 (ATCC CRL-2884) were propagated in DMEM/10% FBS plus L-glutamine and penicillin/streptomycin. All tissue culture containers and coverslips were coated with 50 µg/ml poly-L-lysine (Sigma, P7890) in PBS for at least 30 min at room temperature and then rinsed with distilled water.

Small Molecule Compound Screening

The 96-well plates were coated with poly-1-lysine (50 µg/ml) for 30 minutes at room temperature and then rinsed with distilled water and air dried. In each well, 5,000 primary SCs isolated from rat neonates were seeded and maintained in chemically defined medium composed of in DMEM/10% FBS (Life Technologies), supplemented with 10 ng/ml neuregulin 1 (NRG1; R&D Systems, 396-HB-050), and 5 µM forskolin (Sigma, F6886), plus L-glutamine and penicillin/streptomycin for 2 d before screening. Each compound in the Epigenetics compound library (Cayman, 11076) was diluted to a final concentration of 5 µM in the medium containing DMEM/0.5% FBS with L-glutamine and penicillin/streptomycin. SCs were treated with diluted compounds for 8 hours. Treated SCs were washed with PBS and then treated with SingleShot Cell Lysis Kite (172-5080, BioRad) following the manufacturer's instructions. The cell lysates from each well were collected for qRT-PCR by using iTaq Universal SYBR Green One-Step Kit (BioRad 172-5150,) following the instructions. Each compound was tested in triplicate.

In Vivo Administration of HDAC3 Inhibitors

HDAC3 inhibitors, RGFP966 (MedKoo, 510205; a selective HDAC3 inhibitor with IC50 of 80 nM; half-life ~1 hr) and PDA106 (MedKoo, 406720; preference toward HDAC3 inhibition with Ki of 14 nM; half-life ~8 hr) appear to be blood-brain barrier permeable, benzamide-type HDAC3-selective inhibitors. They were dissolved in DMSO (calculated to be 10% of the final volume) and diluted with 30% hydroxypropyl-β-cyclodextrin, 0.1 M acetate, pH 5.4. PDA106 and RGFP966 were administered at a dose of 100 mg/kg and 10 mg/kg separately as previously described (Malvaez M, et al. HDAC3-selective inhibitor enhances extinction of cocaine-seeking behavior in a persistent manner Proc Natl Acad Sci USA. 2013; 110:2647-2652, which is herein incorporated by reference in its entirety; Rai M, et al. HDAC inhibitors correct frataxin deficiency in a Friedreich ataxia mouse model. PLoS One. 2008; 3:e1958, which is herein incorporated by reference in its entirety). Pups were given subcutaneous injections of drugs daily first week and intraperitoneal injections every 2 days the second week for 3 days. Sciatic nerves were then collected and analyzed at indicated time points. For treatment of adult mice, drugs were injected daily via i.p. after sciatic nerves transection injury first week, and every 2 days after the first week for 3 days and analyzed at corresponding time points. Administrations of the HDAC3 inhibitors were well tolerated and no harmful side effects were observed in the mice throughout the entire period of experiments.

SC-DRG Co-Culture

DRG neurons were isolated from embryonic day 16.5 (E16.5) rat spinal cords and plated as explants on collagen-coated coverslips. Cultures were maintained in serum-free neurobasal medium (NB medium; 2% B27 supplement, 2 mM L-glutamine, 0.4% glucose, and 50 ng/ml 2.5 S NGF (Harlan, 005017). Non-neuronal cells were removed by feeding the cultures with NB medium containing 5-fluorodeoxyuridine and uridine. SC were isolated from postnatal day 2 sciatic nerves and expanded in SC proliferation medium. SC-DRG co-cultures were established by seeding purified DRG neuron cultures with 100,000 SCs in C. media (MEM, 10% FBS, 2 mM L-glutamine, 0.4% glucose, and 50 ng/ml 2.5 S NGF). 3 days after SC plating, C. media was supplemented with 50 µg/ml ascorbic acid (Sigma, A0278) to initiate myelination. SC-DRG co-cultures were allowed to myelinate for 10 days, with fresh media provided every 2 days. To determine the extent of myelination in SC-DRG co-cultures, the total number of MBP segments were counted in micrographs from 10-12 random fields per coverslip.

Tamoxifen Induction of Floxed Allele Deletion

Tamoxifen (Sigma, T5648) was dissolved to a stock concentration of 20 mg/ml in a vehicle of ethanol and sunflower seed oil (1:9 v/v). For perinatal tamoxifen injections, tamoxifen stock was injected i.p. at 2 mg/100 µl to lactating mothers, thus administering tamoxifen to neonatal pups, beginning at P0. Tamoxifen was injected i.p. into pups after P5. Control mice were treated identically. Sciatic nerves of pups were analyzed at indicated dates for immunostaining and EM.

Sciatic Nerve Transection Injury

Young or aging adult mice were under general anesthesia with injection of a mixture of ketamine (90 mg/kg) and xylazine (10 mg/kg). Right sciatic nerves were exposed and transected at the midthigh level. Exposed left sciatic nerves were used as uncut controls. Mice were treated with Hdac3 inhibitors or tamoxifen to delete Hdac3 floxed alleles following injury. Nerves were collected at indicated timepoints post-surgery and processed for immunohistochemistry or EM.

Assessment of Sensory and Motor Recovery

Mice after nerve transection injury were tested for sensory recovery by pinprick assay. An austerlitz insect pin (size 000) (Fine Science Tools Inc.) was gently applied to the plantar surface of the paw without moving the paw or penetrating the skin. The most lateral part of the plantar surface of the hind paw corresponding to the sensory field of the sciatic nerve was divided into 5 areas A-E. The pinprick was applied twice from the most lateral toe to the heel. A response was considered positive when the animal briskly removed its paw, and the mouse was graded 1 for this area, and then tested for the next one. Scoring was done blinded to the genotype.

To assess motor recovery after nerve transection injury, the movement of the toes was evaluated. The reappearance of the toe spreading reflex results from reinnervation of the small muscles of the foot and was scored: 0, no spreading; 1, intermediate spreading with all toes; and 2, full spreading. Full spreading was defined as a complete, wide, and sustained for at least 2 seconds spreading of the toes. Mice were scored when a full response was observed on the contralateral side to the injury. Mice were evaluated twice in each experimental session with at least a 45-minute interval. Scoring was done blinded to the genotype. For rotarod analysis, mice were challenged on a rotarod apparatus specifically designed for mouse usage (Med Associates) to evaluate motor function. Animals were trained for 3 days and tested three times with 1 hour intervals between testing trials. An acceleration setting was used to test motor function, the initial speed started at 4 rotations per minute (rpm) with gradual acceleration to a maximum of 40 rpm. The mean latency to fall (seconds) of three separate trials on the rotarod apparatus was reported. Recordings were performed with the experimenter blinded to treatment groups or mouse genotypes.

Immunofluorescence Staining

The sciatic nerves of mice at defined ages were dissected and fixed for 15 min in 4% PFA in 0.1 M sodium phosphate buffer (pH 7.4), embedded in OCT, cryoprotected in 25% sucrose and sectioned at 12 µm as longitudinal or cross sections using a cryostat or at 30 µm using a vibratome. Tissue sections or cells were permeabilized and blocked in blocking buffer (0.3% Triton X-100 and 5% normal donkey serum in PBS) for 1 h at 25° C., followed by incubation with primary antibodies overnight at 4° C. We used antibodies to HDAC3 (Rabbit; Santa Cruz Biotechnology, sc-11417), MPZ (Rabbit; Abcam, ab31851), MBP (Goat; Santa Cruz Biotechnology, sc-13914 and Mouse; Biolegend, 836501), NF-M (Rabbit, Millipore, AB1987), SOX10 (Goat; Santa Cruz Biotechnology, sc-17342), EGR2 (Rabbit; Santa Cruz, sc-20690), Ki67 (Rabbit; Thermo Scientific, RM-9106), SOX2 (Goat; Santa Cruz Biotechnology, sc-17320), HDAC5 (Mouse; Sigma, H4538), CD31 (Rat; BD Pharmingen, 553370) and CASPR (Mouse; NeuroMab, 75-001). Secondary antibodies conjugated to Cy2, Cy3 or Cy5 were from Jackson ImmunoResearch Laboratories. All images were acquired using a Nikon C2$^+$ confocal microscope.

Electron Microscopy and Morphometric Analysis

Mice were perfused with 4% PFA, 2.5% glutaraldehyde in 0.1 M sodium cacodylate buffer, pH 7.2. Sciatic nerves were dissected and fixed in the same fixative solution overnight. Nerves were rinsed in PBS, postfixed in 1% OsO4 in PBS for 1 hour, dehydrated in graded ethanol, infiltrated with propylene oxide, and embedded in Epon. Semithin sections were stained with toluidine blue, and thin sections were stained with lead citrate. The morphometric measurements were performed in toluidine blue-stained semithin sections. The number of myelinated axons per nerve were analyzed in ultrathin sections using a JEOL 1200 EXII electron microscope as previously described (Wu L M, et al. Zeb2 recruits HDAC-NuRD to inhibit Notch and controls Schwann cell differentiation and remyelination. Nat Neurosci. 2016; 19:1060-1072, which is herein incorporated by reference in its entirety).

Transient Transfections

For plasmid transfections, rat SCs were transfected with expression vectors using Lipofectamine 3000 (Life Technologies) per the manufacturer's protocol and assayed for immunocytochemistry, western blotting or qRT-PCR analysis. Differentiation was assessed by immunostaining for EGR2. Multiple images were taken from each coverslip to obtain representative images from all areas of the coverslip, and at least 400 cells/coverslip were counted using ImageJ (<<https://imagej.nih.gov/ij/>>).

For siRNA knockdown in SCs, we used Lipofectamine RNAiMAX (Life Technologies) per manufacturer's instructions and assayed for qRT-PCR analysis. Hdac3 siRNA: SASI_Rn01_00031908 and SASI_Rn01_00031910; Tead1 siRNA: SASI_Rn02_00327154; Tead2 siRNA: SASI_Rn02_00229556; Tead3 siRNA: SASI_Rn02_00209091; Tead4 siRNA: SASI_Rn02_00317135 and SASI_Rn02_00317137.

Western Blotting

For western blotting, the perineurium and epineurium were removed from sciatic nerves prior to snap-freezing and storage at −80° C. Sciatic nerves and rat SCs were lysed in RIPA buffer, containing protease and phosphatase inhibitors. Western blot analysis was performed as described previously (Zhang L, et al. Hdac3 interaction with p300 histone acetyltransferase regulates the oligodendrocyte and astrocyte lineage fate switch. Dev Cell. 2016; 36:316-330, which is herein incorporated by reference in its entirety). GAPDH (Millipore MAB374) was used as an input control. The antibodies used were HDAC3 (Rabbit; Santa Cruz Biotechnology, sc-11417), MPZ (Rabbit; Abcam, ab31851), MBP (Goat; Santa Cruz Biotechnology, sc-13914), AKT (Rabbit; Cell Signaling Technology, #9272), p-AKT (Rabbit; Cell Signaling Technology, #9271), ERK (Rabbit; Cell Signaling Technology, #4695), p-ERK (Rabbit; Cell Signaling Technology, #4730), p-PI3K (Rabbit; Cell Signaling Technology, #4228), PI3K (Rabbit; Millipore, ABS233), TEAD4 (Rabbit; Santa Cruz Biotechnology, sc-101184), Flag (Rabbit; Cell Signaling Technology, #2368), PTEN (Rabbit; Cell Signaling Technology, #9559) and Acetyl-PTEN (Rabbit; Signalway Antibody, HW139). Corresponding secondary antibodies conjugated to HRP were from Jackson ImmunoResearch Laboratories (catalog numbers 111-035-144 and 111-035-003).

RNA Isolation and Quantitative Real Time-PCR

RNA from purified SCs or sciatic nerves was extracted using TRIZOL (Life Technologies). cDNA was synthesized from 1 µg RNA using iScript Reverse Transcription Supermix (BioRad) according to the manufacturer's instructions. qRT-PCR was performed using the StepOnePlus Real-time PCR System (Applied Biosystems) with quantitative SYBR green PCR mix (BioRad 170-8880) as previously described (Wu L M, et al. Zeb2 recruits HDAC-NuRD to inhibit Notch and controls Schwann cell differentiation and remyelination. Nat Neurosci. 2016; 19:1060-1072, which is herein incorporated by reference in its entirety). PCR primer sequences are available upon request.

RNA-Sequencing and Data Analysis

RNA from control, Hdac3 mutant sciatic nerves were extracted using TRIZOL (Life Technologies) followed by purification using an RNeasy Mini Kit (Qiagen). RNA-seq libraries were prepared using the Illumina RNA-Seq Preparation Kit and sequenced by a HiSeq 2000 sequencer. RNA-seq reads were aligned to mm10 using TopHat with default settings (<<http://tophat.cbcb.umd.edu>>). We used Cuff-diff to (1) estimate FPKM values for known transcripts and (2) analyze differentially expressed transcripts. In all differential expression tests, a difference was considered significant if the q value was less than 0.05 (Cuff-diff default). Heatmap of gene expression was generated using R language (version 3.2.1) and was generated based on log 2 [FPKM]. GO-analysis of gene expression changes was performed using Gene Set Enrichment (GSEA, <<http://www-.broadinstitute.org/gsea/index.jsp>>). We used ToppCluster (<<https://toppcluster.cchmc.org/>>) to construct the network of genes belonging to over-represented GO-term categories.

Chromatin Immunoprecipitation Sequencing (ChIP-Seq) Assays

ChIP assays were performed as described previously with minor modifications (Wu L M, et al. Zeb2 recruits HDAC-NuRD to inhibit Notch and controls Schwann cell differentiation and remyelination. Nat Neurosci. 2016; 19:1060-1072, which is herein incorporated by reference in its entirety). Briefly, purified rat SCs grown in proliferation and differentiation (9 hours in 1 mM cAMP-containing medium) conditions (~20 million cells) were fixed for 10 mM at room temperature with 1% formaldehyde-containing medium. Nuclei were isolated and sonicated in sonication buffer (10 mM Tris-HCl [pH 8.0], 1 mM EDTA, 0.5 mM EGTA, and protease inhibitor cocktail). Sonicated chromatin (~300 µg) was used for immunoprecipitation by incubation with antibodies overnight at 4° C. Pre-rinsed protein A/G plus agarose beads (50 µl) were added to each ChIP reaction and incubated for 1 hour at 4° C. The beads were then incubated in 200 µl elution buffer at 65° C. for 20 minutes to elute immunoprecipitated materials. The ChIP-seq libraries were prepared using NEBNext ChIP-seq Library Prep Master Mix Set for Illumina (NEB catalogue number E6240L) and then run on the Illumina sequencer HiSeq 2000. Two ChIP-seq replicates for diff_HDAC3, p300 and IgG; one replicate for Pro_HDAC3, siHdac3_H3K27ac, Scr_H3K27ac, H3k27ac and H3K4me1. The antibodies used were as follows: HDAC3 (Santa Cruz Biotechnology, sc-11417); p300 (Rabbit, Santa Cruz sc-585), H3K27ac (Rabbit, Abcam, ab4729) and H3K4me1 (Rabbit, Abcam, ab8895).

ChIP-Seq Peak-Calling and Data Analysis

All sequencing data were mapped to rat genome assembly m5 and ChIP-seq peak calling was performed as previously described using MACS (Model-based Analysis of ChIP-seq) version 1.4.2 (<<http://liulab.dfci.harvard.edu/MACS>>) with default parameters, to get primary binding regions. To ensure that our data were of high quality and reproducibility, we called peaks with enrichment ≥10-fold over control ($P \leq 10^{-9}$) and compared the peak sets using the ENCODE overlap rules. These identified primary regions were further filtered using the following criteria, to define a more stringent protein—DNA interactome: (1) the p-value cutoff was set to $\leq 10^{-9}$; (2) an enrichment of 6-fold and peak height >5.

The genome-wide distribution of protein binding regions was determined by HOMER (<<http://homer.salk.edu/homer/index.html>>) in reference to Ensembl RGSC3.4.61 release. For all ChIP-seq data sets, WIG files were generated with MACS, which were subsequently visualized using Mochiview v1.46. Hdac3—p300 co-occupancy was defined as at least a 25% overlap of Hdac3 peak by p300 peak in the genome regions co-occupied by Hdac3-p300 in ChIP-Seq and analyzed with Pearson's correlation and ToppCluster (<<https://toppcluster.cchmc.org/>>). ChIP-seq heatmaps were ordered by strength of binding. The heatmaps were drawn using the Heatmap tools provided by Cistrome (<<http://cistrome.org/ap>>).

Compound Muscle Action Potential Recording

To analyze nerve conduction and motor unit function, single compound muscle action potentials (CMAPs) were recorded in vivo from the lateral gastrocnemius muscles of wildtype littermate controls or cKO mice during electrical stimulation of the sciatic nerve under sodium pentobarbital anesthesia (50 mg/kg, i.p.) as described previously (Wu L M, et al. Zeb2 recruits HDAC-NuRD to inhibit Notch and controls Schwann cell differentiation and remyelination. Nat Neurosci. 2016; 19:1060-1072, which is herein incorporated by reference in its entirety). CMAPs were amplified and obtained using a Micro 1401 data acquisition unit and analyzed using Spike2 software (<<http://ced.co.uk/products/spkovin>>). Three successive electrical stimulations of the sciatic nerve at 2 mA (0.25-0.5 Hz, 0.1 ms duration) were initiated immediately proximal to the tibial, sural and common peroneal branches via a stimulus isolator connected to the Micro 1401. Conduction velocity was calculated after determining the latency of CMAP onset relative to the stimulus artifact induced by electrical stimulation of the sciatic nerve and the distance between recording and stimulating electrodes measured directly on the nerve. Peak CMAP amplitude and CMAP duration were calculated from each stimulation paradigm. The average of the stimulations of the sciatic nerve for each paradigm were obtained and then averaged across animals.

Statistical Analyses

All analyses were done using GraphPad Prism 6.00 (San Diego, Calif., <<www.graphpad.com>>). Data are shown in dot plots or bar graphs as mean±SEM. P<0.05 is deemed statistically significant. Data distribution was assumed to be normal, but this was not formally tested. Statistical analysis was performed by two-tailed unpaired Student's t tests between two samples, and one-way ANOVA with Tukey's post-hoc analysis for multiple comparisons, or as indicated. Quantifications were performed from at least three experimental groups in a blinded fashion. n value was defined as the number of experiments that were repeated independently with similar results. No statistical methods were used to predetermine sample sizes, but our sample sizes are similar to those generally employed in the field. No randomization was used to collect all the data, but they were quantified blindly. No animals or data points were excluded from analyses.

Data Availability.

All high-throughput data mentioned herein are publicly available from GEO under accession GSE93161. Uncropped images of blots can be found in He et al. 2018 and its related supplementary information, as found online. Further information on experimental design is available in the Life Sciences Reporting Summary related to He at al. 2018.

RESULTS

Identification of Inhibitors of SC Myelination by Epigenetic Screening.

EGR2 is a pro-myelinating regulator that serves an indicator of myelinogenic potential. We developed an unbiased gene expression-based assay using real-time quantitative PCR indexing of Egr2 to identify inhibitors of epigenetic enzymes that block SC maturation. Cultured rat SCs were treated a library of epigenetics compounds targeting enzymes including methyltransferases, demethylases, histone acetyltransferases, histone deacetylases (HDACs), and acetylated histone regulators.

Figure 1:
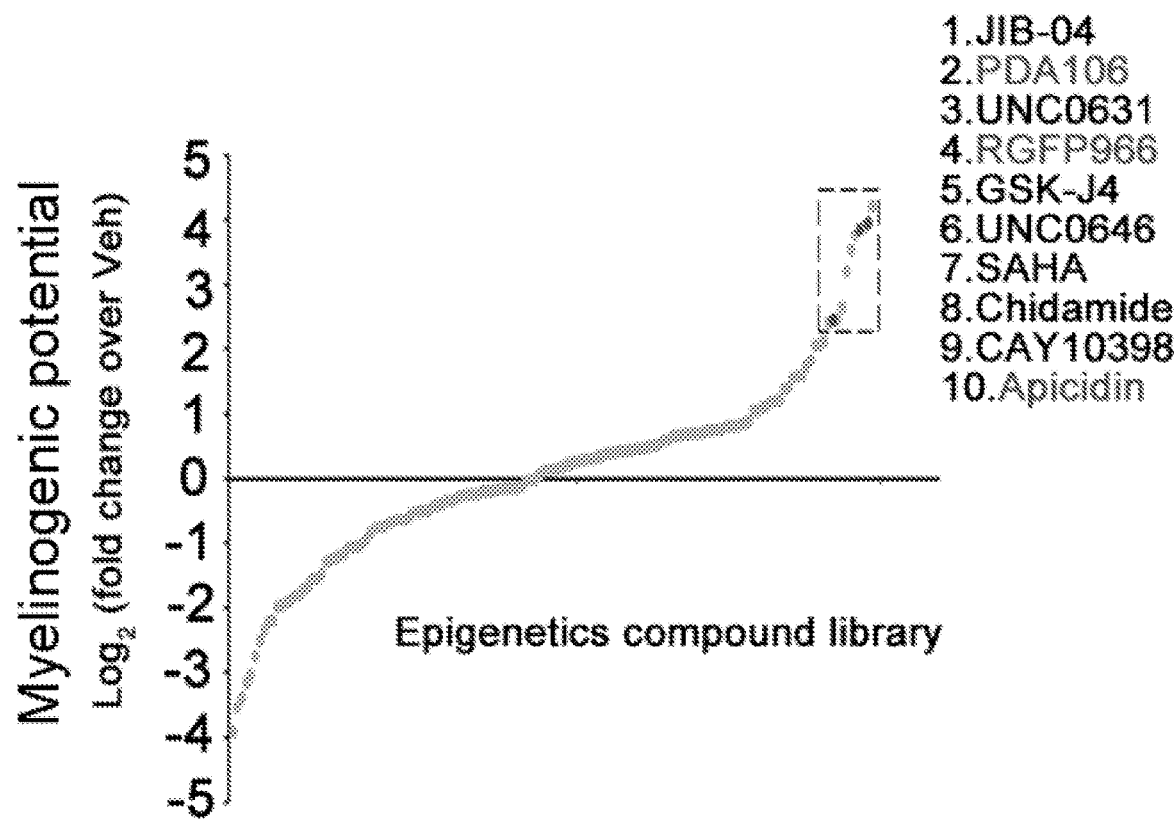
FIG. 1: Small-molecule epigenetic compound library screen for SC myelination inhibitors. (A) Relative expression of Egr2 in rat SC cultures treated with epigenetic drugs (gray dots). Data are presented as mean from three independent experiments. The top ten compounds (boxed) that induced Egr2>5 folds are listed. Red dots: compounds preferentially target HDAC3. (B) Effects of small-molecule epigenetic enzymatic inhibitors on Egr2 expression: Expression of Egr2 was assessed in SCs treated with a library of epigenetic drugs. Each point represents a single compound, with Egr2 expression compared to Veh. The red line indicates upregulation of Egr2 by more than 5-fold. The inhibitors that preferentially target HDAC3 were labeled as red. (C) Effects of small-molecule epigenetic enzymatic inhibitors on Egr2 expression: qPCR quantification of Egr2 expression in SCs treated with eleven compounds that upregulated Egr2 by more than 5-fold. (Data are presented as mean±s.e.m.; n=3 independent experiments; two-tailed unpaired Student's t-test; $P_{Veh\ versus\ JIB\text{-}04}=0.0002$, $t_{Veh\ versus\ JIB04}=12.67$, d.f.=4; $P_{Veh\ versus\ PDA106}=0.0007$, $t_{Veh\ versus\ PDA106}=9.365$, d.f.=4; $P_{Veh\ versus\ UNC0631}=0.0009$, $t_{Veh\ versus\ UNC0631}=8.974$, d.f.=4; $P_{Veh\ versus\ RGFP966}=0.0003$, $t_{Veh\ versus\ RGFP966}=12.25$, d.f.=4; $P_{Veh\ versus\ GSK\text{-}J4}=0.001$, $t_{Veh\ versus\ GSK\text{-}J4}=8.633$, d.f.=4; $P_{Veh\ versus\ UNC0646}=0.0002$, $t_{Veh\ versus\ UNC0646}=12.85$, d.f.=4; $P_{Veh\ versus\ SAHA}<0.0001$, $t_{Veh\ versus\ SAHA}=40.71$, d.f.=4; $P_{Veh\ versus\ Chidamide}<0.0001$, $t_{Veh\ versus\ Chidamide}=16.55$, d.f.=4; $P_{Veh\ versus\ CAY10398}<0.0001$, $t_{Veh\ versus\ CAY10398}=17.2$, d.f.=4; $P_{Veh\ versus\ Apicidin}=0.0003$, $t_{Veh\ versus\ Apicidin}=11.71$, d.f.=4). (D) Representative images of MPZ and phalloidin immunostaining in SC cultures treated with Veh, HDAC1/2i (FK228) HDAC8i (PCI34051), or HDAC3i (PDA106 or RGFP966) for 24 hours. n=3 independent experiments, with 15 images for each experiment. Scale bars: 50 μm. (E) Transcript levels of myelin-related genes Pmp22 and Mpz in SC cultures treated with indicated HDAC inhibitors. Transcript levels, determined by qRT-PCR, were normalized to those in vehicle-treated cells. (Data are presented as mean±s.e.m.; n=3 independent experiments; one-way ANOVA with Tukey's multiple comparisons test; Pmp22, $F_{(4,\ 10)}=154.7$, $P_{Veh\ versus\ FK228}=0.0144$, $P_{Veh\ versus\ PCI34051}>0.9999$, $P_{Veh\ versus\ RGFP966}<0.0001$, $P_{Veh\ versus\ PDA106}<0.0001$; Mpz, $F_{(4,\ 10)}=122.3$, $P_{Veh\ versus\ FK228}=0.0399$, $P_{Veh\ versus\ PCI34051}>0.9999$, $P_{Veh\ versus\ RGFP966}<0.0001$, $P_{Veh\ versus\ PDA106}<0.0001$). (F) Representative images of longitudinal cryosections of sciatic nerves from mice treated with Veh, RGFP966, or PDA106. Immunostaining was performed at P7 with EGR2 (red) and DAPI (blue). n=4 animals/group, with 5 images for each mouse. Scale bar: 20 μm. (G) Quantification at P7 of $EGR2^+$ cells in sciatic nerves of mice treated with Veh or HDAC3 inhibitors. Note that RGFP966 and PDA106 treatments increased the numbers of $EGR2^+$ cells compared to control. (Data are presented as mean±s.e.m.; n=4 animals/group; one-way ANOVA with Tukey's multiple comparisons test; $F_{(2,\ 9)}=14.7$, $P_{Veh\ versus\ RGFP966}=0.0016$, $P_{Veh\ versus\ PDA106}=0.0071$). (H) qRT-PCR showing upregulation of myelination-associated genes in sciatic nerves from Veh-, RGFP966-, or PDA106-treated mice. (Data are presented as mean±s.e.m.; n=3 independent experiments; one-way ANOVA with Tukey's multiple comparisons test; Prx, $F_{(2,\ 6)}=10.56$, $P_{Veh\ versus\ RGFP966}=0.0418$, $P_{Veh\ versus\ PDA106}=0.0103$; Mbp, $F_{(2,\ 6)}=41.28$, $P_{Veh\ versus\ RGFP966}=0.0019$, $P_{Veh\ versus\ PDA106}=0.0003$; Mpz, $F_{(2,\ 6)}=52.8$, $P_{Veh\ versus\ RGFP966}=0.0002$, $P_{Veh\ versus\ PDA106}=0.0008$; Egr2, $F_{(2,\ 6)}=60.53$, $P_{Veh\ versus\ RGFP966}=0.0004$, $P_{Veh\ versus\ PDA106}=0.0001$). (I) Representative electron micrographs of sciatic nerve cross-sections from Veh-, RGFP966-, and PDA106-treated mice at P7. n=3 animals/group, with 10 images for each mouse. Scale bars: 2 (J) Quantification of g ratios of axons in sciatic nerves from Veh-, RGFP966-, and PDA106-treated mice at P7. (Data are presented as mean±s.e.m.; n=301 axons from 3 control mice, 300 axons from 3 RGFP966 treated mice and 240 axons from 3 PDA106 treated mice; one-way ANOVA with Tukey's multiple comparisons test; $F_{(2,\ 838)}=213.9$, $P_{Veh\ versus\ RGFP966}<0.0001$, $P_{Veh\ versus\ PDA106}<0.0001$). (K) Representative electron micrographs of sciatic nerve cross-sections from Veh-, RGFP966-, and PDA106-treated mice at P15. n=3 animals/group, with 10 images for each mouse. Scale bars: 2 (L) Quantification of g ratios of axons in sciatic nerves from Veh-, RGFP966-, and PDA106-treated mice at P15. (Data are presented as mean±s.e.m.; n=300 axons from 3 mice for each group; one-way ANOVA with Tukey's multiple comparisons test; $F_{(2,\ 897)}=540.5$, $P_{Veh\ versus\ RGFP966}<0.0001$, $P_{Veh\ versus\ PDA106}<0.0001$). (M) Quantification of myelinated axons in sciatic nerves from Veh-, RGFP966-, and PDA106-treated mice at P7 and P15. (Data are presented as mean±s.e.m.; n=6 animals/group; one-way ANOVA with Tukey's multiple comparisons test; P7, $F_{(2,\ 15)}=8.807$, $P_{Veh\ versus\ RGFP966}=0.0042$, $P_{Veh\ versus\ PDA106}=0.0111$; P14, $F_{(2,\ 15)}=6.541$, $P_{Veh\ versus\ RGFP966}=0.0136$, $P_{Veh\ versus\ PDA106}=0.0239$). (N) Effects of pharmacological inhibition of HDAC3 on myelination at different stages: Upper: Schematic diagram showing drug treatment scheme. Mice were treated with Veh or PDA106 from P7 to P15. Sciatic nerves were harvested at P24. Bottom: Representative toluidine blue-stained images of cross sections of sciatic nerves from Veh- and PDA106-treated mice. Arrow indicates hypermyelinated axons. n=3 animals/group, with 5 images for each mouse. Scale bars: 20
Figure 1:
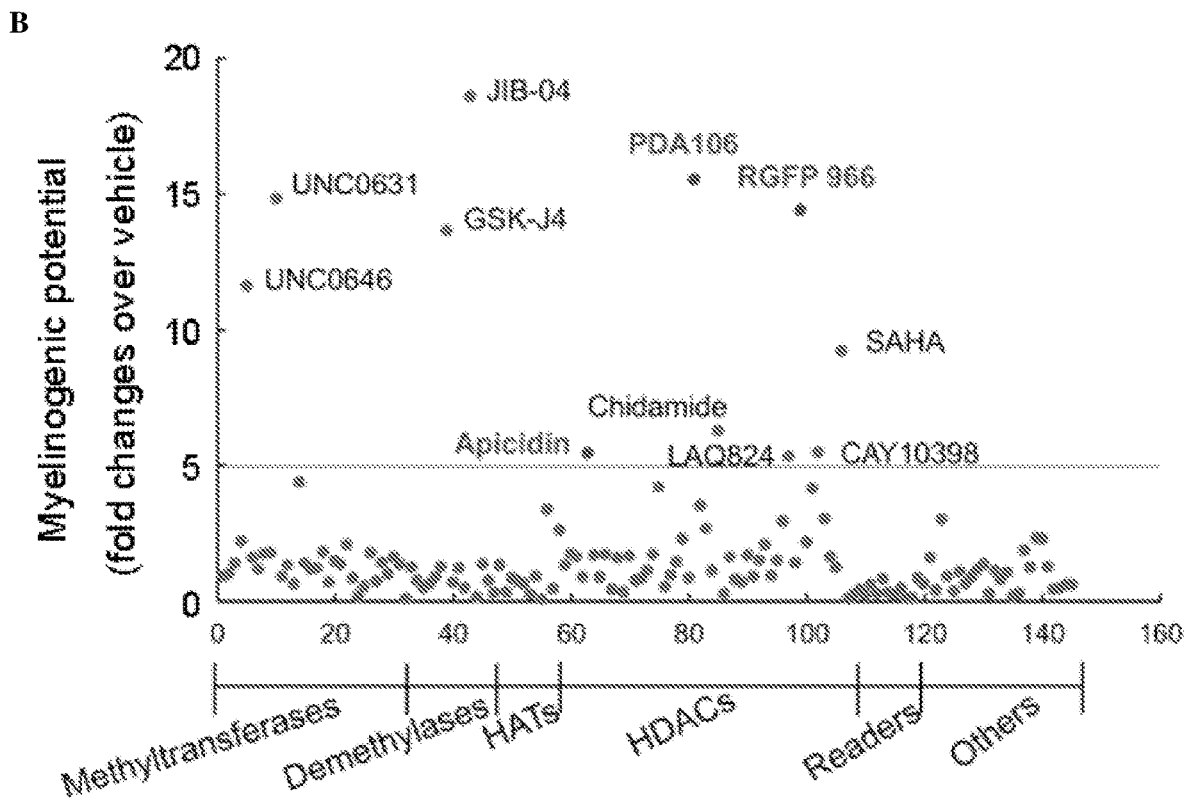
Figure 1:
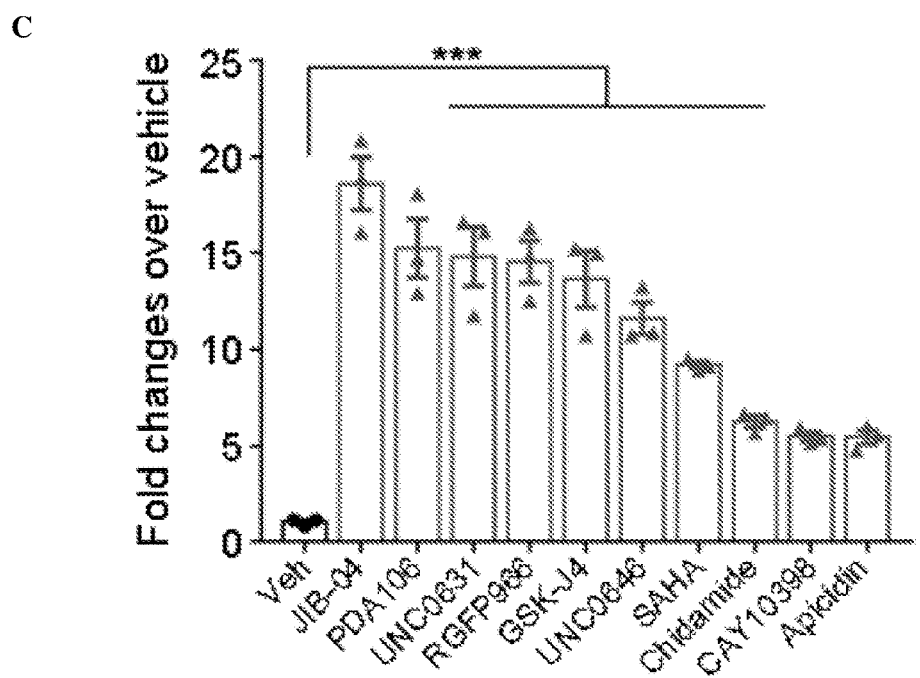
Figure 1:
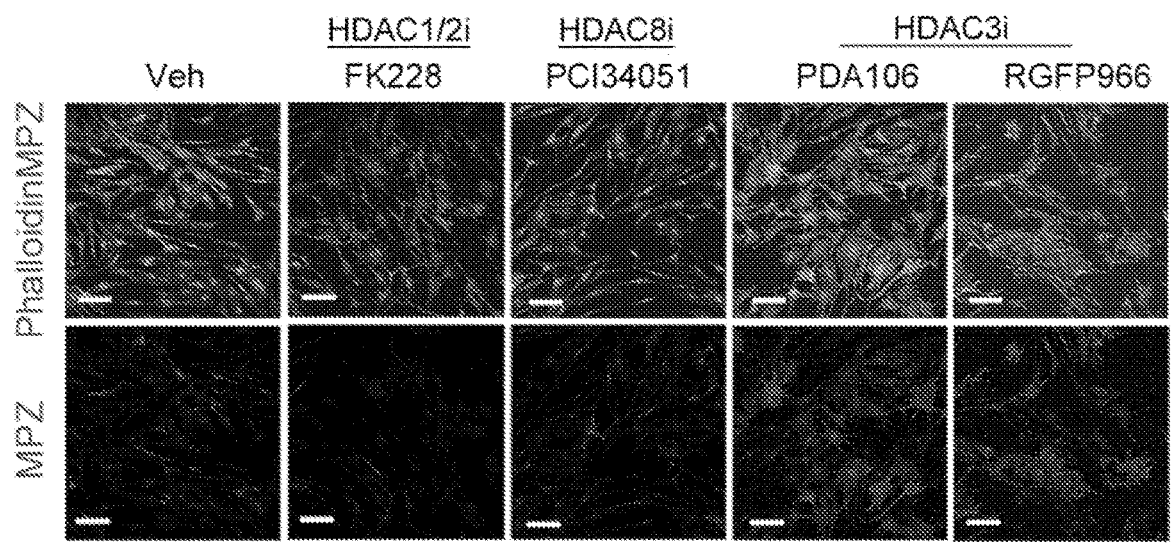
Figure 1:
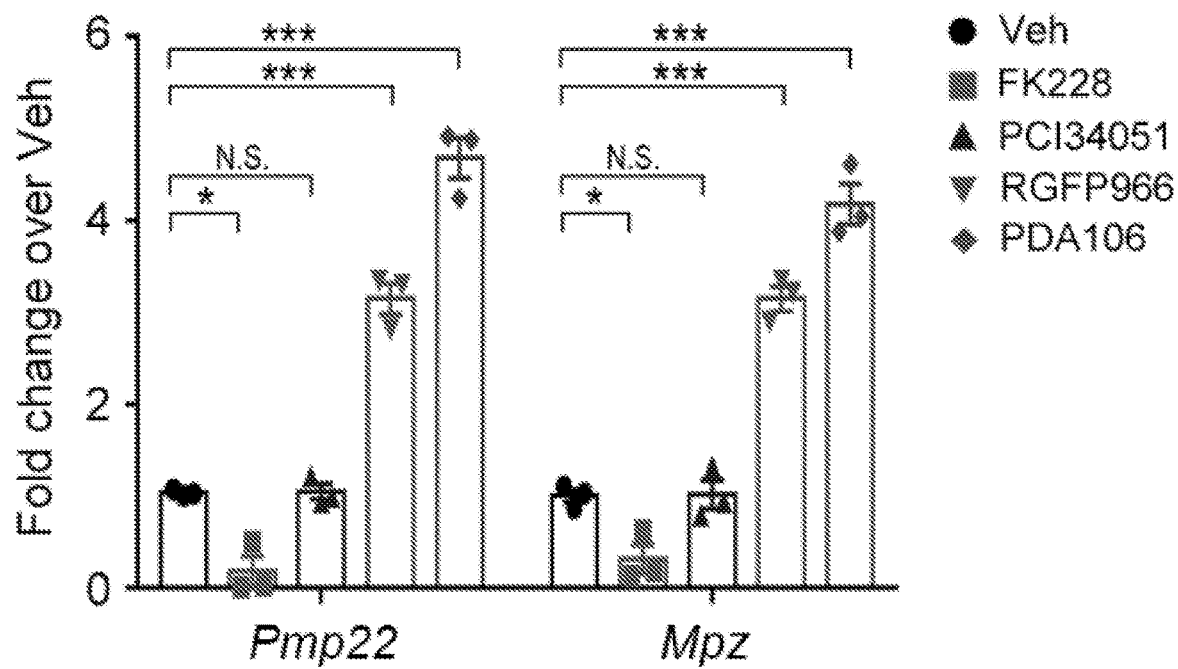
Figure 1:
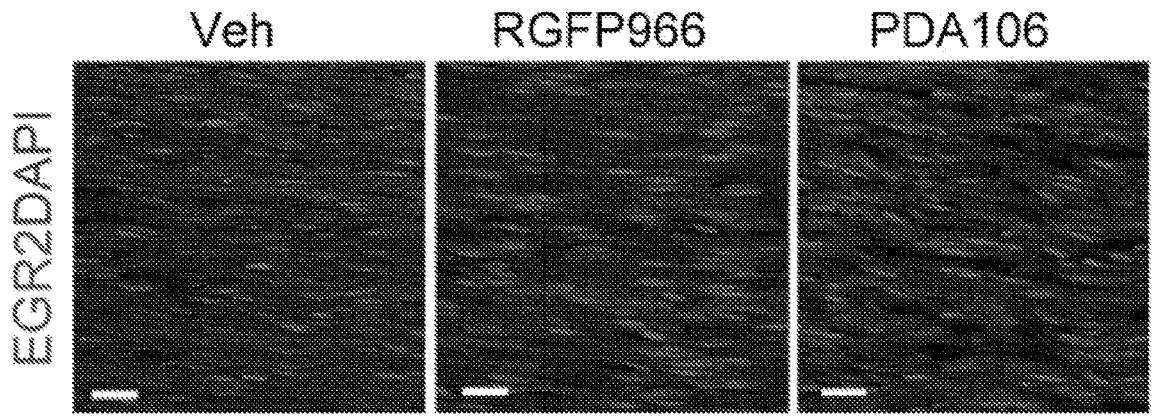
Figure 1:
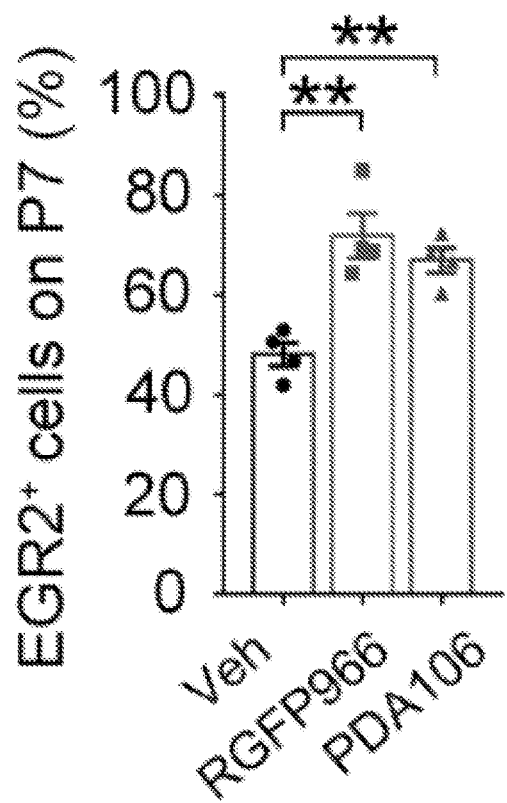
Figure 1:
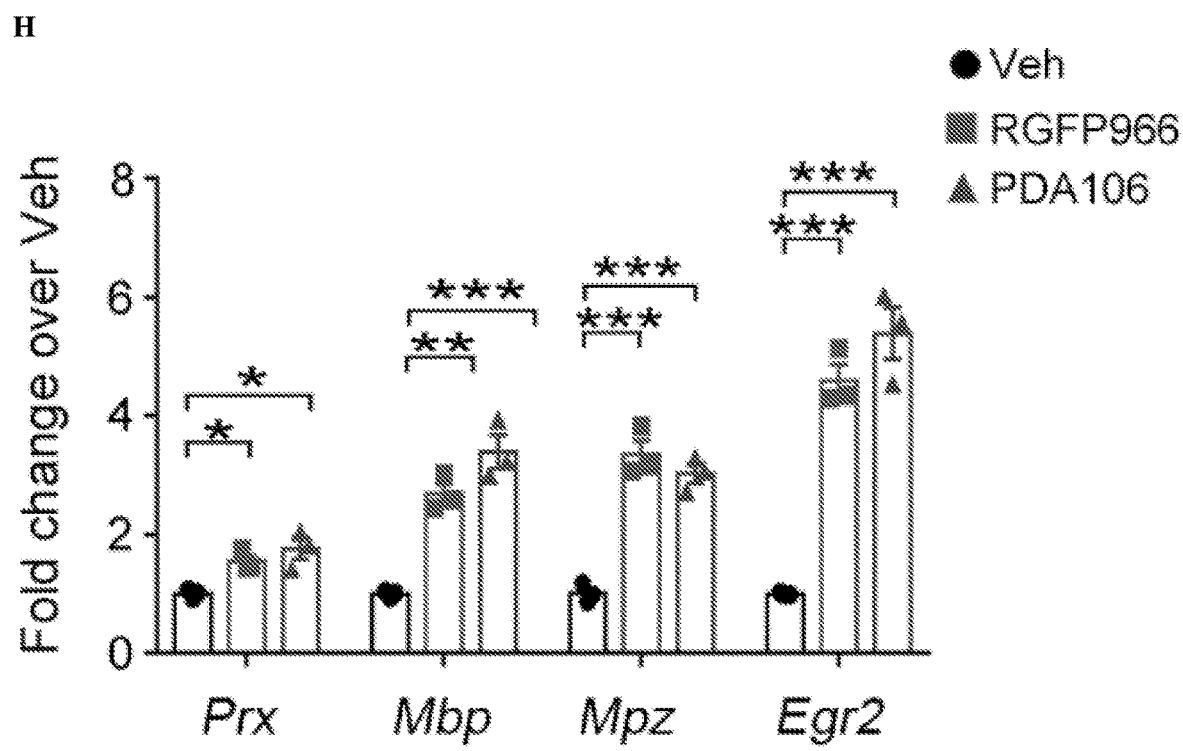
Figure 1:
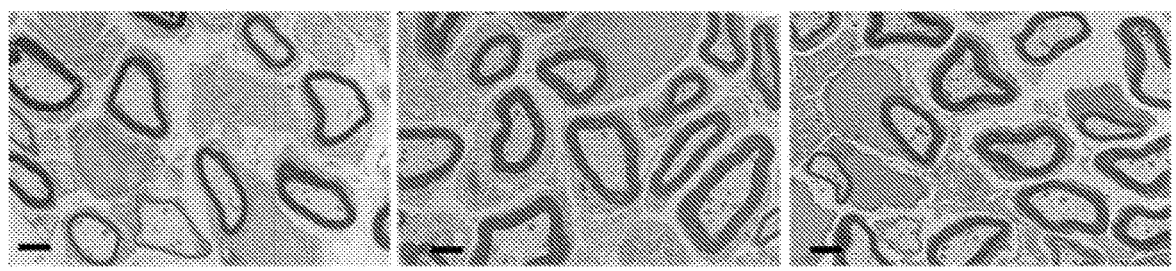
Figure 1:
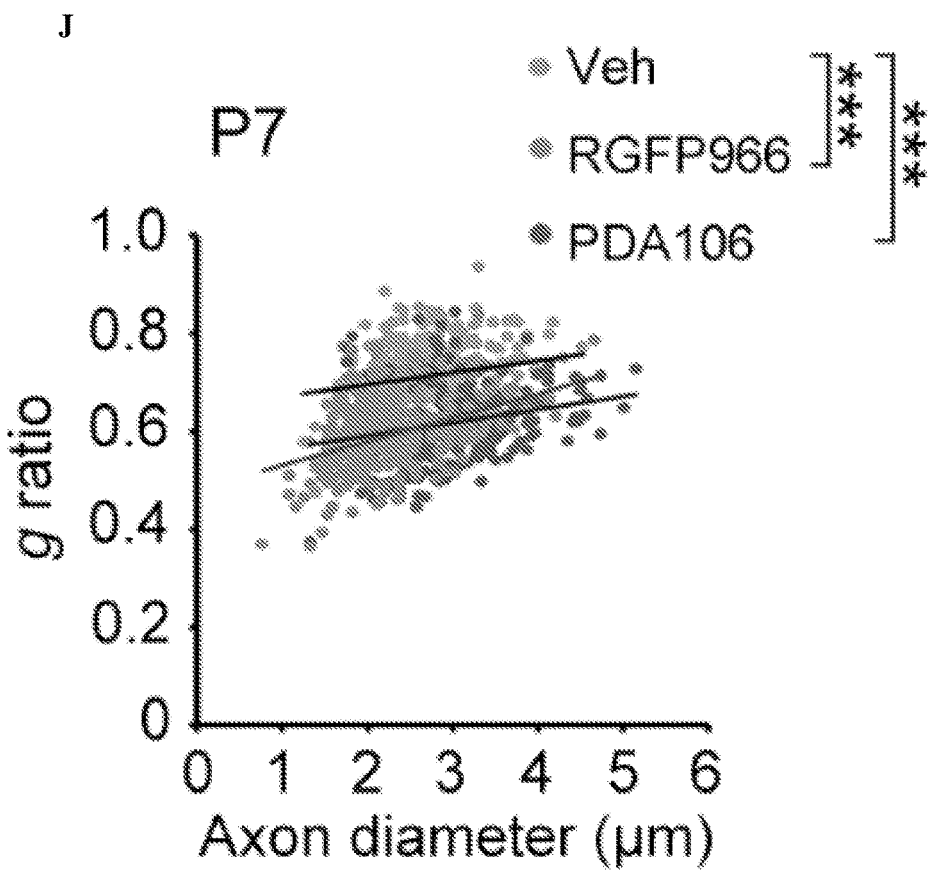
Figure 1:
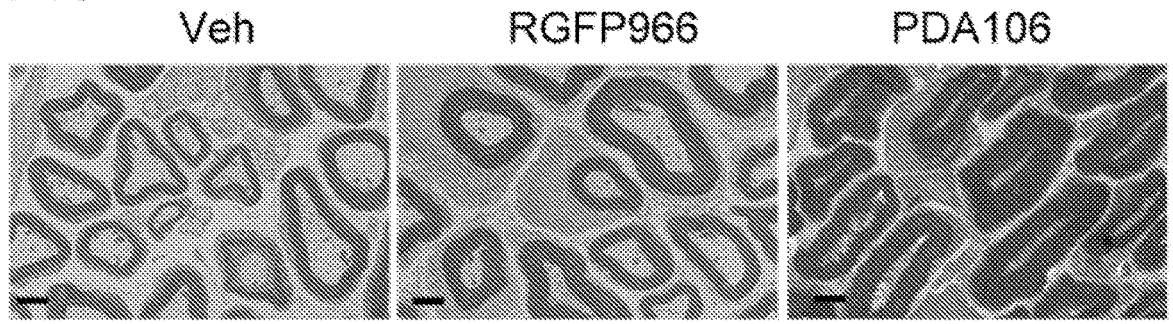
Figure 1:
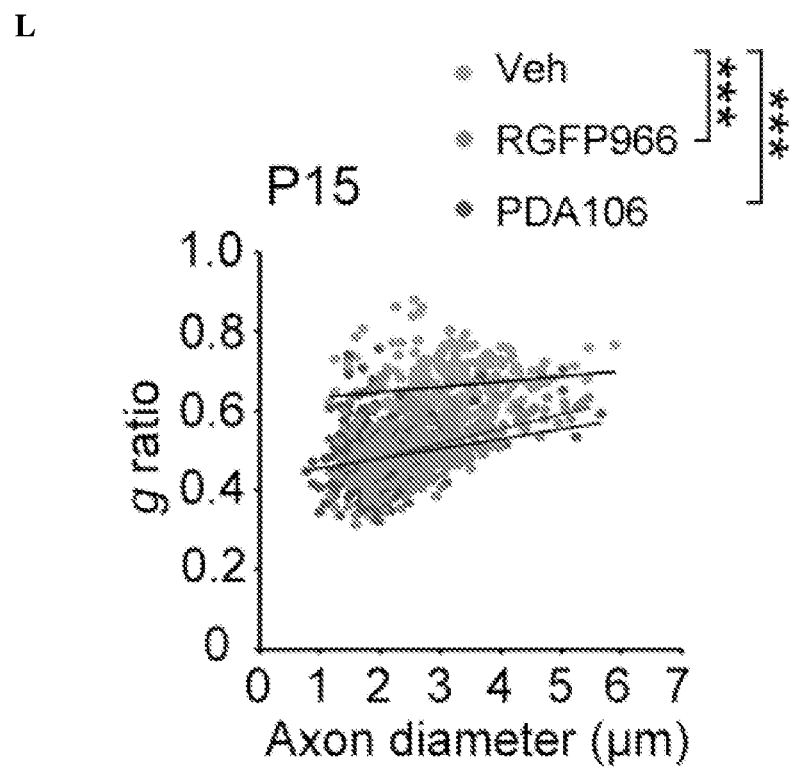
Figure 1:
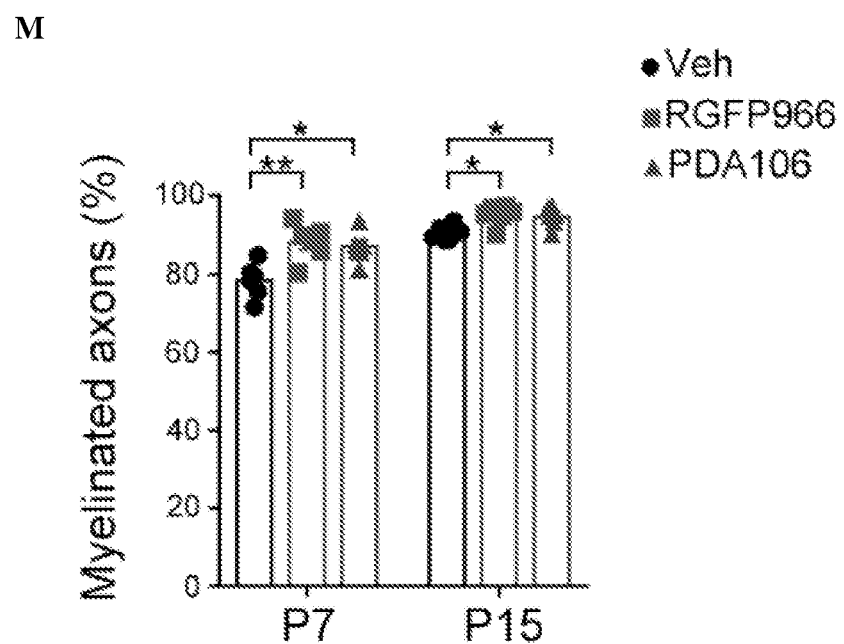
Figure 1:
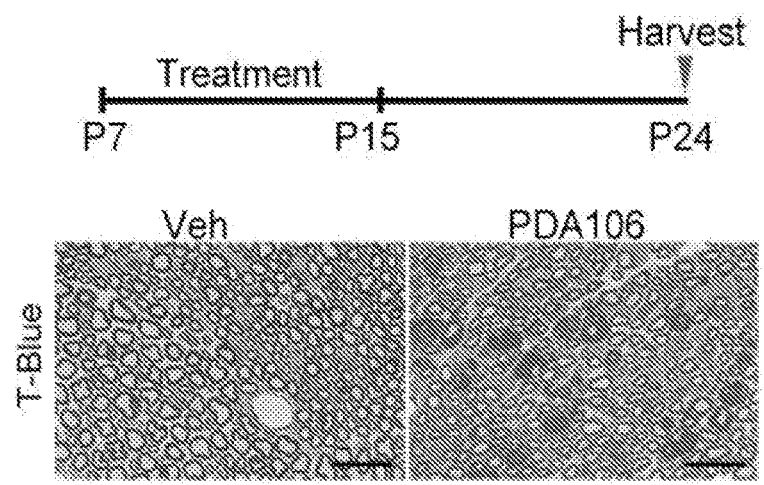
Figure 1:
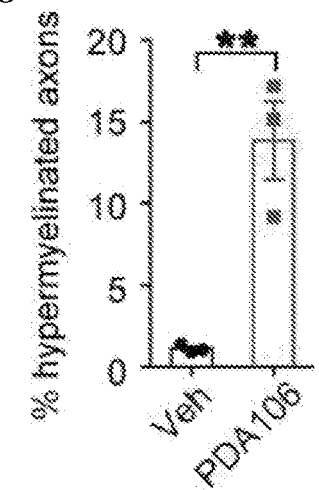
Figure 1:
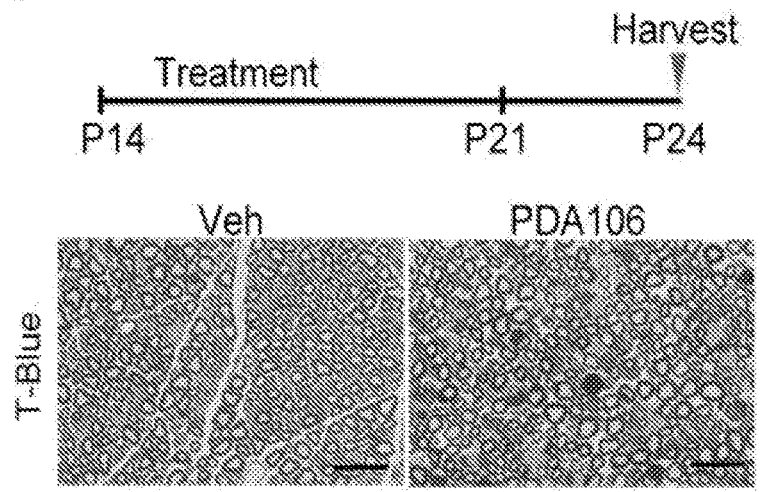
Figure 1:
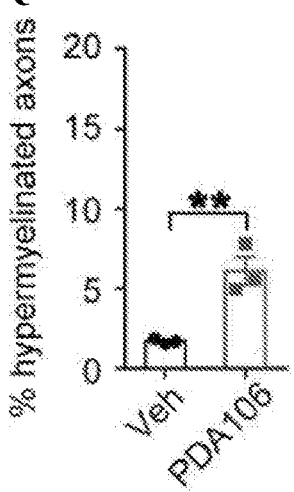
Figure 1:
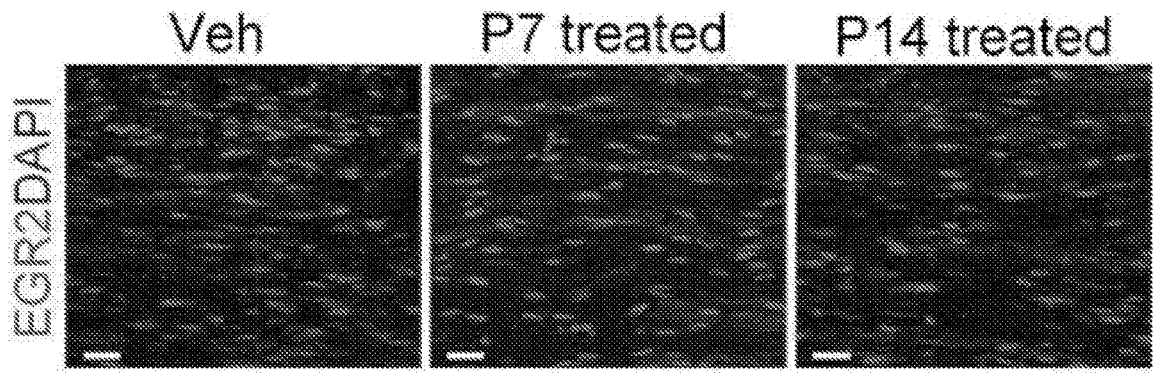
Figure 1:
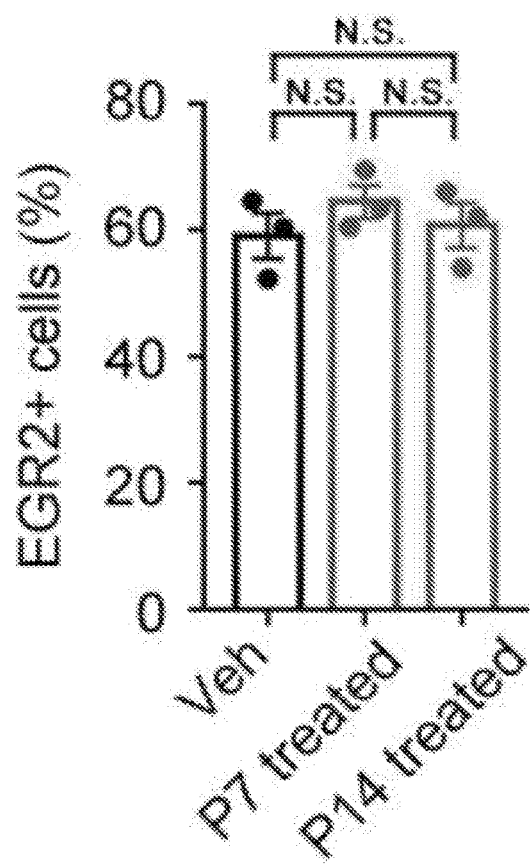

We identified a set of compounds that enhanced Egr2 expression over vehicle treatment by 5-fold or more (FIG. 1A-1C). Among these identified compounds were methyltransferase inhibitors (e.g., UNC0631 and UNC0646), demethylase inhibitors (e.g., JIB-04 and GSK-J4), HDAC inhibitors (SAHA (suberoylanilide hydroxamic acid), chidamide, CAY10398, and LAQ824), and HDAC3 inhibitors (e.g., pimelic diphenylamide (PDA106), RGFP966, and apicidin). The convergent effects of the chemically dissimilar compounds of PDA106, RGFP966, and apicidin suggested that effects were exerted through HDAC3 inhibition.

To investigate the effects of HDAC inhibition on SC maturation, we treated SCs isolated from neonatal rat sciatic nerve with inhibitors of HDAC1/2 (FK228), HDAC8 (PCI34051), and HDAC3 (RGFP966 and PDA106). Treatment with HDAC1/2 inhibitors reduced SC process extension and expression of mature SC markers MPZ and PMP22 (FIGS. 1D & 1E), consistent with the role of HDAC1/2 in SC maturation. HDAC8 inhibition had minimal effects on SC morphology (FIG. 1D). In contrast, treatment with HDAC3 inhibitors resulted in an expansion of cellular processes, actin cytoskeleton augmentation as shown by phalloidin staining, and induction of MPZ and PMP22 expression as assessed by immunocytochemistry and qRT-PCR (FIGS. 1D & 1E), suggesting that inhibition of HDAC3 activity promotes the maturation process of SCs in vitro.

To evaluate the effects HDAC3 inhibition in vivo, we administered RGFP966 or PDA106 by intraperitoneal (i.p.) injection into neonatal mice daily beginning at P1. Treatment continued until sciatic nerves were harvested for analysis at P7 and P15. Consistent with our in vitro data, both HDAC3 inhibitors caused an elevation in the number of EGR2-expressing mature SCs in sciatic nerves (FIGS. 1F & 1G). Treatment also significantly elevated expression of myelination-associated genes, including Prx, Mbp, Mpz, and Egr2, compared to vehicle-treated mice at P7 (FIG. 1H). Ultrastructural analysis of sciatic nerves by electron microscopy (EM) revealed an increase in myelin thickness (assessed by analysis of g ratios, inner axon diameter/outer diameter of the myelinated sheath; FIGS. 1I-1L) and the percentage of myelinated axons (FIG. 1M) in HDAC3 inhibitor-treated mice compared to controls at P7 and P15. While treatment initiated at either P7 or P14 also enhanced myelination, treatment starting at P7 produced a more profound enhancement of myelin thickness than that at P14, although the EGR2$^+$ SC numbers were comparable at P24, indicating that SC myelin sheath growth is more responsive to HDAC3 inhibitors at earlier developmental stages (FIGS. 1N-1S).

HDAC3 Inhibition Enhances SC Remyelination and Functional Recovery after Sciatic Nerve Transection We next evaluated whether treatment with HDAC3 inhibitors after nerve injury would enhance remyelination and functional recovery of nerve conduction, which can depend on the myelination state. We performed sciatic nerve transection of the right hindlimb in a group of 8-week-old adult mice and treated these mice with HDAC3 inhibitors, RGFP966 or PDA106, for two weeks at a dose that resulted in effective inhibition of HDAC3 activity without adverse effects on mice. After peripheral nerve transection, denervated SCs resume proliferation followed by differentiation and remyelination of regenerated axons in mice. We focused our analysis on the regenerating site, defined as a tissue bridge consisting of the SC-axon growth tip proximal to the injury. At 6 days post injury (Dpi) when SCs have migrated into the bridge tissue extensively, the bridge appeared transparent despite considerable axonal regrowth in the vehicle-treated animals, suggesting that little myelin regeneration occurs spontaneously within this time period (FIG. 2A). In contrast, opaque regeneration tracks were observed within the bridges of RGFP966- and PDA106-treated mice (FIG. 2A), suggesting an accelerated myelin sheath regeneration. The percentages of MBP myelinating axons entering the bridge of the regenerating sciatic nerves were significantly higher in RGFP966- and in PDA106-treated mice than vehicle-treated groups (FIGS. 2B & 2C). Treatment with HDAC3 inhibitors increased the proportion of EGR2$^+$ maturing SCs in the tissue bridge (FIGS. 2D & 2E), while the percentage of Ki67$^+$ cells decreased, suggesting increased SC differentiation accompanied by reduced proliferation after HDAC3 inhibitor treatment (FIGS. 2D & 2E). To further assess the extent of remyelination, we performed EM analysis on the regenerating sciatic nerves. At Dpi 14 both RGFP966- and PDA106-treated mice exhibited thicker myelin sheaths in the axons with different calibers in the regenerating bridge (FIGS. 2F-2H) and an increase in myelinated axons compared to vehicle-treated animals (FIG. 2I). Similarly, at Dpi 18 and 35, there was an increase of myelin thickness after HDAC3 inhibitor treatment (FIG. 2J-2M).

To investigate whether the increase in remyelination after HDAC3 inhibition improves motor functions in injured nerves, we measured in vivo conduction velocity and compound muscle action potentials (CMAPs) in injured sciatic nerves at different stages (Dpi 18 and 35) after treatment of injured adult mice with RGFP966 or PDA106 for two weeks (FIG. 2N). At Dpi 18, CMAP activity was barely detectable after electrical stimulation of vehicle-treated injured nerves. In contrast, an increase in conduction velocity and CMAP amplitude was observed in injured nerves of inhibitor-treated mice (FIGS. 2O & 2P). At Dpi 35, electrophysiological recordings indicated low CMAP activity in vehicle-treated injured nerves, whereas treatment with RGFP966 improved motor nerve function (FIGS. 2Q & 2R).

Furthermore, we found that the short-term treatment with HDAC3 inhibitors for ten days enhanced recovery of both sensory functions as measured by responses to pinprick stimulation (FIGS. 2S-2U) and motor functions assessed by toe spreading reflexes (FIGS. 2V & 2W) at Dpi 24. This result was even observed 3 months after treatment (Dpi 94) (FIGS. 2U & 2W), when nerve function remained compromised in vehicle-treated control mice, in keeping with the increase in myelin thickness in HDAC3 inhibitor-treated animals at this stage (FIGS. 2X & 2Y). Moreover, the rotarod test confirmed functional improvement in motor performance after inhibitor treatment (FIG. 2Z).

Myelin morphology in uninjured intact nerves on the left hindlimb was unaltered during the treatment period (FIGS. 2AA & 2AB), indicating that transient HDAC3 inhibitor administration did not elicit hypermyelination in uninjured adult nerves. There was an age-related decline of SC HDAC3 levels in adult compared to developing peripheral nerves (FIGS. 2AC & 2AD). Given the age-associated deficits in functional recovery after nerve injury compared with young adult mice, we assessed the efficacy of HDAC3 inhibition in 10-12 month-old mice and found that treatment enhanced nerve conductivity in these mice after sciatic nerve transection (FIG. 2AE-2AH). These data show that pharmacological attenuation of HDAC3 activity after sciatic nerve transection accelerates SC remyelination and improves functional recovery.

Ablation of Hdac3 in SCs Leads to Hypermyelination in Sciatic Nerves

To determine whether the effect of HDAC3 inhibitors on promoting myelination is intrinsic to SCs, we transfected rat SC culture with an siRNA designed to silence Hdac3 expression (FIG. 3A). Hdac3 silencing resulted in increased amounts of myelin proteins MBP and MPZ (FIG. 3A). To assess the myelination capacity of SCs, we performed an SC-neuronal co-culture assay in which primary rat SCs (SOX10$^+$) treated with or without siHdac3 were seeded onto dorsal root ganglion (DRG) cultures. After 10 days under pro-myelinating conditions, the extent of myelination, assayed by MBP immunolabeling, was greater in Hdac3-deficient SC cultures than the control-transfected SCs (FIG. 3B). Further, the number of myelinated segments was increased by approximately 4 fold in Hdac3-deficient SC cultures relative to controls (FIG. 3C).

To assess the cell-intrinsic role of HDAC3 in SC myelination in vivo, we generated mice lacking Hdac3 in SCs by crossing Hdac3$^{fl/fl}$ mice[31] with a SC lineage-expressing Cnp-Cre line[32] (FIG. 3D). HDAC3 expression was lower in the sciatic nerves of Hdac3$^{fl/fl}$; Cnp-Cre$^{+/-}$ (referred to here as Hdac3-cKO) mice compared to controls (FIG. 3D-3F). Hdac3$^{fl/+}$; Cnp-Cre$^{+/-}$ or Hdac3$^{fl/fl}$ littermates were phenotypically normal during SC development and were used as controls.

The numbers of SOX10-expressing SC lineage cells were comparable between control and Hdac3-cKO mutant sciatic nerves, and the proportion of EGR2$^+$ differentiated SCs was higher in Hdac3-cKO mutants than controls at P7 (FIGS. 3G & 3H). Ultrastructural analysis of sciatic nerves from Hdac3-cKO neonates at P1 showed an increase in myelinated axons compared to controls, indicating an accelerated onset of myelination in the absence of Hdac3 (FIGS. 3I & 3J). By P7, an active phase of myelinogenesis, Hdac3-cKO axons were hypermyelinated with more layers of myelin lamellae than observed in controls (FIGS. 3K & 3L). At P12, the formation of localized myelin protrusions or out-foldings appeared in hypermyelinated fibers (FIG. 3M). At P18, massive myelin lamellar wrapping was observed in toluidine-blue-stained semi-thin sections and EM graphs of Hdac3-cKO sciatic nerves in cross-sections (FIG. 3N) and longitudinal sections (FIG. 3O), eventually leading to demyelination in adulthood (FIG. 3P). Similar phenotypes were also detected in Hdac3$^{fl/fl}$; Dhh$^{Cre+/-}$ (Hdac3-cKO$^{Dhh}$) mice (FIG. 3Q-3T), in which Hdac3 was deleted in another SC lineage-expressing Dhh-Cre line[33].

To exclude effects of Hdac3 deletion on embryonic SC development, we inactivated Hdac3 in postnatal SCs using an inducible Plp1-CreERT driver[34] with tamoxifen administration from P0 to P10 (FIG. 3U). At P15, Hdac3$^{fl/fl}$; Plp1-CreERT (Hdac3-iKO) mice exhibited hypermyelination in sciatic nerves compared to controls (FIGS. 3U & 3V).

To further examine effects of Hdac3 deletion on premyelinating SCs, we ablated Hdac3 by treatment of Hdac3-iKO mice from P6 to P34 with tamoxifen (FIG. 3W) and harvested the sciatic nerves at P108. The redundant myelin sheaths in SCs were considerably thicker, even to the point of causing axonal resection, in Hdac3-iKO mice treated with tamoxifen than in controls (FIGS. 3W & 3X). Ablation of Hdac3 induced at the early postnatal stage P11 exerted a more robust effect on enhancing myelin thickness than ablation at P30 (FIG. 3Y-3AD). In contrast, tamoxifen administration after mice had reached adulthood did not alter myelin morphology substantially, despite a modest increase of myelin thickness in small diameter axons (FIG. 3AE-3AG), consistent with the low expression levels of HDAC3 in adult nerves.

Hdac3 Deletion Enhances SC Remyelination and Myelin Thickness after Injury

To test whether the effect of HDAC3 inhibitors on remyelination was due to inhibition of HDAC3 in SCs and not because of activity on other cell-types, we used a cell-type-specific inducible strategy to ablate HDAC3 in SCs after nerve transection injury. HDAC3 expression was detected in denervated SCs marked by SOX10, and these HDAC3$^+$ SCs increased in the regenerating bridge tissues after nerve transection at Dpi 14 compared to uninjured adult sciatic nerves (FIG. 4A). We ablated HDAC3 by treating 8-week old Hdac3-iKO and control mice with tamoxifen before and after sciatic nerve transection. This treatment efficiently removed HDAC3 specifically from SCs of Hdac3-iKO mice (FIG. 4B). At 14 Dpi, a time point at which remyelination of the distal stump occurs, we observed an increase in EGR2$^+$ differentiating SCs in the tissue bridge of Hdac3-iKO mice compared to controls (FIGS. 4C & 4D), while the SC proliferation rate and number of SOX2$^+$ immature SCs were reduced in Hdac3 (FIG. 4E-4H).

By EM analysis at Dpi 14, Hdac3-iKO mice had thicker myelin in transected sites compared to controls (FIGS. 4I & 4J), although the number of myelinating axons was comparable (FIG. 4K). At Dpi 28, myelin sheaths were much thicker in the regenerating region of Hdac3-iKO nerves compared to controls (FIG. 4L) with significantly lower g ratios than in control lesion sites or contralateral regions of intact nerves (FIG. 4M). The tamoxifen treatment during this period did not alter myelin thickness in the uninjured nerves (FIG. 4M).

At Dpi 20, in vivo CMAP activity was barely detectable after electrical stimulation of injured nerves in control mice (FIG. 4N). In contrast, we observed significantly greater CMAP signals in injured nerves of Hdac3-iKO mice, as reflected by elevated conduction velocities and mean peak amplitudes (FIGS. 4O & 4P). Furthermore, Hdac3-iKO mice exhibited enhanced sensory functions as measured by pinprick stimulation (FIG. 4Q) and motor functions as assayed by toe spreading reflexes and rotarod tests (FIGS. 4R & 4S). These observations suggest that HDAC3 inhibition in denervated SCs accelerates SC maturation, enhances remyelination, and improves functional recovery.

HDAC3 Negatively Regulates NRG1/PI3K/AKT Signaling to Repress SC Myelination

The hypermyelinating phenotype observed in Hdac3-cKO mice resembles that of mice overexpressing NRG1 type III. Since we did not detect significant differences in the activation of NRG1 receptors ERBB2 or 3, assayed by the ratio of phospho-ErbB/ErbB, between control and Hdac3-cKO nerves at P13 (FIG. 5A), we hypothesized that the effect of HDAC3 on SC myelination was due to activation of downstream pathways such as PI3K/AKT and MAPK/ERK. Indeed, we detected an increase in the levels of phosphorylated AKT, PI3K, and ERK in Hdac3-cKO nerves at P13 compared to controls (FIG. 5B). Similarly, inhibition of HDAC3 by PDA106 in purified rat SCs led to an elevation in p-AKT, p-PI3K, and p-ERK levels (FIG. 5C). In addition, HDAC3 inhibitor or Hdac3 siRNA treatment increased the level of acetylated PTEN (FIG. 5D), which results in a reduction of PTEN activity, leading to activation of PI3K/AKT signaling.

Treatment of primary rat SCs with the recombinant NRG1 type III for 1 hour led to upregulation of HDAC3 expression (FIG. 5F). This effect appeared to be occluded by a NRG1 signaling inhibitor gefitinib (FIG. 5G), which blocks the signaling of ERBB2/3 receptors activated by NRG1 engagement. Conversely, HDAC3 overexpression inhibited phosphorylation of AKT and ERK induced by NRG1 in SCs (FIG. 5E). In addition, treatment with NRG1 or the HDAC3 inhibitor PDA106 increased the p-ERK and p-AKT levels in SCs (FIGS. 5H & 5I), and combined treatment of NRG1 together with the HDAC3 inhibitor further enhanced p-ERK levels (FIGS. 5H & 5I). These observations suggest that NRG1 may induce expression of HDAC3, which in turn acts as a negative regulator of NRG1 signaling pathway.

HDAC3 Inhibits Pro-Myelinating Programs and Recruits p300 to Activate a Myelination-Inhibitory Network While the Hdac3-mutant phenotype resembles that of NRG1 overexpressing mice, unique features such as myelin outfoldings, which are not induced by NRG1 overexpression, suggest that HDAC3 might regulate additional regulatory networks independent of NRG1 that block peripheral myelin overgrowth. To define the HDAC3-regulated genetic program that controls SC myelin sheath formation, we performed unbiased transcriptome profiling of control, Hdac3-cKO$^{Cnp}$, and Hdac3-cKO$^{Dhh}$ sciatic nerves at P6, an active phase of SC differentiation. We applied weighted gene co-expression network analysis (WGCNA) to the data to identify co-expressed gene modules with the most significant changes in both Hdac3-mutant models (FIG. 5J). Our data indicate an upregulation of genes associated with myelination, lipid metabolic and biosynthetic processes, HIPPO signaling, and integrin signaling processes in Hdac3 mutants (FIGS. 5K & 5L); all are processes known to be useful for SC myelination.

To further identify HDAC3 target genes with expression altered in Hdac3-cKO mutants, we performed chromatin-immunoprecipitation sequencing (ChIP-seq) analysis of HDAC3 genomic occupancy in SCs cultured under proliferation and differentiation conditions. The intensity of HDAC3-binding sites was higher in differentiating SCs than proliferating SCs (FIGS. 5M & 5N). Recent studies indicate that, in the absence of histone acetyltransferase (HAT) co-activator p300, HDAC3 occupancy represses target gene expression, while in the presence of p300, HDAC3 and p300 co-occupancy coordinately targets the enhancers marked by H3K27ac to promote expression of target genes with overall increase in net HAT activity. HDAC3 targeted a distinct set of genes that are different from p300-targeted ones in SCs (FIG. 5O). These HDAC3-targeted genes with minimal p300 co-occupancy included myelin-related genes Pmp22, Mpz, Mbp, Erbb2, and Gjb1 and pro-myelinating transcriptional regulatory genes such as Egr2, Zeb2, and Srebf1 (FIG. 5P). Consistently, expression of these genes was increased in Hdac3-cKO sciatic nerves (FIG. 5J-5L), while overexpression of HDAC3 inhibited expression of these myelination-related genes (FIG. 5Q). Furthermore, knockdown of HDAC3 in SCs led to an increased level of the activating histone mark H3K27ac on the enhancers of myelination-associated gene loci (FIGS. 5R & 5S).

These data revealed that HDAC3 and p300 co-occupancy targeted a common set of genes in differentiating SCs that coincide with the enhancer elements marked by H3K27ac (FIGS. 5O & 5T). The gene loci bound by both HDAC3 and p300 were significantly enriched for those genes encoding cell-growth-related factors and negative regulators of myelination (FIG. 5U). These include Notch1, Hes5, Id2/4, Sox2, and Ngfr/p75 (FIG. 5V), as well as Pten and Dlg1, which are negative regulators of PI3K/AKT signaling (FIG. 5V). Accordingly, the expression of these genes was downregulated in Hdac3-cKO mutant nerves (FIG. 5W). Similarly, at Dpi 14 expression of HDAC3/p300-targeted negative regulators of myelination was upregulated in the regenerating tissue bridge, while myelin genes and pro-myelination regulators were downregulated (FIGS. 5X & 5Y). Our data position coordination between HDAC3 and p300 at the apex of a gene regulatory network that controls both activation and inhibition of SC myelination via distinct mechanisms.

HIPPO Effector TEAD4, an HDAC3/p300 Target, is an Inhibitor of SC Myelin Growth

To identify novel regulatory factors that inhibit myelin overgrowth, we then examined potential transcription factors regulated by the coordinated action of HDAC3 and p300. Tead4 was identified among the transcription factor gene loci co-occupied by both HDAC3 and p300 (Table 1). The Tead4 locus is enriched with histone marks H3K27ac and H3K4me1 for active and poised enhancers, respectively, on HDAC3/p300 co-targeted elements (FIG. 6A), suggesting that the HDAC3 and p300 co-occupancy may activate Tead4 expression. In contrast, the loci of other TEAD family members Tead1, 2, and 3 were mainly targeted by HDAC3 but not p300 (FIG. 6B). Overexpression of HDAC3 and p300 in SCs promoted Tead4 expression to a greater extent than did either HDAC3 or p300 overexpression alone (FIG. 6C). Conversely, Tead4 expression was downregulated in siHdac3-treated SCs and sciatic nerves of Hdac3-cKO mice (FIG. 6D).

TABLE 1

The loci of genes associated with negative regulation targeted by HDAC3 and p300 co-occupancy

| | Gene_Symbol | Peak* corelation coefficient score | Peak overlapped score | Summed Score |
|---|---|---|---|---|
| 1 | Nr1i2 | 0.41 | 1.396256669 | 1.80625667 |
| 2 | Tead4 | 0.37 | 0.854454454 | 1.22445445 |
| 3 | Nr4a3 | 0.34 | 0.867280785 | 1.20728079 |
| 4 | Nr1d1 | 0.47 | 0.706914565 | 1.17691457 |
| 5 | Nr4a2 | 0.44 | 0.730941704 | 1.1709417 |
| 6 | Irf2 | 0.4 | 0.760646166 | 1.16064617 |
| 7 | Nr1d1 | 0.4 | 0.706914565 | 1.10691457 |
| 8 | Hnf1a | 0.32 | 0.740466102 | 1.0604661 |

TABLE 1-continued

The loci of genes associated with negative regulation targeted by HDAC3 and p300 co-occupancy

| Gene_Symbol | Peak* corelation coefficient score | Peak overlapped score | Summed Score |
|---|---|---|---|
| 9 Zfp251 | 0.42 | 0.630936228 | 1.05093623 |
| 10 Bach1 | 0.45 | 0.591905565 | 1.04190557 |
| 11 Rest | 0.28 | 0.712514092 | 0.99251409 |
| 12 Hes7 | 0.38 | 0.579545455 | 0.95954546 |
| 13 Tcf3 | 0.26 | 0.649484536 | 0.90948454 |
| 14 Deaf1 | 0.37 | 0.506972112 | 0.87697211 |
| 15 Id3 | 0.27 | 0.573134328 | 0.84313433 |
| 16 Nanog | 0.14 | 0.701550388 | 0.84155039 |
| 17 Mlx | 0.28 | 0.559691913 | 0.83969191 |
| 18 Esrra | 0.43 | 0.368802902 | 0.7988029 |
| 19 D1x1 | 0.32 | 0.475155279 | 0.79515528 |
| 20 Zbtb3 | 0.32 | 0.442231076 | 0.76223108 |
| 21 Tfeb | 0.16 | 0.567596567 | 0.72759657 |
| 22 Sim2 | 0.16 | 0.511811024 | 0.67181102 |
| 23 Smad3 | 0.22 | 0.443050193 | 0.66305019 |
| 24 Erf | 0.37 | 0.285350318 | 0.65535032 |
| 25 Mta2 | 0.22 | 0.433784287 | 0.65378429 |
| 26 Hexim2 | 0.34 | 0.279323513 | 0.61932351 |
| 27 Zbtb4 | 0.28 | 0.331864905 | 0.61186491 |
| 28 Nr2f2 | 0.29 | 0.29970617 | 0.58970617 |
| 29 Irf1 | 0.14 | 0.43963964 | 0.57963964 |
| 30 Ovol2 | 0.22 | 0.336683417 | 0.55668342 |
| 31 Tbx6 | 0.37 | 0.15045045 | 0.52045045 |
| 32 Scrt2 | 0.23 | 0.290368272 | 0.52036827 |
| 33 Hes2 | 0.21 | 0.306318681 | 0.51631868 |
| 34 Runx2 | 0.18 | 0.237948718 | 0.41794872 |
| 35 Id2 | 0.38 | 0 | 0.38 |
| 36 Mxi1 | 0.37 | 0 | 0.37 |
| 37 Mier1 | 0.16 | 0.197468354 | 0.35746835 |
| 38 Scrt1 | 0.32 | 0 | 0.32 |
| 39 Irf3 | 0.32 | 0 | 0.32 |
| 40 Etv3l | 0.32 | 0 | 0.32 |
| 41 Sox2 | 0.31 | 0 | 0.31 |
| 42 Satb2 | 0.31 | 0 | 0.31 |
| 43 Nr2f1 | 0.3 | 0 | 0.3 |
| 44 Glis2 | 0.29 | 0 | 0.29 |
| 45 Ddit3 | 0.28 | 0 | 0.28 |
| 46 Nfx1 | 0.28 | 0 | 0.28 |
| 47 Tbx3 | 0.27 | 0 | 0.27 |
| 48 Rara | 0.27 | 0 | 0.27 |
| 49 Junb | 0.26 | 0 | 0.26 |
| 50 Homez | 0.26 | 0 | 0.26 |
| 51 Foxh1 | 0.26 | 0 | 0.26 |
| 52 Klf16 | 0.25 | 0 | 0.25 |
| 53 Elk4 | 0.25 | 0 | 0.25 |
| 54 Mef2d | 0.25 | 0 | 0.25 |
| 55 Zbtb7b | 0.25 | 0 | 0.25 |
| 56 Smad2 | 0.24 | 0 | 0.24 |
| 57 Maff | 0.24 | 0 | 0.24 |
| 58 Smad2 | 0.23 | 0 | 0.23 |
| 59 Hoxb4 | 0.23 | 0 | 0.23 |
| 60 Zbtb26 | 0.23 | 0 | 0.23 |
| 61 Foxk1 | 0.22 | 0 | 0.22 |
| 62 Hivep2 | 0.22 | 0 | 0.22 |
| 63 Zhx1 | 0.21 | 0 | 0.21 |
| 64 Hic2 | 0.21 | 0 | 0.21 |
| 65 Ovol1 | 0.2 | 0 | 0.2 |
| 66 Egr1 | 0.2 | 0 | 0.2 |
| 67 Nr2f6 | 0.19 | 0 | 0.19 |
| 68 Foxs1 | 0.19 | 0 | 0.19 |
| 69 Etv3 | 0.19 | 0 | 0.19 |
| 70 Mxd1 | 0.17 | 0 | 0.17 |
| 71 Arntl | 0.16 | 0 | 0.16 |
| 72 Stat3 | 0.15 | 0 | 0.15 |
| 73 Rbak | 0.15 | 0 | 0.15 |
| 74 Id4 | 0.15 | 0 | 0.15 |
| 75 Hes3 | 0.14 | 0 | 0.14 |
| 76 Stat6 | 0.13 | 0 | 0.13 |
| 77 Hhex | 0.13 | 0 | 0.13 |
| 78 Foxo3 | 0.13 | 0 | 0.13 |
| 79 Snai3 | 0.12 | 0 | 0.12 |
| 80 Kdm5b | 0.12 | 0 | 0.12 |
| 81 Zeb1 | 0.11 | 0 | 0.11 |
| 82 Zbtb1 | 0.11 | 0 | 0.11 |
| 83 Ahrr | 0.099 | 0 | 0.099 |
| 84 Smad7 | 0.096 | 0 | 0.096 |
| 85 Nfil3 | 0.092 | 0 | 0.092 |
| 86 Prox2 | 0.089 | 0 | 0.089 |
| 87 Lhx9 | 0.087 | 0 | 0.087 |
| 88 Elf2 | 0.079 | 0 | 0.079 |
| 89 Hsf4 | 0.075 | 0 | 0.075 |
| 90 Bach2 | 0.074 | 0 | 0.074 |
| 91 Nr1h2 | 0.069 | 0 | 0.069 |
| 92 Runx1 | 0.061 | 0 | 0.061 |
| 93 Foxm1 | 0.057 | 0 | 0.057 |
| 94 Runx3 | 0.046 | 0 | 0.046 |
| 95 Tbx1 | 0.036 | 0 | 0.036 |
| 96 Aebp2 | 0.028 | 0 | 0.028 |
| 97 Pax4 | 0.025 | 0 | 0.025 |
| 98 Jdp2 | 0.015 | 0 | 0.015 |
| 99 Gata2 | 0.011 | 0 | 0.011 |

*ChIP-seq peaks in genomic regions near TSS (−40 kb to −1 kb).

Depletion of Tead4, but not Tead1, 2, or 3, increased expression of myelination-associated genes Egr2, Pmp22, Mbp, and Mpz (FIG. 6E), while repressing the genes associated with SC differentiation inhibition such as Id2, Id4, and Sox2 (FIG. 6F). The change in gene expression patterns upon depleting Tead4 correlated with increased myelination in DRG-SC co-culture paradigm: the knockdown of Tead4 in SCs produced an increased number of myelin segments compared to control siRNA-treated SCs (FIGS. 6G & 6H), which was confirmed by the elevation of myelin proteins MBP and MPZ in SCs (FIG. 6I). These results identify TEAD4 as a direct target of HDAC3-p300 regulation, which negatively regulates SC myelination.

To determine whether genetic ablation of Tead4 in the SC lineage produces hypermyelination phenotypes similar to Hdac3 deletion in vivo, we selectively ablated the expression of Tead4 in SC lineage cells by breeding mice with the floxed Tead4 allele with the SC-lineage expressing Dhh-Cre line (FIG. 6J-6L). The Tead4$^{fl/fl}$; Dhh$^{Cre+/−}$ (Tead4-cKO) animals were born at the expected Mendelian frequency. At early postnatal stages, morphometric analysis did not reveal substantial alterations in expression of mature SC markers (FIG. 6M-6P), while myelin thickness was increased slightly relative to control animals (FIGS. 6Q & 6R). The myelin internodal length was not significantly altered in Tead4-cKO mice at P14 (FIGS. 6S & 6T). In contrast, in adult sciatic nerves, Tead4-cKO mutants developed hypermyelination and excessive myelin profiles as shown by toluidine blue staining, ultrastructure and g ratio analyses (FIGS. 6U & 6V), suggesting that sustained absence of TEAD4 leads to myelin overgrowth. Accordingly, we also observed an increase in expression of the major myelination-related genes in Tead4-cKO nerves by qRT-PCR (FIG. 6W), while overexpression of TEAD4 in SCs inhibited expression of myelination-related genes (FIG. 6X).

To test whether Tead4 loss is responsible for upregulation of myelin genes in Hdac3-deficient SCs, we inhibited Hdac3 expression using siRNA and then overexpressed Tead4. Silencing of Hdac3 led to an upregulation in expression of myelination-associated genes, whereas Tead4 overexpression repressed their expression (FIG. 6Y). Conversely, Hdac3 overexpression inhibited myelination gene expression, and Tead4 inhibition partially restored their expression (FIG. 6Z).

DISCUSSION

Functional regeneration and recovery after nerve injury includes not only axonal regrowth but also remyelination of the regenerated axons. Despite the remarkable axonal regeneration capacity in peripheral nerves, myelin sheaths regenerated after injury are thinner than myelin formed during development. Slow and compromised remyelination could contribute to the limited restoration of sensory and motor functions observed after proximal nerve injury in humans In a small-molecule epigenetic screen we found that pharmacological inhibitors of HDAC3 markedly elevated myelinogenic potential. Further, transient inhibition of HDAC3 activity accelerated myelination and promoted functional recovery after peripheral nerve injury in mice. Since peripheral nerve regeneration involves multiple processes (e.g., including but not limited to axonal regeneration, SC migration, macrophage infiltration, and endothelial cell growth), HDAC3 inhibitors may also influence remyelination in a non-cell autonomous manner as pharmacological inhibition of HDAC3 enhanced axonal regrowth and blood vessel formation after nerve injury (FIG. 7A-7D). Nonetheless, cell-type-specific genetic ablation demonstrated that Hdac3 loss in SC lineage cells sufficed to increase SC maturation and myelinogenesis during nerve development and promoted denervated SC re-differentiation and myelination.

Inhibition of HDAC3 enhanced nerve conductivity after nerve injury not only in young adult mice but also in aging mice, suggesting that targeting HDAC3 may rejuvenate the age-related decline in functional recovery after nerve injury. Since the axonal regeneration rate is comparable between young and aged mice after nerve injury, enhancement of SC myelination by HDAC3 inhibition may contribute to conductivity restoration in aging animals, suggesting a potential therapeutic strategy for improving myelin repair in elderly individuals who often suffer from idiopathic peripheral neuropathy.

Although nuclear export of HDAC5 in DRG neurons occurs for nerve regeneration, we did not detect nuclear translocation of HDAC5 in SCs during nerve regeneration (FIG. 7E). HDAC3 exerts unique functions distinct from other class I HDACs, as inhibition of HDAC1/2 suppresses, rather than promotes, myelin sheath growth and blocks SC remyelination (although transient pharmacological inhibition of HDAC1/2 increases repair cells to promote axonal regrowth). This suggests distinct functions among individual HDAC family members in SC myelination and remyelination. In contrast to its later function as an inhibitor of SC maturation and myelinogenesis, HDAC3 promotes oligodendrocyte specification early in development. Thus, HDAC3 may have a distinct role in myelinating cell development in the central and peripheral nervous systems. Both in vitro and in vivo pharmacological and genetic approaches described here provide evidence that HDAC3 acts cell-intrinsically on immature or pre-myelinating SCs to delimit myelin growth and regeneration.

Our results suggest that HDAC3 functions in a negative regulatory loop that may restrain the activity of the NRG1/PI3K/AKT signaling to ensure proper myelination and myelin growth. We found that HDAC3 antagonizes NRG1 signaling and its downstream myelinogenic program by blocking the activation of PI3K/AKT and ERK at the cellular level. It is possible that HDAC3, which can shuttle between the cytoplasm and nucleus, may regulate the acetylation state of PTEN or PI3K/AKT to control kinase activity or turnover as in other contexts. Alternatively, HDAC3 may indirectly regulate factors that inhibit NRG1/PI3K/AKT signaling. Our genomic occupancy and expression profiling analyses revealed that HDAC3, in coordination with p300, directly activates expression of Pten and Dlg1. In contrast to the loss of Pten-associated Dlg1, which leads to a transient increase of myelin thickness during development, deletion of Hdac3 in SCs resulted in profound, sustained myelin sheath growth.

The HDAC3 expression pattern appears to parallel that of NRG1 type III, which increases during perinatal stages and then decreases in adulthood. Downregulation of HDAC3 in adult nerves may correlate with a low level of NRG1; therefore, a minimal level of inhibition exerted by HDAC3 appears sufficient to maintain myelin homeostasis in adult nerves. Alternatively, the low HDAC3 levels in adulthood could be related to previous formation of deacetylated chromatin or heterochromatin over myelination gene loci, obviating the need for histone deacetylation in adulthood. Thus, a developmental window of opportunity may exist for modulating HDAC3 activity in immature or premyelinating SCs. Our observations suggest a potential role for a balance between NRG1/PI3K/AKT signaling and HDAC3 activity in fine-tuning myelin sheath thickness for optimal conduction velocity and nerve functions during development and recovery from injury.

Our genome-wide analysis of HDAC3 occupancy and transcriptome profiling revealed that HDAC3 inhibits the transcription of pro-myelinating genes in SCs. Inhibition of HDAC3 increased transcription of these genes and the deposition of activating H3K27ac marks on their enhancers and promoters. Thus, our observations suggest that HDAC3 exerts an inhibitory effect on SC myelination at least in part through epigenetic silencing of the pro-myelination program. We found that HDAC3 co-occupies with p300 in the regulatory elements of genes, including Notch, Id2/4, and Pten/Dlg1, associated with myelination inhibition. Coordination between HDAC3 and p300, which have similar temporal expression patterns (FIG. 7F), exerts net activating effects to activate a myelination-inhibitory network. Thus, HDAC3 may act as a dual-function switch by exerting the inhibitory effect through the epigenetic silencing of pro-myelination genes and through the recruitment of p300 to activate genes that inhibit SC myelination. The genome-wide HDAC3/p300 targeting analyses revealed the epigenetic landscape that underlies regulation of myelin growth and indicates regulatory networks that block peripheral myelin regrowth post-injury.

The genomic occupancy analyses further identified an HDAC3/p300 target TEAD4 as a previously unrecognized inhibitor of SC myelin growth. In contrast to TEAD1, which cooperates with YAP/TAZ to activate myelination programs, TEAD4 can also inhibit expression of SC myelination-associated genes, indicating a function divergent from other TEAD family members in SC myelination. Over-expressing YAP with TEAD4 led to net stimulation of Egr2 promoter activity in vitro, while TEAD4 overexpression alone in the absence of YAP inhibited Egr2 expression, suggesting context-dependent TEAD4 functions in gene regulation. Nonetheless, deletion of Tead4 in mice led to elevation of Egr2 and hypermyelination, consistent with the notion that TEAD4 functions as a default repressor and that YAP promotes tissue growth by relieving TEAD-mediated repression.

Our data uncovered a previously unrecognized HDAC3-dependent pathway and epigenetic silencing that impacts SC myelin growth and regeneration, providing epigenetic mechanisms underlying myelinopathy-associated diseases and nerve injury. Although it is possible that there is an insufficient supply of NRG1 after peripheral nerve injury, we found that numbers of HDAC3-expressing SCs increase after nerve injury. Thus, HDAC3 appears to counter the activity of pro-myelinating signals such as PI3K/AKT/ERK signaling.

Although excessive hypermyelination seen with sustained Hdac3 ablation would not sometimes be a desirable endpoint, the potent activity of the druggable enzyme HDAC3 in the regulation of myelin sheath growth nevertheless highlights a therapeutic potential for time- or dose-delimited and controlled HDAC3 attenuation, which might allow SC re-entry into active myelinogenesis, overcoming the remyelination block in patients with demyelinating neuropathies or nerve damage. In the mouse models described here, acceleration of myelin repair by measured and limited treatment with HDAC3 inhibitors facilitated timely recovery of conduction velocity as well as sensory and motor functions. The myelin morphology in uninjured nerves was unaltered by treatment with HDAC3 inhibitors, indicating that transient HDAC3 inhibition does not appear to be detrimental to uninjured nerves. Treatment with pharmacological HDAC3 inhibitors activated expression of myelination-associated genes in human SC-derived cell lines (FIG. 7G), suggesting that HDAC3 inhibition will promote the myelination program in human SCs. Given that HDAC inhibitors are generally well-tolerated and have been clinically approved, attenuation of HDAC3 activity (e.g., by HDAC3 inhibitors and other means) and its regulatory circuits (including its downstream effector TEAD4) is a therapy to, for example, provide enhancement of myelin repair in patients suffering from peripheral neuropathies and nerve trauma.

Example Set B

Unless otherwise indicated, the methods and materials used in Example Set B are the same as those used in Example Set A.

Inhibition of HDAC3 Treats Experimental Autoimmune Encephalomyelitis (EAE)

8-week-old female C57BL/6 (Charles River lab) mice received injections of 200 μg of myelin oligodendrocyte glycoprotein (MOG) 35-55 peptide emulsified in complete Freund's adjuvant (BD Biosciences), supplemented with 600 μg of *Mycobacterium tuberculosis* (strain H37Ra; BD Biosciences). 24 and 72 hours after immunization, mice were given two intraperitoneal injections of 400 ng of pertussis toxins (List Biological Laboratories, Cat # NC9675592). EAE onset was monitored daily and scored with Clinical scores (0=healthy; 1=flaccid tail; 2=ataxia and/or paresis of hindlimbs; 3=paralysis of hindlimbs and/or paresis of forelimbs; 4=tetraparalysis; 5=moribund or death). Once disease symptoms peaked (day 15; clinical score ~3) they were randomized into 2 treatment groups, DMSO and PDA106 were delivered the animals by i.p. for 10 days, at a dose of 100 mg/kg body weight.

In the experimental autoimmune encephalomyelitis (EAE) demyelinating mouse model induced by myelin peptide MOG35-55, the most commonly used animal model of multiple sclerosis (BITTNER et al., "Myelin oligodendrocyte glycoprotein (MOG35-55) induced experimental autoimmune encephalomyelitis (EAE) in C57BL/6 mice" J Vis Exp. (2014) Vol. 86, Article 51275 (doi: 10.3791/51275)), HDAC3 inhibitor administration improved motor function reflected in clinical scores as well as in remyelination.

FIG. 8A shows the promotion of myelination of Schwann cells in sciatic nerve cells at P15 from mice treated with vehicle or an HDAC3 inhibitor PDA106 from P3-P8. In addition, FIGS. 8B and 8C indicate that HDAC3 inhibition also promotes oligodendrocyte myelination in the central nervous system. FIG. 8B shows the clinical score in chronic progressive demyelinating EAE mice treated with DMSO or PDA106 daily (at a dose of 100 mg/kg body weight) for 10 days beginning at the peak of disease at post-immunization day (PID) 15 (black arrow). FIG. 8C shows electron microscopy images of the lesion areas at PID 25 in ventral spinal cords of mice treated with DMSO or PDA106.

HDAC3 inhibitor administration improves the motor function (FIG. 8B, decrease in clinical score) and remyelination in the spinal cord (shown in FIG. 8C). Thus, attenuation of HDAC3 activity (e.g., by HDAC3 inhibitors) appears beneficial for myelin repair in the peripheral nervous system and the central nervous system after damage resulting from neurodegenerative diseases (e.g., multiple sclerosis).

Inhibition of HDAC3 Provides Remyelination in LPC-Induced Demyelination Lesion

In the lysolecithin (also referred to as lysophosphatidylcholine (LPC)) induced demyelination animal model in the spinal cord, we observed that genetic ablation of HDAC3 in oligodendrocytes of HDAC3$^{PlpcreERT}$ mice (~8-week old) by injection of tamoxifen accelerated remyelination in LPC-induced lesions (FIG. 9). In this experiment, LPC (0.5 μl of 1% w/v lysolecithin) was injected into the ventral white matter of the spinal cord, which was followed by five additional days of tamoxifen administration in the mice, and the lesioned spinal cords were harvested at 14 dpl (14 days post-LPC-lesion-inducement). Thus, attenuation of HDAC3 activity (e.g., by genetic ablation or HDAC3 inhibitors) appears beneficial for myelin repair in the peripheral nervous system and the central nervous system after damage resulting from neurodegenerative diseases (e.g., leukodystrophies).

Inhibition of HDAC3 Promotes Axon Regeneration in the Central Nervous System.

Immediately after optic tract transection, 8-week-old adult mice (wild type mice) were treated with an HDAC3 inhibitor (RGFP966 at a dose of 10 mg/kg body weight) daily over the first week and every 2 days during the second week for a total of 3 days.

Axon regeneration was assayed by examining axonal fibers labeled with the anterograde tracer, cholera toxin β (CTB, shown in white color), in the optic nerve sections across the lesion site.

FIG. 10 shows long-distance axon regeneration in mice treated with DMSO (top) and RGFP966 (middle and bottom from two different mice) at 28 days after injury. Thus, inhibition of HDAC3 appears to result in long-distance axon regeneration after nerve injury (e.g., by transection)

Inhibition of HDAC3 can Decrease Inflammation after Nerve Injury.

Injury to the optic nerves in the CNS can induce inflammation and tissue damage, which can create scar barriers to prevent regeneration.

Crush injury to the optic nerves of mice (wild type mice) was accomplished with the aid of a pair of cross-action forceps, applying a crush injury to the optic nerve at about 2 mm from the eyeball for about 3 seconds in wildtype mice. After the crush injury, we treated the optic nerves with an HDAC3 inhibitor (RGFP966) (10 mg/kg body weight, i.p.

injection daily over the first week and every 2 days during the second week) and examined the optic nerve at 10 day post injury, a time point representing peak phagocytic activity of microglia after injury. FIG. 11 shows that the number of CD68 inflammatory microglia/macrophage cells at the injury site at 10 dpi was decreased in RGFP966-treated animals vs. DMSO controls.

Thus, inhibition of HDAC3 appears to suppress inflammation after nerve injury (e.g., by a crush injury).

The headings used in the disclosure are not meant to suggest that all disclosure relating to the heading is found within the section that starts with that heading. Disclosure for any subject may be found throughout the specification.

It is noted that terms like "preferably," "commonly," and "typically" are not used herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

As used in the disclosure, "a" or "an" means one or more than one, unless otherwise specified. As used in the claims, when used in conjunction with the word "comprising" the words "a" or "an" means one or more than one, unless otherwise specified. As used in the disclosure or claims, "another" means at least a second or more, unless otherwise specified. As used in the disclosure, the phrases "such as", "for example", and "e.g." mean "for example, but not limited to" in that the list following the term ("such as", "for example", or "e.g.") provides some examples but the list is not necessarily a fully inclusive list. The word "comprising" means that the items following the word "comprising" may include additional unrecited elements or steps; that is, "comprising" does not exclude additional unrecited steps or elements.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

Detailed descriptions of one or more embodiments are provided herein. It is to be understood, however, that the present invention may be embodied in various forms. Therefore, specific details disclosed herein (even if designated as preferred or advantageous) are not to be interpreted as limiting, but rather are to be used as an illustrative basis for the claims and as a representative basis for teaching one skilled in the art to employ the present invention in any appropriate manner Indeed, various modifications of the invention in addition to those described herein will become apparent to those skilled in the art from the foregoing description and the accompanying figures. Such modifications are intended to fall within the scope of the appended claims.

What is claimed is:

1. A method for treating an animal for disease or nerve injury, comprising administration of a composition comprising a myelination enhancing inhibitor to the animal, wherein (a) the myelination enhancing inhibitor used for treatment is CUDC-907, Quisinostat, RG2833, CUDC-101, Resminostat, 4SC-202, Mocetinostat, Entinostat, Citarinostat, Abexinostat, Pracinostat, PDA106, CAY10398, chidamide, LAQ824, SAHA, GSK-J4, JIB-04, UNC0631, or UNC0646, and the disease or nerve injury is myelopathy, myelitis, vascular myelopathy, cervical spondylotic myelopathy, spondylosis, spinal stenosis, demyelinating disease, any disease of the nervous system where the myelin sheath of a neuron is damaged, CNS demyelinating disease, PNS demyelinating disease, genetic demyelinating disease, infectious demyelinating disease, autoimmune demyelinating disease, demyelinating myelinoclastic disease, demyelinating leukodystrophic disease, Devic's disease, CNS neuropathies, diseases resulting in vitamin B12 deficiency, central pontine myelinolysis, myelopathies, tabes *dorsalis*, leukoencephalopathies, progressive multifocal leukoencephalopathy, leukodystrophies, optic neuritis, transverse myelitis, neuromyelitis optica, Guillain-Barré syndrome, chronic inflammatory demyelinating polyneuropathy, anti-MAG peripheral neuropathy, Charcot-Marie-Tooth disease, Hereditary neuropathy with liability to pressure palsy, copper deficiency associated conditions, peripheral neuropathy, myelopathy, optic neuropathy, progressive inflammatory neuropathy, multiple sclerosis (MS), MS-type clinically isolated syndrome, relapsing-remitting MS, primary progressive MS, or secondary progressive MS; or (b) the myelination enhancing inhibitor used for treatment is CUDC-907, Quisinostat, CUDC-101, Resminostat, 4SC-202, Mocetinostat, Entinostat, Citarinostat, Abexinostat, Pracinostat, RGFP966, CAY10398, chidamide, LAQ824, GSK-J4, JIB-04, UNC0631, or UNC0646, and the disease or nerve injury is spinal cord injury, traumatic brain injury, acquired brain injury, hypoxic ischemic brain injury, strokes, periventricular leukomalacia (PVL), white-matter brain injury, CNS nerve injury, PNS nerve injury, crush nerve injury, or transection nerve injury.

2. The method of claim 1, wherein the myelination enhancing inhibitor used for treatment is CUDC-907, Quisinostat, RG2833, CUDC-101, Resminostat, 4SC-202, Mocetinostat, Entinostat, Citarinostat, Abexinostat, Pracinostat, PDA106, CAY10398, chidamide, LAQ824, SAHA, GSK-J4, JIB-04, UNC0631, or UNC0646, and the disease or nerve injury is myelopathy, myelitis, vascular myelopathy, cervical spondylotic myelopathy, spondylosis, spinal stenosis, demyelinating disease, any disease of the nervous system where the myelin sheath of a neuron is damaged, CNS demyelinating disease, PNS demyelinating disease, genetic demyelinating disease, infectious demyelinating disease, autoimmune demyelinating disease, demyelinating myelinoclastic disease, demyelinating leukodystrophic disease, Devic's disease, CNS neuropathies, diseases resulting in vitamin B12 deficiency, central pontine myelinolysis, myelopathies, tabes *dorsalis*, leukoencephalopathies, progressive multifocal leukoencephalopathy, leukodystrophies, optic neuritis, transverse myelitis, neuromyelitis optica, Guillain-Barré syndrome, chronic inflammatory demyelinating polyneuropathy, anti-MAG peripheral neuropathy, Charcot-Marie-Tooth disease, Hereditary neuropathy with liability to pressure palsy, copper deficiency associated conditions, peripheral neuropathy, myelopathy, optic neuropathy, progressive inflammatory neuropathy, multiple sclerosis (MS), MS-type clinically isolated syndrome, relapsing-remitting MS, primary progressive MS, or secondary progressive MS.

3. The method of claim 1, wherein the myelination enhancing inhibitor used for treatment is CUDC-907, Quisinostat, CUDC-101, Resminostat, 4SC-202, Mocetinostat, Entinostat, Citarinostat, Abexinostat, Pracinostat, RGFP966, CAY10398, chidamide, LAQ824, GSK-J4, JIB-04, UNC0631, or UNC0646, and the disease or nerve injury is spinal cord injury, traumatic brain injury, acquired brain injury, hypoxic ischemic brain injury, strokes, periventricular leukomalacia (PVL), white-matter brain injury, CNS nerve injury, PNS nerve injury, crush nerve injury, or transection nerve injury.

4. The method of claim 1, wherein the method comprises more than one administration of the composition comprising the myelination enhancing inhibitor to the animal.

5. The method of claim 1, wherein the amount of the myelination enhancing inhibitor is from about 0.0001% (by weight total composition) to about 99%.

6. The method of claim 1, wherein the composition further comprises a formulary ingredient.

7. The method of claim 1, wherein the composition is a pharmaceutical composition.

8. The method of claim 1 wherein the administration comprises parenteral administration, mucosal administration, intravenous administration, depot injection, subcutaneous administration, topical administration, intradermal administration, oral administration, sublingual administration, intranasal administration, or intramuscular administration.

9. The method of claim 1, wherein the administration comprises a depot injection or an oral administration.

10. The method of claim 1, wherein if there is more than one administration at least one composition used for at least one administration is different from the composition of at least one other administration.

11. The method of claim 1, wherein the myelination enhancing inhibitor of the composition is administered to the animal in an amount of from about 0.005 mg/kg animal body weight to about 100 mg/kg animal body weight.

12. The method of claim 1, wherein the animal is a human, a rodent, or a primate.

13. The method of claim 1, wherein the animal is in need of treatment of disease or nerve injury.

14. The method of claim 2, wherein the method is for treating MS, MS-type clinically isolated syndrome, relapsing-remitting MS, primary progressive MS, or secondary progressive MS.

15. The method of claim 2, wherein the method is for treating inflammation, remyelination, or both in MS, MS-type clinically isolated syndrome, relapsing-remitting MS, primary progressive MS, or secondary progressive MS.

16. The method of claim 2, wherein the method is for treating CNS demyelinating disease, PNS demyelinating disease, or MS.

17. The method of claim 3, wherein the method is for treating traumatic brain injury, acquired brain injury, hypoxic ischemic brain injury, strokes, periventricular leukomalacia (PVL), white-matter brain injury, CNS nerve injury, PNS nerve injury, crush nerve injury, or transection nerve injury.

18. The method of claim 3, wherein the method is for treating CNS nerve injury, PNS nerve injury, crush nerve injury, or transection nerve injury.

19. The method of claim 1, wherein the method further comprises one or more other treatments.

20. The method of claim 2, wherein the myelination enhancing inhibitor is PDA106, RG2833, CAY10398, chidamide, LAQ824, SAHA, GSK-J4, JIB-04, UNC0631, or UNC0646.

21. The method of claim 3, wherein the myelination enhancing inhibitor is CUDC-907, Quisinostat, CUDC-101, Resminostat, 4SC-202, Mocetinostat, Entinostat, Citarinostat, Abexinostat, Pracinostat, or RGFP966.

22. The method of claim 2, wherein the method is for treating an animal for MS, comprising administration of a composition comprising PDA106 to the animal.

23. The method of claim 3, wherein the method is for treating an animal for crush nerve injury or transection nerve injury, comprising administration of a composition comprising RGFP966 to the animal.

24. The method of claim 2, wherein the myelination enhancing inhibitor is PDA106.

25. The method of claim 3, wherein the myelination enhancing inhibitor is RGFP966.

26. A method for treating an animal for MS, comprising administration of a composition comprising PDA106 to the animal.

27. A method for treating an animal for crush nerve injury or transection nerve injury, comprising administration of a composition comprising RGFP966 to the animal.

* * * * *